US009505766B2

(12) United States Patent
Taunton, Jr. et al.

(10) Patent No.: US 9,505,766 B2
(45) Date of Patent: Nov. 29, 2016

(54) KINASE INHIBITORS

(71) Applicant: The Regents of the University of California, Oakland, CA (US)

(72) Inventors: John William Taunton, Jr., San Francisco, CA (US); Rebecca Maglathlin, San Francisco, CA (US); Iana Serafimova, San Francisco, CA (US); Michael S. Cohen, New York, NY (US); Rand Miller, San Francisco, CA (US); Ville Paavilainen, San Francisco, CA (US); Jesse McFarland, Oakland, CA (US); Shyam Krishnan, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/462,158

(22) Filed: Aug. 18, 2014

(65) Prior Publication Data

US 2015/0045343 A1    Feb. 12, 2015

Related U.S. Application Data

(63) Continuation of application No. 13/510,272, filed as application No. PCT/US2010/056890 on Nov. 16, 2010, now abandoned.

(60) Provisional application No. 61/261,696, filed on Nov. 16, 2009, provisional application No. 61/330,271, filed on Apr. 30, 2010.

(51) Int. Cl.
| | |
|---|---|
| *A61K 31/00* | (2006.01) |
| *C07D 487/04* | (2006.01) |
| *C07D 207/416* | (2006.01) |
| *C07D 231/56* | (2006.01) |
| *C07D 471/04* | (2006.01) |
| *C07D 473/00* | (2006.01) |
| *C07D 473/34* | (2006.01) |

(52) U.S. Cl.
CPC ......... *C07D 487/04* (2013.01); *C07D 207/416* (2013.01); *C07D 231/56* (2013.01); *C07D 471/04* (2013.01); *C07D 473/00* (2013.01); *C07D 473/34* (2013.01)

(58) Field of Classification Search
None
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 5,514,711 A | 5/1996 | Kitano et al. | |
| 5,663,346 A | 9/1997 | Buzetti | |
| 5,792,771 A | 8/1998 | App et al. | |
| 6,331,555 B1 | 12/2001 | Hirth et al. | |
| 2005/0026945 A1 | 2/2005 | Kafka et al. | |
| 2006/0058297 A1 | 3/2006 | Roifman et al. | |
| 2007/0232668 A1 | 10/2007 | Priebe et al. | |
| 2007/0232688 A1 | 10/2007 | Orchansky et al. | |
| 2010/0113520 A1 | 5/2010 | Miller | |
| 2010/0144705 A1 | 6/2010 | Miller | |
| 2012/0028981 A1 | 2/2012 | Miller | |

FOREIGN PATENT DOCUMENTS

| | | |
|---|---|---|
| EP | 0041215 A2 | 12/1981 |
| EP | 0093908 A1 | 11/1983 |
| EP | 0189071 A2 | 7/1986 |
| EP | 0450073 A1 | 10/1991 |
| WO | WO 91/13055 A2 | 9/1991 |
| WO | WO 94/14808 A1 | 7/1994 |
| WO | WO 95/24190 A2 | 9/1995 |
| WO | WO 95/26341 A1 | 10/1995 |
| WO | WO 99/43673 A1 | 9/1999 |
| WO | WO 2007/043401 A1 | 4/2007 |
| WO | WO 2008/005954 A2 | 1/2008 |
| WO | WO 2008/079460 A2 | 7/2008 |

OTHER PUBLICATIONS

Anderson (Chem and Biol 10:787-797, 2003).*
Thiel (Nature Biotechnol 2:513-519, 2004).*
Basheer, Ahmad et al. "Enols of Substituted Cyanomalonamides", *Journal of Organic Chemistry* 72:5297-5312, 2007.
CAS RN 26272-41-3 (entered into STN Nov. 16, 1984).
CAS RN 63431-27-6 (entered into STN Nov. 16, 1984).
Cohen, Michael S. et al., "Structural Bioinformatics-Based Design of Selective, Irreversible Kinase Inhibitors", *Science* 308:1318-1321, 2005.
Database CA [Online] Chemical Abstracts Service, Columbus, Ohio, US; Ilavsky, D. et al: "Preparation and spectral properties of the derivatives of 3-N-arylamino-2-cyanopropenoic acid", retrieved from STN Database accession No. 1986:207183, 1 page.
Database CA [Online] Chemical Abstracts Service, Columbus, Ohio, US; Khan, Misbahul Ain et al: "Synthesis of pyrido[2',3':3,4]pyrazolo[1,5-a]pyrimidine derivatives", retrieved from STN Database accession No. 1988:570356, 2 pages.
Database CA [Online] Chemical Abstracts Service, Columbus, Ohio, US; Ho, Yuh-Wen et al: "Synthesis of some new 6,8-disubstituted 7,8-dihydropyrimido[2,3:4,3]pyrazolo[1,5-a]pyrimidines and 6,7,8-trisubstituted pyrimido[2,3:4,3]pyrazolo[1,5-a]pyrimidine derivatives", retrieved from STN Database accession No. 2003:527006, 2 pages.

(Continued)

*Primary Examiner* — Craig Ricci
(74) *Attorney, Agent, or Firm* — Mintz Levin Cohn Ferris Glovsky and Popeo, P.C.

(57) ABSTRACT

Methods of inhibiting kinases using kinase inhibitors having olefin moieties are disclosed.

10 Claims, 12 Drawing Sheets

(56) References Cited

OTHER PUBLICATIONS

Donald, Alastair et al. "Rapid Evolution of 6-Phenylpurine Inhibitors of Protein Kinase B through Structure-Based Design", *Journal of Medicinal Chemistry* 50:2289-2292, 2007.
Examination Report dated Jun. 12, 2014 in counterpart European Application No. EP10830919.6, 9 pages.
International Preliminary Report on Patentability and Written Opinion dated May 22, 2012 for International Application No. PCT/US2010/056890, 10 pages.
International Search Report dated Jul. 28, 2011 for International Application No. PCT/US2010/056890, 7 pages.
Kakehi et al., "Synthesis Using Allylidenedihydropyridines. VIII.[1)] Facile Preparation of 2-Alkylthio-3-vinylpyrazolo[1,5-a]pyridines". *Bull. Chem. Soc. Jpn.*, 1980, 1775-1776.
Kakehi et al., "Synthesis Using Allylidenedihydropyridines I. Convenient Synthesis of 3-Ethenylpyrazolo[1,5-a] Pyridines", *Chemistry Letters*, 1977, pp. 545-546.
Kamath, Shantaram et al., "Receptor-Guided Alignment-Based Comparative 3D-QSAR Studies of Benzylidene Malonitrile Tyrphostins as EGFR and HER-2 Kinase Inhibitors", *Journal of Medicinal Chemistry* 46:4657-4668, 2003.
Knight, Zachary A. et al., "A membrane capture assay for lipid kinase activity", *Nature Protocols* 2(10):2459-2466, 2007.
Milata et al., "Alkylated benzimidazole and benzotriazole derivatives of 3-amino-2-propenoic acid", *Collection of Czechoslovak Chemical Communications*, 1989, 54(3):713-724.
Milata et al., "4-Aminoethylene derivatives of 2-Methylbenzotriazole", *Collection of Czechoslovak Chemical Communications*, 1990, 55(4):1038-1048.
Office Action dated Apr. 12, 2013 in related Chinese Application No. 201080061570.1.
Proença, Fernanda et al., "A simple and eco-friendly approach for the synthesis of 2-imino and 2-oxo-2H-chromene-3-carboxamides", *Green Chemistry* 10:995-998, 2008.
Radwan, S.M., "Synthesis and reactions of some new heterocyclic compounds containing thieno[2,3-c] pyridazine moiety", *Phosphorus, Sulfur and Silicon*, 2000, 163:153-169.
Rellos, Peter et al., "Structure and Regulation of the Human Nek2 Centrosomal Kinase*", *Journal of Biological Chemistry* 282(9):6833-6842, 2007.
Romano et al., "Reactions of 1,2-diaminobenzimidazoles with β-dielectrophiles: Synthesis of pyrimido[1,2-α] benzimidazole derivatives." *Heterocycles*, 1990, 31(2):267-276.
Sammes, M.P. et al., "α-Cyano-sulphonyl Chlorides" Their Preparation and Reactions with Amines, Alcohols, and Enamines, *Journal of the Chemical Society* 2151-2155, 1971.

Santilli, Arthur A. et al., "8,9,10,11-Tetrahydro-12H-benzo[5,6]quinoxalino-[2,3-e][1,4]diazepin-12-ones. Examples of a New Heterocyclic Ring System", *Journal of Organic Chemistry* 29:2066-2068, 1964.
Strakova et al., "Synthesis and reactions of 1-(2-pyridyl)-3-methyl-4-chloro-5-formyl-6,7-dihydroindazoles", *Chemistry of Heterocyclic Compounds*, 1998, 34(6):669-673.
Vinogradov et al., "Synthesis and reactions of 1-aryl-3-formyl-4,6-dinitro-1H-indazoles". *Mendeleev Commun.*, 2002, 12(5):198-200.
Wang, Kan et al., "Cyanoacetamide Multicomponent Reaction (I): Parallel Synthesis of Cyanoacetamides", *Journal of Combinatorial Chemistry* 11:920-927, 2009.
Wells, Geoffrey et al., "Structural Studies on Bioactive Compounds. 32.[1] Oxidation of Tyrphostin Protein Tyrosine Kinase Inhibitors with Hypervalent Iodine Reagents", *Journal of Medicinal Chemistry* 43:1550-1562, 2000.
Non-Final Office Action dated May 24, 2013 in parent U.S. Appl. No. 13/510,272, 7 pages.
Final Office Action dated Dec. 18, 2013 in parent U.S. Appl. No. 13/510,272, 8 pages.
Buzzetti et al., "Cinnamamide Analogs as Inhibitors of Protein Tryrosine Kinases", *IL Farmaco, Elsevier France*, 1993, 48(5):615-636.
Gazit et al., "Tyrphostins. 5. Potent Inhibitors of Platelet-Derived Growth Factor Receptor Tyrosine Kinase: Structure-Activity Relationships in Quinoxalines, Quinolines, and Indole Tyrphostins", *Journal of Medicinal Chemistry, American Chemical Society*, 1996, 39(11):2170-2177.
Gazit et al, "Tyrphostins. 6. Dimeric Benzylidenemalononitrile Tyrphostins: Potent Inhibitors of EGF Receptor Tyrosine Kinase in Vitro", *Journal of Medicinal Chemistry*, 1996, 4905-4911.
Montgomery et al., "Synthesis and antiproliferative activity of unsaturated quinolone derivatives", *Anti-Cancer Drug Design*, 2000, 15(3): 171-181.
Zwaans et al., "Ab initio calculations on 2-, 3- and 4- substituted quinolones in relation with their activity as protein tyrosine kinase inhibitors", *Journal of Molecular Structure: Theo Chem*, 1996, 362(1):51-68.
Extended European Search Report dated Jun. 14, 2013 in counterpart European Application No. EP 10830919.6, 12 pages.
Office Action dated Mar. 7, 2014 in counterpart Mexican Application No. MX/a/2012/005678, 22 pages (English Translation).
Office Action dated Sep. 30, 2014 in counterpart Mexican Application No. MX/a/2012/005678, 13 pages (English Translation).

* cited by examiner

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 1

Arg Arg Gln Leu Phe Arg Gly Phe Ser Phe Val Ala Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Leu Glu Ile Tyr Gly Glu Phe Lys Lys Lys
1               5                   10
```

KINASE INHIBITORS

CROSS-REFERENCES TO RELATED APPLICATIONS

This application is a continuation of U.S. application Ser. No. 13/510,272, filed Oct. 23, 2013, which in turn is a U.S. National Stage of International Appl. No. PCT/US10/56809, filed Nov. 16, 2010, which in turn claims the benefit of U.S. Application No. 61/261,696, filed Nov. 16, 2009, and U.S. Application No. 61/330,271, filed Apr. 30, 2010, each of which is incorporated by reference in its entirety for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 84850-011711USUS_ST25.TXT, created on Aug. 15, 2014, 1,004 bytes, machine format IBM-PC, MS Windows operating system, is hereby incorporated by reference.

STATEMENT AS TO RIGHTS TO INVENTIONS MADE UNDER FEDERALLY SPONSORED RESEARCH AND DEVELOPMENT

This invention was made with government support under GM071434 awarded by the National Institutes of Health. The Government has certain rights in the invention.

BACKGROUND OF THE INVENTION

The human genome contains at least 500 genes encoding protein kinases. In fact, protein kinase genes constitute about 2% of all human genes. Protein kinases modify up to 30% of all human proteins and regulate the majority of cellular pathways, particularly those pathways involved in signal transduction.

Because of the profound effects on cells, the activities of protein kinases are highly regulated. Indeed, unregulated kinase activity frequently causes disease related to control of cell growth, cell movement and cell death, particularly cancer. A large body of research is currently being conducted to find drugs capable of inhibiting specific kinases to treat a variety of diseases. Some such drugs are already in clinical use, including Gleevec (imatinib) and Iressa (gefitinib). To increase potency and selectivity, irreversible electrophilic inhibitors, which form a covalent bond with a cysteine in the kinase active site, have been developed. Several of these irreversible kinase inhibitors are currently in clinical trials (e.g., neratinib, tovok) Inhibition of proteins through irreversible binding of an inhibitor to the protein, however, often leads to toxicity and/or immunogenic problems when used to treat diseases. Therefore, reversible kinase inhibitors are needed to inhibit kinases while minimizing the risk of toxicity. The present invention addresses these and other needs in the art.

BRIEF SUMMARY OF THE INVENTION

In a first aspect, kinase inhibitors are provided. In some embodiments, the kinase inhibitor has the structure of Formula I:

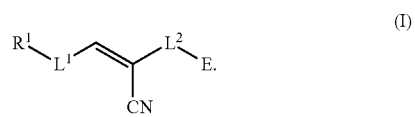

(I)

In Formula I, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ is bond, —C(O)—, —C(O)N($L^3R^2$)—, —C(O)O—, —S(O)$_n$—, —O—, —N($L^3R^2$)—, —P(O)(O$L^3R^2$)O—, —SO$_2$N($L^3R^2$)—, —P(O)(N$L^3R^2$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol n is 0, 1 or 2.

$L^2$ is a bond, —C(O)—, —C(O)N($L^{3.4}R^{2.4}$)—, —C(O)O—, —S(O)$_t$—, —O—, —N($L^{3.4}R^{2.4}$)—, —P(O)(O$L^{3.4}R^{2.4}$)O—, —SO$_2$N($L^{3.4}R^{2.4}$)—, —P(O)(N$L^{3.4}R^{2.4}$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol t is 0, 1 or 2.

$L^3$ and $L^{3.4}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol w is 0, 1 or 2.

$R^2$ and $R^{2.4}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

E is an electron withdrawing group or together with $L^2$ forms an electron withdrawing group.

In another aspect, methods of inhibiting protein kinases are provided. The methods include contacting a protein kinase with an effective amount of a kinase inhibitor provided herein. The kinase inhibitor may have the structure of Formula I or Formula II (or any of the embodiments thereof described herein).

In another aspect, a method of treating a disease associated with kinase activity in a subject in need of such treatment. The method includes administering to the subject an effective amount of a kinase inhibitor provided herein. The kinase inhibitor may have the structure of Formula I or Formula II (or any of the embodiments thereof described herein).

DETAILED DESCRIPTION OF THE INVENTION

I. Definitions

Figure 1A:
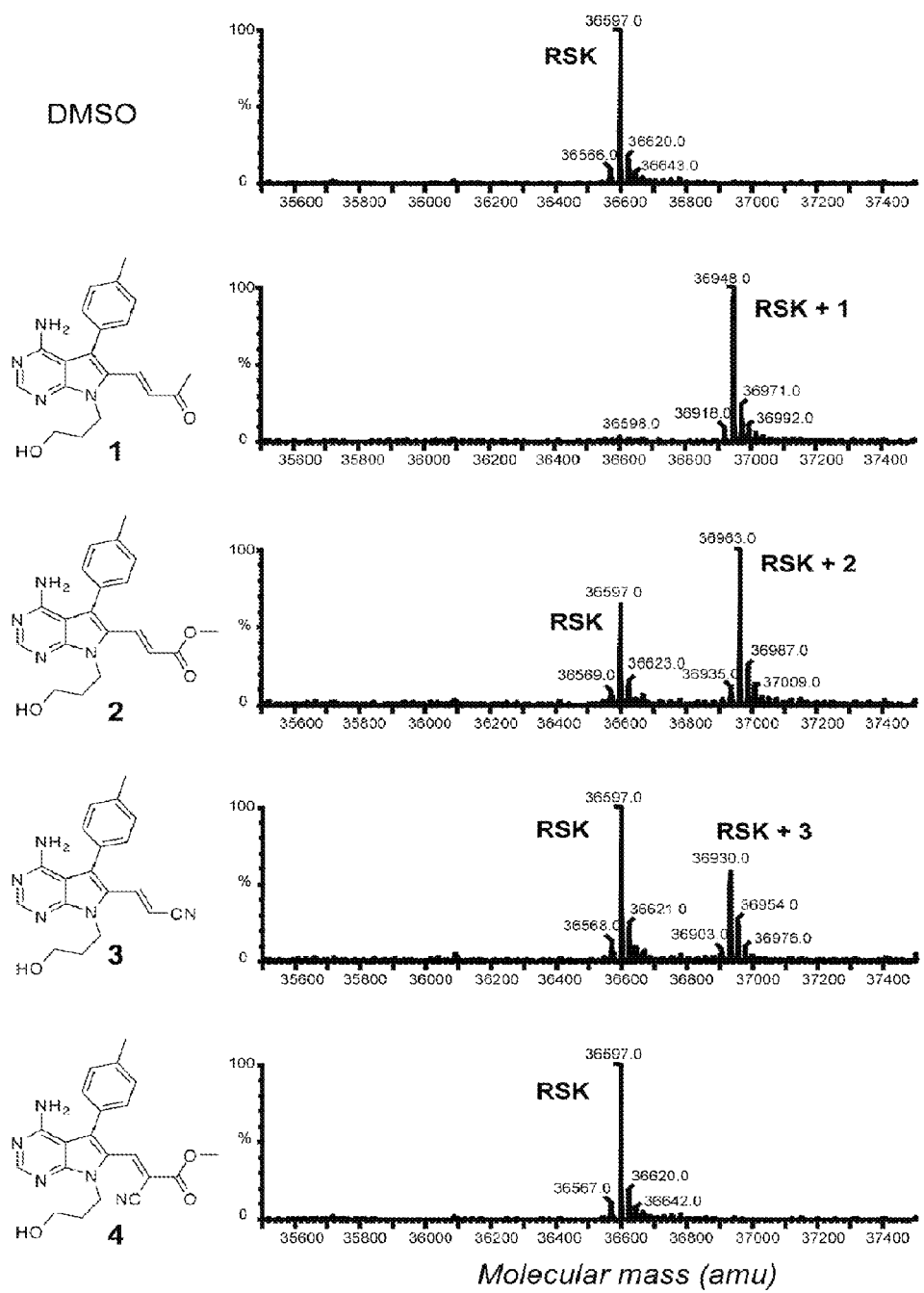
FIG. 1A and FIG. 1B provide mass spectrometric results following incubation of DMSO or Cmpds 1-4 (FIG. 1A), and Cmpds 5-8 (FIG. 1B) with human RSK2 CTD for 1 hr at room temperature.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene" by itself or as part of another substituent means a divalent radical derived from an alkyl, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, a polyunsaturated, aromatic, hydrocarbon substituent which can be a single ring or multiple rings (preferably from 1 to 3 rings) which are fused together (i.e. a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e. multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent means a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S($O_2$)—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR$SO_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR$SO_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Where a substituent of a compound provided herein is "R-substituted" (e.g. $R^7$-substituted), it is meant that the substituent is substituted with one or more of the named R groups (e.g. $R^7$) as appropriate. In some embodiments, the substituent is substituted with only one of the named R groups.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and or causing remission of cancer.

An "effective amount" is an amount of a kinase inhibitor sufficient to contribute to the treatment, prevention, or reduction of a symptom or symptoms of a disease, or to inhibit the activity or a protein kinase relative to the absence of the kinase inhibitor. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an osteoclast or leukocyte relative to the absence of the antagonist.

The terms "kinase," "protein kinase" and the like, refer to an enzyme that transfers a phosphate group from a donor molecule (e.g. ATP) to a substrate. The process of transferring a phosphate group from a donor to a substrate is conventionally known as phosphorylation. The term "substrate" in the context of protein phosphorylation refers to a compound (e.g. protein) which accepts a phosphate group and is thus phosphorylated.

II. Kinase Inhibitors

In a first aspect, kinase inhibitors are provided. The kinase inhibitors are typically reversible kinase inhibitors. In some embodiments, the kinase inhibitor has the structure of Formula I:

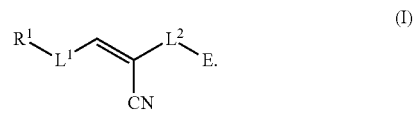

In Formula I, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^{1A}$-$R^{1A}$. $R^{1A}$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $L^1$-$R^1$ and/or $R^1$ is/are generally designed to fit within a kinase ATP binding site and/or bind to amino acids within the kinase ATP binding site (e.g. a kinase ATP binding site moiety).

$L^1$ is a bond, —C(O)—, —C(O)N($L^3R^2$)—, —C(O)O—, —S(O)$_n$—, —O—, —N($L^3R^2$)—, —P(O)(O$L^3R^2$)O—, —SO$_2$N($L^3R^2$)—, —P(O)(N$L^3R^2$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol n is 0, 1 or 2. In some embodiments, $L^1$ is a bond. $L^{1A}$ is a bond, —C(O)—, —C(O)N($L^{3'}R^{2'}$)—, —C(O)O—, —S(O)$_n$—, —O—, —N($L^{3'}R^{2'}$)—, —P(O)(O$L^{3'}R^{2'}$)O—, —SO$_2$N($L^{3'}R^{2'}$)—, —P(O)(N $L^{3'}R^{2'}$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol n' is 0, 1 or 2.

$L^2$ is a bond, —C(O)—, —C(O)N($L^{3A}R^{2A}$)—, —C(O)O—, —S(O)$_t$—, —O—, —N($L^{3A}R^{2A}$)—, —P(O)(O$L^{3A}R^{2A}$)O—, —SO$_2$N($L^{3A}R^{2A}$)—, —P(O)(N$L^{3A}R^{2A}$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol t is 0, 1 or 2.

$L^3$, $L^{3'}$ and $L^{3A}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol w is 0, 1 or 2.

$R^2$, $R^{2'}$ and $R^{2A}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

E is an electron withdrawing group or together with $L^2$ forms an electron withdrawing group (e.g. $-L^2$-E may form an electron withdrawing group). In some embodiments, E is ring A or $R^4$, wherein $R^4$ and ring A are is as defined below. Thus, E may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or $-L^{5A}-R^{4A}$. E may also be hydrogen, $R^{23A}$-substituted or unsubstituted alkyl, $R^{23A}$-substituted or unsubstituted heteroalkyl, $R^{23A}$-substituted or unsubstituted cycloalkyl, $R^{23A}$-substituted or unsubstituted heterocycloalkyl, $R^{23A}$-substituted or unsubstituted aryl, or $R^{23A}$-substituted or unsubstituted heteroaryl. In some embodiments, E is a substituted or unsubstituted heteroaryl (e.g. $R^{23A}$-substituted or unsubstituted heteroaryl) or substituted or unsubstituted heterocycloalkyl (e.g. $R^{23A}$-substituted or unsubstituted heterocycloalkyl).

In some embodiments, where $-L^2$-E is an electron withdrawing group, E may simply be hydrogen. The term "electron withdrawing group" refers to a chemical substituent that modifies the electrostatic forces acting on a nearby chemical reaction center by withdrawing negative charge from that chemical reaction center. Thus, electron withdrawing groups draw electrons away from a reaction center. As a result, the reaction center is fractionally more positive than it would be in the absence of the electron-withdrawing group. In some embodiments, the chemical reaction center is one of the two carbons forming the carbon-carbon double bond (olefin). In some embodiments, the chemical reaction center is the olefin carbon attached to $-L^1-R^1$. The electron withdrawing group functions to draw charge or electrons away from this olefin carbon thereby making the olefin carbon electron deficient (relative to the absence of the electron withdrawing group). The electron deficient olefin carbon is thereby rendered more reactive toward electron rich chemical groups, such as the sulfhydryl of a kinase active site cysteine.

E and $-L^2$-E are typically substituents that sufficiently withdraw electrons from the reaction center olefin carbon to reversibly bind to the sulfhydryl of a kinase active cite cysteine (e.g. measurably reversibly binding when the kinase is fully denatured or partly denatured). Methods of testing the reversibility of the bond between the reaction center olefin carbon and the sulfhydryl of a kinase active site cysteine (or a thiol compound proxy) are provided in the Assays and Examples provided below.

In some embodiments, $-L^2$-E is as set forth in one of the Formulae set forth below For example, in Formula II $-L^2$-E is $-C(O)X(L^4-R^3)_z(L^5-R^4)$, in Formula IIIc $-L^2$-$NR^3R^4$, in Formula IIIc $-L^2$-E is $-WNR^3R^4$, etc. Thus, $-L^2$-E may be as set forth in the Formulae provided herein and combined with the definitions and embodiments of $-L^1-R^1$ provided herein. Likewise, $-L^1-R^1$ may be as set forth in the Formulae provided herein (e.g. Formula IIIa to IIIe wherein $-L^1-R^1$ includes a pyrrolopyrimidinyl) and combined with the definitions of $-L^2$-E as provided herein.

Some non-limiting examples of groups capable of withdrawing electrons from a reaction center include, but are not limited to, $-NO_2$, $-N(R_2)$, $-N(R_3)^+$, $-N(H_3)^+$, $-SO_3H$, $-SO_3R'$, $-S(O_2)R'$ (sulfone), $-S(O)R'$ (sulfoxide), $-S(O_2)NH_2$ (sulfonamide), $-SO_2NHR'$, $-SO_2NR'_2$, $-PO(OR')_2$, $-PO_3H_2$, $-PO(NR'_2)_2$, pyridinyl (2-, 3-, 4-), pyrazolyl, indazolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, a 5 or 6-membered heteroaryl with a C=N double bond optionally fused to a 5 or 6 membered heteroaryl, pyridinyl N-oxide, $-C\equiv N$, $-CX'_3$, $-C(O)X'$, $-COOH$, $-COOR'$, $-C(O)R'$, $-C(O)NH_2$, $-C(O)NHR'$, $-C(O)NR'_2$, $-C(O)H$, $-P(O)(OR')OR''$ and X', wherein X' is independently halogen (e.g. chloro of fluoro) and R, R' and R'' are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or similar Substituents (e.g. a substituent group, a size limited substituent group or a lower substituent group). The term "electron withdrawing group" is distinguished from an "electron donating group" as known in the art.

Thus, in some embodiments, the kinase inhibitors provided herein (e.g. compounds of Formula I above or the Formulae provided below) are reversible kinase inhibitors, and may measurably dissociate from the protein kinase when the protein kinase is not denatured, partially denatured, or fully denatured. In some embodiments, the covalent reversible kinase inhibitor measurably dissociates from the protein kinase only when the protein kinase is fully denatured or partially denatured, but does not measurably dissociate from the protein kinase when the protein kinase is intact, or dissociates at least 10, $1\times10^2$, $1\times10^3$, $1\times10^4$, $1\times10^5$, $1\times10^6$, $1\times10^7$, $1\times10^8$, $1\times10^9$, $1\times10^{10}$ fold slower when the protein kinase is intact relative to the dissociation when the protein kinase is fully or partially denatured (referred to herein as a "covalent reversible denatured kinase inhibitor"). In some embodiments, the protein kinase is denatured or fully denatured (i.e. not intact) when placed in denaturing solution, such as 6 N guanidine, 1% SDS, 50% MeCN, or similar protein denaturant, for seconds or minutes (e.g. 30 to 120 seconds, such as 60 seconds). In some embodiments, the reversible kinase inhibitors described herein, after covalently binding to the kinase active site cysteine residue, are capable of dissociating from the kinase within seconds or minutes after denaturing/unfolding the kinase with 6 N guanidine, 1% SDS, 50% MeCN, or similar protein denaturant.

In some embodiments of the kinase inhibitors provided herein, if $L^1$ is a bond and $R^1$ is (3-(4-amino-5-p-tolyl-7H-pyrrolo[2,3-d]pyrimidin-7-yl)propan-1-ol)-6-yl, then $-L^2$-E is not $-C(O)NH_2$. In other embodiments, where $L^1$ is a bond and $R^1$ is a substituted 4-amino pyrrolopyrimidinyl, then $-L^2$-E is not $-C(O)NH_2$. In other embodiments, where $L^1$ is a bond and $R^1$ is a substituted pyrrolopyrimidinyl, then $-L^2$-E is not $-C(O)NH_2$. In certain embodiments, where $L^1$ is a bond and $R^1$ is a substituted or unsubstituted pyrrolopyrimidinyl, then $-L^2$-E is not $-C(O)NH_2$. In other embodiments, where $R^1$ is a substituted or unsubstituted pyrrolopyrimidinyl, then $-L^2$-E is not $-C(O)NH_2$.

In other embodiments, $-L^2$-E is not $-C(O)NH_2$. In other embodiments, $-L^2$-E is not $-C(O)OH$, or $-C(O)OR''$, wherein R'' is an unsubstituted $C_1$-$C_{10}$ alkyl (e.g. unsubstituted $C_1$-$C_5$ alkyl such as methyl). In some embodiments, -$L^2$-E is not —C(O)N(CH$_3$)$_2$ or —C(O)NH(CH$_3$).

In some embodiments of Formula I above or the Formulae provided below, $R^1$ and $R^{14}$ are independently $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl.

$R^7$ is independently hydrogen, halogen, —CN, —OH, —NH$_2$, —COOH, —CF$_3$, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, $R^8$-substituted or unsubstituted heteroaryl, or -$L^6$-$R^{7A}$. $L^6$ is —O—, —NH—, —C(O)—, —C(O)NH—, —S(O)$_m$—, or —S(O)$_m$NH—, where m is 0, 1, or 2.

$R^{7A}$ is independently hydrogen, halogen, —CN, —OH, —NH$_2$, —COOH, —CF$_3$, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl. $R^8$ is independently hydrogen, halogen, —CN, —OH, —NH$_2$, —COOH, —CF$_3$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, $R^9$-substituted or unsubstituted heteroaryl or -$L^9$-$R^{9A}$. In some embodiments, $R^8$ is independently —OH or unsubstituted alkyl. $L^9$ is —O—, —NH—, —C(O)—, —C(O)NH—, —S(O)$_{m'}$—, or —S(O)$_{m'}$NH—, where m' is 0, 1, or 2.

$R^{9A}$ is independently hydrogen, halogen, —CN, —OH, —NH$_2$, —COOH, —CF$_3$, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^9$ is independently hydrogen, halogen, —CN, —OH, —NH$_2$, —COOH, —CF$_3$, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^{10}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^1$ and $R^{14}$ are independently $R^7$-substituted or unsubstituted 6,5 fused ring heteroaryl, $R^7$-substituted or unsubstituted 5,6 fused ring heteroaryl, $R^7$-substituted or unsubstituted 5,5 fused ring heteroaryl, $R^7$-substituted or unsubstituted 6,6 fused ring heteroaryl, or $R^7$-substituted or unsubstituted 5 or 6 membered heteroaryl having at least 2 (e.g. 2 to 4) ring nitrogens. In certain embodiments, $R^1$ and $R^{14}$ are independently $R^7$-substituted phenyl, $R^7$-substituted piperidinyl, $R^7$-substituted 6-membered heterocycloalkyl, $R^7$-substituted or unsubstituted 6,5 fused ring heteroaryl, $R^7$-substituted or unsubstituted 5,6 fused ring heteroaryl. $R^7$ may be halogen, —CN, —OH, —NH$_2$, —COOH, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl or -$L^6$-$R^{7A}$. $R^{7A}$ may be $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl. $L^6$ may be —O—, —NH—, —C(O)—, —C(O)NH—, —S(O)$_m$—, or —S(O)$_m$NH—. $R^8$ may be —OH, or $R^9$-substituted or unsubstituted alkyl. In some related embodiments, $R^7$ is independently $R^8$-substituted or unsubstituted cycloalkyl, $R^8$-substituted or unsubstituted heterocycloalkyl, $R^8$-substituted or unsubstituted aryl, $R^8$-substituted or unsubstituted heteroaryl, or -$L^6$-$R^{7A}$. In other related embodiments, $R^7$ is $R^8$-substituted or unsubstituted heteroaryl, or -$L^6$-$R^{7A}$. $L^6$ may be —C(O)—. $R^{7A}$ may be $R^8$-substituted or unsubstituted heteroaryl.

In some embodiments, $R^1$ or $R^{14}$ is a substituted or unsubstituted heteroaryl, such as an $R^7$-substituted or unsubstituted heteroaryl. The heteroaryl may be a substituted or unsubstituted pyrrolopyrimidinyl, substituted or unsubstituted indolyl, substituted or unsubstituted pyrazolyl, substituted or unsubstituted indazolyl, substituted or unsubstituted imidazolyl, substituted or unsubstituted thiazolyl, substituted or unsubstituted benzothiazolyl, substituted or unsubstituted oxazolyl, substituted or unsubstituted benzimidazolyl, substituted or unsubstituted benzoxazolyl, substituted or unsubstituted isoxazolyl, substituted or unsubstituted benzisoxazolyl, substituted or unsubstituted triazolyl, substituted or unsubstituted benzotriazolyl, substituted or unsubstituted quinolinyl, substituted or unsubstituted isoquinolinyl, substituted or unsubstituted quinazolinyl, substituted or unsubstituted pyrimidinyl, substituted or unsubstituted pyridinyl N-oxide, substituted or unsubstituted furanyl, substituted or unsubstituted thiophenyl, substituted or unsubstituted benzofuranyl, substituted or unsubstituted benzothiophenyl, substituted or unsubstituted imidazo[1,2b]pyridazinyl. In some embodiments, $R^1$ or $R^{14}$ is a substituted or unsubstituted 6,5 fused ring heteroaryl, a substituted or unsubstituted 5,6 fused ring heteroaryl, a substituted or unsubstituted 5,5 fused ring heteroaryl, or a substituted or unsubstituted 6,6 fused ring heteroaryl. In other embodiments, $R^1$ or $R^{14}$ is a substituted or unsubstituted 5 or 6 membered heteroaryl having at least 2 (e.g. 2 to 4) ring nitrogens. As discussed above any $R^1$ substituent may be $R^7$-substituted, including the substituents recited in this paragraph.

$R^1$ and/or -$L^1$-$R^1$ is/are generally designed to be a kinase ATP binding site moiety. It has also been found herein that compounds of Formula I in which $R^1$ and/or -$L^1$-$R^1$ is/are attached to the remainder of the compound via an sp2 carbon, stability of the compound is improved. A "kinase ATP binding site moiety," as used herein, is a moiety capable of fitting within a kinase ATP binding site and/or binding to amino acids within the kinase ATP binding site. Kinase ATP binding sites are well known for wide variety of kinases, and may be easily determined from the primary amino acid structure of a kinase using computer modeling techniques commonly employed in the art. In certain embodiments, -$L^1$-$R^1$ is a kinase ATP binding site moiety and the electron deficient olefin carbon binds to a sulfhydryl of a kinase active site cysteine. Thus, in some embodiments the kinase inhibitors provided herein bind to at least two points of the protein kinase: at least one residue within the ATP binding site moiety and a sulfhydryl of a kinase active site cysteine. In some embodiments, -$L^1$-$R^1$ does not have the formula:

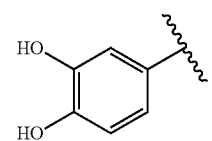

In other embodiments, -L$^1$-R$^1$ is not a phenyl substituted with hydroxyl. In some embodiments, -L$^1$-R$^1$ includes a substituted or unsubstituted heteroaryl or substituted or unsubstituted heteroarylene group.

In some embodiments, L$^1$-R$^1$ and/or R$^1$ is substituted or unsubstituted aryl or substituted or unsubstituted heteroaryl. In other embodiments, L$^1$ is a bond and R$^1$ is substituted or unsubstituted aryl or substituted or unsubstituted heteroaryl. In other embodiments, L$^1$ is a substituted or unsubstituted arylene or substituted or unsubstituted heteroarylene and R$^1$ or R$^{1A}$ is a substituted or unsubstituted aryl or substituted or unsubstituted heteroaryl. For example, L$^1$ may be substituted or unsubstituted arylene and R$^1$ or R$^{1A}$ may be substituted or unsubstituted heteroaryl. In related embodiments, L$^{1A}$ is —C(O)—, —C(O)NH—, —C(O)O—, —S(O)—, —SO$_2$—, —S—, —O—, —NH— or —SO$_2$NH—.

In some embodiments, L$^1$ is a bond and R$^1$ is an R$^7$-substituted phenyl. In some related embodiments, R$^7$ is -L$^6$-R$^{7A}$ or R$^8$-substituted or unsubstituted heteroaryl, wherein R$^{7A}$ is R$^8$-substituted or unsubstituted heteroaryl. In some further related embodiments, L$^6$ is a bond or —C(O)—. In other related embodiment, the R$^8$-substituted or unsubstituted heteroaryl is an R$^8$-substituted or unsubstituted 6,5 fused ring heteroaryl or R$^8$-substituted or unsubstituted 5,6 fused ring.

In other embodiments, L$^1$ is a bond and R$^1$ is an R$^7$-substituted phenyl, R$^7$-substituted piperidinyl, R$^7$-substituted piperizinyl, R$^7$-substituted pyrrolidinyl, R$^7$-substituted piperidinyl, R$^7$-substituted azepanyl, or R$^7$-substituted azetidinyl. In some related embodiments, R$^7$ is -L$^6$-R$^{7A}$ or R$^8$-substituted or unsubstituted heteroaryl, wherein R$^{7A}$ is R$^8$-substituted or unsubstituted heteroaryl. In some further related embodiments, L$^6$ is a bond or —C(O)—. In other related embodiment, the R$^8$-substituted or unsubstituted heteroaryl is an R$^8$-substituted or unsubstituted 6,5 fused ring heteroaryl or R$^8$-substituted or unsubstituted 5,6 fused ring.

In some embodiment, L$^1$ is a substituted or unsubstituted arylene (e.g. phenylene) and R$^1$ or R$^{1A}$ is a substituted or unsubstituted heteroaryl (e.g. R$^7$-substituted). In other embodiments, L$^1$ is a substituted or unsubstituted heteroarylene.

In some embodiments of Formula I above or the Formulae provided below, L$^1$ is a bond, —C(O)—, —C(O)N(L$^3$R$^2$)—, —C(O)O—, —S(O)$_n$—, —O—, —S—, —N(L$^3$R$^2$)—, —P(O)(OL$^3$R$^2$)O—, —SO$_2$N(L$^3$R$^2$)—, —P(O)(NL$^3$R$^2$)N—, R$^{11}$-substituted or unsubstituted alkylene, R$^{11}$-substituted or unsubstituted heteroalkylene, R$^{11}$-substituted or unsubstituted cycloalkylene, R$^{11}$-substituted or unsubstituted heterocycloalkylene, R$^{11}$-substituted or unsubstituted arylene, or R$^{11}$-substituted or unsubstituted heteroarylene. L$^{1A}$ may be a bond, —C(O)—, —C(O)N(L$^3$R$^2$)—, —C(O)O—, —S(O)$_n$—, —O—, —N(L$^3$R$^2$)—, —P(O)(OL$^3$R$^2$)O—, —SO$_2$N(L$^3$R$^2$)—, —P(O)(N L$^3$R$^2$)N—, R$^{11}$-substituted or unsubstituted alkylene, R$^{11}$-substituted or unsubstituted heteroalkylene, R$^{11}$-substituted or unsubstituted cycloalkylene, R$^{11}$-substituted or unsubstituted heterocycloalkylene, R$^{11}$-substituted or unsubstituted arylene, or R$^{11}$-substituted or unsubstituted heteroarylene.

L$^1$ and L$^{1A}$ may also independently be a bond, R$^{11}$-substituted or unsubstituted alkylene, R$^{11}$-substituted or unsubstituted heteroalkylene, R$^{11}$-substituted or unsubstituted cycloalkylene, R$^{11}$-substituted or unsubstituted heterocycloalkylene, R$^{11}$-substituted or unsubstituted arylene, or R$^{11}$-substituted or unsubstituted heteroarylene.

R$^{11}$ is independently hydrogen, halogen, —CN, —OH, —NH$_2$, —COOH, —CF$_3$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl, or R$^{12}$-substituted or unsubstituted heteroaryl. R$^{12}$ is independently hydrogen, halogen, —CN, —OH, —NH$_2$, —COOH, —CF$_3$, R$^{13}$-substituted or unsubstituted alkyl, R$^{13}$-substituted or unsubstituted heteroalkyl, R$^{13}$-substituted or unsubstituted cycloalkyl, R$^{13}$-substituted or unsubstituted heterocycloalkyl, R$^{13}$-substituted or unsubstituted aryl, or R$^{13}$-substituted or unsubstituted heteroaryl. R$^{13}$ is independently hydrogen, halogen, —CN, —OH, —NH$_2$, —COOH, —CF$_3$, R$^{14}$-substituted or unsubstituted alkyl, R$^{14}$-substituted or unsubstituted heteroalkyl, R$^{14}$-substituted or unsubstituted cycloalkyl, R$^{14}$-substituted or unsubstituted heterocycloalkyl, R$^{14}$-substituted or unsubstituted aryl, or R$^{14}$-substituted or unsubstituted heteroaryl. R$^{14}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

L$^2$ may be a bond, —C(O)N(L$^{3A}$R$^{2A}$)—, —C(O)O—, —S(O)$_r$—, —O—, —S—, —N(L$^{3A}$R$^{2A}$)—, —C(O)—P(O)(OL$^3$R$^2$))—, —SO$_2$N(L$^3$R$^2$)—, —P(O)(NL$^3$R$^2$)N—, R$^{19}$-substituted or unsubstituted alkylene, R$^{19}$-substituted or unsubstituted heteroalkylene, R$^{19}$-substituted or unsubstituted cycloalkylene, R$^{19}$-substituted or unsubstituted heterocycloalkylene, R$^{19}$-substituted or unsubstituted arylene, or R$^{19}$-substituted or unsubstituted heteroarylene.

R$^{19}$ is independently hydrogen, halogen, —CN, —OH, —NH$_2$, —COOH, —CF$_3$, R$^{20}$-substituted or unsubstituted alkyl, R$^{20}$-substituted or unsubstituted heteroalkyl, R$^{20}$-substituted or unsubstituted cycloalkyl, R$^{20}$-substituted or unsubstituted heterocycloalkyl, R$^{20}$-substituted or unsubstituted aryl, or R$^{20}$-substituted or unsubstituted heteroaryl. R$^{20}$ is independently hydrogen, halogen, —CN, —OH, —NH$_2$, —COOH, —CF$_3$, R$^{21}$-substituted or unsubstituted alkyl, R$^{21}$-substituted or unsubstituted heteroalkyl, R$^{21}$-substituted or unsubstituted cycloalkyl, R$^{2'}$-substituted or unsubstituted heterocycloalkyl, R$^{2'}$-substituted or unsubstituted aryl, or R$^{21}$-substituted or unsubstituted heteroaryl. R$^{21}$ is independently hydrogen, halogen, —CN, —OH, —NH$_2$, —COOH, —CF$_3$, R$^{22}$-substituted or unsubstituted alkyl, R$^{22}$-substituted or unsubstituted heteroalkyl, R$^{22}$-substituted or unsubstituted cycloalkyl, R$^{22}$-substituted or unsubstituted heterocycloalkyl, R$^{22}$-substituted or unsubstituted aryl, or R$^{22}$-substituted or unsubstituted heteroaryl. R$^{22}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, L$^3$, L$^{3'}$, and L$^{3A}$ are independently a bond, R$^{27}$-substituted or unsubstituted alkylene, R$^{27}$-substituted or unsubstituted heteroalkylene, R$^{27}$-substituted or unsubstituted cycloalkylene, R$^{27}$-substituted or unsubstituted heterocycloalkylene, R$^{27}$-substituted or unsubstituted arylene, or R$^{27}$-substituted or unsubstituted heteroarylene. R$^{27}$ is independently hydrogen, halogen, —CN, —OH, —NH$_2$, —COOH, —CF$_3$, R$^{28}$-substituted or unsubstituted alkyl, R$^{28}$-substituted or unsubstituted heteroalkyl, R$^{28}$-substituted or unsubstituted cycloalkyl, R$^{28}$-substituted or unsubstituted heterocycloalkyl, R$^{28}$-substituted or unsubstituted aryl, or R$^{28}$-substituted or unsubstituted heteroaryl. R$^{28}$ is independently hydrogen, halogen, —CN, —OH, —NH$_2$, —COOH, —CF$_3$, R$^{29}$-substituted or unsubstituted alkyl, R$^{29}$-substituted or unsubstituted heteroalkyl, R$^{29}$-substituted or unsubstituted cycloalkyl, R$^{29}$-substituted or unsubstituted heterocycloalkyl, R$^{29}$-substituted or unsubstituted aryl, or $R^{29}$-substituted or unsubstituted heteroaryl. $R^{29}$ is independently hydrogen, halogen, —CN, —OH, —NH$_2$, —COOH, —CF$_3$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. $R^{30}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^2$, $R^{2'}$, and $R^{2A}$ are independently hydrogen, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{15}$ is independently hydrogen, halogen, —CN, —OH, —NH$_2$, —COOH, —CF$_3$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, $R^{16}$-substituted or unsubstituted heteroaryl, or -$L^7$-$R^{15A}$. $L^7$ is independently —O—, —C(O)—, —C(O)NH—, —S(O)$_y$—, or —S(O)$_y$NH—, where y is 0, 1, or 2. $R^{15A}$ is independently hydrogen, halogen, —CN, —OH, —NH$_2$, —COOH, —CF$_3$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, $R^{16}$-substituted or unsubstituted heteroaryl. $R^{16}$ is independently hydrogen, halogen, —CN, —OH, —NH$_2$, —COOH, —CF$_3$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl. $R^{17}$ is independently hydrogen, halogen, —CN, —OH, —NH$_2$, —COOH, —CF$_3$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. $R^{18}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the kinase inhibitor has the structure of Formula II:

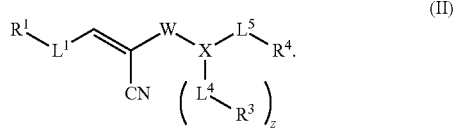

(II)

Regarding Formula II, W is —C(O)— or —S(O)$_2$—, X is O or N, and z is 0 or 1, provided, however, that if X is O, then z is 0. $L^1$ and $R^1$ are defined as disclosed above for Formula I. In some embodiments, X is N. In other embodiments, X is O.

$R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or -$L^{5A}$-$R^{4A}$. $R^{4A}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^3$ and $R^4$ may be joined together with X to form a substituted or unsubstituted heterocycloalkyl or substituted or unsubstituted heteroaryl. $R^3$ and $R^{4A}$ may be joined together with X to form a substituted or unsubstituted heterocycloalkyl or substituted or unsubstituted heteroaryl.

$L^4$ and $L^5$ are independently a bond, —C(O)—, —C(O)N($L^{3A}R^{2A}$)—, —C(O)O—, —S(O)$_t$—, —O—, —N($L^{3A}R^{2A}$)—, —P(O)(O$L^{3A}R^{2A}$)O—, —SO$_2$N($L^{3A}R^{2A}$)—, —P(O)(N$L^{3A}R^{2A}$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{3A}$, $R^{2A}$, t are as defined above. $L^{5A}$ is a bond, —C(O)—, —C(O)N($L^{3A'}R^{2A'}$)—, —C(O)O—, —S(O)$_t$—, —O—, —N($L^{3A'}R^{2A'}$)—, —P(O)(O$L^{3A'}R^{2A'}$)O—, —SO$_2$N($L^{3A'}R^{2A'}$)—, —P(O)(N$L^{3A'}R^{2A'}$)N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol t' is 0, 1 or 2.

$R^{2A'}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{2A'}$ is independently hydrogen, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl. $R^{15}$ is as defined above.

$L^{3A'}$ is independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In some embodiments, $L^{3A'}$ is a bond, $R^{27}$-substituted or unsubstituted alkylene, $R^{27}$-substituted or unsubstituted heteroalkylene, $R^{27}$-substituted or unsubstituted cycloalkylene, $R^{27}$-substituted or unsubstituted heterocycloalkylene, $R^{27}$-substituted or unsubstituted arylene, or $R^{27}$-substituted or unsubstituted heteroarylene. $R^{27}$ is as defined above.

In some embodiments, $L^4$ and $L^5$ are independently a bond, —C(O)—, —C(O)N($L^{3A}R^{2A}$)—, —C(O)O—, —S(O)$_t$—, —O—, —N($L^{3A}R^{2A}$)—, —P(O)(O$L^{3A}R^{2A}$)O—, —SO$_2$N($L^{3A}R^{2A}$)—, —P(O)(N$L^{3A}R^{2A}$)N—, $R^{19}$-substituted or unsubstituted alkylene, $R^{19}$-substituted or unsubstituted heteroalkylene, $R^{19}$-substituted or unsubstituted cycloalkylene, $R^{19}$-substituted or unsubstituted heterocycloalkylene, $R^{19}$-substituted or unsubstituted arylene, or $R^{19}$-substituted or unsubstituted heteroarylene. In some embodiments, $L^{5A}$ is a bond, —C(O)—, —C(O)N($L^{3A}R^{2A}$)—, —C(O)O—, —S(O)$_t$—, —O—, —N($L^{3A'}R^{2A'}$)—, —P(O)(O$L^{3A'}R^{2A'}$)O—, —$SO_2$N($L^{3A'}R^{2A'}$)—, —P(O)(N$L^{3A'}R^{2A'}$)N—, $R^{19}$-substituted or unsubstituted alkylene, $R^{19}$-substituted or unsubstituted heteroalkylene, $R^{19}$-substituted or unsubstituted cycloalkylene, $R^{19}$-substituted or unsubstituted heterocycloalkylene, $R^{19}$-substituted or unsubstituted arylene, or $R^{19}$-substituted or unsubstituted heteroarylene. $R^{19}$ is as defined above.

In some embodiments, at least one of $L^5$-$R^4$ or $L^4$-$R^3$ includes a substituted or unsubstituted heteroaryl or substituted or unsubstituted heteroarylene. In some embodiments, one of $L^5$-$R^4$ or $L^4$-$R^3$ includes a substituted or unsubstituted heteroaryl or substituted or unsubstituted heteroarylene. In some embodiments, one of $L^5$-$R^4$ or $L^4$-$R^3$ is a hydrogen.

In some embodiments, if $L^1$ is a bond and $R^1$ is (3-(4-amino-5-p-tolyl-7H-pyrrolo[2,3-d]pyrimidin-7-yl)propan-1-ol)-6-yl, then at least one of $R^3$ and $R^4$ are not hydrogen.

In some embodiments of Formula I or Formula II, $R^1$ or $R^{1A}$ is $R^7$-substituted or unsubstituted heterocycloalkyl, $R^7$-substituted or unsubstituted aryl, or $R^7$-substituted or unsubstituted heteroaryl, wherein $R^7$ is as described above.

In some embodiments, $R^3$ is hydrogen, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

$R^{23}$ is independently hydrogen, halogen, —CN, —OH, —$NH_2$, —COOH, —$CF_3$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, $R^{24}$-substituted or unsubstituted heteroaryl, or -$L^8$-$R^{23A'}$. $L^8$ is independently —O—, —C(O)—, —C(O)NH—, —S(O)$_p$—, or —S(O)$_p$NH—, wherein p is 0, 1, or 2. $R^{23A'}$ is independently hydrogen, halogen, —CN, —OH, —$NH_2$, —COOH, —$CF_3$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, $R^{24}$-substituted or unsubstituted heteroaryl. $R^{24}$ is independently hydrogen, halogen, —CN, —OH, —$NH_2$, —COOH, —$CF_3$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. $R^{25}$ is independently hydrogen, halogen, —CN, —OH, —$NH_2$, —COOH, —$CF_3$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl. $R^{26}$ is independently halogen, —CN, —OH, —$NH_2$, —COOH, —$CF_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^3$ and $R^4$ are joined together with X to form a substituted or unsubstituted heteroaryl or substituted or unsubstituted heterocycloalkyl (e.g. $R^{23}$-substituted or unsubstituted heteroaryl or $R^{23}$-substituted or unsubstituted heterocycloalkyl). In some embodiments, $R^3$ and $R^4$ are joined together with X to form a 4 to 8 membered substituted or unsubstituted heterocycloalkyl or a 5 to 6 membered substituted or unsubstituted heteroaryl (e.g. $R^{23}$-substituted species thereof). In some embodiments, $R^3$ and $R^4$ are joined together with X to form a 4 to 7 membered substituted or unsubstituted heterocycloalkyl or a 5 to 6 membered substituted or unsubstituted heteroaryl (e.g. $R^{23}$-substituted species thereof). In some embodiments, $R^3$ and $R^4$ are joined together with X to form a 5 to 7 membered substituted or unsubstituted heterocycloalkyl or a 5 to 6 membered substituted or unsubstituted heteroaryl (e.g. $R^{23}$-substituted species thereof). In some embodiments, $R^3$ and $R^4$ are joined together with X to form a substituted or unsubstituted morpholino, substituted or unsubstituted thiomorpholino (or oxidated ring thereof), substituted or unsubstituted pyridinyl, substituted or unsubstituted pyrazyinyl, substituted or unsubstituted pyrrolidinyl, substituted or unsubstituted piperidinyl, substituted or unsubstituted piperizinyl, substituted or unsubstituted pyrrolidinyl, substituted or unsubstituted azepanyl, or substituted or unsubstituted azetidinyl (e.g. $R^{23}$-substituted substituents thereof).

In some embodiments relating to Formula II, $R^4$ and $R^{4A}$ are hydrogen, $R^{23A}$-substituted or unsubstituted alkyl, $R^{23A}$-substituted or unsubstituted heteroalkyl, $R^{23A}$-substituted or unsubstituted cycloalkyl, $R^{23A}$-substituted or unsubstituted heterocycloalkyl, $R^{23A}$-substituted or unsubstituted aryl, or $R^{23A}$-substituted or unsubstituted heteroaryl. In some embodiments, $R^4$ and $R^{4A}$ are not hydrogen.

$R^{23A}$ is hydrogen, halogen, —CN, —OH, —$NH_2$, —COOH, —$CF_3$, $R^{24A}$-substituted or unsubstituted alkyl, $R^{24A}$-substituted or unsubstituted heteroalkyl, $R^{24A}$-substituted or unsubstituted cycloalkyl, $R^{24A}$-substituted or unsubstituted heterocycloalkyl, $R^{24A}$-substituted or unsubstituted aryl, $R^{24A}$-substituted or unsubstituted heteroaryl, or -$L^{7A}$-$R^{24B}$. $L^{7A}$ is independently —O—, —C(O)—, —C(O)NH—, —S(O)$_{y'}$—, or —S(O)$_{y'}$NH—, wherein y' is 0, 1, or 2. $R^{24B}$ is independently hydrogen, halogen, —CN, —OH, —$NH_2$, —COOH, —$CF_3$, $R^{24A}$-substituted or unsubstituted alkyl, $R^{24A}$-substituted or unsubstituted heteroalkyl, $R^{24A}$-substituted or unsubstituted cycloalkyl, $R^{24A}$-substituted or unsubstituted heterocycloalkyl, $R^{24A}$-substituted or unsubstituted aryl, $R^{24A}$-substituted or unsubstituted heteroaryl. $R^{24A}$ is independently hydrogen, halogen, —CN, —OH, —$NH_2$, —COOH, —$CF_3$, $R^{25A}$-substituted or unsubstituted alkyl, $R^{25A}$-substituted or unsubstituted heteroalkyl, $R^{25A}$-substituted or unsubstituted cycloalkyl, $R^{25A}$-substituted or unsubstituted heterocycloalkyl, $R^{25A}$-substituted or unsubstituted aryl, or $R^{25A}$-substituted or unsubstituted heteroaryl. $R^{25A}$ is independently hydrogen, halogen, —CN, —OH, —$NH_2$, —COOH, —$CF_3$, $R^{26A}$-substituted or unsubstituted alkyl, $R^{26A}$-substituted or unsubstituted heteroalkyl, $R^{26A}$-substituted or unsubstituted cycloalkyl, $R^{26A}$-substituted or unsubstituted heterocycloalkyl, $R^{26A}$-substituted or unsubstituted aryl, or $R^{26A}$-substituted or unsubstituted heteroaryl. $R^{26A}$ is independently halogen, —CN, —OH, —$NH_2$, —COOH, —$CF_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^4$ or $R^{4A}$ is $R^{23A}$-substituted or unsubstituted alkyl. In some embodiments, $R^3$ is substituted or unsubstituted pyridinyl (2-, 3-, 4-), substituted or unsubstituted pyrazolyl, substituted or unsubstituted indazolyl, substituted or unsubstituted imidazolyl, substituted or unsubstituted thiazolyl, substituted or unsubstituted benzothiazolyl, substituted or unsubstituted oxazolyl, substituted or unsubstituted benzimidazolyl, substituted or unsubstituted benzoxazolyl, substituted or unsubstituted isoxazolyl, substituted or unsubstituted benzisoxazolyl, substituted or unsubstituted triazolyl, substituted or unsubstituted benzotriazolyl, substituted or unsubstituted quinolinyl, substituted or unsubstituted isoquinolinyl, substituted or unsubstituted quinazolinyl, substituted or unsubstituted pyrimidinyl, substituted or unsubstituted pyridinyl N-oxide, or a substituted or unsubstituted 5 or 6-membered heteroaryl with at least one ring nitrogen (e.g. a C—N double bond), optionally fused to a 5 or 6 membered heteroaryl. In some embodiments where the substituents in the preceding sentence are substituted, the substituent is $R^{15}$-substituted.

Further regarding compounds with the structure of Formula II, in some embodiments $L^1$, $L^4$ and $L^5$ are independently a bond, and $R^1$ is $R^7$-substituted or unsubstituted heterocycloalkyl, $R^7$-substituted or unsubstituted aryl, or $R^7$-substituted or unsubstituted heteroaryl. In some embodiments, $R^7$ is independently —$NH_2$, $R^8$-substituted or unsubstituted alkyl, $R^8$-substituted or unsubstituted aryl, $R^8$-substituted or unsubstituted heteroaryl, or -$L^6$-$R^{7A}$. $L^6$ may be —C(O)—. $R^{7A}$ may be $R^8$-substituted or unsubstituted alkyl, $R^8$-substituted or unsubstituted aryl, $R^8$-substituted or unsubstituted heteroaryl. $R^8$ may be —OH or $R^9$-substituted or unsubstituted alkyl. $R^4$ may be hydrogen or $R^{15}$-substituted or unsubstituted alkyl, and $R^3$ may be hydrogen or $R^{23}$-substituted or unsubstituted alkyl. $R^3$ and $R^4$ may optionally be joined together with X to form a 4-7 membered (e.g. 5-7) membered heterocycloalkyl (e.g. an $R^{23}$ substituted species thereof).

In some embodiments, $R^7$ is $R^8$-substituted or unsubstituted heteroaryl, or -$L^6$-$R^{7A}$. $L^4$ may be —C(O)—, and $R^{7A}$ is $R^8$-substituted or unsubstituted heteroaryl. $R^7$, $R^8$, $L^6$, $R^{7A}$ are as defined above.

In some embodiments, in the compound having the structure of Formula I or II, $R^1$ is $R^7$-substituted phenyl. In some related embodiments, $R^7$ is $R^8$-substituted or unsubstituted heteroaryl or -$L^6$-$R^{7A}$. $L^6$ may be —C(O)—, and $R^{7A}$ may be $R^8$-substituted or unsubstituted heteroaryl. In further embodiments of Formula II, $R^3$ and $R^4$ are hydrogen.

In some embodiments, $R^7$ is $R^8$-substituted or unsubstituted purinyl, $R^8$-substituted or unsubstituted pyrimidinyl, $R^8$-substituted or unsubstituted imidazolyl, $R^8$-substituted or unsubstituted 1H-pyrrolo[2,3-b]pyridinyl, $R^8$-substituted or unsubstituted pyrimidinyl, $R^8$-substituted or unsubstituted 1H-indazolyl, or $R^8$-substituted or unsubstituted 7H-pyrrolo[2,3-d]pyrimidinyl. $R^7$ may also be $R^8$-substituted or unsubstituted pyrrolopyrimidinyl, $R^8$-substituted or unsubstituted indolyl, $R^8$-substituted or unsubstituted pyrazolyl, $R^8$-substituted or unsubstituted indazolyl, $R^8$-substituted or unsubstituted imidazolyl, $R^8$-substituted or unsubstituted thiazolyl, $R^8$-substituted or unsubstituted benzothiazolyl, $R^8$-substituted or unsubstituted oxazolyl, $R^8$-substituted or unsubstituted benzimidazolyl, $R^8$-substituted or unsubstituted benzoxazolyl, $R^8$-substituted or unsubstituted isoxazolyl, $R^8$-substituted or unsubstituted benzisoxazolyl, $R^8$-substituted or unsubstituted triazolyl, $R^8$-substituted or unsubstituted benzotriazolyl, $R^8$-substituted or unsubstituted quinolinyl, $R^8$-substituted or unsubstituted isoquinolinyl, $R^8$-substituted or unsubstituted quinazolinyl, $R^8$-substituted or unsubstituted pyrimidinyl, $R^8$-substituted or unsubstituted pyridinyl N-oxide, $R^8$-substituted or unsubstituted furanyl, $R^8$-substituted or unsubstituted thiophenyl, $R^8$-substituted or unsubstituted benzofuranyl, $R^8$-substituted or unsubstituted benzothiophenyl, $R^8$-substituted or unsubstituted imidazo[1,2b]pyridazinyl. In some embodiments, $R^1$ is $R^8$-substituted or unsubstituted 6,5 fused ring heteroaryl, $R^8$-substituted or unsubstituted 5,6 fused ring heteroaryl, $R^8$-substituted or unsubstituted 5,5 fused ring heteroaryl, or $R^8$-substituted or unsubstituted 6,6 fused ring heteroaryl. In other embodiments, $R^1$ is a $R^8$-substituted or unsubstituted 5 or 6 membered heteroaryl having at least 2 (e.g. 2 to 4) ring nitrogens.

In certain embodiments, $R^7$ is -$L^4$-$R^{7A}$ and $R^{7A}$ is $R^8$-substituted or unsubstituted 1H-pyrrolo[2,3-b]pyridinyl.

In certain embodiments, X is N, and $R^1$ is $R^7$-substituted 6-membered heterocycloalkyl. $R^7$ may be $R^8$-substituted or unsubstituted heteroaryl. $R^1$ may be $R^7$-substituted piperidinyl. $R^7$ may be $R^8$-substituted or unsubstituted purinyl, $R^8$-substituted or unsubstituted pyrimidinyl, $R^8$-substituted or unsubstituted imidazolyl, $R^8$-substituted or unsubstituted 1H-pyrrolo[2,3-b]pyridinyl, $R^8$-substituted or unsubstituted pyrimidinyl, $R^8$-substituted or unsubstituted 1H-indazolyl, or $R^8$-substituted or unsubstituted 7H-pyrrolo[2,3-d]pyrimidinyl. In certain embodiments, $R^3$ and $R^4$ are hydrogen.

In yet further embodiments, $R^1$ is $R^7$-substituted or unsubstituted 6,5 fused ring heteroaryl, or $R^7$-substituted or unsubstituted 5,6 fused ring heteroaryl. $R^7$ may be —$NH_2$, $R^8$-substituted or unsubstituted alkyl, $R^8$-substituted or unsubstituted aryl, and $R^8$ is independently —OH or unsubstituted alkyl. In other embodiments, $R^1$ is $R^7$-substituted or unsubstituted indazolyl, or $R^7$-substituted or unsubstituted 7H-pyrrolo[2,3-d]pyrimidinyl. In certain embodiments, $R^3$ and $R^4$ are hydrogen.

In certain embodiments of compounds having the structure of Formula I or II, $R^1$ is $R^7$-substituted or unsubstituted indazole, or $R^7$-substituted or unsubstituted 7H-pyrrolo[2,3-d]pyrimidinyl, $R^3$ is unsubstituted alkyl, and $R^4$ is hydrogen. In further embodiments, $R^3$ is phenylmethyl, and $R^4$ is hydrogen. In some embodiments, $R^3$ and $R^4$ join with N to form a $R^{23}$-substituted or unsubstituted pyrrolidinyl.

In certain embodiments contemplating compounds having structure of Formula I or II, X is O, $R^1$ is $R^7$-substituted or unsubstituted 6,5 fused ring heteroaryl, or $R^7$-substituted or unsubstituted 5,6 fused ring heteroaryl. $R^7$ may be —$NH_2$, $R^8$-substituted or unsubstituted alkyl, or $R^8$-substituted or unsubstituted aryl. $R^8$ may be —OH or unsubstituted alkyl, and $R^3$ may be unsubstituted alkyl. In certain further embodiments, $R^1$ is $R^7$-substituted 7H-pyrrolo[2,3-d]pyrimidine, and $R^7$ is —$NH_2$, $R^8$-substituted or unsubstituted alkyl, or $R^8$-substituted or unsubstituted phenyl.

In some embodiments, the —C(O)X($L^4$-$R^3$)$_z$($L^5$-$R^4$) substituent of Formula II is an electron withdrawing group. Therefore, the —C(O)X($L^4$-$R^3$)$_z$($L^5$-$R^4$) is capable of withdrawing negative charge from the olefin moiety to which it is attached. In some embodiments, the —C(O)X($L^4$-$R^3$)$_z$($L^5$-$R^4$) is capable of sufficiently withdrawing negative charge from the olefin moiety to which it is attached to allow a thiol adduct to form between an olefin carbon and the sulfhydryl of a kinase active site cysteine as discussed herein.

In certain embodiments of Formula I and Formula II, $R^1$ is substituted or unsubstituted heteroaryl. In other embodiments, $R^1$ is substituted or unsubstituted pyrazolopyrimidinyl (e.g. $R^7$-substituted or unsubstituted pyrazolopyrimidinyl). In other embodiments, $R^1$ is substituted or unsubstituted pyrrolopyrimidinyl (e.g. $R^7$-substituted or unsubstituted pyrrolopyrimidinyl).

In some embodiments, the kinase inhibitor has the structure:

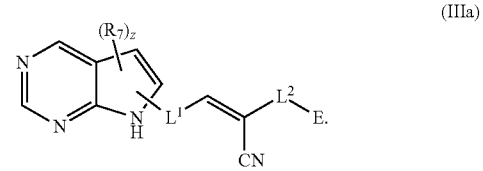

(IIIa)

In Formula IIIa, z is an integer from 1 to 4. $L^1$, $L^2$ and $R^7$ are as defined above. In some embodiments, $L^1$ is a bond.

In some embodiments, the kinase inhibitor has the structure:

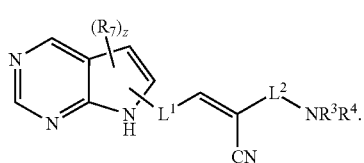

(IIIb)

In Formula IIIb, z is an integer from 1 to 4. $L^1$, $L^2$, $R^3$, $R^4$ and $R^7$ are as defined above. In some embodiments, $L^1$ is a bond.

In some embodiments, the kinase inhibitor has the structure:

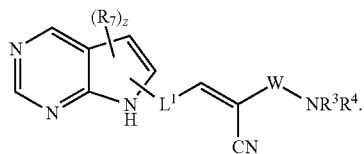

(IIIc)

In Formula IIIc, W is —C(O)— or —S(O)$_2$—, z is an integer from 1 to 4. $L^1$, $R^3$, $R^4$ and $R^7$ are as defined above. In some embodiments, $L^1$ is a bond.

In some embodiments, the kinase inhibitor has the structure:

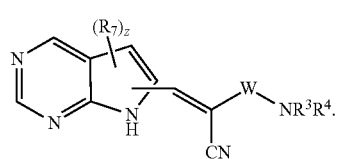

(IIId)

In Formula IIId, W is —C(O)— or —S(O)$_2$—, z is an integer from 1 to 4. $L^1$, $L^2$, $R^3$, $R^4$ and $R^7$ are as defined above. In some embodiments, $L^1$ is a bond. Ins some embodiments. In some embodiment, the kinase inhibitor is compound 43, 44, 45, 46, 47, 48, 49 and 50.

In some embodiments, the kinase inhibitor has the structure:

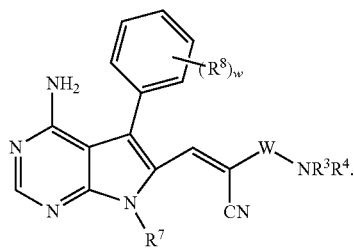

(IIIe)

In Formula IIIe, W is —C(O)— or —S(O)$_2$—, w is an integer from 1 to 5 (e.g. 1). $L^1$, $L^2$, $R^3$, $R^4$, $R^7$ and $R^8$ are as defined above.

In another embodiment of Formula I or Formula II, $L^1$ is substituted or unsubstituted arylene. In some embodiments, $L^1$ is substituted or unsubstituted phenylene.

In some embodiments, the kinase inhibitor has the structure:

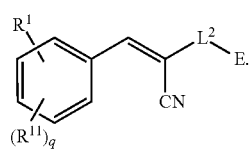

(IVa)

In Formula IVa, $R^1$, $L^2$, E and $R^{11}$ are as defined above. The symbol q is an integer from 1 to 4. In some embodiments $R^{11}$ is hydrogen. In some embodiments, $R^1$ is substituted or unsubstituted heteroaryl. In further embodiments, $R^1$ is substituted or unsubstituted pyrrolopyrimidine. In certain embodiments of Formula IVa, $R^1$ is substituted or unsubstituted heteroaryl, q is 0, and $L^1$ is substituted or unsubstituted phenylene.

In some embodiments, the kinase inhibitor has the structure:

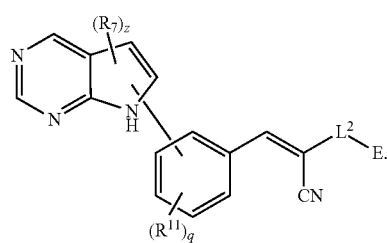

(IVb)

In Formula IVb, $R^7$, $L^2$, E and $R^{11}$ are as defined above. The symbol q is an integer from 0 to 4. In some embodiments $R^{11}$ is hydrogen. The symbol z is an integer from 1 to 4.

In some embodiments, the kinase inhibitor has the structure:

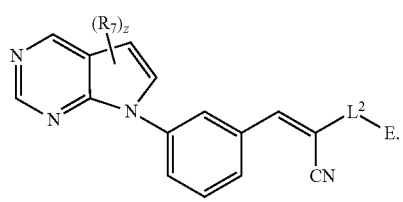

(IVc)

In Formula IVc, $R^7$, $L^2$, and E are as defined above. The symbol z is an integer from 1 to 4. In further embodiments, E is —NR$^3$R$^4$ (as defined above).

In some embodiments, the kinase inhibitor has the structure:

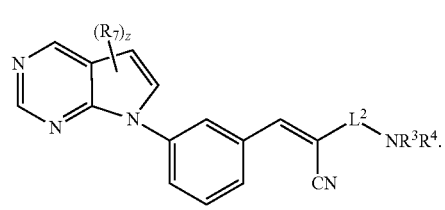

(IVd)

In Formula IVd, $R^7$, $L^2$, $R^3$ and $R^4$ are as defined above. The symbol z is an integer from 1 to 4. In further embodiments, $L^2$ is —C(O)—.

In some embodiments, the kinase inhibitor has the structure:

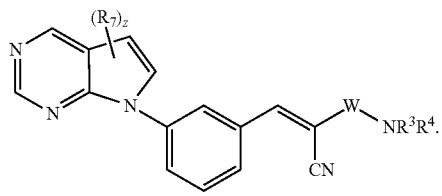
(IVe)

In Formula IVe, W is —C(O)— or —S(O)$_2$—, $R^7$, $R^3$ and $R^4$ are as defined above. The symbol z is an integer from 1 to 4. In some embodiments, $R^7$ is independently —NH$_2$, or substituted or unsubstituted aryl. In some embodiments, one of $R^7$ is —NH$_2$, and another $R^7$ is substituted aryl.

In some embodiments, the kinase inhibitor has the structure:

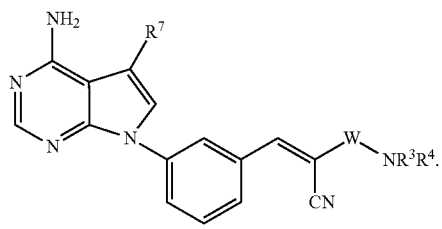
(IVf)

In Formula IVf, W is —C(O)— or —S(O)$_2$—, $R^7$, $R^3$ and $R^4$ are as defined above. In certain further embodiments, $R^3$ and $R^4$ are independently hydrogen, unsubstituted or substituted alkyl, or joined together to form a substituted or unsubstituted heteroalkyl. $R^7$ may be substituted or unsubstituted phenyl. In some embodiments, the kinase inhibitor is compound 51, 52, 53, 54, 55, 56, 57, 58, 59, 60 or 61.

In some embodiments, the kinase inhibitor has the structure:

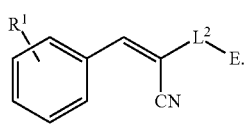
(Va)

In Formula (Va), $R^1$, $L^2$ and E are as defined above. In certain embodiments, E is —NR$^3$R$^4$ as defined above). $L^2$ may be —C(O)—.

In some embodiments, the kinase inhibitor has the structure:

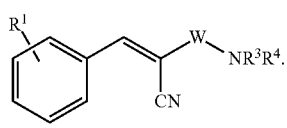
(Vb)

In Formula Vb, W is —C(O)— or —S(O)$_2$—, $R^1$, $R^3$ and $R^4$ are as defined above. In certain embodiments, $R^1$ is substituted alkyl.

In some embodiments, the kinase inhibitor has the structure:

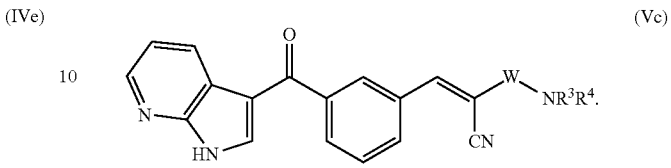
(Vc)

In Formula Vc, W is —C(O)— or —S(O)$_2$—, $R^3$ and $R^4$ are as defined above. In certain embodiments, the kinase inhibitor is compound 38 or 39.

In some embodiments, $R^1$ is substituted or unsubstituted indazolyl, and the kinase inhibitor has the structure of Formula VIa following, wherein $R^7$ is as defined herein.

In some embodiments, the kinase inhibitor has the formula:

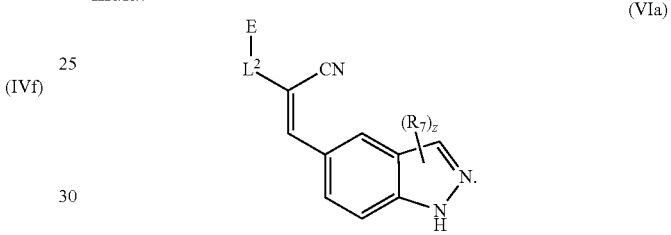
(VIa)

In Formula VIa, $L^2$, E and $R^7$ are as defined above. The symbol z is an integer from 1 to 4.

In some embodiments, the kinase inhibitor has the formula:

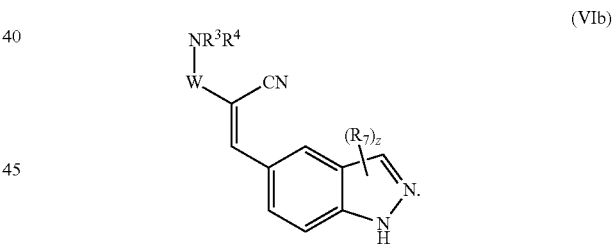
(VIb)

In Formula VIb, W is —C(O)— or —S(O)$_2$—, $R^3$, $R^4$ and $R^7$ are as defined above. The symbol z is an integer from 1 to 4.

In some embodiments, the kinase inhibitor has the formula:

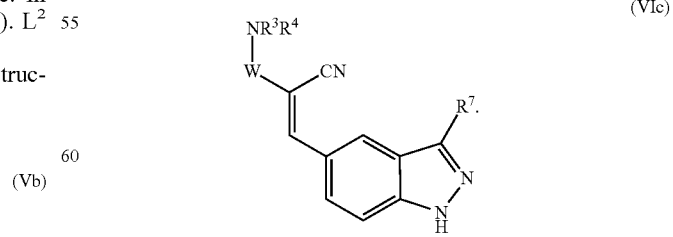
(VIc)

In Formula VIc, W is —C(O)— or —S(O)$_2$—, $R^3$, $R^4$ and $R^7$ are as defined above. In some embodiments, the kinase inhibitor is compound 37, 40, 41 or 42.

In another embodiment of Formula I, $L^1$ is substituted or unsubstituted heterocycloalkylene, $L^2$ is —C(O)—. In further embodiments, $R^1$ is substituted or unsubstituted heteroaryl, E is —$NR^3R^4$. In some embodiments, $L^1$ is piperidinyl. In further embodiments, $R^1$ is purinyl.

In some embodiments, the kinase inhibitor has the formula:

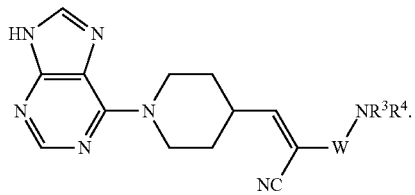

(VII)

In Formula (VII), W is —C(O)— or —$S(O)_2$—, $R^3$ and $R^4$ are as defined above. In some embodiments, the kinase inhibitor is compound 36.

The kinase inhibitor may be a reversible kinase inhibitor (as discussed herein). In some embodiments, the kinase inhibitor is a reversible denatured kinase inhibitor (as discussed herein). In some embodiments, the kinase inhibitor is a covalent reversible kinase inhibitor (as discussed herein). In other embodiments, the kinase inhibitor is a covalent reversible denatured kinase inhibitor (as discussed herein). And in certain embodiments, the kinase inhibitor is a thiol covalent reversible denatured kinase inhibitor (as discussed herein).

In some embodiments, the compounds of the Formulae provided herein, and embodiments thereof, are stable at pH 7.5 (e.g. in phosphate-buffered saline at 37° C.). In some embodiments, where the compound of Formula I or II, and embodiments thereof, are stable at pH 7.5, the compound has a half life of greater than 6 hours, 12 hours, 24 hours, or 48 hours. In some embodiments, where the compounds of the Formulae provided herein, and embodiments thereof, are stable at pH 7.5, the compound has a half life of greater than 12 hours. In some embodiments, where the compounds of the Formulae provided herein, and embodiments thereof, are stable at pH 7.5, the compound has a half life of greater than 24 hours. In some embodiments, where the compounds of the Formulae provided herein, and embodiments thereof, are stable at pH 7.5, the compound has a half life of greater than 48 hours. In certain embodiments, the compounds of the Formulae provided herein, and embodiments thereof, exhibit kinase inhibition within a cell. In some embodiments, the cell is a prokaryote or eukaryote. The cell may be a eukaryote (e.g. protozoan cell, fungal cell, plant cell or an animal cell). In some embodiments, the cell is a mammalian cell such as a human cell, cow cell, pig cell, horse cell, dog cell and cat cell, mouse cell, or rat cell. In some embodiments, the cell is a human cell. The cell may form part of an organ or an organism. In certain embodiments, the cell does not form part of an organ or an organism.

In some embodiments, each substituted group described above in the compounds of the Formulae provided herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted or unsubstituted cycloalkylene, substituted or unsubstituted heterocycloalkylene, substituted or unsubstituted arylene, or substituted or unsubstituted heteroarylene described above in the compounds of the Formulae provided herein is substituted with at least one substituent group. In other embodiments, at least one or all of these groups are substituted with at least one size-limited substituent group. Alternatively, at least one or all of these groups are substituted with at least one lower substituent group.

In other embodiments of the compounds of the Formulae provided herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene substituted or unsubstituted $C_4$-$C_8$ cycloalkylene, and each substituted or unsubstituted heterocycloalkylene is a substituted or unsubstituted 4 to 8 membered heterocycloalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene substituted or unsubstituted $C_5$-$C_6$ cycloalkylene, and each substituted or unsubstituted heterocycloalkylene is a substituted or unsubstituted 5 to 7 membered heterocycloalkylene.

In some embodiments, the compounds of the Formulae provided herein is one or more of the compounds set forth in Table 1 and or Tables 2a-2e below. In other embodiments, the compound is one or more of the following:

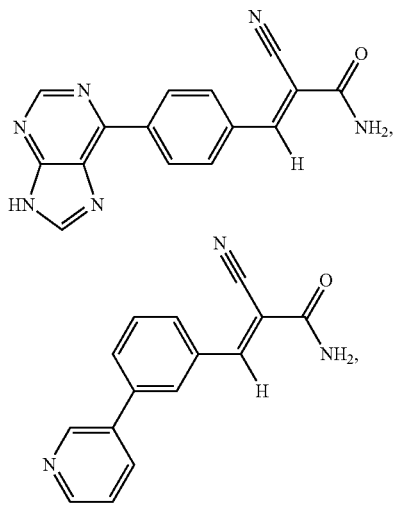

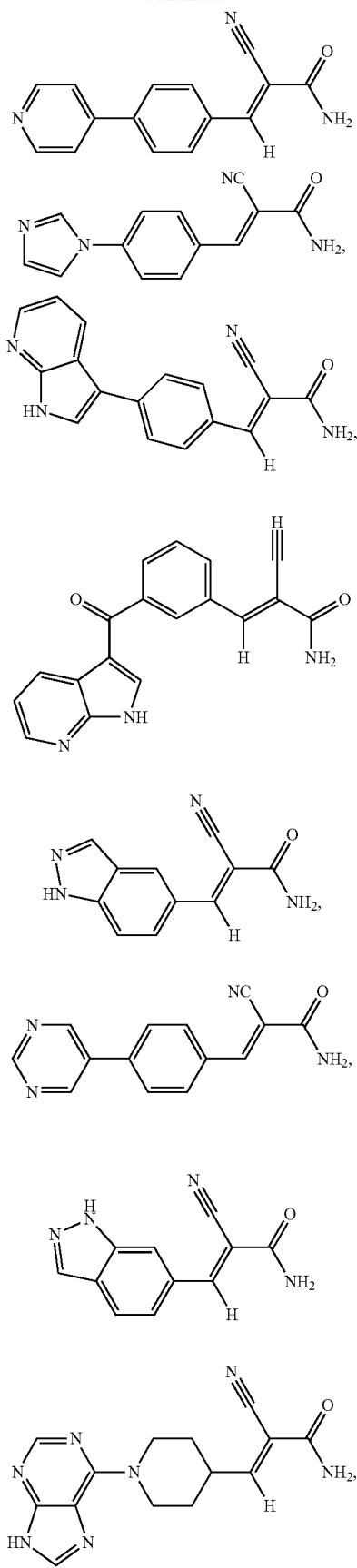
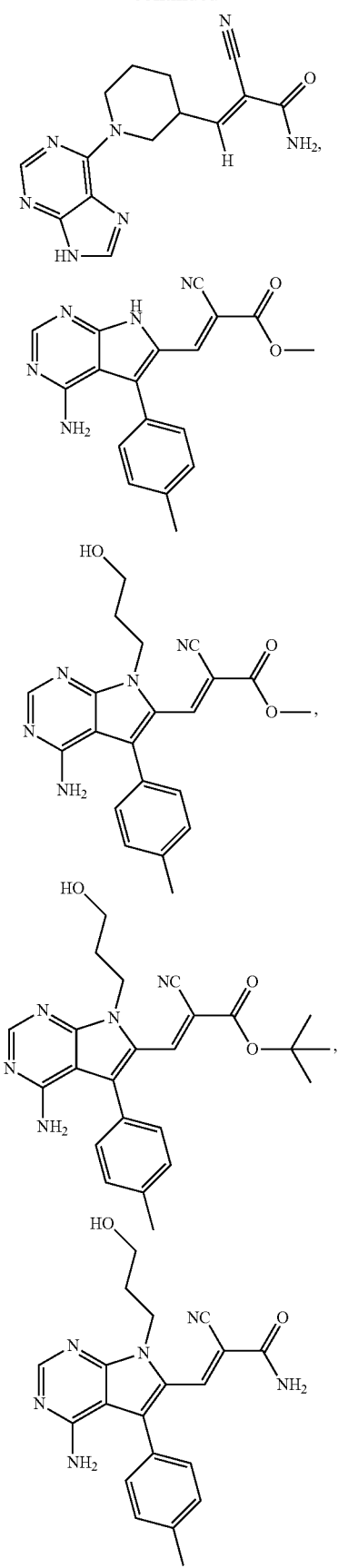

31
-continued
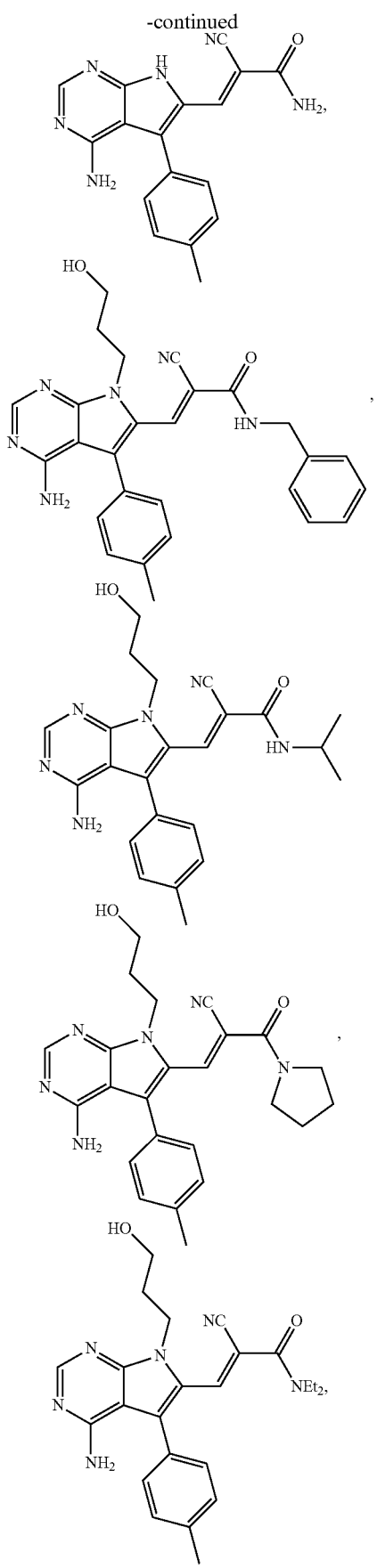
32
-continued
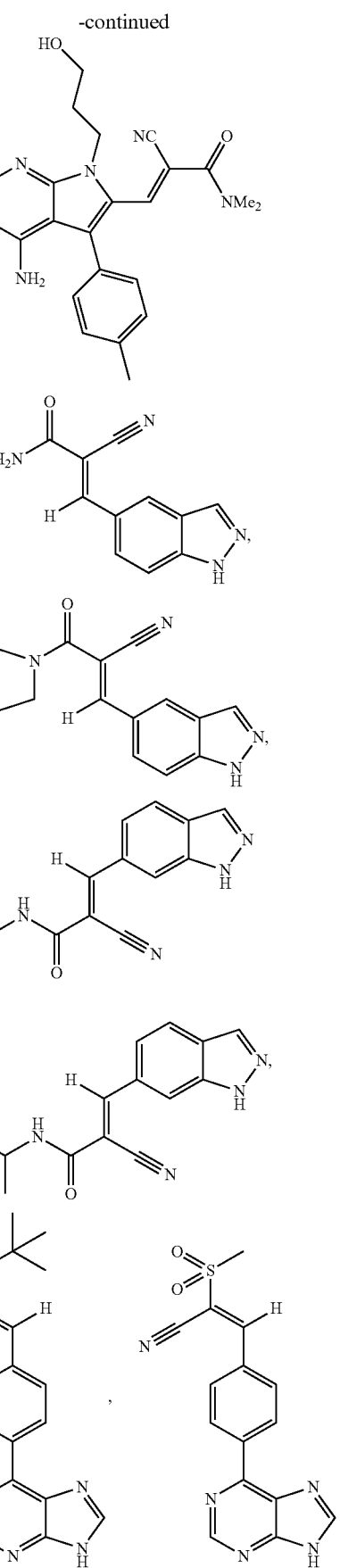

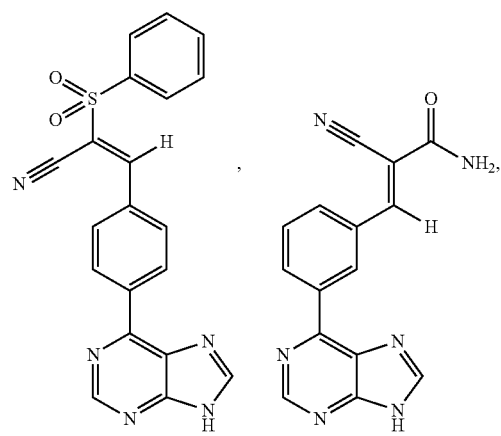
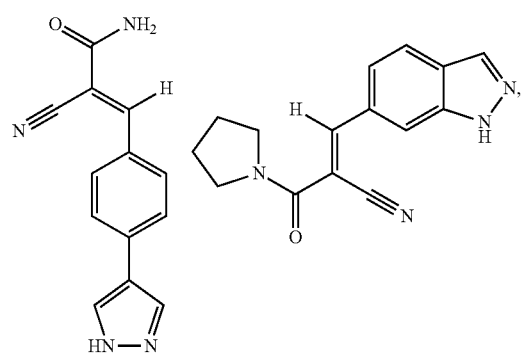
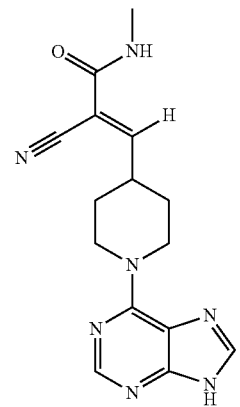
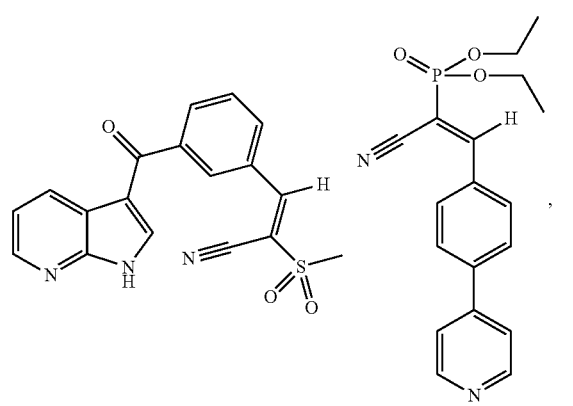
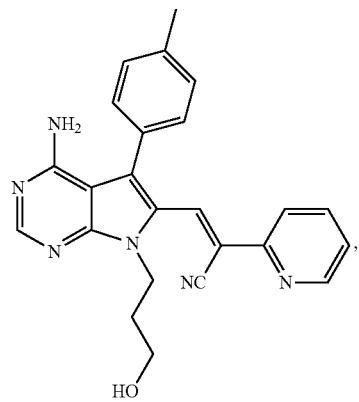
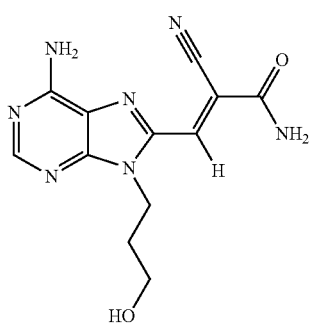
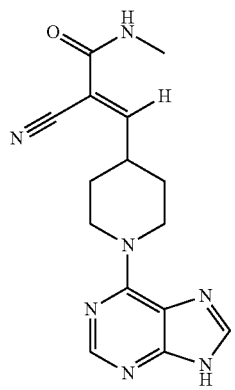
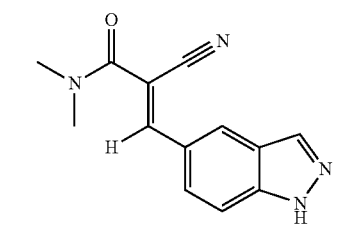
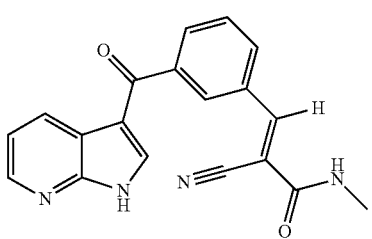

35
-continued
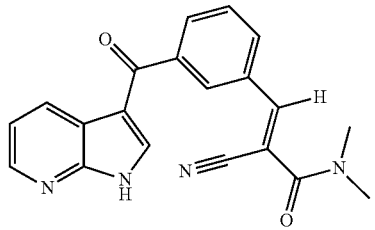
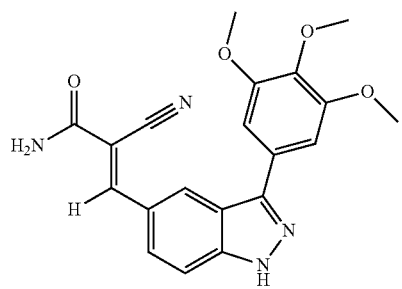
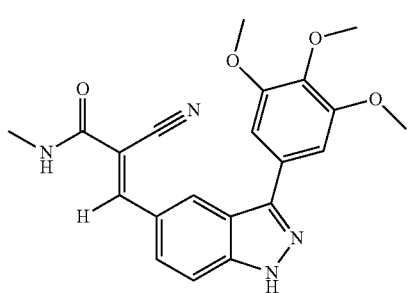
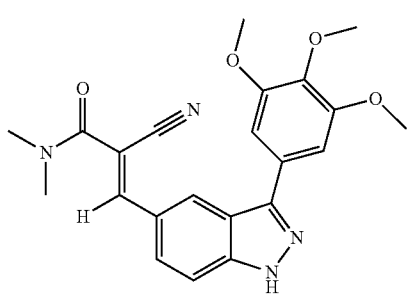
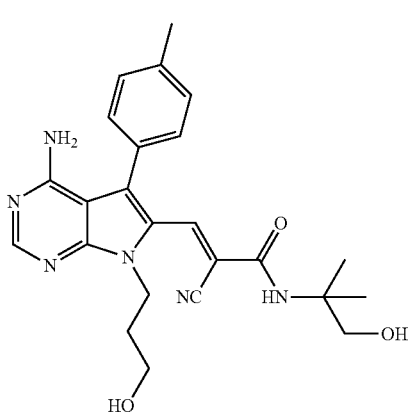
36
-continued
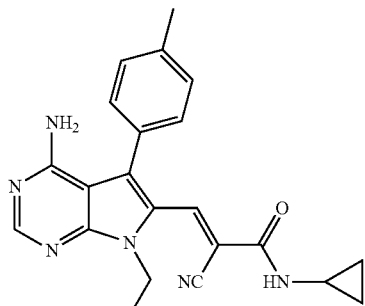
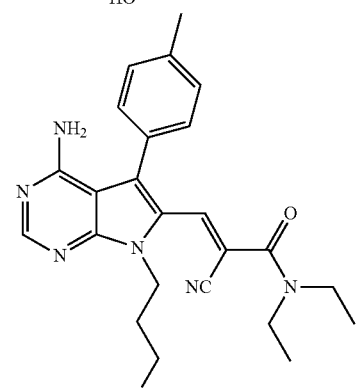
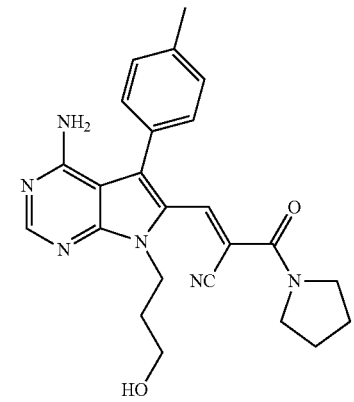
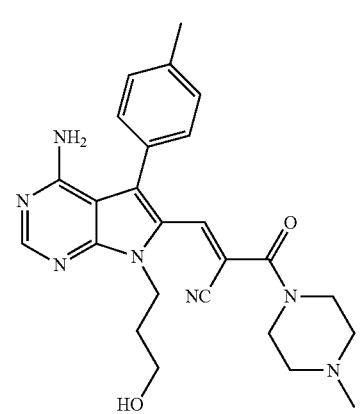

37
-continued
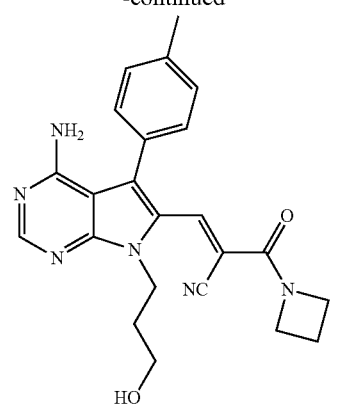
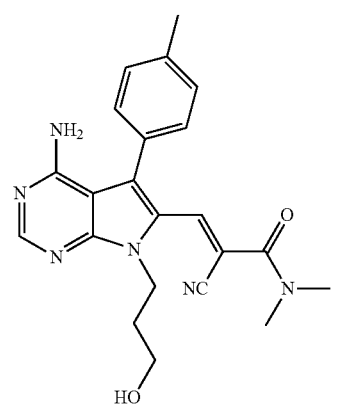
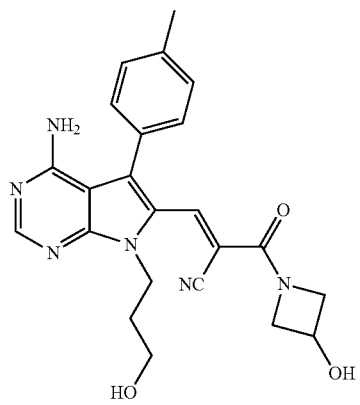
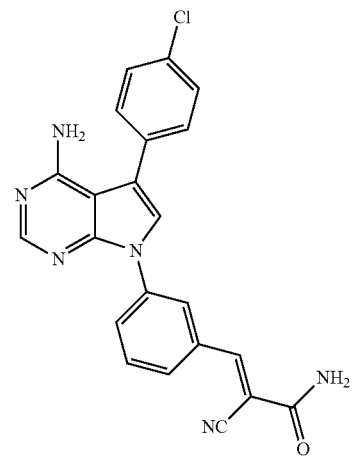
38
-continued
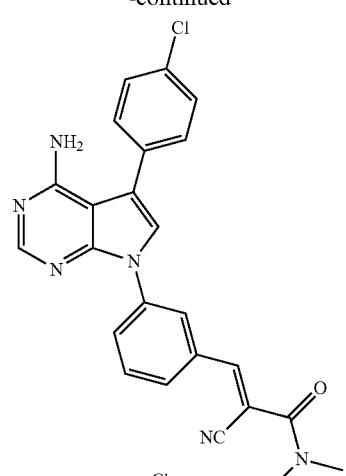
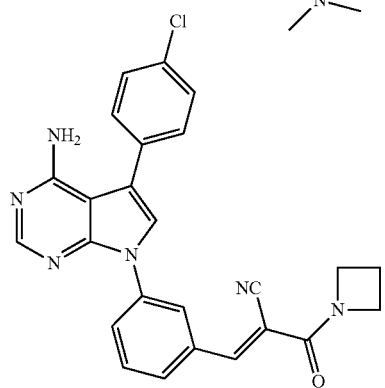
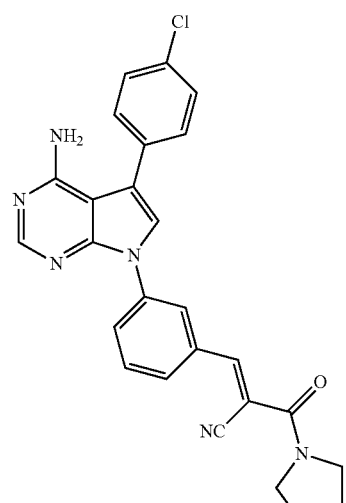
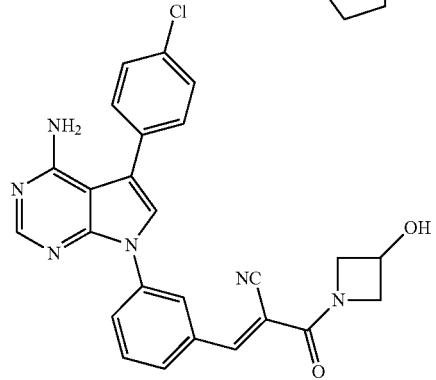

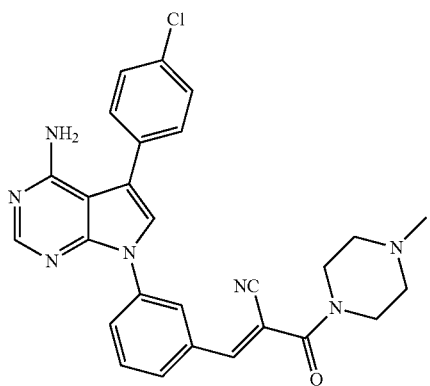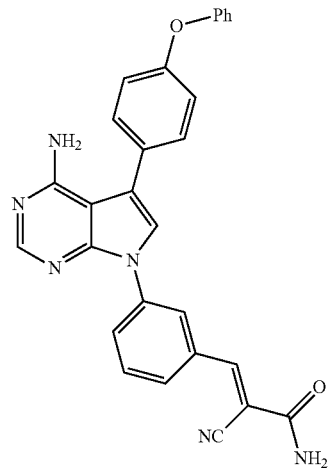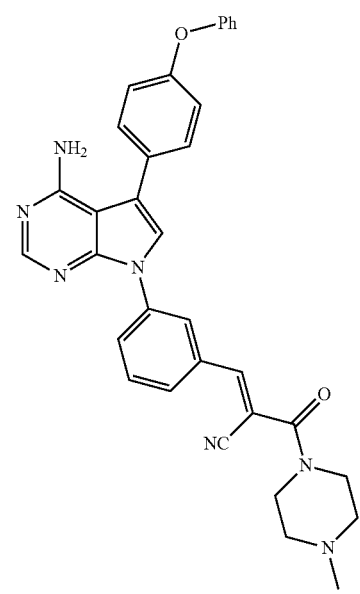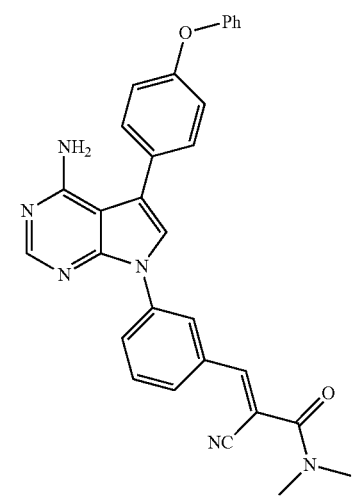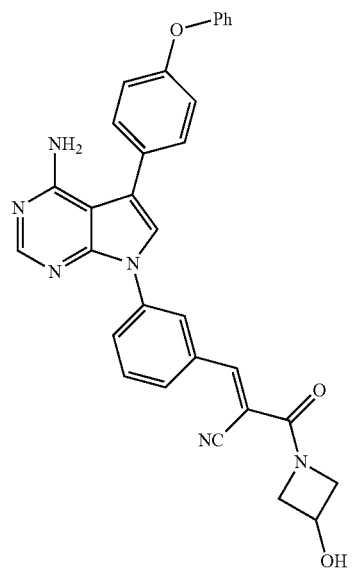

41
-continued
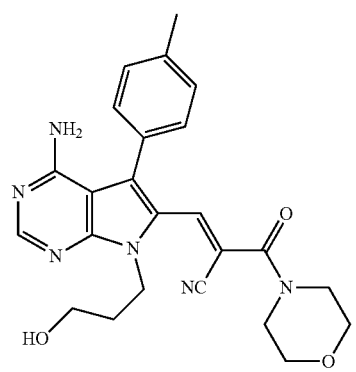
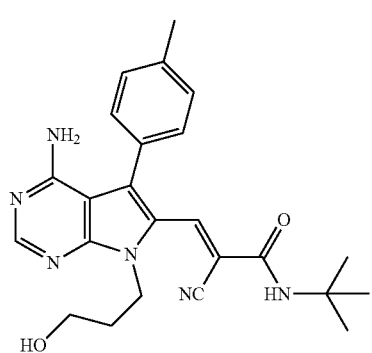
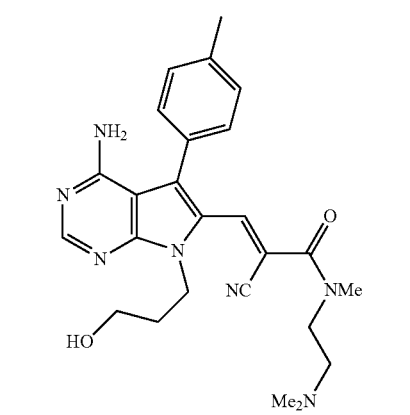
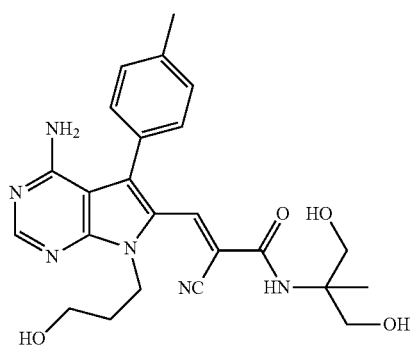
42
-continued
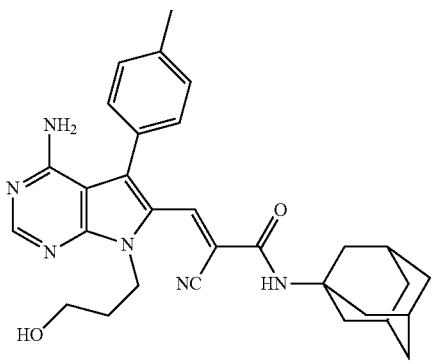
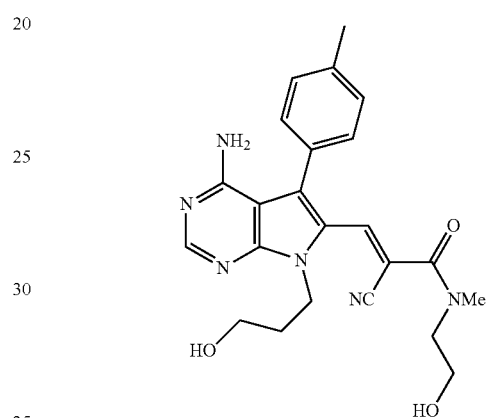
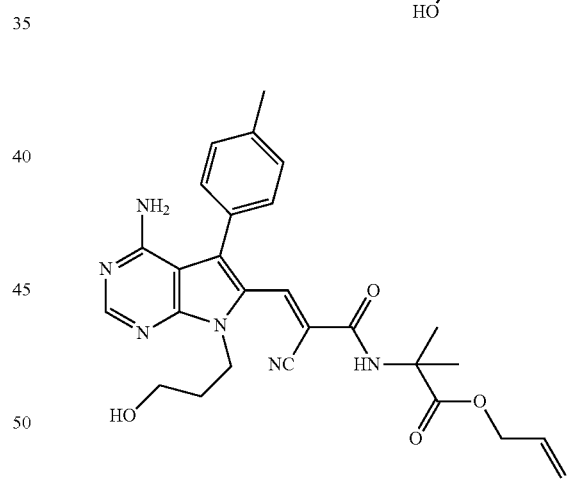
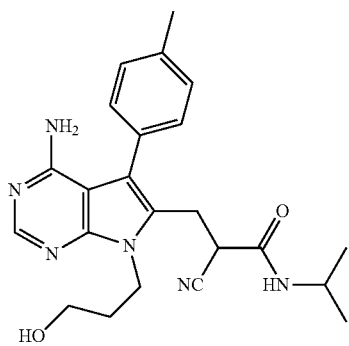

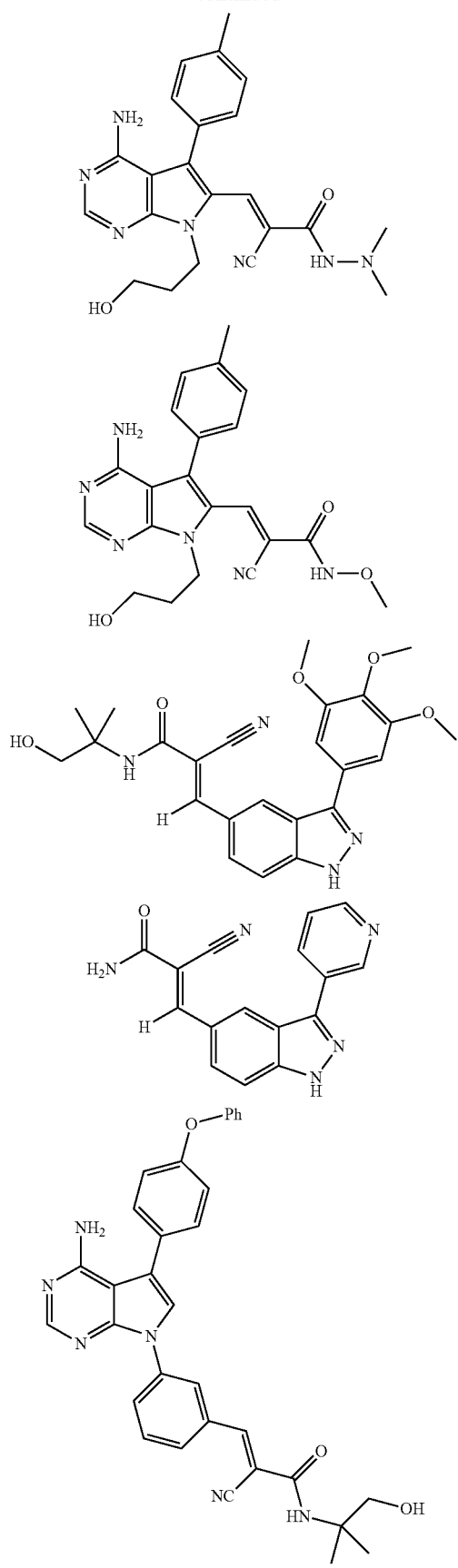

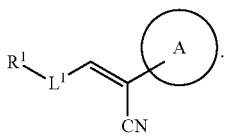

In some embodiments, the kinase inhibitor has the structure of Formula VIII:

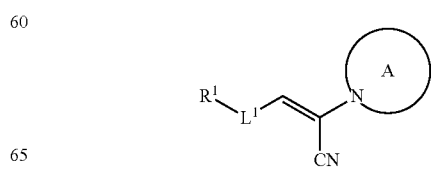

(VIII)

In Formula VIII and other Formulae provided herein, ring A is a substituted or unsubstituted heteroaryl, such as an $R^{31}$-substituted or unsubstituted heteroaryl. $R^1$ and $L^1$ are as defined above.

$R^{31}$ is $R^{23A}$ as defined above, or is hydrogen, halogen, —CN, —OH, —NH$_2$, —COOH, —CF$_3$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

$R^{33}$ is independently hydrogen, halogen, —CN, —OH, —NH$_2$, —COOH, —CF$_3$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^{34}$ is independently hydrogen, halogen, —CN, —OH, —NH$_2$, —COOH, —CF$_3$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

$R^{35}$ is independently halogen, —CN, —OH, —NH$_{25}$—COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the kinase inhibitor has the structure of Formula IX:

(IX)

In Formula IX, ring A is a substituted or unsubstituted heteroaryl, such as an $R^{31}$-substituted or unsubstituted heteroaryl as set fort above. $R^1$ and $L^1$ are as defined above.

In some embodiments of Formulae VIII and IX above, ring A is $R^{31}$-substituted or unsubstituted heteroaryl. In some embodiments of Formulae VIII and IX above, ring A is five-membered $R^{31}$-substituted or unsubstituted heteroaryl or six-membered $R^{31}$-substituted or unsubstituted heteroaryl.

In some embodiments, the kinase inhibitor has the structure of Formula Xa:

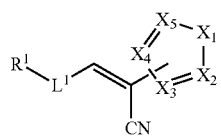

(Xa)

In Formula Xa, $X_1$ is —$C(R^{31}R^{32})$—, —$N(R^{31})$—, —S— or —O— when $X_1$ is not the point of attachment. When $X_1$ is the point of attachment, then $X_1$ is $C(R^{31})$ or N. $X_2$, $X_3$, $X_4$ and $X_5$ are independently —$C(R^{31})$= or —N= when not the point of attachment. When $X_2$, $X_3$, $X_4$ or $X_5$ is the point of attachment, then the $X_2$, $X_3$, $X_4$ or $X_5$ that is the point of attachment is C. At least one of $X_1$, $X_2$, $X_3$, $X_4$ and $X_5$ is not carbon (i.e. not —$C(R^{31}R^{32})$—, $C(R^{31})$ or —$C(R^{31})$= as appropriate). For example, in some embodiments at least one of $X_1$, $X_2$, $X_3$, $X_4$ and $X_5$ is nitrogen (i.e. —$N(R^{31})$— or —N= as appropriate). Typically, at least 2 of $X_1$, $X_2$, $X_3$, $X_4$ and $X_5$ is a carbon (e.g. —$C(R^{31}R^{32})$—, $C(R^{31})$ or —$C(R^{31})$=).

$R^{31}$ is as defined above. $R^{32}$ is hydrogen, halogen, —CN, —OH, —$NH_2$, —COOH, —$CF_3$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. $R^{33}$ is defined as disclosed above.

In some embodiments, the kinase inhibitor has the structure of Formula Xb:

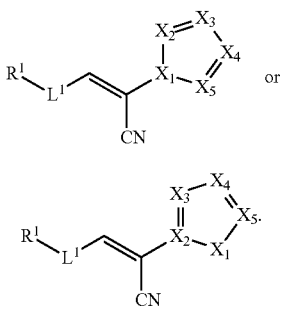

(Xb')

or (Xb")

In Formula Xb', $X_1$ is $C(R^{31})$ or N. $X_2$, $X_3$, $X_4$ and $X_5$ are independently —$C(R^{31})$= or —N=, provided, however, that at least one of $X_1$, $X_2$, $X_3$, $X_4$ and $X_5$ is N. Typically, at least 2 of $X_1$, $X_2$, $X_3$, $X_4$ and $X_5$ is a carbon. In Formula Xb", $X_2$ is C. $X_1$ is —$C(R^{31}R^{32})$—, —$N(R^{31})$—, —S— or —O—. $X_3$, $X_4$ and $X_5$ are independently —$C(R^{31})$= or —N=, provided, however, that at least one of $X_1$, $X_3$, $X_4$ and $X_5$ is not carbon. $L^1$, $R^1$ and $R^{31}$ are defined as disclosed above. Typically, at least one of $X_1$, $X_3$, $X_4$ and $X_5$ is carbon.

In some embodiments, the kinase inhibitor has the structure of Formula Xc:

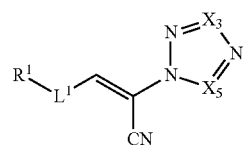

(Xc)

In Formula Xc, $X_3$ and $X_5$ are independently —$C(R^{31})$=. $L^1$, $R^1$ and $R^{31}$ are as defined above.

In some embodiments, the kinase inhibitor has the structure of Formula Xd:

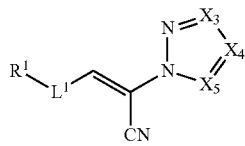

(Xd)

In Formula Xd, $X_3$, $X_4$ and $X_5$ are independently —$C(R^{31})$=. $L^1$, $R^1$ and $R^{31}$ are defined as disclosed above.

In some embodiments, the kinase inhibitor has the structure of Formula Xe:

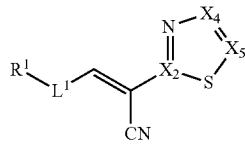

(Xe)

In Formula Xe, $X_4$ and $X_5$ are independently —$C(R^{31})$=. $X^2$ is C. $L^1$, $R^1$ and $R^{31}$ are as defined as disclosed above.

In some embodiments, the kinase inhibitor has the structure of Formula Xf:

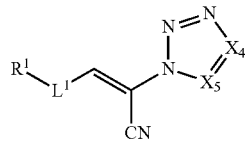

(Xf)

In Formula Xf, $X_4$ and $X_5$ are independently —$C(R^{31})$=. $L^1$, $R^1$ and $R^{31}$ are defined as disclosed above.

In some embodiments, the kinase inhibitor has the structure of Formula XIa:

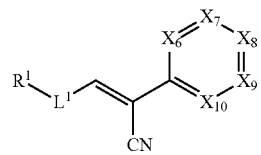

(XIa)

In Formula XIa, $X_6$, $X_7$, $X_8$, $X_9$ and $X_{10}$ are independently —C($R^{31}$)=, —N=, or +N—O—, provided, however, that at least one of $X_6$, $X_7$, $X_8$, $X_9$ and $X_{10}$ is N or +N—O—. $L^1$, $R^1$ and $R^{31}$ are defined as disclosed above.

In some embodiments, the kinase inhibitor has the structure of Formula XIb:

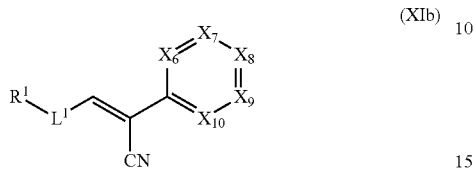

(XIb)

In Formula XIb, $X_6$, $X_7$, $X_9$ and $X_{10}$ are independently —C($R^{31}$)=. $X_8$ is N or +N—O—. $L^1$, $R^1$ and $R^{31}$ are defined as disclosed above.

In some embodiments, the kinase inhibitor has the structure of Formula XIc:

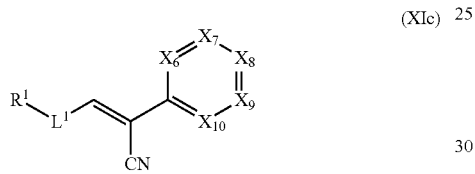

(XIc)

In Formula XIc, $X_6$, $X_8$, $X_9$ and $X_{10}$ are independently —C($R^{31}$)=. $X_7$ is N or +N—O—. $L^1$, $R^1$ and $R^{31}$ are defined as disclosed above.

In some embodiments of Formulae VIII and IX above, ring A is $R^{31}$-substituted or unsubstituted furyl, $R^{31}$-substituted or unsubstituted thienyl, $R^{31}$-substituted or unsubstituted pyrrolyl, $R^{31}$-substituted or unsubstituted imidazolyl, $R^{31}$-substituted or unsubstituted pyrazolyl, $R^{31}$-substituted or unsubstituted oxazolyl, $R^{31}$-substituted or unsubstituted isoxazolyl, $R^{31}$-substituted or unsubstituted thiazolyl, $R^{31}$-substituted or unsubstituted isothiazolyl, $R^{31}$-substituted or unsubstituted triazolyl, $R^{31}$-substituted or unsubstituted oxadiazolyl, $R^{31}$-substituted or unsubstituted pyridyl, $R^{31}$-substituted or unsubstituted pyrimidyl, $R^{31}$-substituted or unsubstituted pyridazinyl, $R^{31}$-substituted or unsubstituted pyrrolinyl, $R^{31}$-substituted or unsubstituted pyrazinyl, $R^{31}$-substituted or unsubstituted tetrazolyl, $R^{31}$-substituted or unsubstituted furanyl, $R^{31}$-substituted or unsubstituted dihydrothieno-pyrazolyl, $R^{31}$-substituted or unsubstituted thianaphthenyl, $R^{31}$-substituted or unsubstituted carbazolyl, $R^{31}$-substituted or unsubstituted benzothienyl, $R^{31}$-substituted or unsubstituted benzofuranyl, $R^{31}$-substituted or unsubstituted indolyl, $R^{31}$-substituted or unsubstituted quinolinyl, $R^{31}$-substituted or unsubstituted benzotriazolyl, $R^{31}$-substituted or unsubstituted benzothiazolyl, $R^{31}$-substituted or unsubstituted benzooxazolyl, $R^{31}$-substituted or unsubstituted benzimidazolyl, $R^{31}$-substituted or unsubstituted isoquinolinyl, $R^{31}$-substituted or unsubstituted isoindolyl, $R^{31}$-substituted or unsubstituted acridinyl, $R^{31}$-substituted or unsubstituted benzoisazolyl. $R^{31}$ is defined as disclosed above.

In some embodiments of Formulae VIII, IX, Xa-Xf, and XIa-XIc above, $R^1$ is $R^7$-substituted or unsubstituted heterocycloalkyl, $R^7$-substituted or unsubstituted aryl, or $R^7$-substituted or unsubstituted heteroaryl. $L^1$ is a bond.

In some embodiments, a compound of Formulae I is one or more compounds set forth in Table 1, Tables 2a-2e below, or the following compounds:

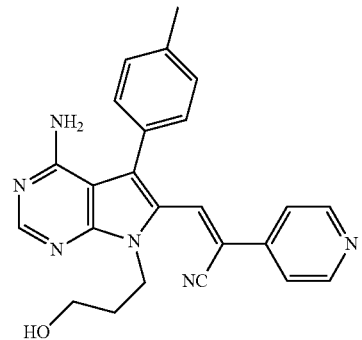

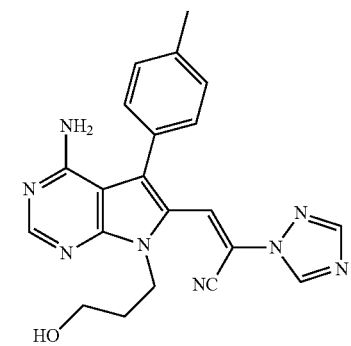

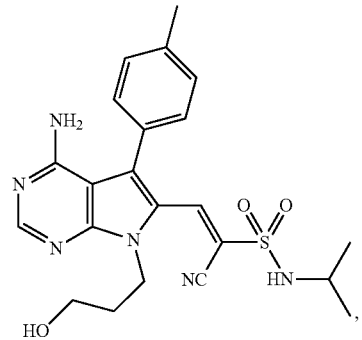

,

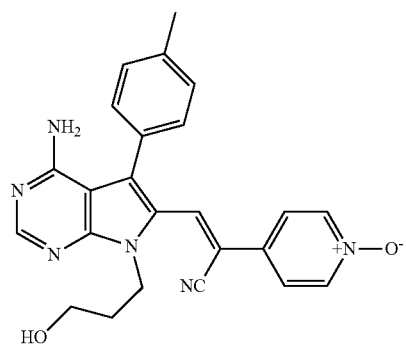

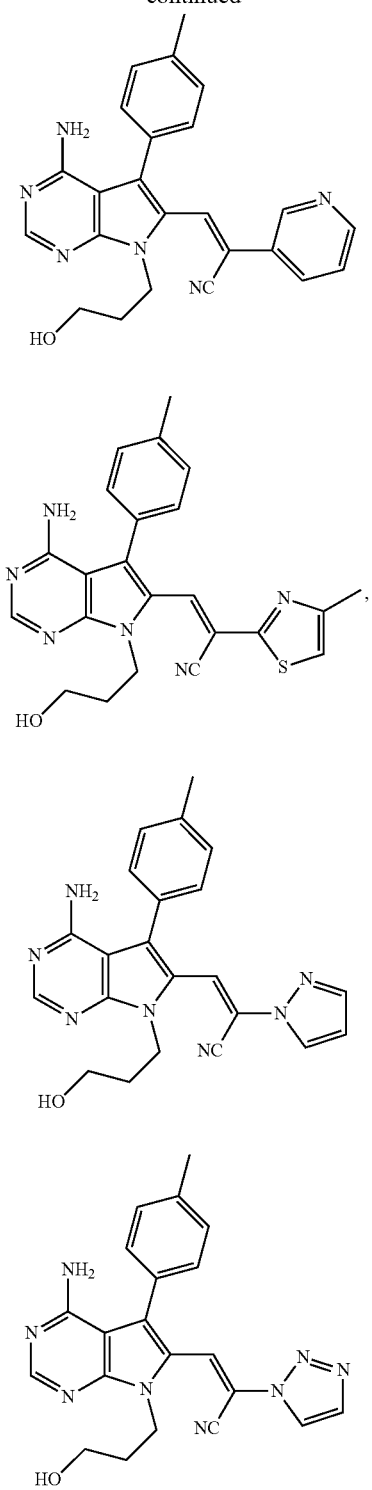

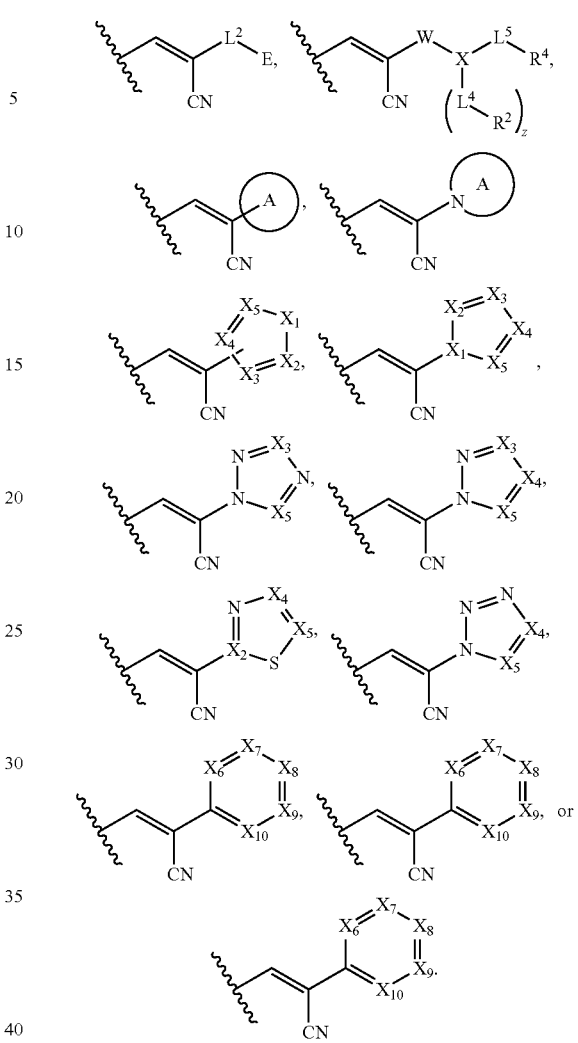

W, $L^2$, $L^4$, $L^5$, E, $R^3$, $R^4$, ring A, $X_1$, $X_2$, $X_3$, $X_4$, $X_5$, $X_6$, $X_7$, $X_8$, $X_9$, $X_{10}$, and z are as defined above. The symbol ⸹ represents the point of attachment of the substituent to the remained of the compound or solid support.

In another aspect, there is provided a protein adduct comprising a protein bound to a kinase inhibitor provided herein. In some embodiments, the adduct has the formula:

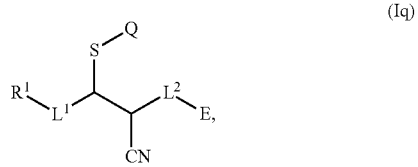

(Iq)

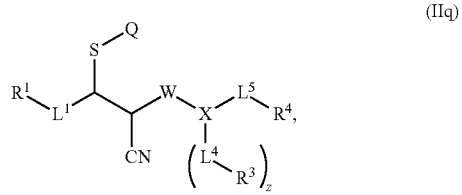

(IIq)

Using chemical synthesis techniques generally known in the art and the synthesis techniques set forth in the Examples section, a person having ordinary skill in the art would be able to synthesize the compounds of Formula I. In another aspect, a method of making a reversible kinase inhibitor is provided. The method includes the step of modifying a known non-reversible or irreversible kinase inhibitor to include a substituent having the formula:

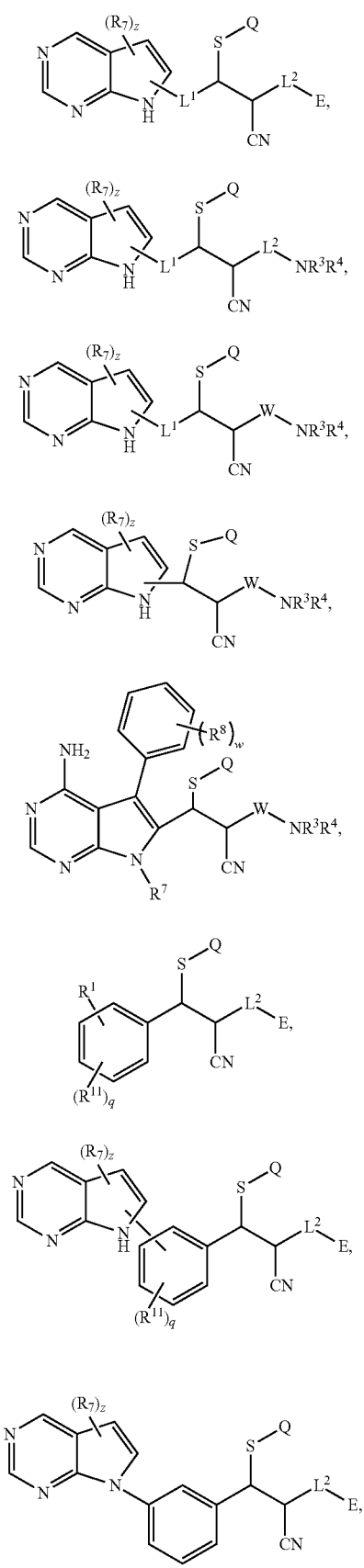
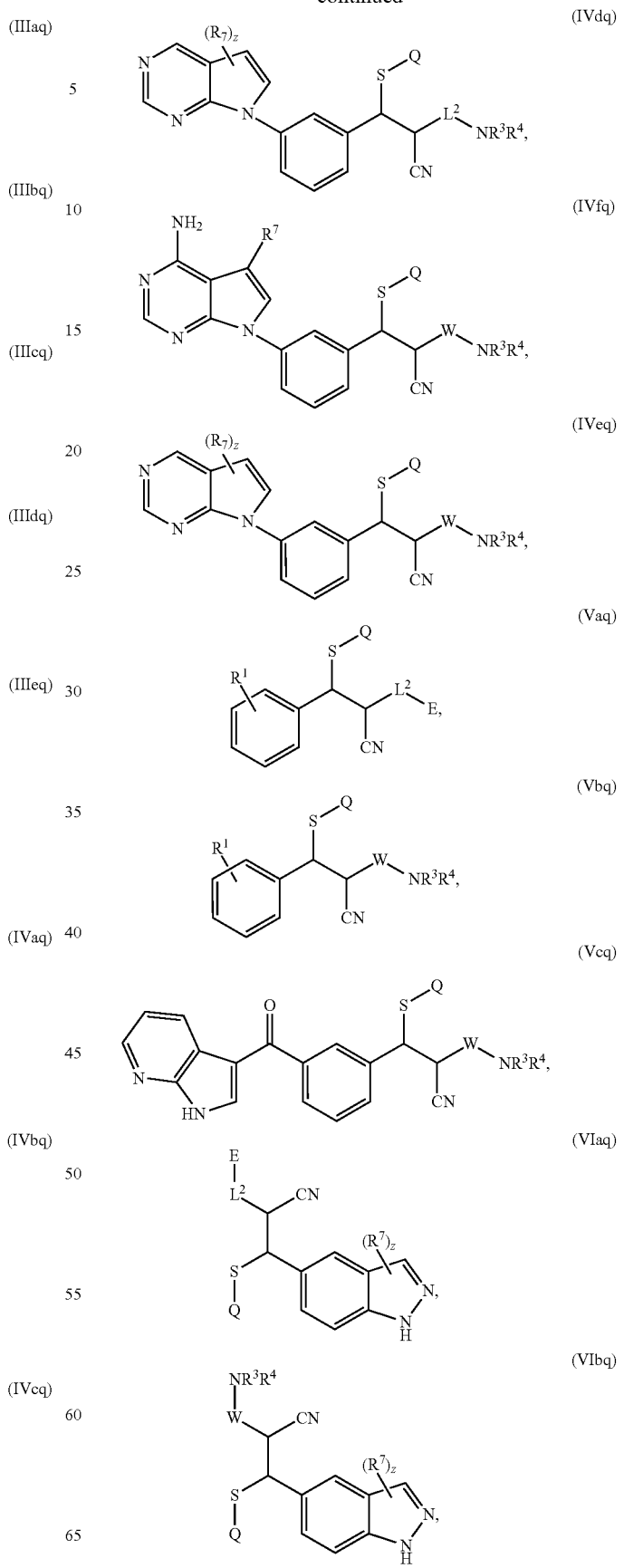

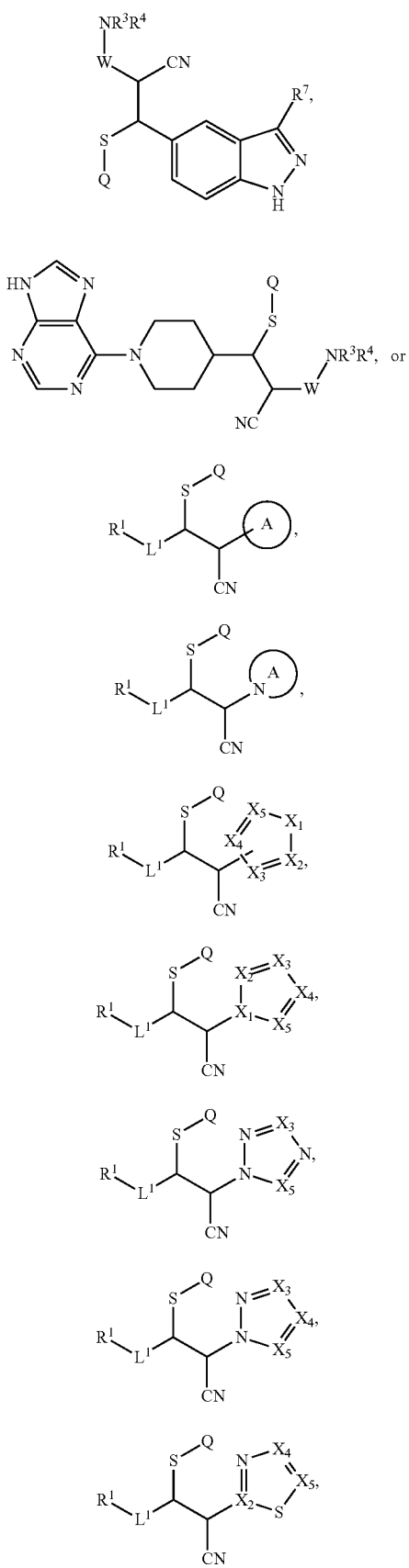
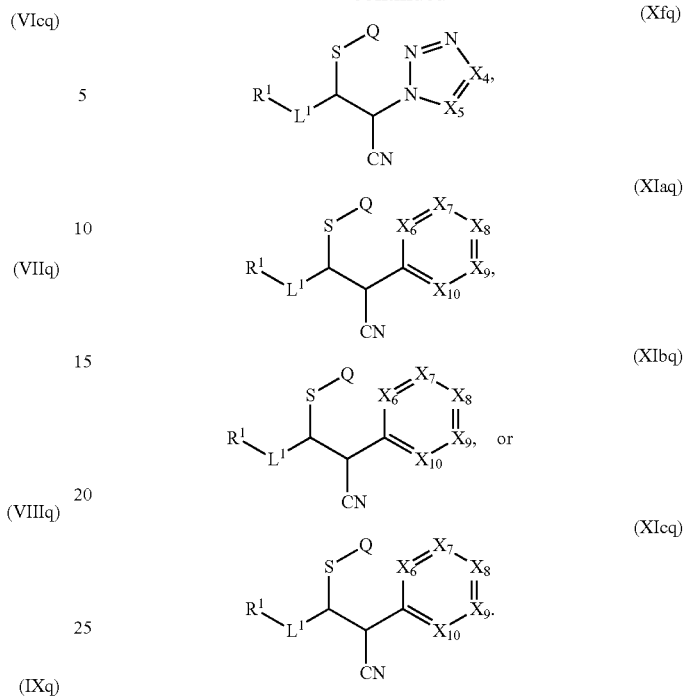

The symbols in the protein adduct formulae (e.g. W, E, $R^1$, $R^3$, $R^4$, $R^7$, $R^{11}$, ring A, $X_1$, $X_2$, $X_3$, $X_4$, $X_5$, $X_6$, $X_7$, $X_8$, $X_9$, $X_{10}$, etc.) are as defined above. The symbol Q represents a protein (e.g. peptide). The sulfur attached to the Q typically forms part of a cysteine amino acid. In some embodiments, the cysteine linked to the inhibitor compounds is Cys-481 of BTK, Cys-909 of JAK3, or Cys-436 of RSK2.

III. Methods of Inhibiting Protein Kinases

In another aspect, methods of inhibiting protein kinases are provided. The methods include contacting a protein kinase with an effective amount of a kinase inhibitor provided herein. The kinase inhibitor may have the structure of the Formulae provided herein (or any of the embodiments thereof described above). In some embodiments, the methods of inhibiting a protein kinase are conducted within a cell. Thus, in certain embodiments, methods of inhibiting a protein kinase within a cell are provided. The method includes contacting a cell with an effective amount of a kinase inhibitor provided herein. The kinase inhibitor may have the structure of the Formulae provided herein (or any of the embodiments thereof described above). In some embodiments, the cell is a prokaryote or eukaryote. The cell may be a eukaryote (e.g. protozoan cell, fungal cell, plant cell or an animal cell). In some embodiments, the cell is a mammalian cell such as a human cell, cow cell, pig cell, horse cell, dog cell and cat cell, mouse cell, or rat cell. In some embodiments, the cell is a human cell. The cell may form part of an organ or an organism. In certain embodiments, the cell does not form part of an organ or an organism.

The kinase inhibitor may be a reversible kinase inhibitor. A reversible kinase inhibitor is a kinase inhibitor, as disclosed herein (e.g. the compounds of the Formulae provided herein and embodiments thereof), is capable of measurably dissociating from the protein kinase when the protein kinase is intact (i.e. not denatured) or denatured (e.g. partially denatured or fully denatured). A "denatured" kinase is a kinase without sufficient tertiary or secondary structure sufficient to retain kinase activity. An "intact" kinase is a kinase with sufficient tertiary or secondary structure sufficient to retain kinase activity. Therefore, in some embodiments, the method of inhibiting a protein kinase includes contacting a protein kinase with a reversible kinase inhibitor and allowing the reversible kinase inhibitor to reversibly bind to an active site cysteine residue, thereby inhibiting the protein kinase.

In some embodiments, the reversible kinase inhibitor measurably dissociates from the protein kinase only when the protein kinase is denatured, but does not measurably dissociate from the protein kinase when the protein kinase is intact (or dissociates at least 1, $1\times10^2$, $1\times10^3$, $1\times10^4$, $1\times10^5$, $1\times10^6$, $1\times10^7$, $1\times10^8$, $1\times10^9$, $1\times10^{10}$ fold slower relative to the dissociation when the protein kinase is denatured). A reversible kinase inhibitor that measurably dissociates (or dissociates at least 1, $1\times10^2$, $1\times10^3$, $1\times10^4$, $1\times10^5$, $1\times10^6$, $1\times10^7$, $1\times10^8$, $1\times10^9$, $1\times10^{10}$ fold slower relative to the dissociation when the protein kinase is denatured) from the protein kinase only when the protein kinase is denatured, but does not measurably dissociate from the protein kinase when the protein kinase is intact is referred to herein as a "reversible denatured kinase inhibitor." After dissociating from the kinase, the reversible denatured kinase inhibitor can bind to the same or another kinase.

In certain embodiments, the method of inhibiting the protein kinase includes contacting the protein kinase with a kinase inhibitor wherein the kinase inhibitor inhibits the protein kinase with an inhibition constant of less than 100 nM. And where the protein kinase inhibitor is a reversible protein kinase inhibitor, the method of inhibiting the protein kinase includes contacting the protein kinase with a reversible kinase inhibitor wherein the reversible kinase inhibitor inhibits the protein kinase with an inhibition constant of less than 100 nM.

Where a kinase (also referred to herein as a protein kinase) is inhibited using a kinase inhibitor described herein, it is meant that kinase activity (i.e. phosphorylation of a substrate molecule (e.g. a protein substrate)) is decreased when contacted with the kinase inhibitor relative to the activity of the kinase in the absence of the kinase inhibitor. In some embodiments, the kinase inhibitor decreases the kinase activity 1, 2, 3, 4, 5, 6, 7, 8, 9, 10, 25, 50, 100, 250, 500, 1000, 5000, 10,000, 100,000, 500,000, 1,000,000, or more fold. In some embodiments, the kinase inhibitor inhibits the activity of the kinase with an inhibition constant ($K_i$) of less than 100 µM, 10 µM, 5 µM, 1 µM, 500 nM, 250 nM, 100 nM, 75 nM, 50 nM, 25 nM, 10 nM, 1 nM, 500 pM, 250 pM, 100 pM, 75 pM, 50 pM, 25 pM, 10 pM, or 1 pM. In some embodiments, the kinase inhibitor inhibits the activity of the kinase with an $IC_{50}$ of less than 100 µM, 10 µM, 5 µM, 1 µM, 500 nM, 250 nM, 100 nM, 75 nM, 50 nM, 25 nM, 10 nM, 1 nM, 500 pM, 250 pM, 100 pM, 75 pM, 50 pM, 25 pM, 10 pM, or 1 pM, when measured under the conditions set forth in the examples section.

Where a reversible kinase inhibitor provided herein reversibly binds to an active site cysteine residue, a reversible bond is formed between the active site cysteine residue and the reversible kinase inhibitor. The reversible bond is typically a covalent bond. A "covalent reversible kinase inhibitor," as used herein, refers to a reversible kinase inhibitor that forms a covalent bond with the kinase. Where the covalent reversible kinase inhibitor forms a reversible bond with an active site cysteine residue, the covalent reversible kinase inhibitor is referred to herein as a "thiol covalent reversible kinase inhibitor." In some embodiments, the covalent reversible kinase inhibitor measurably dissociates from the protein kinase only when the protein kinase is denatured, but does not measurably dissociate (or dissociates at least 1, $1\times10^2$, $1\times10^3$, $1\times10^4$, $1\times10^5$, $1\times10^6$, $1\times10^7$, $1\times10^8$, $1\times10^9$, $1\times10^{10}$ fold slower relative to the dissociation when the protein kinas is fully or partially denatured) from the protein kinase when the protein kinase is intact (referred to herein as a "covalent reversible denatured kinase inhibitor"). In some embodiments, the protein kinase is denatured (i.e. not intact) when placed in denaturing solution, such as 6 N guanidine, 1% SDS, 50% MeCN, or similar protein denaturant, for second or minutes (e.g. 30 to 120 seconds, such as 60 seconds). A covalent reversible denatured kinase inhibitor that forms a reversible bond with an active site cysteine residue is termed a "thiol covalent reversible denatured kinase inhibitor."

In some embodiments, the thiol covalent reversible kinase inhibitor forms a bond between the cysteine sulfhydryl groups and a carbon atom forming part of the carbon-carbon double bond (i.e. olefin) of the compound of the Formulae provided herein. Thus, in some embodiments, electrons of the sulfur atom of the active site cysteine sulfhydryl group attacks an electron deficient carbon atom of the carbon-carbon double bond (olefin). In some embodiments, the electron deficient carbon atom of the carbon-carbon double bond is distal to the electron withdrawing cyano group and the electron withdrawing $-L^2$-E substituent of the kinase inhibitor of the Formulae provided herein and embodiments thereof (i.e. the carbon attached to $-L^1$-$R^1$). In this way, a thiol adduct is formed (e.g., Michael reaction with cysteine). Therefore, in some embodiments, the combination of cyano and $-L^2$-E electron withdrawing groups bound to the olefinic moiety increases the reactivity of the olefin to form a thiol adduct with the active site cysteine residue. In some embodiments, the resulting thiol adduct is stable at about pH 2 to about pH 7 (e.g. about pH 3). In some embodiments, the reversible kinase inhibitors described herein, after covalently binding to the kinase active site cysteine residue as described herein, is capable of dissociating from the kinase within seconds or minutes after denaturing/unfolding the kinase with 6 N guanidine, 1% SDS, 50% MeCN, or similar protein denaturant.

In some embodiments, in addition to increasing the reactivity of the olefin towards the active site cysteine sulfhydryl group, the cyano and $-L^2$-E electron withdrawing groups function to increase the reversibility of thiol adduct that is formed. Thus, in some embodiments, the reversible kinase inhibitors set forth herein is completely reversible. The term "completely reversible" means the reversible kinase inhibitor exhibits a measurable dissociation rate under conditions in which the kinase is not denatured. In some embodiments, the kinase inhibitors provided herein are not completely reversible (i.e. do not exhibit a measurable dissociation rate under conditions in which the kinase is intact). Dissociation may be measured using any appropriate means, including dialysis and mass spectrometry. Specific methods of measuring dissociation are set forth in the Examples section below.

In some embodiments, the reversible denatured kinase inhibitor binds reversibly to cellular components other than the protein kinase that the reversible denatured kinase inhibitor inhibits (or specifically inhibits). The cellular components may be GSH, proteins or protein fragments that are not targeted kinases (e.g. a kinase that does not include an active site cysteine or does not include an active site cysteine within sufficient proximity to an ATP binding site), protein fragments of targeted kinases (e.g. a kinase that has been digested such that the number of bonding points to the kinase reversible denatured kinase inhibitor has been decreased such that the reversible denatured kinase inhibitor dissociates from the kinase). Thus, in some embodiments, the reversible denatured kinase inhibitor measurably dissociates from the kinase where the kinase is partly or fully digested. The ability of a reversible denatured kinase inhibitor to measurably dissociate from cellular components other than the intact of full length protein kinase that the reversible denatured kinase inhibitor inhibits may provide decreased toxicity, including decreased immunogenic toxicity. In certain embodiments, the -$L^1$-$R^1$ group of the reversible denatured kinase inhibitor is a kinase ATP binding site moiety and the electron deficient olefin carbon binds to a sulfhydryl of a kinase active site cysteine. Thus, in some embodiments the kinase inhibitors provided herein bind to at least two points of the protein kinase: at least one residue within the ATP binding site moiety and a sulfhydryl of a kinase active site cysteine.

In some embodiments, physiological concentrations of glutathione (e.g. 5 or 10 mM GSH) have little or no measurable effect on the ability of the reversible kinase inhibitors (e.g. provided herein to inhibit a protein kinase (e.g. reversible denatured kinase inhibitor only reversibly binds to GSH thereby enabling increased binding to the target kinase). In some embodiments, the IC50 or $K_i$ of the reversible kinase inhibitor is increased no more than 20%, 15%, 10%, 9%, 8%, 7%, 6%, 5%, 4%, 3%, 2%, 1%, 0.5%, 0.1%, 0.01% or 0.001% in the presence of physiological concentrations of glutathione(e.g. 5 or 10 mM GSH). In other embodiments, the IC50 or $K_i$ of the reversible kinase inhibitor is not measurably increased by the presence of physiological concentrations of glutathione (e.g. 5 or 10 mM GSH). In some embodiments, the physiological concentrations of glutathione (e.g. 5 or 10 mM GSH) have little or no measurable effect on the ability of the reversible kinase inhibitors provided herein to inhibit a protein kinase wherein the reversible kinase inhibitor is present at low concentrations (e.g. less than 100 nM, 75 nM, 50 nM, 25 nM, 10 nM, 5 nM, 3 nM, 1 nM, 500 μM, 250 μM, 100 μM, 75 μM, 50 μM, 25 μM, 10 μM, or 1 μM). In some embodiments, the physiological concentrations of glutathione (e.g. 5 or 10 mM GSH) have little or no measurable effect on the ability of the reversible kinase inhibitors provided herein to inhibit a protein kinase wherein the reversible kinase inhibitor is present at a concentration of less than 10 nM, 5 nM, 4 nM 3 nM, 2 nM or 1 nM. In certain embodiments, the physiological concentrations of glutathione (e.g. 5 or 10 mM GSH) have little or no measurable effect on the ability of the reversible kinase inhibitors provided herein to inhibit a protein In some embodiments, physiological concentrations of adenosine triphosphate (e.g. 1 mM ATP) have little or no measurable effect on the ability of the reversible kinase inhibitors provided herein to inhibit a protein kinase. In some embodiments, the IC50 or $K_i$ of the reversible kinase inhibitor is increased no more than 10%, 9%, 8%, 7%, 6%, 5%, 4%, 3%, 2%, 1%, 0.5%, 0.1%, 0.01% or 0.001% in the presence of physiological concentrations of adenosine triphosphate (e.g. 1 mM ATP). In other embodiments, the IC50 or $K_i$ of the reversible kinase inhibitor is not measurably increased by the presence of physiological concentrations of adenosine triphosphate (e.g. 1 mM ATP).

In certain embodiments, the reversible kinase inhibitors provided herein reacts reversibly with GSH. In certain embodiments, the reversible kinase inhibitors provided herein react rapidly and reversibly with GSH. Thus, in certain embodiments, the reversible kinase inhibitors provided herein react reversibly with GSH (e.g. rapidly and reversibly) while also reversibly binding to an active site cysteine residue (e.g. at a concentration of less than 10 nM, 5 nM, 4 nM 3 nM, 2 nM or 1 nM). The GSH may be at physiological concentration (e.g. 5-10 mM). Without being bound by any particular mechanistic theory, it is believed that the ability of reversible kinase inhibitors provided herein to react rapidly and reversibly with cellular glutathione protects most non-targeted cellular proteins from the electrophilic qualities of the reversible kinase inhibitor.

The protein kinase may be any appropriate kinase. In some embodiments, the protein kinase includes a cysteine residue in the active site. A protein kinase active site is a portion of the protein kinase in which the protein kinase substrate is phosphorylated. The kinase active site is typically a pocket or cleft containing amino acid residues that bind to a substrate (also referred to herein as kinase active site binding residues) and amino acid residues that participate in the catalytic phosphorylation reaction (also referred to herein as kinase active site catalytic residues). The reversible kinase inhibitors provided herein are capable of inhibiting the kinase catalytic action by fitting into the kinase active site and disrupting the ability of the kinase to phosphorylate the substrate. The active sites of many protein kinases are known in the art through structure determinations (e.g. X-ray crystallography or three dimensional NMR techniques). Where the three dimensional structure has not been determined, the structure of an active site of a protein kinase may be determined by the primary amino acid sequence using computer software modeling programs generally known in the art.

Protein kinases inhibited using the kinase inhibitors provided herein include, but are not limited to, serine/threonine-specific protein kinases, tyrosine-specific protein kinases, receptor tyrosine kinases, receptor-associated tyrosine kinases, histidine-specific protein kinases, and aspartic acid/glutamic acid-specific protein kinases, as known in the art. In some embodiments, the kinase is a tyrosine protein kinase or serine/threonine protein kinases. Examples of kinases include SRC, YES, FGR, CHK2, FGFR1-4, BTK, EGFR, HER2, HER4, HER3, JAK3, PLK1-3, MPS1, RON, MEK1/2, ERK1/2, VEGFR, KIT, KDR, PDGFR, FLT3, CDK8, MEK7, ROR1, RSK1-4, MSK1/2, MEKK1, NEK2, MEK5, MNK1/2, MEK4, TGFbR2, ZAP70, WNK1-4, BMX, TEC, TXK, ITK, BLK, MK2/3, LIMK1, TNK1, CDK11, p70S6 Kb, EphB3, ZAK, and NOK.

IV. Methods of Treating Disease

In another aspect, a method of treating a disease associated with kinase activity in a subject in need of such treatment. The method includes administering to the subject an effective amount (e.g. a therapeutically effective amount) of a compound having the structure of the Formulae provided herein (or an embodiment thereof as described above).

In some embodiments, the disease associated with kinase activity is chronic disease. The disease may be cancer, epilepsy, HIV infection, autoimmune disease (e.g. arthritis), ischemic disease (e.g. heart attack or stroke), stroke, neurodegenerative diseases, metabolic or inflammation. In certain embodiments, the disease is cancer, including, for example, leukemia, carcinomas and sarcomas, such as cancer of the brain, breast, cervix, colon, pancreas, head & neck, liver, kidney, lung, non-small cell lung, prostate, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas. In some embodiments, the disease is liver cancer, colon cancer, breast cancer, melanoma, acute myelogenous leukemia, chronic myelogenous leukemia, or nonsmall-cell lung cancer. In some embodiments, the disease is cancers which have metastasized. In some embodiments, the disease is rheumatoid arthritis, systemic lupus erythematosus, multiple sclerosis, scleroderma or polymyositis. In some embodiments, the disease is diabetes, obesity, or lipid disorders. In some embodiments, the disease may be caused by an infectious agent such as caused by bacteria, parasite or virus. In some embodiments, the disease is acute such as myocardial infarction, stroke or asthma. In some embodiments the disease is Parkinson's disease or amyotrophic lateral sclerosis.

V. Assays

Using techniques known in the art and the guidance provided herein, candidate kinase inhibitors may be easily assayed for their ability to inhibit any known protein kinase. For example, candidate kinase inhibitors having the structure of the Formulae provided herein or embodiments thereof may be first assayed using computer modeling techniques in order to assess potential binding contacts between kinase active site binding residues and/or kinase active site catalytic residues. Such computer modeling techniques may also be referred to as in silico techniques. As discussed above, the kinase active site binding residues and/or kinase active site catalytic residues are known or easily determined for any kinase in which the primary amino acid structure is known. In particular, computer modeling techniques may be employed to assess the ability of candidate kinase inhibitors to react with a kinase active site cysteine residue with the electron deficient olefin carbon to form a thiol adduct. For example, where the kinase inhibitor electron deficient olefin carbon is within 10 Å of the kinase active site cysteine sulfhydryl, the potency and/or selectivity of kinase inhibitor may be improved (e.g. by 1000-10,000-fold).

Likewise, computer modeling techniques may be used to assess the ability of candidate kinase inhibitors to fit into the kinase active site without creating stearic clashes. As described above, in some embodiments, —$R^1$ or -L-$R^1$ to fit within the kinase ATP binding site and/or make contacts with amino acid residues within the kinase ATP binding site. Therefore, computer modeling techniques may be used to assess the ability of —$R^1$ or -L-$R^1$ to fit within the kinase ATP binding site and/or make contacts with amino acid residues within the kinase ATP binding site. The computer modeling assays described above may be used to assess the kinase inhibition ability of candidate kinase inhibitors having different general chemical scaffolds within the structure of the Formulae provided herein or embodiments thereof. In this way, new classes of chemical scaffolds may be assessed using computer modeling prior to performing in vitro activity assays.

In vitro assays may also be used to assess the kinase inhibiting properties of candidate kinase inhibitors having the structure of the Formulae provided herein or embodiments thereof. In vitro kinase assays are well known in the art. High throughput techniques are known and useful for quickly assessing large numbers of kinase inhibitor candidates using binding assays for a large number of kinase panels. See, for example, Karaman et al., *Nat. Biotechnol.* 2008 January; 26(1):127-32.

Compounds that decrease kinase catalytic activity may also be identified and tested using biologically active protein kinases, either recombinant or naturally occurring. Protein kinases can be found in native cells, isolated in vitro, or co-expressed or expressed in a cell. Certain protein kinases specifically phosphorylate particular substrates. Where specific substrates are known, the ability of a candidate kinase inhibitor to reduce phosphorylation of the specific substrate may be assayed. General, or non-specific, kinase substrates may also be employed.

The kinase inhibitors provided herein may also be tested in vitro for their ability to inhibit a mutant of a kinase that does not contain an active site cysteine. The ability of a kinase inhibitor to decrease the catalytic activity of a kinase having an active site cysteine while not having the ability (or having measurably decreased ability) to decrease the catalytic activity of a mutant of the kinase that does not contain an active site cysteine is indicative of a kinase inhibitor that inhibits the kinase by binding to the active cite cysteine. For example, the C436V mutant of RSK2 may be resistant to certain kinase inhibitors (IC50>10 uM) that show strong inhibitory activity against the wild type RSK2. This result supports the conclusion that RSK2 inhibition requires the formation of a covalent bond between Cys436 and the inhibitor.

As described above, E and -$L^2$-E are typically substituents that sufficiently withdraw electrons from the reaction center olefin carbon to reversibly bind to the sulfhydryl of a kinase active cite cysteine (e.g. when the kinase is partly or fully denatured). The kinase inhibitors provided herein may also be tested in vitro for their ability to reversibly bind to the active site cysteine of a protein kinase by measuring association and dissociation of the kinase inhibitor from the protein kinase (e.g. partially or fully denatures) or from a thiol compound (e.g. 2-mercaptoethanol (BME)). The ability of the reaction center carbon of a kinase inhibitor provided herein to reversibly bind to the sulfhydryl of a kinase active cite cysteine may be measured using any appropriate means, including dialysis, mass spectrometry, NMR and UV detection (see Examples section for more details). For example, the kinase inhibitors may be assayed by detecting the binding of a thiol compound such as BME. The binding may be assessed using UV detection of compounds that typically become less UV active upon binding to a thiol compound or by detecting the binding using proton NMR. Typically, the assays are conducted by titering in the thiol compound and examining a change in the endpoint binding detection parameter (e.g. UV activity or proton NMR). Reversibility is assessed by dilution. Specific examples are provided below in the Examples section (see Example 82).

The kinase inhibitors provided herein may also be tested in vitro for their stability at pH 7.5. Any appropriate method may be used to determine the stability of a kinase inhibitor set forth herein at pH 7.5. Appropriate methods include, for example, LC-MS (e.g. HPLC-MS) as well as measuring changes in UV absorption where the kinase inhibitor includes a chromophore group. UV absorption may be measured using high-throughput techniques (e.g. multiwell plated for scanning large numbers of kinase inhibitors simultaneously). Stability may be assessed using phosphate-buffered saline at pH 7.5 at 37° C. Compounds having half-lives greater than 6 hours, 12 hours, 24 hours, or 48 hours may be may be selected.

Cellular assays may also be used to assess the kinase inhibiting properties of candidate kinase inhibitors having the structure of the Formulae provided herein or embodiments thereof. Cellular assays include cells from any appropriate source, including plant and animal cells (such as mammalian cells). The cellular assays may also be conducted in human cells. Cellular assays of kinase inhibition are well known in the art, and include methods in which a kinase inhibitor is delivered into the cell (e.g. by electroporation, passive diffusion, microinjection and the like) and a kinase activity endpoint is measured, such as the amount of phosphorylation of a cellular substrate, the amount of expression of a cellular protein, or some other change in the cellular phenotype known to be affected by the catalytic activity of the particular kinase being measured. For example, phosphorylation of a particular cellular substrate may be assessed using a detection antibody specific or the phosphorylated cellular substrate followed by western blotting techniques and visualization using any appropriate means (e.g. fluorescent detection of a fluorescently labeled antibody).

Measuring the reduction in the protein kinase catalytic activity in the presence of a kinase inhibitor disclosed herein relative to the activity in the absence of the inhibitor may be performed using a variety of methods known in the art, such as the assays described in the Examples section below. Other methods for assaying the activity of kinase activity are known in the art. The selection of appropriate assay methods is well within the capabilities of those having ordinary skill in the art.

Once kinase inhibitors are identified that are capable of reducing kinase catalytic activity in vitro and/or in a cell, the compounds may be further tested for their ability to selectively inhibit kinase activity in animal models (e.g. whole animals or animal organs). Thus, kinase inhibitors may be further tested in cell models or animal models for their ability to cause detectable changes in phenotype related to a particular kinase activity. In addition to cell cultures, animal models may be used to test inhibitors of kinases for their ability to treat, for example, cancer in an animal model.

VI. Pharmaceutical Formulations

In another aspect, the present invention provides pharmaceutical compositions comprising a kinase inhibitor compound of the invention or a kinase inhibitor compound in combination with a pharmaceutically acceptable excipient (e.g. carrier).

The pharmaceutical compositions include optical isomers, diastereomers, or pharmaceutically acceptable salts of the inhibitors disclosed herein. For example, in some embodiments, the pharmaceutical compositions include a compound of the present invention and citrate as a pharmaceutically acceptable salt. The kinase inhibitor included in the pharmaceutical composition may be covalently attached to a carrier moiety, as described above. Alternatively, the kinase inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

A. Formulations

The kinase inhibitors of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of administered to a mammal can vary depending upon a variety of factors, including a disease that results in increased activity of kinase, whether the mammal suffers from another disease, and the route of administration; size, age, sex, health, body weight, body mass index, and diet of the recipient; nature and extent of symptoms of the disease being treated (e.g., cancer), type of concurrent treatment, complications from the disease being treated or other health-related problems. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of reducing the level of kinase catalytic activity, as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side-effects. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

D. Additional Agents and Therapeutic Modalities

In some embodiments, the kinase inhibitors provided herein may be used in combination with other therapeutic agents or therapeutic modalities. In some embodiments, the additional therapeutic agent is an anticancer agent. The therapeutic agent may be a chemotherapeutic agents, a biologic agent, hormonal therapy agent, or a kinase inhibitor that is not a kinase inhibitor of the Formulae provided herein (or embodiments thereof). The additional therapeutic agent may additionally be an alkylating agent, an anthracylcines, a monoclonal antibody, a cytokine, a nucleoside analog, prednisone, a taxane, estrogen, progesterone, hormone antagonists, a vinca alkaloid, an anti-metabolites or the like.

In some embodiments, the kinase inhibitors provided herein may be used in combination with other therapeutic modalities such as radiation therapy and surgery.

VII. Examples

The following examples are offered to illustrate, but not to limit the claimed invention.

General Chemistry Methods.

Low-resolution electrospray ionization mass spectra ($ESI^+$-MS) were recorded on a Waters Micromass ZQ 4000 spectrometer. LC/MS (MS: $ESI^+$) was performed on a Waters AllianceHT LC/MS with a flow rate of 0.2 ml $min^{-1}$ (monitored at 210 nm, 260 nm, and/or 350 nm) using an Xterra MS C18 column (Waters). For air- and water-sensitive reactions, glassware was oven- or flame-dried prior to use and reactions were performed under argon. Dichloromethane, dimethylformamide, methanol, tetrahydrofuran, toluene, and diisopropylamine were dried using the solvent purification system manufactured by Glass Contour, Inc. (Laguna Beach, Calif.). All other solvents were of ACS chemical grade (Fisher) and used without further purification unless otherwise indicated. Analytical and preparative thin layer chromatography were performed with silica gel 60 $F_{254}$ glass plates (EM Science). Flash chromatography was conducted with 230-400 mesh silica gel (Selecto Scientific). Preparative high performance liquid chromatography (HPLC) was performed on a Prostar 210 (Varian) with a flow rate of 10 ml $min^{-1}$ (monitored at 210 nm and 260 nm) using a COMBI-A C18 preparatory column (Peeke Scientific).

General Procedure for JAK2 and JAK3 Kinase Assays.

Active JAK2 (Human, residues 808-end) and JAK3 (Human, residues 781-end) was purchased from Millipore. Active kinase (3 nM) in 8 mM HEPES, pH 7.0, 200 uM EDTA, 10 mM $MgCl_2$, 0.2 mg/mL BSA, 100 uM ATP and 10 mM GSH were pre-incubated with inhibitors (eight or ten concentrations, in duplicate) for 30 minutes at room temperature. Kinase reactions were initiated by the addition of 0.3 µCi/µL of γ-$^{32}$P-ATP (6000 Ci/mmol, NEN) and 100 uM peptide substrate (JAK3-tide for JAK3 or PDK-tide for JAK2, Millipore) and incubated for 30 minutes at room temperature. Kinase activity was determined by spotting 5 µL of each reaction onto sheets of phosphocellulose. Each blot was washed once with 1% AcOH solution, twice with 0.1% $H_3PO_4$ solution, and once with MeOH (5-10 minutes per wash). Dried blots were exposed for 30 minutes to a storage phosphor screen and scanned by a Typhoon imager (GE Life Sciences). The data were quantified using the SPOT program (Knight, Z. et al. *Nature Protocols,* 2 (10), 2459-66) and plotted using GraphPad Prism 4.0 software.

General Procedure for Btk Kinase Assay.

Btk (human, full length) was purchased (Invitrogen, catalog number PV3363) and used as specified in the product literature. Btk (2 nM final concentration) was pre-incubated with inhibitors (six or ten concentrations, in duplicate) for 30 minutes at room temperature. Kinase reactions were initiated by the addition of 0.16 µCi/µL of γ-$^{32}$P-ATP (6000 Ci/mmol, NEN) and 0.2 mg/mL substrate (poly[Glu:Tyr], 4:1 Glu:Tyr) and incubated for 30 minutes at room temperature. Kinase activity was determined by spotting 6 µL of each reaction onto sheets of phosphocellulose. Each blot was washed once with 1% AcOH solution, twice with 0.1% $H_3PO_4$ solution, and once with MeOH (5-10 minutes per wash). Dried blots were exposed for 30 minutes to a storage phosphor screen and scanned by a Typhoon imager (GE Life Sciences). The data were quantified using ImageQuant (v. 5.2, Molecular Dynamics) and plotted using GraphPad Prism 4.0 software.

Example 1

3-(4-(9H-purin-6-yl)phenyl)-2-cyanoacrylamide

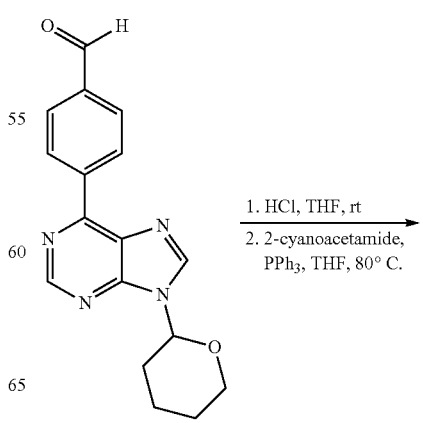

-continued

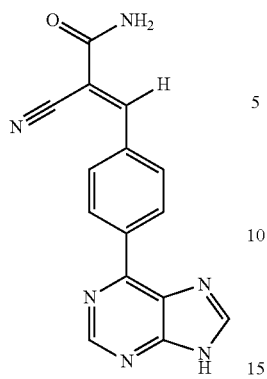

To a solution of 1-tetrahydropyran-1-yl-6-(p-formylphenyl)purine (Donald, A. et al. *J. Med. Chem.* 2007, 50, 2289-2292) (170 mg, 0.55 mmol) in 6 mL THF was added 20 drops of aqueous 1 N HCl. The reaction was stirred at room temperature overnight. After 18 hours a white precipitate had formed, and all starting material had been consumed as determined by TLC. The reaction was diluted with EtOAc, washed with saturated NaHCO$_3$, and the organic layer was dried with Na$_2$SO$_4$. Rotary evaporation afforded 100 mg (81%) of 2 as a light yellow solid that was carried on without further purification. Exact mass: 224.07, M/z found: 225.3 (M+H)$^+$.

A slurry of the deprotected 6-(p-formylphenyl)-purine (10.9 mg, 0.049 mmol), 2-cyanoacetamide (5.4 mg, 0.064 mmol), and PPh$_3$ (13 mg, 0.049 mmol) in THF (0.5 mL) was heated to 80° C. in a sealed vial. The mixture was stirred at 80° C. for 12 hours and concentrated in vacuo. The residue was chromatographed on silica with 9:1 CH$_2$Cl$_2$:MeOH, affording 9.6 mg (87%) of 3-(4-(9H-purin-6-yl)phenyl)-2-cyanoacrylamide (mixture of E/Z isomers) as a light yellow solid. Exact mass: 290.09, M/z found: 291.3 (M+H)$^+$.

Example 2

4-(1-tosyl-1H-pyrrolo[2,3-b]pyridin-3-yl)benzaldehyde

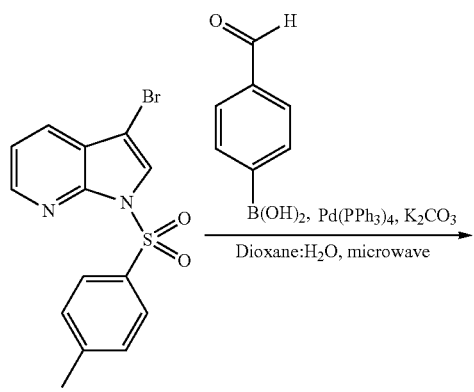

-continued

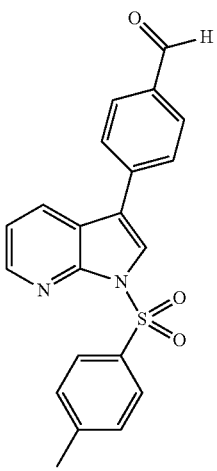

A slurry of 3-bromo-1-tosyl-1H-pyrrolo[2,3-b]pyridine (100 mg, 0.29 mmol), 4-formylphenyl boronic acid (66 mg, 0.44 mmol) and K$_2$CO$_3$ (126 mg, 0.87 mmol) in 5:1 dioxane:water (2 mL) was degassed argon for 30 minutes in a microwave vial. Pd(PPh$_3$)$_4$ (33 mg, 0.029 mmol) was added and the vessel was purged with argon. The vial was heated to 150° C. for 15 minutes in a microwave reactor, cooled to room temperature, diluted with EtOAc, washed with water, the organic layer dried with Na$_2$SO$_4$ and concentrated in vacuo. The residue was chromatographed on silica with 1:1 hexanes:EtOAc, affording 92 mg (86%) of 4-(1-tosyl-1H-pyrrolo[2,3-b]pyridin-3-yl)benzaldehyde as a yellow solid.

Example 3

4-(1H-pyrrolo[2,3-b]pyridin-3-yl)benzaldehyde

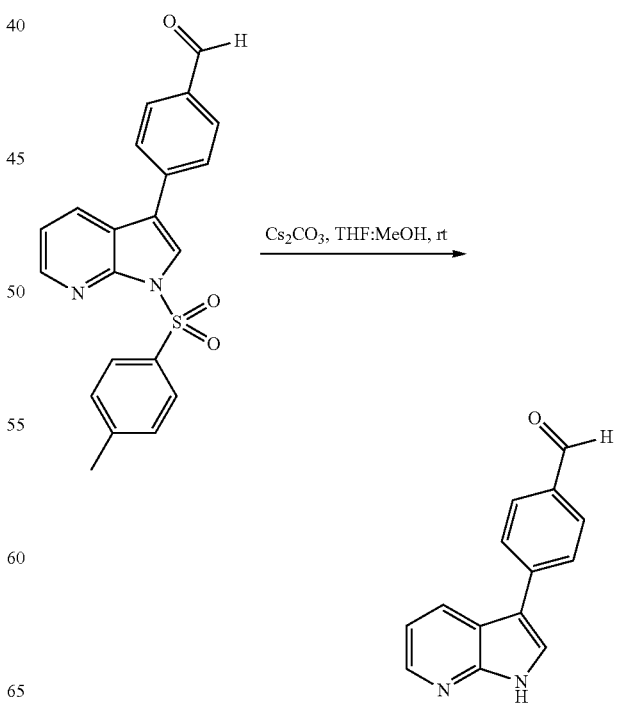

To a solution of 4-(1-tosyl-1H-pyrrolo[2,3-b]pyridin-3-yl)benzaldehyde (162 mg, 0.45 mmol) in 2:1 THF:MeOH (2 mL) was added Cs₂CO₃ (435 mg, 1.34 mmol). The solution turned yellow upon addition of the carbonate base, and was stirred at room temperature for 18 hours. After complete consumption of starting material, monitored by TLC, the light orange solution was concentrated in vacuo, the residue taken up in 10 mL of water, and the resulting slurry stirred vigorously for 30 minutes. The yellow precipitate was filtered, washed with water, and dried under vacuum to afford 74 mg of 4-(1H-pyrrolo[2,3-b]pyridin-3-yl)benzaldehyde as a bright yellow solid. Exact Mass: 222.08, M/z found: 223.3 (M+H)⁺.

Example 4

3-(4-(1H-pyrrolo[2,3-b]pyridin-3-yl)phenyl)-2-cyanoacrylamide

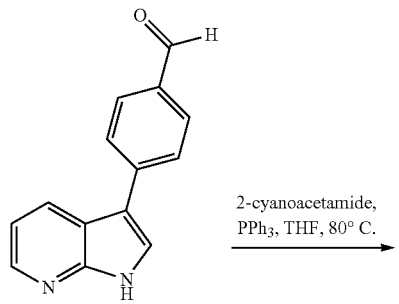

To a slurry of 4-(1H-pyrrolo[2,3-b]pyridin-3-yl)benzaldehyde (8 mg, 0.036 mmol) in 1:1 THF:MeOH was added 2-cyanoacetamide (4 mg, 0.043 mmol) and PPh₃ (5 mg, 0.018 mmol). The reaction mixture was heated to 80° C. for 48 hours, and after significant evolution of product, monitored by LCMS, the reaction was concentrated and taken up in a small volume of THF. EtOH was added and the resulting yellow precipitate filtered and dried in vacuo to afford 1.2 mg of 3-(4-(1H-pyrrolo[2,3-b]pyridin-3-yl)phenyl)-2-cyanoacrylamide (mixture of E/Z isomers) as a brilliant yellow solid. Exact mass: 288.30, M/z found: 289.3 (M+H)⁺.

Example 5

3-(1H-pyrrolo[2,3-b]pyridine-3-carbonyl)benzaldehyde

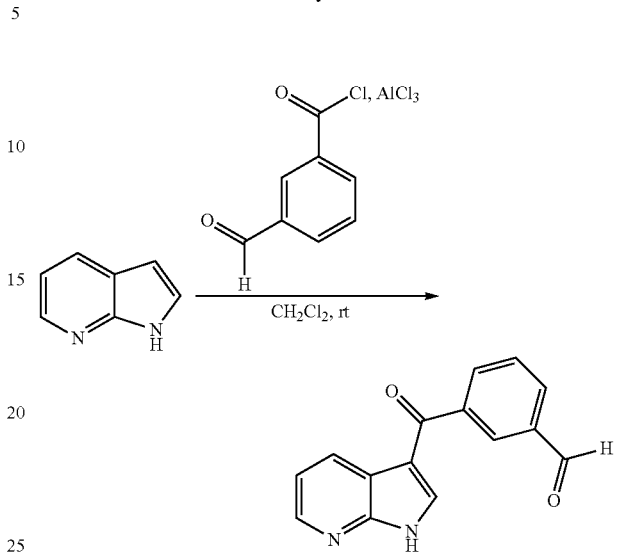

7-azaindole (182 mg, 1.5 mmol) and AlCl₃ (945 mg, 7.4 mmol) were combined in dry CH₂Cl₂ (50 mL) in a flame-dried round bottom flask under argon. The heterogeneous yellow mixture was allowed to stir at room temperature for one hour, at which time 3-formyl benzoyl chloride (505 mg, 2.9 mmol) was added dropwise via syringe under positive pressure of argon. The mixture slowly became a translucent yellow solution. After two additional hours of stirring at room temperature, MeOH (~20 mL) was added slowly to quench excess acid chloride. The solvent was removed in vacuo and the residue chromatographed on silica with 9:1 EtOAc:MeOH to afford 42 mg (11%) of 3-(1H-pyrrolo[2,3-b]pyridine-3-carbonyl)benzaldehyde as a white solid. Exact mass: 250.07, M/z found: 251.3 (M+H)⁺.

Example 6

3-(3-(1H-pyrrolo[2,3-b]pyridine-3-carbonyl)phenyl)-2-cyanoacrylamide

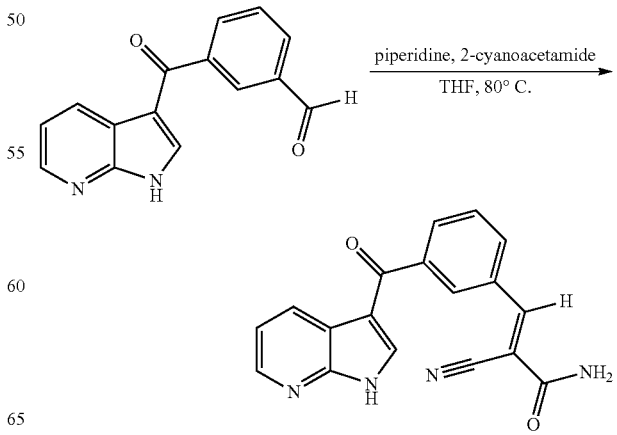

To a solution of 3-(1H-pyrrolo[2,3-b]pyridine-3-carbonyl)benzaldehyde (19.5 mg, 0.08 mmol) in THF (1 mL) was added 2-cyanoacetamide (15 mg, 0.17 mmol) and piperidine (10 μL, 0.096 mmol) and the slurry was stirred at 80° C. for three hours with evolution of a white precipitate. The precipitate was collected by filtration to afford 1.5 mg (6%) of 3-(3-(1H-pyrrolo[2,3-b]pyridine-3-carbonyl)phenyl)-2-cyanoacrylamide (mixture of E/Z isomers) as a white solid. Exact mass: 316.10, M/z found: 317.3 (M+H)$^+$.

Example 7

2-cyano-3-(1H-indazol-5-yl)acrylamide

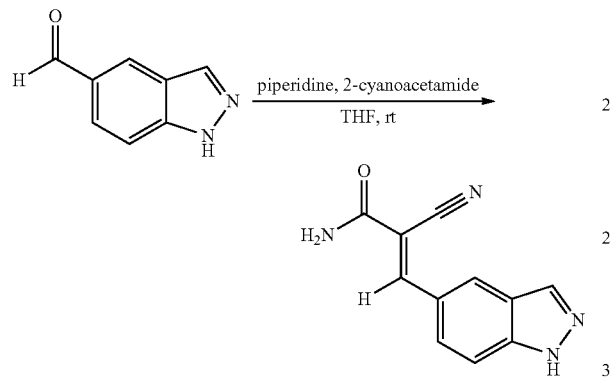

To a solution of 5-formyl-1H-indazole (102.5 mg, 0.7 mmol) in THF (2 mL) was added 2-cyanoacetamide (75 mg, 0.9 mmol) and piperidine (20 μL, 0.2 mmol). The reaction was stirred for 18 hours at room temperature, followed by addition of a spatula-tip of cyanoacetamide. The reaction was stirred for another three hours and yellow solids began to precipitate. The reaction was filtered and the solids were washed with THF and dried in vacuo to afford 65 mg (44%) of 2-cyano-3-(1H-indazol-5-yl)acrylamide (mixture of E/Z isomers) as a yellow solid. Exact mass: 212.07, M/z found: 213.4 (M+H)$^+$.

Example 8

3-(1H-indazol-5-yl)-2-(pyrrolidine-1-carbonyl)acrylonitrile

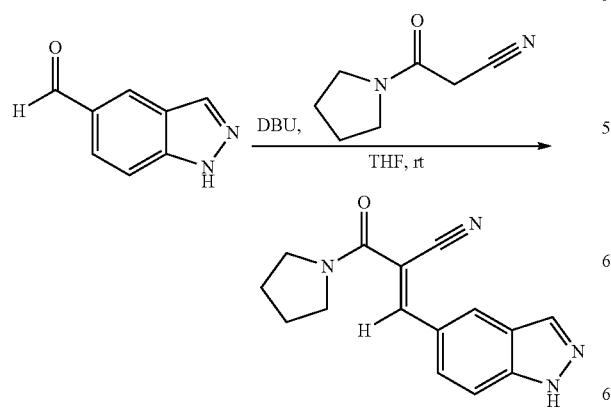

To a solution of 6-formyl-1H-indazole (115 mg, 0.8 mmol) in THF (2 mL) was added 2-cyano-N-isopropylacetamide (100 mg, 0.7 mmol) and DBU (130 μL, 1.05 mmol). The resulting brown solution was stirred at room temperature for 18 hours, monitored by TLC. An additional spatula tip of 2-cyano-N-isopropylacetamide was added, and the reaction stirred for another 18 hours with minimal evolution of additional product. The reaction was concentrated, taken up in a small volume of EtOAc, and purified by preparative TLC to afford 43 mg (20%) of 3-(1H-indazol-6-yl)-2-(pyrrolidine-1-carbonyl)acrylonitrile (mixture of E/Z isomers) as an amorphous tan solid. Exact mass: 266.12, M/z found: 267.5 (M+H)$^+$.

Example 9

2-cyano-3-(1H-indazol-6-yl)acrylamide

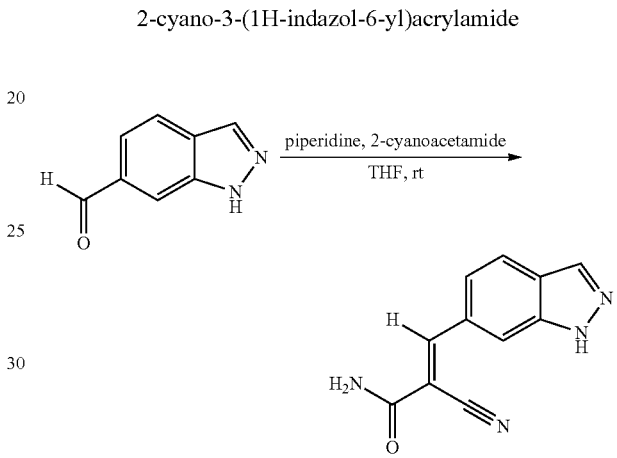

To a solution of 6-formyl-1H-indazole (102.5 mg, 0.7 mmol) in THF (2 mL) was added 2-cyanoacetamide (78.2 mg, 0.7 mmol) and piperidine (50 μL, 0.5 mmol). The reaction was stirred for 18 hours at room temperature with production of a white precipitate. The reaction was filtered and the solids were washed with THF and dried in vacuo to afford 69 mg (46%) of 2-cyano-3-(1H-indazol-6-yl)acrylamide (mixture of E/Z isomers) as a white solid. Exact mass: 212.07, M/z found: 213.4 (M+H)$^+$.

Example 10

2-cyano-3-(1H-indazol-6-yl)-N-methylacrylamide

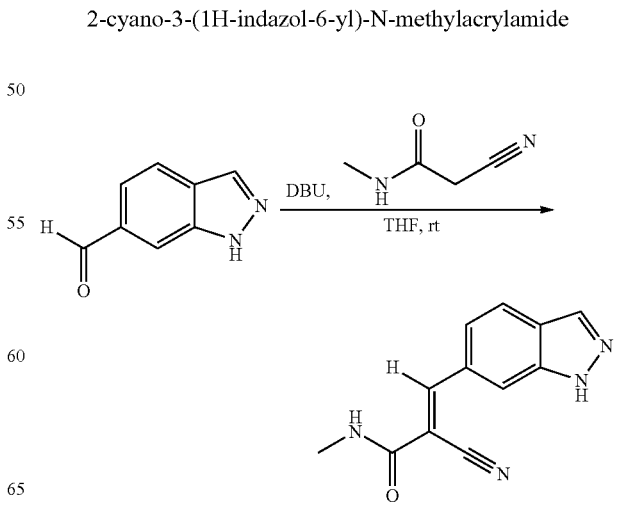

To a solution of 6-formyl-1H-indazole (103.5 mg, 0.7 mmol) in THF (1 mL) was added 2-cyano-N-methylacetamide (70 mg, 0.7 mmol) and DBU (130 μL, 1.05 mmol). Immediately upon DBU addition, the yellow slurry became a clear orange solution, followed by rapid evolution of an orange precipitate. After an hour of stirring at room temperature, the reaction was concentrated, taken up in a small volume of 1:1 EtOAc:H₂O and sonicated vigorously to break up the residue. The resulting solids were filtered, washed with EtOAc and H₂O and dried to afford 21 mg (13%) of 2-cyano-3-(1H-indazol-6-yl)-N-methylacrylamide (mixture of E/Z isomers) as a tan solid. Exact mass: 226.09, M/z found: 227.4 (M+H)⁺.

Example 11

2-cyano-3-(1H-indazol-6-yl)-N-isopropylacrylamide

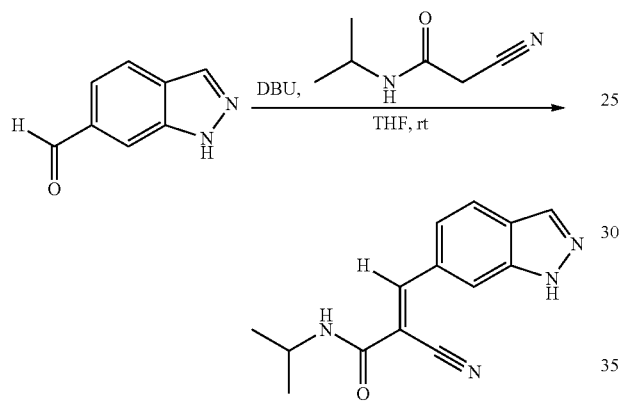

To a solution of 6-formyl-1H-indazole (101.5 mg, 0.7 mmol) in THF (1 mL) was added 2-cyano-N-isopropylacetamide (99.9 mg, 0.8 mmol) and DBU (130 μL, 1.05 mmol). After 1 hour, complete consumption of starting material was observed, monitored by TLC. The reaction was diluted with EtOAc and washed with H₂O and brine. Hexanes was added slowly to the remaining organic layer until a light precipitate formed, which was collected by filtration to afford 48 mg (27%) of 2-cyano-3-(1H-indazol-6-yl)-N-isopropylacrylamide (mixture of E/Z isomers) as a white solid.

Example 12

(1-(9H-purin-6-yl)piperidin-4-yl)methanol

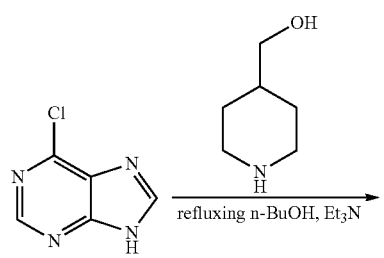

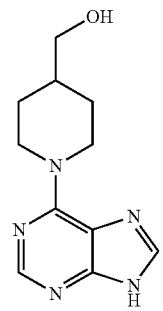

6-Chloropurine (509 mg, 3.2 mmol), 4-piperidine methanol (737 mg, 6.4 mmol) and Et₃N (2.25 mL, 25.6 mmol) was dissolved in n-BuOH (30 mL) and heated to 100° C. in a sealed vessel. The light orange solution was heated overnight, cooled to room temperature, and concentrated to afford a tan solid. The residue was triturated with 3:1 hexanes:MeOH (10 mL) and dried in vacuo to afford 401 mg (57%) of (1-(9H-purin-6-yl)piperidin-4-yl)methanol as a bright white solid.

Example 13

1-(9H-purin-6-yl)piperidine-4-carbaldehyde

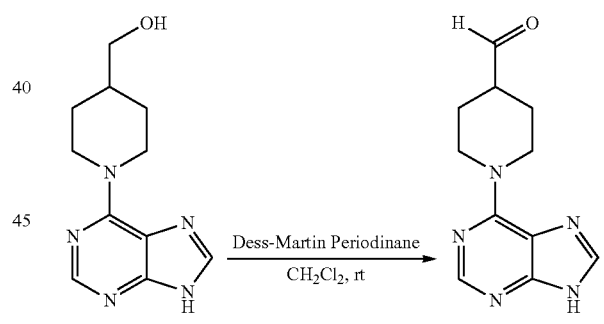

(1-(9H-purin-6-yl)piperidin-4-yl)methanol (250 mg, 1.1 mmol) and Dess-Martin periodinane (700 mg, 1.65 mmol) were combined in dry CH₂Cl₂ (30 mL) and the slurry stirred vigorously until it became a yellow, heterogeneous solution. Water (20 μL) in CH₂Cl₂ (20 mL) was added dropwise to the reaction, which became cloudy upon addition of ~1 molar equivalent of water. After an additional 30 minutes of vigorous stirring, the reaction mixture was diluted in EtOAc (~100 mL) and washed with 1:1 saturated NaS₂O₄:NaHCO₃, water, and brine. The aqueous layer was back-extracted with EtOAc, the combined organic layers dried with Na₂SO₄ and concentrated. The residue was chromatographed on silica with 9:1 CH₂Cl₂:MeOH to afford 124 mg (48%) of 1-(9H-purin-6-yl)piperidine-4-carbaldehyde as a waxy, colorless solid.

Example 14

3-(1-(9H-purin-6-yl)piperidin-4-yl)-2-cyanoacrylamide

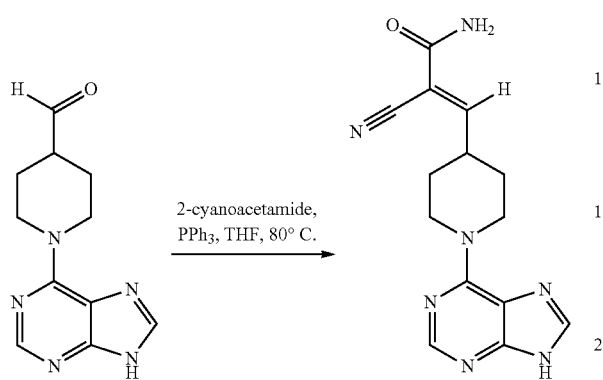

1-(9H-purin-6-yl)piperidine-4-carbaldehyde (11.2 mg, 0.048 mmol), 2-cyanoacetamide (6 mg, 0.071 mmol) and PPh$_3$ (6 mg, 0.023 mmol) were combined in THF (1 mL) and heated to 80° C. in a sealed vial. After 18 hours of heating, a white precipitate had formed but TLC indicated the presence of significant quantities of starting material. A spatula tip of 2-cyanoacetamide was added to the reaction and it was stirred for an additional 18 hours at 80° C. The reaction was cooled and the precipitate collected by filtration to afford 6 mg (46%) of 3-(1-(9H-purin-6-yl)piperidin-4-yl)-2-cyanoacrylamide (mixture of E/Z isomers) as a white solid. Exact mass: 297.13, M/z found: 298.3 (M+H)$^+$.

Example 15

2-(2-oxo-2-p-tolylethyl)isoindoline-1,3-dione

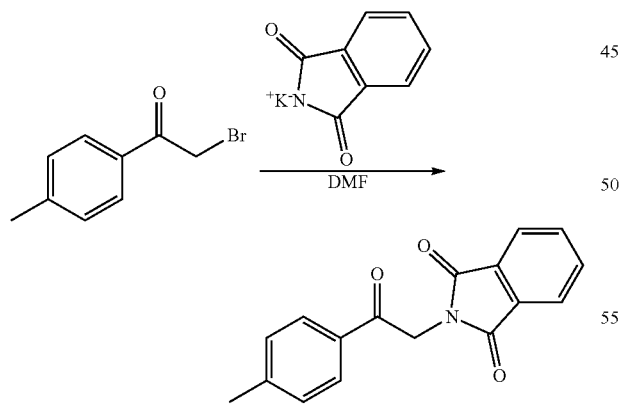

2-bromo-1-p-tolylethanone (20 g, 93.8 mmol) was dissolved in 100 mL DMF. Potassium phthalamide (19.9 g, 103.2 mmol) was added and the reaction was stirred at room temperature for 3 hours. The reaction was diluted to a total volume of 200 mL with CH$_3$Cl and the product precipitated out of solution. The precipitated product was collected by filtration. The leftover filtrate was concentrated, redissolved in 100 mL CH$_3$Cl, and then washed with water, saturated sodium bicarbonate and brine. The aqueous layer was extracted with CH$_2$Cl$_2$+10% MeOH, and the resulting organic layer was dried over Na$_2$SO$_4$ and concentrated in vacuo. The total amount of 2-(2-oxo-2-p-tolylethyl)isoindoline-1,3-dione obtained was 24.4 g (94% yield).

Example 16

2-amino-4-p-tolyl-1H-pyrrole-3-carbonitrile

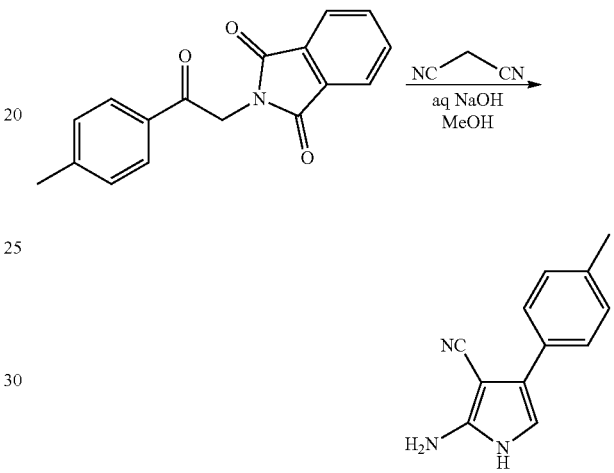

To a solution of malononitrile (1.23 g, 18.6 mmol) in MeOH (22.5 ml)/48% w/v aq. NaOH (3.5 ml)/H$_2$O (7.5 ml) was added 2-(2-oxo-2-p-tolylethyl)isoindoline-1,3-dione (4 g, 14.3 mmol). The reaction mixture was stirred at room temperature for 3 hours after which the product precipitated out of solution. The solid was collected by filtration and washed with water. To the leftover filtrate was added water and the resulting precipitation was filtered off and combined with the product. The solid product was dried under vacuum overnight to give 2.3 g (82% yield) of 2-amino-4-p-tolyl-1H-pyrrole-3-carbonitrile.

Example 17 methyl N-3-cyano-4-p-tolyl-1H-pyrrol-2-ylformimidate

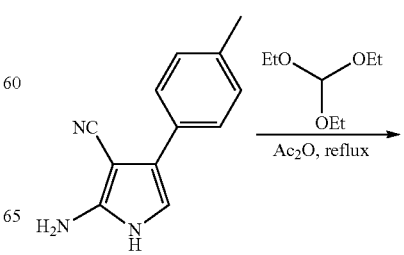

78

Example 19

5-p-tolyl-7H-pyrrolo[2,3-d]pyrimidin-4-amine

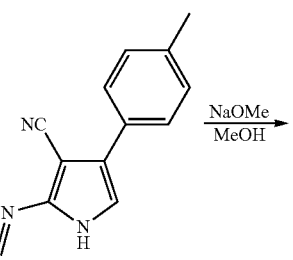

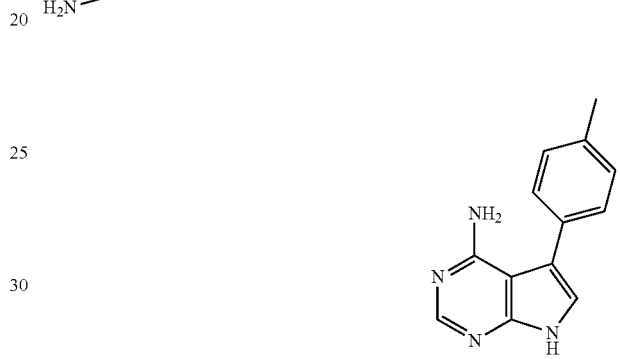

N'-(3-cyano-4-p-tolyl-1H-pyrrol-2-yl)formimidamide (2.27 g, 10.2 mmol) was dissolved in MeOH (30 ml) and heated to reflux. Sodium methoxide (1.5 m, 25% wt in MeOH, 5.1 mmol) was added and the reaction was stirred at reflux for 3 hours after which the product precipitated out of solution. After cooling to room temperature, the solid was isolated by filtration and dried under high vacuum to give 2.3 g (100%) of pure 5-p-tolyl-7H-pyrrolo[2,3-d]pyrimidin-4-amine as a tan solid.

Example 20

7-(3-(tert-butyldimethylsilyloxy)propyl)-5-p-tolyl-7H-pyrrolo[2,3-d]pyrimidin-4-amine

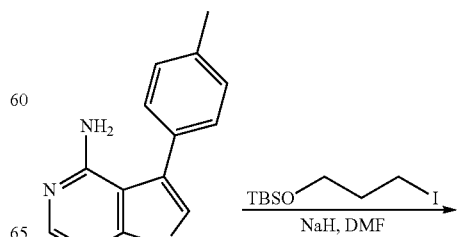

77

-continued

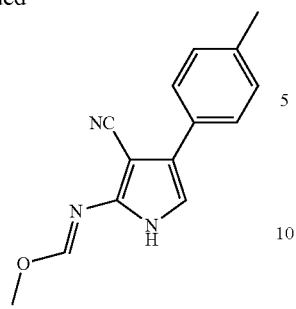

To a solution of 2-amino-4-p-tolyl-1H-pyrrole-3-carbonitrile (2.3 g, 11.6 mmol) in triethyl orthoformate (10 ml) was added acetic anhydride (110 µl, 1.1 mmol) and the mixture was refluxed for 1 hour. After cooling to room temperature, the solvent was removed in vacuo. The 2.88 g (99% yield) of crude methyl N-3-cyano-4-p-tolyl-1H-pyrrol-2-yl-formimidate was azeotropically dried with toluene and carried on directly to the next step.

Example 18

N'-(3-cyano-4-p-tolyl-1H-pyrrol-2-yl)formimidamide

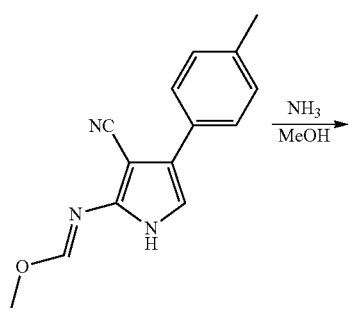

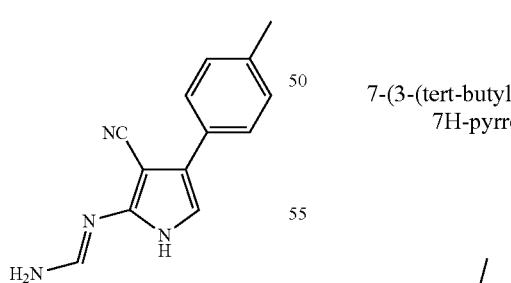

The crude methyl N-3-cyano-4-p-tolyl-1H-pyrrol-2-yl-formimidate (2.88 g, 11.5 mmol) was dissolved in 7 N NH₃ in MeOH (80 ml) and stirred at room temperature in a capped round bottom flask for 4 hours. The solvent was removed in vacuo and the crude N'-(3-cyano-4-p-tolyl-1H-pyrrol-2-yl)formimidamide product was dried on high vacuum overnight to give 2.27 g (88% yield) of product.

-continued

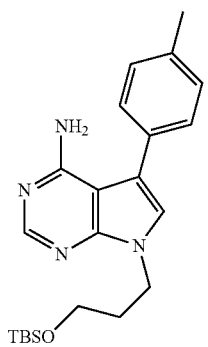

To a 0° C. slurry of 5-p-tolyl-7H-pyrrolo[2,3-d]pyrimidin-4-amine (5.01 g, 22.3 mmol) in DMF (120 mL) was added NaH (0.98 g of 60% oil dispersion, 24.6 mmol) and the resulting mixture was allowed to warm to room temperature. After stirring for 30 min, 3-(t-butyldimethylsilyloxy)propyl iodide (7.38 g, 24.6 mmol) was added dropwise over 10 min. After stirring for an additional 4 hours the reaction was quenched by adding 100 ml water and the precipitated product was filtered and dried under high vacuum to give 7.78 g (88% yield) of 7-(3-(tert-butyldimethylsilyloxy)propyl)-5-p-tolyl-7H-pyrrolo[2,3-d]pyrimidin-4-amine. Exact Mass 396.23. Found 397.5 [M+H]+.

Example 21

6-bromo-7-(3-(tert-butyldimethylsilyloxy)propyl)-5-p-tolyl-7H-pyrrolo[2,3-d]pyrimidin-4-amine

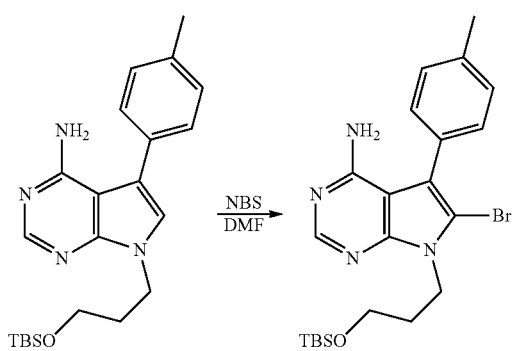

To a solution of 7-(3-(tert-butyldimethylsilyloxy)propyl)-5-p-tolyl-7H-pyrrolo[2,3-d]pyrimidin-4-amine (1.22 g, 3 mmol) in DMF (20 ml) was added N-bromosuccinimide (0.65 g, 3.6 mmol) and the mixture was stirred for 24 hours protected from light. The reaction was diluted with EtOAc (25 ml) and washed with water and brine. The combined organic fractions were dried over anhydrous Na₂SO₄, filtered, concentrated and purified by flash column chromatography (40% ethyl acetate/hexanes) to give 0.9 g (62% yield) of 6-bromo-7-(3-(tert-butyldimethylsilyloxy)propyl)-5-p-tolyl-7H-pyrrolo[2,3-d]pyrimidin-4-amine. Exact Mass: 474.15. Found 475 [M]+ and 477 [M+2]+.

Example 22

7-(3-(tert-butyldimethylsilyloxy)propyl)-5-p-tolyl-6-vinyl-7H-pyrrolo[2,3-d]pyrimidin-4-amine

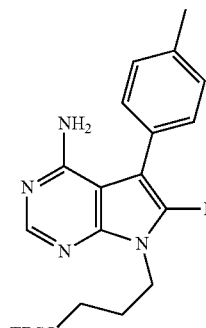

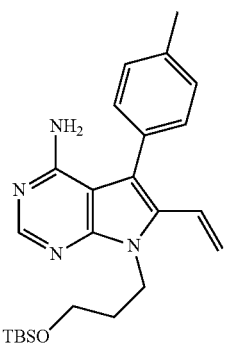

To a solution of 6-bromo-7-(3-(tert-butyldimethylsilyloxy)propyl)-5-p-tolyl-7H-pyrrolo[2,3-d]pyrimidin-4-amine (1.0 g, 2.1 mmol) in toluene (30 ml) was added tributylvinyltin (0.8 ml, 2.73 mmol). Argon gas was bubbled through the solution for 10 min. Tetrakis(triphenylphosphine)palladium (244 mg, 0.21 mmol) was quickly added, and argon gas was bubbled through the solution for another 10 min. The reaction was then stirred at reflux for 3 h. The reaction was filtered through Celite and the filtrate was concentrated. The product was purified by flash column chromatography in 50% EtOAc/hexanes to give a light yellow residue that was lyophilized from benzene to give 757 mg (85% yield) of 7-(3-(tert-butyldimethylsilyloxy)propyl)-5-p-tolyl-6-vinyl-7H-pyrrolo[2,3-d]pyrimidin-4-amine as a light yellow powder. Exact Mass 422.25. Found 423.1 [M+H]+.

Example 23

4-amino-7-(3-(tert-butyldimethylsilyloxy)propyl)-5-p-tolyl-7H-pyrrolo[2,3-d]pyrimidine-6-carbaldehyde

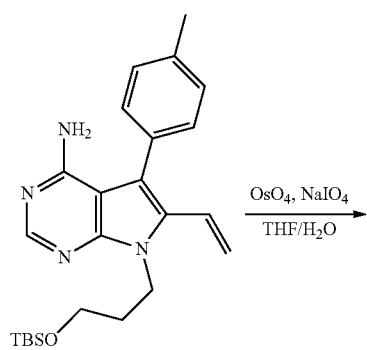

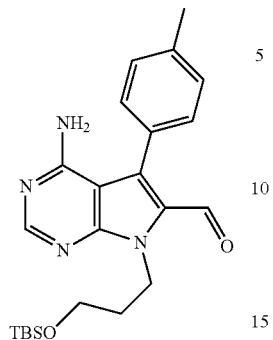

To a solution of 7-(3-(tert-butyldimethylsilyloxy)propyl)-5-p-tolyl-6-vinyl-7H-pyrrolo[2,3-d]pyrimidin-4-amine (760 mg, 1.8 mmol) in 3:1 THF:H₂O (11.3 ml) under argon was dropwise added osmium tetroxide (1.75 ml, 0.18 mmol, 2.5% in t-BuOH). The reaction was stirred at room temperature under argon for 20 min. Sodium periodate (860 mg, 3.6 mmol, dissolved in 2.4 ml warm water) was added dropwise to the reaction over a period of 30 min. The reaction was stirred for 1.5 h at room temperature and was then diluted with ethyl acetate. The organic layer was washed with saturated aqueous sodium thiosulfate and the aqueous layer was back extracted with ethyl acetate. The combined organic layers were dried over sodium sulfate, filtered and concentrated. The residue was purified by flash column chromatography in 50% EtOAc/hexanes to give 417 mg (55% yield) of a yellowish oil that solidified upon standing. Exact Mass 424.23. Found 425.1 [M+H]⁺.

To a solution of 4-amino-7-(3-(tert-butyldimethylsilyloxy)propyl)-5-p-tolyl-7H-pyrrolo[2,3-d]pyrimidine-6-carbaldehyde (52 mg, 0.123 mmol) in dry THF (1.5 ml) was added DBU (22 µl, 0.147 mmol) and methyl 2-cyanoacetate (13 mg, 0.135 mmol). The reaction was stirred at room temperature for 1 hr after which conversion had reached 90%. The reaction was concentrated and the residue was purified by preparatory thin layer chromatography in 50% EtOAc/hexanes to give 51 mg (80% yield) of the TBS-protected cyanoacrylate as a yellow film. To a solution of the TBS-protected cyanoacrylate (51 mg, 0.098 mmol) in THF (1.5 ml) was added 1N aqueous HCl (500 µl). The reaction was stirred at room temperature for 1 hr and then diluted with ethyl acetate. The organic layer was washed with saturated aqueous sodium bicarbonate and brine, then dried over sodium sulfate, filtered, and concentrated. The yellow residue was purified by precipitation from methanol/hexanes (1:3) to give 12 mg (25% yield) of methyl 3-(4-amino-7-(3-hydroxypropyl)-5-p-tolyl-7H-pyrrolo[2,3-d]pyrimidin-6-yl)-2-cyanoacrylate (mixture of E/Z isomers) as a yellow solid. Exact Mass 391.16. Found 392.0 [M+H]⁺.

Example 24

Methyl 3-(4-amino-7-(3-hydroxypropyl)-5-p-tolyl-7H-pyrrolo[2,3-d]pyrimidin-6-yl)-2-cyanoacrylate Example 25 tert-butyl 3-(4-amino-7-(3-hydroxypropyl)-5-p-tolyl-7H-pyrrolo[2,3-d]pyrimidin-6-yl)-2-cyanoacrylate

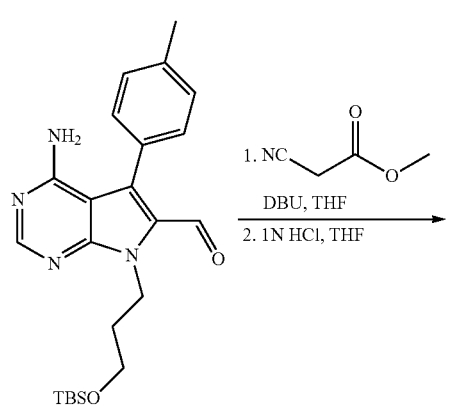

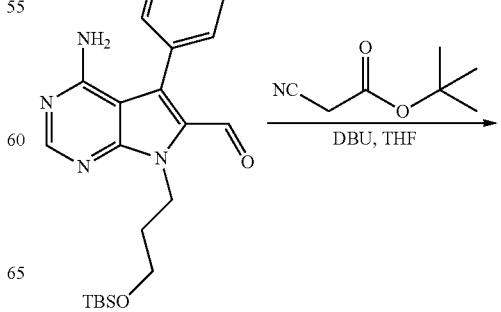

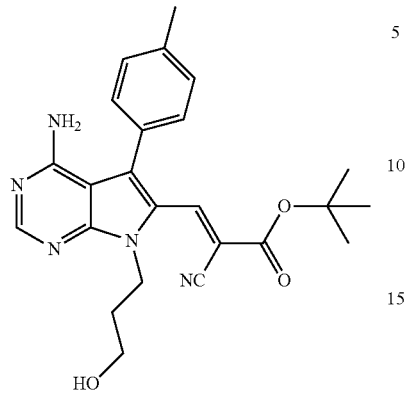

To a solution of 4-amino-7-(3-(tert-butyldimethylsilyloxy)propyl)-5-p-tolyl-7H-pyrrolo[2,3-d]pyrimidine-6-carbaldehyde (100 mg, 0.235 mmol) in dry THF (2 ml) was added DBU (45 μl, 0.306 mmol) and tert-butyl 2-cyanoacetate (34 μl, 0.235 mmol). The reaction was stirred at room temperature for 2 hours after which it was diluted with ethyl acetate. The organic layer was washed with aqueous 0.1 N HCl solution and brine, then dried over sodium sulfate, filtered, and concentrated. The residue was purified by flash column chromatography in 50% EtOAc/hexanes and then by HPLC purification (gradient 30-100% MeOH over 35 min, 10 ml min$^{-1}$ flow rate, retention time 9.34 min) to give 21.3 mg (21% yield) of tert-butyl 3-(4-amino-7-(3-hydroxypropyl)-5-p-tolyl-7H-pyrrolo[2,3-d]pyrimidin-6-yl)-2-cyanoacrylate (mixture of E/Z isomers). Chemical Formula: $C_{24}H_{27}N_5O_3$ Exact Mass 433.21. Found 434.1 [M+H]$^+$.

Example 26

3-(4-amino-7-(3-hydroxypropyl)-5-p-tolyl-7H-pyrrolo[2,3-d]pyrimidin-6-yl)-2-cyanoacrylamide

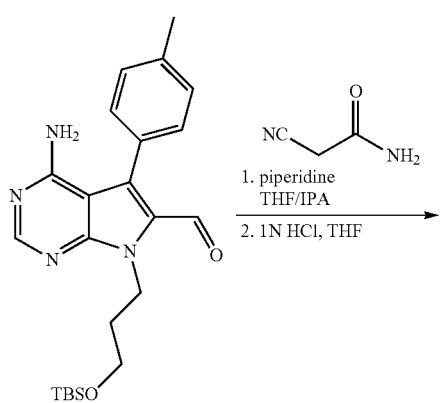

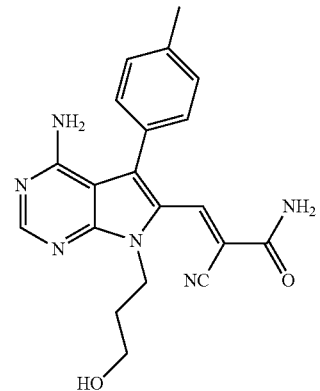

To a solution of 4-amino-7-(3-(tert-butyldimethylsilyloxy)propyl)-5-p-tolyl-7H-pyrrolo[2,3-d]pyrimidine-6-carbaldehyde (120 mg, 0.283 mmol) in dry THF (2 ml) and isopropanol (1 ml) was added piperidine (28 μl, 0.283 mmol) and 2-cyanoacetamide (23 mg, 0.283 mmol). The reaction was stirred at room temperature for 16 hours after which another equivalent of 2-cyanoacetamide and piperidine were added. After 10 days the reaction was diluted with ethyl acetate and the organic layer was washed with water and then dried over sodium sulfate, filtered and concentrated. The crude residue was dissolved in 3 ml dry THF and 1.2 ml of 1N HCl was added. The reaction was stirred for 1.5 hours, then diluted with ethyl acetate. The organic layer was washed with saturated aqueous sodium bicarbonate followed by brine and then dried over sodium sulfate, filtered, and concentrated. The residue was purified by flash column chromatography in 3-5% MeOH/DCM to give 38 mg (42% yield) of 3-(4-amino-7-(3-hydroxypropyl)-5-p-tolyl-7H-pyrrolo[2,3-d]pyrimidin-6-yl)-2-cyanoacrylamide (mixture of E/Z isomers) as a yellow powder. Exact Mass: 376.16. Found 377.4 [M+H]$^+$.

Example 27

2-Cyano-N-benzylacetamide

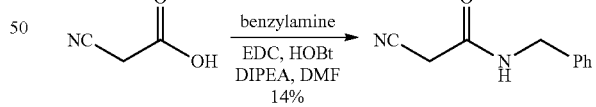

To stirred solution of diisopropylethyl amine (506 μl, 3 mmol) and benzylamine (327 μl, 3 mmol) in DMF was added cyanoacetic acid (85 mg, 1 mmol), EDC (625 mg, 3 mmol), and HOBt (208 mg, 1.5 mmol). The reaction was stirred room temperature overnight. The reaction was then diluted with ether and the organic layer was washed twice with 1N HCl and once with brine. The organic layer was dried over sodium sulfate, filtered and concentrated by rotary evaporation. The clear residue was lyophilized from benzene to give 24 mg (14% yield) of an off-white powder that needed no further purification.

Example 28

2-Cyano-N-isopropylacetamide

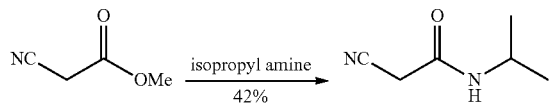

To stirred methyl cyanoacetate (2.0 g, 20 mmol) at 0° C. was added isopropylamine (1.7 ml, 20 mmol) dropwise, keeping the temperature below 10° C. The reaction was stirred at 0° C. for 1 h, after which 2 ml of 15% aqueous NaOH were added and the reaction was stirred at room temperature for 5 min. The mixture was diluted with ethyl acetate and washed with water. The organic layer was dried over sodium sulfate, filtered and concentrated to give 1.06 g (42% yield) of a white solid that needed no further purification. Ref: Basheer, A. et. al. *J. Org. Chem.* (2007), 72: 5297-5312.

Example 29

3-(4-amino-7-(3-hydroxypropyl)-5-p-tolyl-7H-pyrrolo[2,3-d]pyrimidin-6-yl)-N-benzyl-2-cyanoacrylamide

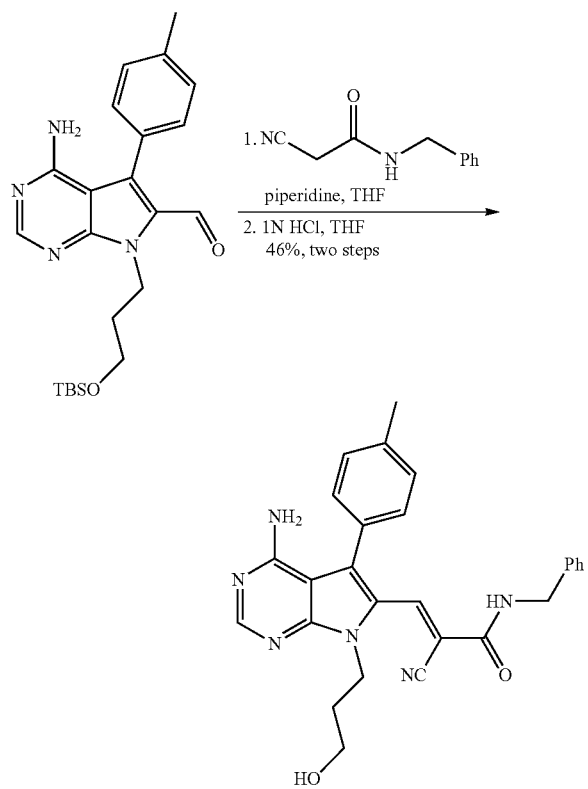

To a solution of 4-amino-7-(3-(tert-butyldimethylsilyloxy)propyl)-5-p-tolyl-7H-pyrrolo[2,3-d]pyrimidine-6-carbaldehyde (58 mg, 0.138 mmol) in dry THF (1 ml) was added piperidine (29 μl, 0.276 mmol) and N-benzyl cyanoacetamide (24 mg, 0.138 mmol). The reaction was stirred at room temperature for 2 days after which conversion had reached 50% and stopped. The reaction was concentrated and the residue was purified by flash column chromatography in 50% EtOAc/hexanes to give a yellow powder that was dissolved in THF (1 ml) and 100 μl 1 N HCl was added. The reaction was stirred at room temperature for 1 hour, diluted with ethyl acetate, and the layers were separated. The organic layer was washed with saturated aqueous sodium bicarbonate followed by brine and then dried over sodium sulfate, filtered, and concentrated. The yellow oil was purified by flash column chromatography, eluting with 100% EtOAc to 5% MeOH/EtOAc, to give a yellow residue that was lyophilized from benzene to give 9.8 mg (46% yield) of 3-(4-amino-7-(3-hydroxypropyl)-5-p-tolyl-7H-pyrrolo[2,3-d]pyrimidin-6-yl)-N-benzyl-2-cyanoacrylamide (mixture of E/Z isomers) as a yellow powder. Exact Mass: 466.21. Found: 467.5 [M+H]$^+$.

Example 30

3-(4-amino-7-(3-hydroxypropyl)-5-p-tolyl-7H-pyrrolo[2,3-d]pyrimidin-6-yl)-2-cyano-N-isopropylacrylamide

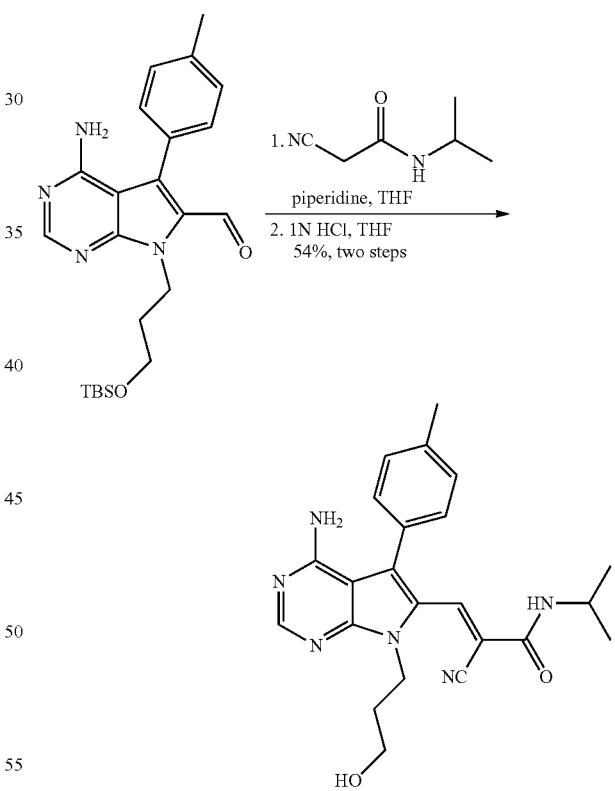

To a solution of 4-amino-7-(3-(tert-butyldimethylsilyloxy)propyl)-5-p-tolyl-7H-pyrrolo[2,3-d]pyrimidine-6-carbaldehyde (100 mg, 0.236 mmol) in dry THF (1.5 ml) was added piperidine (50 μl, 0.476 mmol) and N-isopropyl cyanoacetamide (60 mg, 0.476 mmol). The reaction was stirred at room temperature for 4 days after which conversion had reached 50%. The reaction was concentrated and the residue was purified by flash column chromatography in 50% EtOAc/hexanes to give a yellow foam that was dissolved in THF (1 ml) and 1 N HCl (100 μl). The reaction was stirred at room temperature for 1.5 hours, diluted with ethyl acetate, and the layers were separated. The organic layer was washed with saturated aqueous sodium bicarbonate followed by brine and then dried over sodium sulfate, filtered and concentrated. The yellow oil was purified by flash column chromatography, eluting with 100% EtOAc to 5% MeOH/EtOAc, to give a yellow oil that was lyophilized from benzene to give 26 mg (54% yield) of 3-(4-amino-7-(3-hydroxypropyl)-5-p-tolyl-7H-pyrrolo[2,3-d]pyrimidin-6-yl)-2-cyano-N-isopropylacrylamide (mixture of E/Z isomers) as a yellow powder. Exact Mass: 418.21. Found: 419.5 [M+H]+.

Example 31

6-bromo-5-p-tolyl-7H-pyrrolo[2,3-d]pyrimidin-4-amine

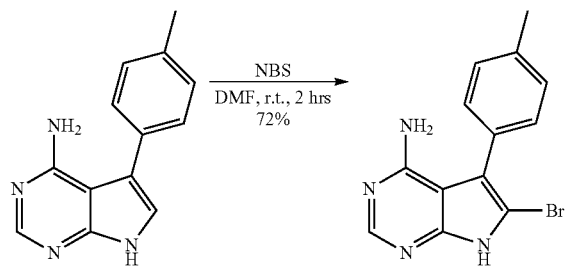

5-p-tolyl-7H-pyrrolo[2,3-c]pyrimidin-4-amine (1.5 g, 6.7 mmol) was dissolved in hot DMF and then allowed to cool to room temperature. The cloudy suspension was stirred under argon and protected from light as NBS (1.4 g, 8.04 mmol) was added in portions over 20 minutes. One hour after addition the solution went clear and a precipitate began to form. After 2 hours, the reaction was filtered and the solid was washed with DMF. The combined filtrates were concentrated and stirred in water for 10 minutes to provide a second crop of solid. The grey solids were combined to give 1.464 g (72% yield).

Example 32

5-p-tolyl-6-vinyl-7H-pyrrolo[2,3-d]pyrimidin-4-amine

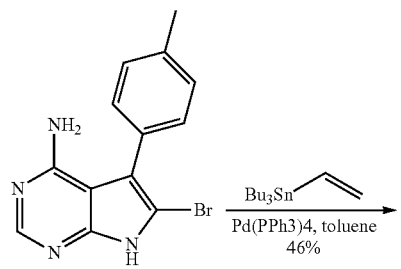

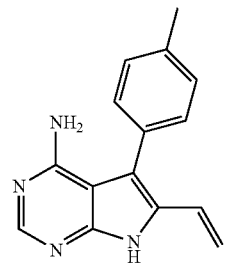

To a stirred solution of 6-bromo-5-p-tolyl-7H-pyrrolo[2,3-c]pyrimidin-4-amine (500 mg, 1.65 mmol) was added tributylvinylstannane (579 μl, 1.98 mmol) and the solution was degassed for 5 minutes. Palladium tetrakistriphenylphosphine (134 mg, 0.116 mg) was added and the reaction was brought to reflux and stirred overnight. The reaction mixture was filtered through a pad of Celite, and the solid was washed 3 times with hot toluene. The filtrate was concentrated and the residue was recrystallized from EtOAc/hexanes to give 190 mg (46% yield) of a grey solid.

Example 33

(E)-3-(4-amino-5-p-tolyl-7H-pyrrolo[2,3-d]pyrimidin-6-yl)-2-cyanoacrylamide

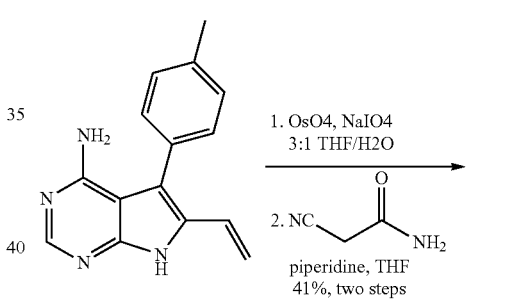

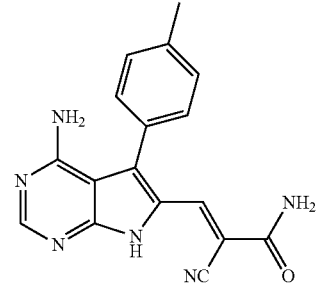

A 2.5% solution (w/v) of osmium tetroxide in tert-butanol (136 μl, 0.013 mmol) was added dropwise to a stirred solution of 5-p-tolyl-6-vinyl-7H-pyrrolo[2,3-d]pyrimidin-4-amine (190 mg, 0.68 mmol) in 3:1 THF/H₂O (5.2 ml). The suspension was stirred at room temperature for 10 minutes followed by the dropwise addition of NaIO₄ (262 mg, 1.224 mmol) suspended in 1 ml of H₂O. The reaction was then stirred at room temperature overnight. The reaction was diluted with ethyl acetate and quenched with saturated aqueous sodium thiosulfate. The organic layer was separated and the aqueous layer was extracted 3 times with ethyl acetate. The combined organic layers were concentrated to give a yellow solid that was dissolved in 2:1 isopropanol/

THF (3 ml). To this solution was added cyanoacetamide (30 mg, 0.359 mmol) and piperidine (35 μl, 0.359 mmol). The reaction was stirred at room temperature overnight during which a yellow precipitate formed. This was filtered to give 46 mg (41% yield, two steps) of 2-cyano-3-(7-p-tolyl-5H-pyrrolo[3,2-d]pyrimidin-6-yl)acrylamide. Exact Mass: 318.12. Found: 319.00 [M+H]+.

Example 34

(E)-3-(4-amino-7-(3-hydroxypropyl)-5-p-tolyl-7H-pyrrolo[2,3-d]pyrimidin-6-yl)acrylonitrile

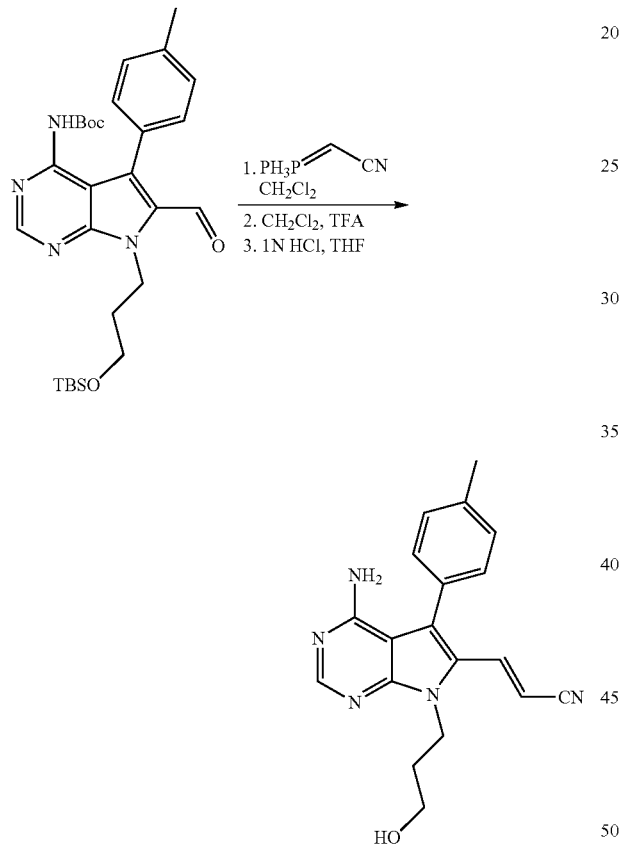

To a flame-dried flask were added tert-butyl 7-(3-(tert-butyldimethylsilyloxy)propyl)-6-formyl-5-p-tolyl-7H-pyrrolo[2,3-d]pyrimidin-4-ylcarbamate (218 mg, 0.416 mmol), (triphenylphosphoranylidene)acetonitrile (500.9 mg, 1.664 mmol) and dry CH$_2$Cl$_2$ (10 ml). The reaction was stirred under argon at room temperature for 16 hours after which the reaction was concentrated and the crude residue was purified by flash column chromatography in 25% EtOAc/hexanes to give 196 mg (87% yield) of 3-(4-amino-7-(3-hydroxypropyl)-5-p-tolyl-7H-pyrrolo[2,3-d]pyrimidin-6-yl)acrylonitrile as a mixture of isomers. 3-(4-amino-7-(3-hydroxypropyl)-5-p-tolyl-7H-pyrrolo[2,3-d]pyrimidin-6-yl)acrylonitrile (80 mg, 0.139 mmol) was dissolved in 2 ml CH$_2$Cl$_2$ and cooled to 0° C. after which 2 ml of TFA was added. The reaction was stirred at 0° C. for 1 hour and then allowed to reach room temperature. After 16 hours, the reaction was concentrated and the crude residue was dissolved in 3 ml dry THF and 1 ml of 1 N HCl was added. The reaction was stirred for 15 hours, then diluted with ethyl acetate and the organic layer was washed with saturated aqueous sodium bicarbonate, followed by brine, then dried over sodium sulfate, filtered, and concentrated. The residue was purified by flash column chromatography in 3% MeOH/DCM to give 9.1 mg (19% yield) of (E)-3-(4-amino-7-(3-hydroxypropyl)-5-p-tolyl-7H-pyrrolo[2,3-d]pyrimidin-6-yl)acrylonitrile and 24.6 mg (53% yield) of (Z)-3-(4-amino-7-(3-hydroxypropyl)-5-p-tolyl-7H-pyrrolo[2,3-d]pyrimidin-6-yl)acrylonitrile. Chemical Formula C$_{19}$H$_{19}$N$_5$O Exact Mass: 333.16. Found 334.5 [M+H]+.

Example 35

3-(1-(9H-purin-6-yl)piperidin-4-yl)-2-cyano-N-methylacrylamide

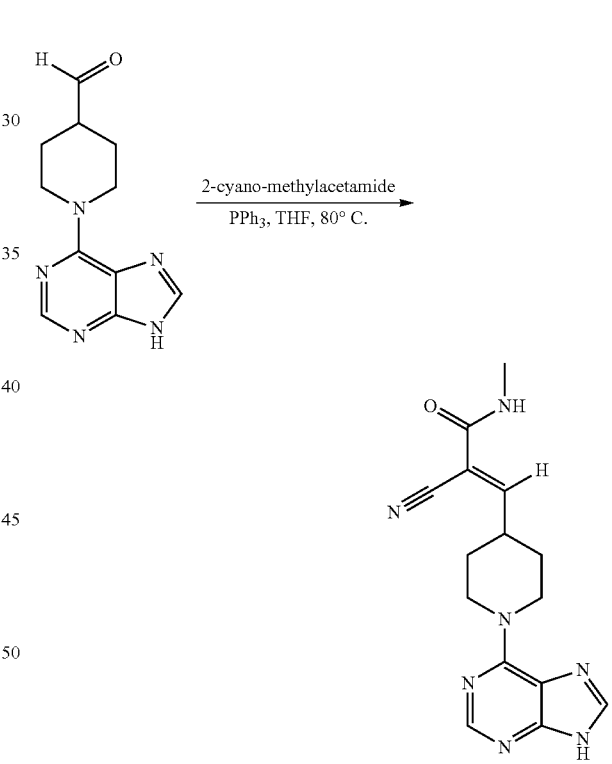

1-(9H-purin-6-yl)piperidine-4-carbaldehyde (17 mg, 0.086 mmol), 2-cyano-methylacetamide (11 mg, 0.112 mmol) and PPh$_3$ (28 mg, 0.106 mmol) were combined in THF (1 mL) and heated to 110° C. in a sealed vial. After 18 hours of heating, the reaction mixture was diluted with EtOAc (2 mL) and washed with water (1 mL). The organic layer was concentrated and submitted to preparative TLC (eluting with 9:1 CH$_2$Cl$_2$:MeOH) to afford 6 mg (23%) of 3-(1-(9H-purin-6-yl)piperidin-4-yl)-2-cyano-N-methylacrylamide as a white solid. Exact mass: 311.15, M/z found: 312.05 (M+H)+

Example 36

2-cyano-3-(1H-indazol-5-yl)-N,N-dimethylacrylamide

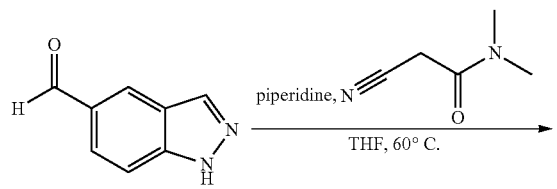

To a solution of 6-formyl-1H-indazole (101 mg, 0.7 mmol) in THF (1 mL) was added 2-cyano-N-dimethylacetamide (80 mg, 0.7 mmol) and DBU (67 μL, 0.7 mmol). The resulting brown solution was stirred at room temperature for 18 hours, followed by 4 hours at 60° C. Starting material remained, so the reaction was stirred for another 18 hours with minimal evolution of additional product. The reaction was concentrated, taken up in a small volume of EtOAc and the resulting white precipitate was collected by filtration to afford 30 mg of 2-cyano-3-(1H-indazol-5-yl)-N,N-dimethylacrylamide (19%) as a white solid. Exact mass: 240.10, M/z found: 241.09 (M+H)$^+$.

Example 37

3-(3-(1H-pyrrolo[2,3-b]pyridine-3-carbonyl)phenyl)-2-cyano-N-methylacrylamide

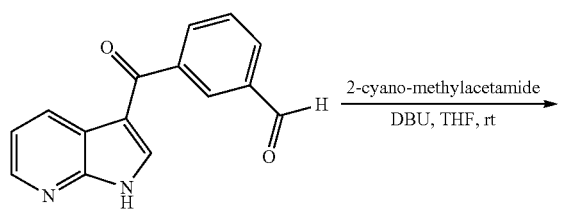

To a solution of 3-(1H-pyrrolo[2,3-b]pyridine-3-carbonyl)benzaldehyde (47 mg, 0.2 mmol) in THF (1 mL) was added 2-cyanoacetamide (19 mg, 0.2 mmol) and DBU (20 μL, 0.2 mmol) and the slurry was stirred at room temperature for five minutes. A few drops of MeOH were added to the reaction to keep a gummy precipitate from sticking to the walls, and the reaction was stirred overnight with evolution of a yellowish precipitate. The precipitate was collected by filtration to afford 8 mg (12%) of 3-(3-(1H-pyrrolo[2,3-b]pyridine-3-carbonyl)phenyl)-2-cyano-N-methylacrylamide as a white solid. Exact mass: 330.11, M/z found: 331.05 (M+H)$^+$.

Example 38

3-(3-(1H-pyrrolo[2,3-b]pyridine-3-carbonyl)phenyl)-2-cyano-N,N-dimethylacrylamide

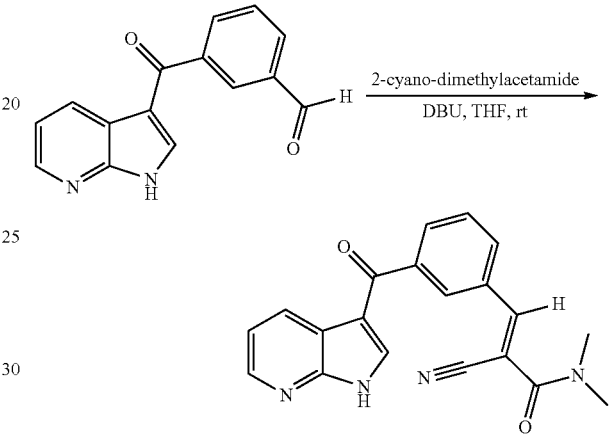

To a solution of 3-(1H-pyrrolo[2,3-b]pyridine-3-carbonyl)benzaldehyde (47 mg, 0.2 mmol) in THF (1 mL) was added 2-cyanoacetamide (19 mg, 0.2 mmol) and DBU (20 μL, 0.2 mmol) and the slurry was stirred at room temperature for several hours, at which point the brown slurry became a clear yellow solution. The following day, the reaction was concentrated to a brown, waxy solid, resuspended in EtOAc:MeOH (2:1), and the resultant precipitate was collected by filtration to afford 12 mg (17%) of 3-(3-(1H-pyrrolo[2,3-b]pyridine-3-carbonyl)phenyl)-2-cyano-N,N-dimethylacrylamide as a white solid. Exact mass: 344.13, M/z found: 345.09 (M+H)$^+$.

Example 39

3-(3,4,5-trimethoxyphenyl)-1H-indazole-5-carbaldehyde

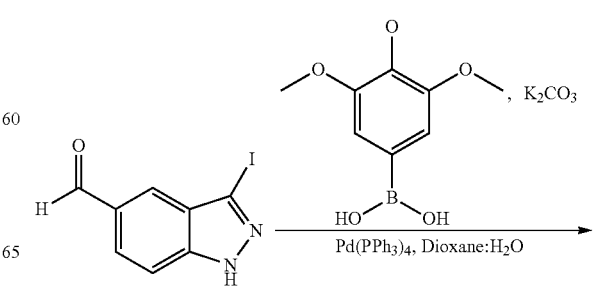

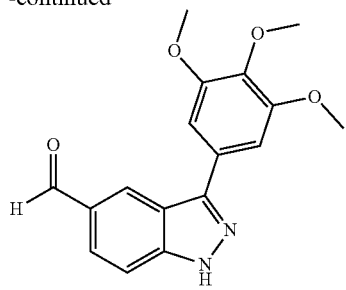

3-iodo-5-formylindazole (210 mg, 0.735 mmol), trimethoxyphenyl boronic acid (187 mg, 0.882 mmol) and K$_2$CO$_3$ (309 mg, 2.21 mmol) were combined in 5:1 Dioxane:H$_2$O (2 mL) and degassed with bubbling argon for 20 minutes. Pd(PPh$_3$)$_4$ (123 mg, 0.106 mmol) was added, and the reaction vessel purged with argon. The reaction was microwaved at 150° C. for fifteen minutes. The crude reaction mixture was diluted with EtOAc (20 mL), washed with 1M HCl (10 mL), H$_2$O (10 mL) and brine (10 mL), dried with Na$_2$SO$_4$, and concentrated. The residue was purified on silica, eluting with 3:2 Hex:EtOAc, and the impure fractions containing product were concentrated to a yellow solid. This yellow solid was suspended in EtOAc and the white solids filtered to afford 140 mg (83%) of 3-(3,4,5-trimethoxyphenyl)-1H-indazole-5-carbaldehyde as a white solid.

Example 40

2-cyano-3-(3-(3,4,5-trimethoxyphenyl)-1H-indazol-5-yl)acrylamide

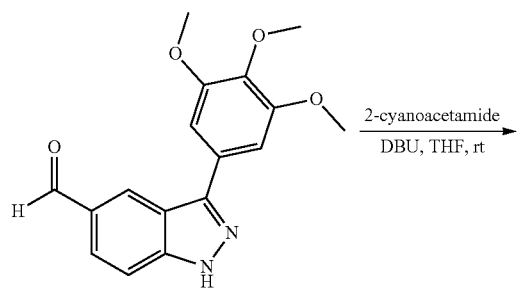

To a solution of 3-(3,4,5-trimethoxyphenyl)-1H-indazole-5-carbaldehyde (52.0 mg, 0.16 mmol) and 2-cyanoacetamide (13.2 mg, 0.16 mmol) in THF (1 mL) was added DBU (16 mL, 0.16 mmol). The colorless solution became bright yellow upon addition of DBU, and slowly turned bright red over the course of 15 minutes. After four hours, the reaction mixture was taken up in EtOAc (10 mL), and washed with 1M HCl (10 mL), NaHCO$_3$ (10 mL) and brine (10 mL). The organic layer was concentrated and purified by preparative TLC, eluting with 9:1 CH$_2$Cl$_2$:MeOH, to afford 5.3 mg (9%) of 2-cyano-3-(3-(3,4,5-trimethoxyphenyl)-1H-indazol-5-yl)acrylamide as a bright yellow solid. Exact mass: 378.13, M/z found: 379.03 (M+H)$^+$.

Example 41

2-cyano-N-methyl-3-(3-(3,4,5-trimethoxyphenyl)-1H-indazol-5-yl)acrylamide

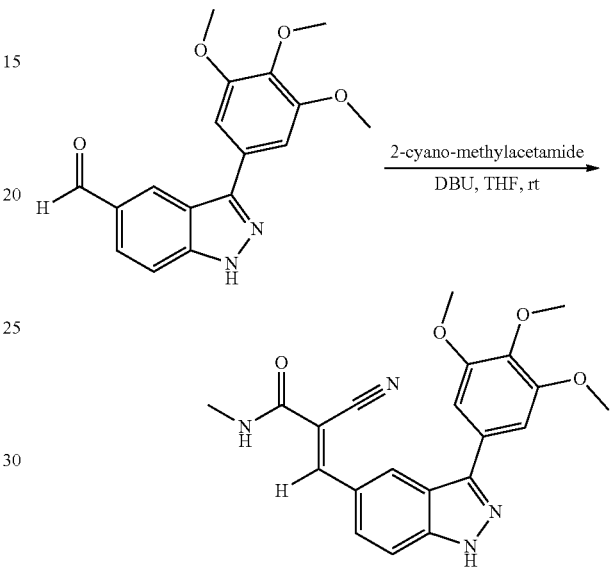

To a solution of 3-(3,4,5-trimethoxyphenyl)-1H-indazole-5-carbaldehyde (30 mg, 0.100 mmol) and 2-cyano-N-methylacetamide (9.6 mg, 0.100 mmol) in THF (1 mL) was added DBU (10 mL, 0.10 mmol). The colorless solution became bright yellow upon addition of DBU, and slowly turned bright red over the course of 15 minutes. After four hours, the reaction mixture was taken up in EtOAc (10 mL), and washed with 1M HCl (10 mL), NaHCO$_3$ (10 mL) and brine (10 mL). The organic layer was concentrated and purified by preparative TLC, eluting with 9:1 CH$_2$Cl$_2$:MeOH, to afford 17 mg (43%) of 2-cyano-N-methyl-3-(3-(3,4,5-trimethoxyphenyl)-1H-indazol-5-yl)acrylamide as a bright yellow solid. Exact mass: 392.15, M/z found: 393.07 (M+H)$^+$.

Example 42

2-cyano-N,N-dimethyl-3-(3-(3,4,5-trimethoxyphenyl)-1H-indazol-5-yl)acrylamide

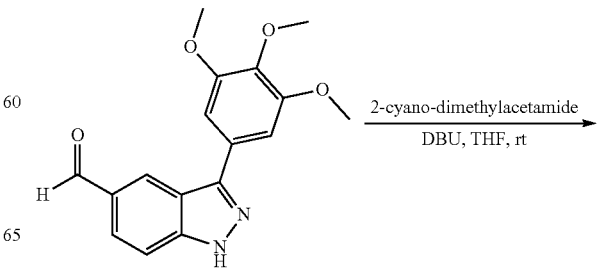

-continued

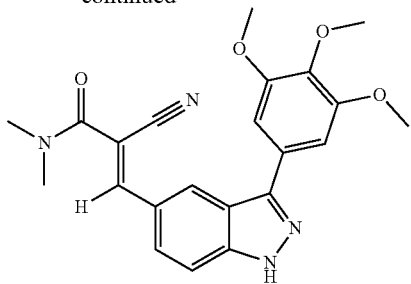

To a solution of 3-(3,4,5-trimethoxyphenyl)-1H-indazole-5-carbaldehyde (50 mg, 0.16 mmol) and 2-cyano-N-methylacetamide (17.6 mg, 0.16 mmol) in THF (1 mL) was added DBU (16 mL, 0.16 mmol). The colorless solution became bright yellow upon addition of DBU, and slowly turned bright red over the course of 15 minutes. After four hours, the reaction mixture was taken up in EtOAc (10 mL), and washed with 1M HCl (10 mL), NaHCO$_3$ (10 mL) and brine (10 mL). The organic layer was concentrated and purified by preparative TLC, eluting with 9:1 CH$_2$Cl$_2$:MeOH, to afford 17 mg (26%) of 2-cyano-N,N-dimethyl-3-(3-(3,4,5-trimethoxyphenyl)-1H-indazol-5-yl)acrylamide as a bright yellow solid. Exact mass: 406.16, M/z found: 407.05 (M+H)$^+$.

Example 43

4-Amino-7-(3-hydroxypropyl)-5-p-tolyl-7H-pyrrolo[2,3-d]pyrimidine-6-carbaldehyde

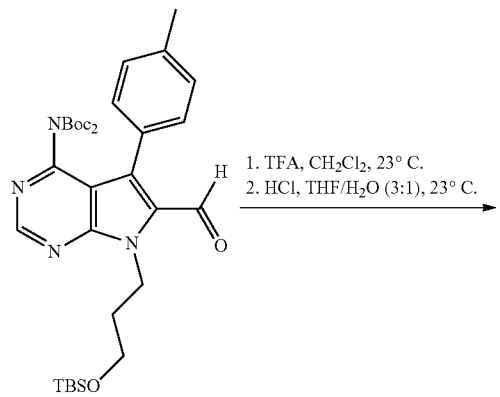

To a solution of 4-Di-tert-butyloxycarbonylamino-7-(3-tert-butyldimethylsiloxypropyl)-5-p-tolyl-7H-pyrrolo[2,3-d]pyrimidine-6-carbaldehyde (1.43 g, 2.28 mmol) in dichloromethane (12 mL) was added TFA (5 mL). The reaction mixture was maintained at ambient temperature for 12 hours, then concentrated under reduced pressure. The residue was redissolved in THF (12 mL), and 1M aq. HCl (4 mL) was added. The reaction mixture was stirred at ambient temperature for 24 hours and then diluted with EtOAc (50 mL) and satd. aq. NaHCO$_3$ (50 mL). The phases were separated and the aqueous phase was extracted with EtOAc (50 mL). The combined organic extracts were washed with brine (50 mL), then concentrated under reduced pressure. The residue was azeotroped with benzene (50 mL) and dried in vacuo to afford 0.99 g of the deprotected aldehyde (wet), which was used without further purification.

Example 44

Azetidine (X=H), and 3-hydroxyazetidine (X=OH) cyanoacetamides

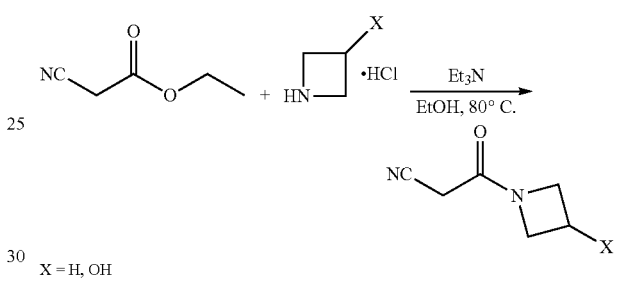

X = H, OH

Ethylcyanoacetate (1.0 equiv.), azetidine (X=H), or 3-hydroxyazetidine (X=OH) hydrochloride (1.1 equiv.) and triethylamine (1.5 equiv.) in EtOH (6 mL) were heated at 80° C. for 6 hours. The reaction mixture was concentrated and the residue was partitioned between EtOAc (25 mL) and DI water (25 mL). The aqueous phase was extracted with EtOAc (2×30 mL). The combined organic extracts were dried (Na$_2$SO$_4$) and concentrated to afford a residue, which was purified by silica gel chromatography (4:1 EtOAc/Hexanes for X=H; 16:1 EtOAc/MeOH for X=OH) to afford the desired cyanoacetamide. Ethylcyanoacetate (550 mg, 4.86 mmol) and azetidine hydrochloride (500 mg) afforded 196.5 mg (33% yield) of azetidine cyanoacetamide. Ethylcyanoacetate (469.4 mg, 4.15 mmol) and 3-hydroxyazetidine hydrochloride (500 mg) afforded 89 mg (15% yield) of azetidine cyanoacetamide.

Example 45

Synthesis of Cyanoacrylamides

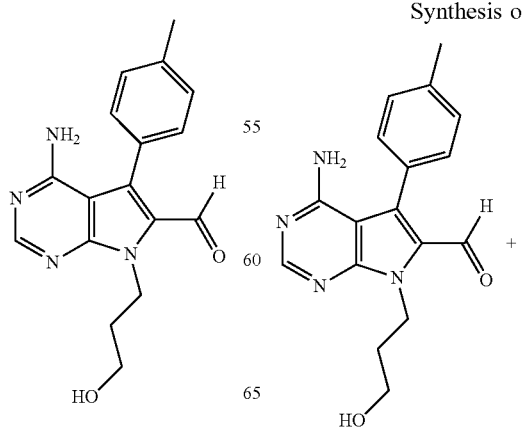

-continued

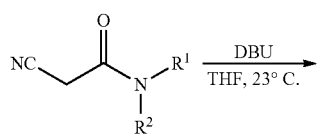

General Procedure for Synthesis of Cyanoacrylamide Derivatives:

4-Amino-7-(3-hydroxypropyl)-5-p-tolyl-7H-pyrrolo[2,3-d]pyrimidine-6-carbaldehyde (1.0 equiv.), the appropriate cyanoacetamide (1.2-1.5 equiv.) and DBU (1.5-2.0 equiv.) were stirred in THF (2 mL) at ambient temperature for 1-3 days. The reaction mixture was then concentrated and purified by preparative TLC to afford the cyanoacrylamide as a mixture of (E)- and (Z)-isomers.

Example 45a 3-(4-amino-7-(3-hydroxypropyl)-5-p-tolyl-7H-pyrrolo[2,3-d]pyrimidin-6-yl)-2-cyano-N,N-dimethylacrylamide

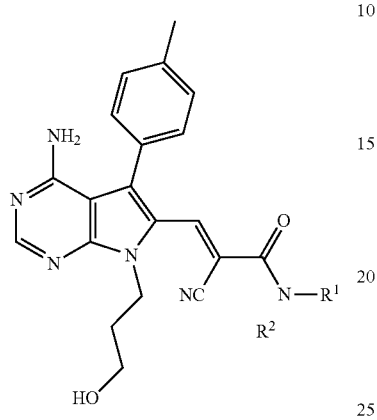

Compound prepared from N,N-dimethylcyanoacetamide. See Basheer, A.; Yamataka, H.; Ammal, S. C.; Rappoport, Z. J. Org. Chem. 2007, 72, 5297-5312. Yield: 33.8 mg (24%, E:Z=1.7:1). ESI-MS: 405.2 (MH+)

Example 45b 3-(4-amino-7-(3-hydroxypropyl)-5-p-tolyl-7H-pyrrolo[2,3-d]pyrimidin-6-yl)-2-cyano-N-(1-hydroxy-2-methylpropan-2-yl)acrylamide

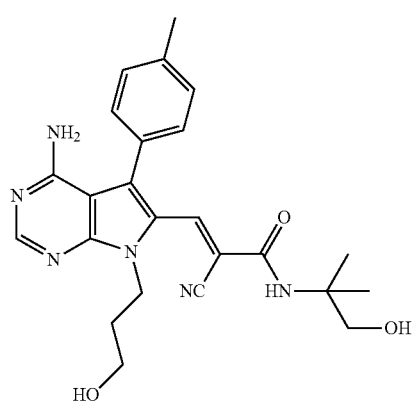

Compound Prepared from 2-cyano-N-(1-hydroxy-2-methylpropan-2-yl)acetamide. See Santilli, A. A.; Osdene, T. S. J. Org. Chem. 1964, 29, 2066-2068. Yield: 17.2 mg (39%), ESI-MS: 449.2 (MH+)

Example 45c 3-(4-amino-7-(3-hydroxypropyl)-5-p-tolyl-7H-pyrrolo[2,3-d]pyrimidin-6-yl)-2-cyano-N,N-diethylacrylamide

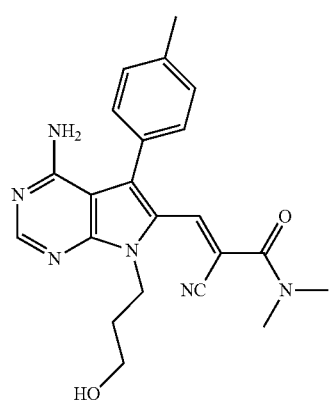 [SMILES: Cc1ccc(-c2c(/C=C(\C#N)C(=O)N(C)C)n(CCCO)c3ncnc(N)c23)cc1]

Compound prepared from N,N-diethylcyanoacetamide. See Wang, K.; Nguyen, K.; Huang, Y.; Domling, A. J. Comb. Chem. 2009, 11, 920-927. Yield: 9.2 mg (8%), ESI-MS: 433.2 (MH+)

Example 45d 3-(4-amino-7-(3-hydroxypropyl)-5-p-tolyl-7H-pyrrolo[2,3-d]pyrimidin-6-yl)-2-(pyrrolidine-1-carbonyl)acrylonitrile

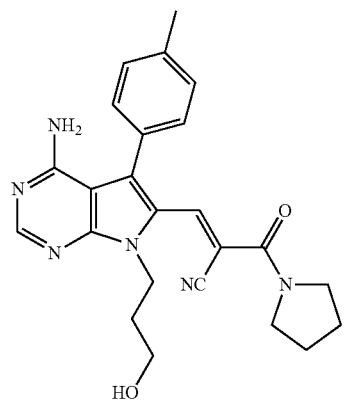 [SMILES: Cc1ccc(-c2c(/C=C(\C#N)C(=O)N3CCCC3)n(CCCO)c3ncnc(N)c23)cc1]

Compound Prepared from N-(2-cyanoacetyl)pyrrolidine. See Wang et al., Id. Yield: 1.6 mg (3%), ESI-MS: 431.2 (MH+)

Example 45e 3-(4-amino-7-(3-hydroxypropyl)-5-p-tolyl-7H-pyrrolo[2,3-d]pyrimidin-6-yl)-2-(azetidine-1-carbonyl)acrylonitrile

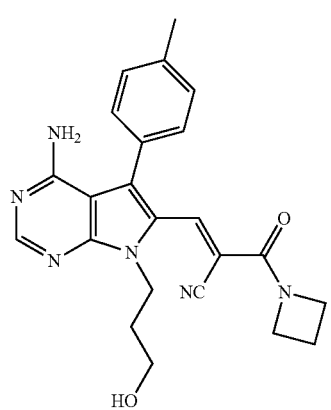 [SMILES: Cc1ccc(-c2c(/C=C(\C#N)C(=O)N3CCC3)n(CCCO)c3ncnc(N)c23)cc1]

Yield: 16.5 mg (32%), ESI-MS: 417.2 (MH+).

Example 45f 3-(4-amino-7-(3-hydroxypropyl)-5-p-tolyl-7H-pyrrolo[2,3-d]pyrimidin-6-yl)-2-(3-hydroxyazetidine-1-carbonyl)acrylonitrile

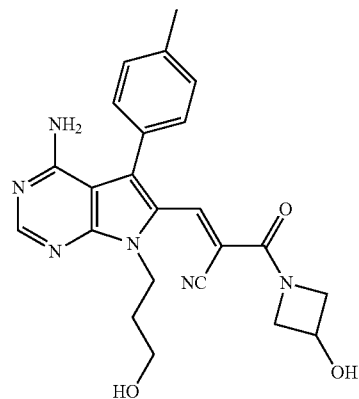 [SMILES: Cc1ccc(-c2c(/C=C(\C#N)C(=O)N3CC(O)C3)n(CCCO)c3ncnc(N)c23)cc1]

Yield: 20.1 mg (38%), ESI-MS: 433.2 (MH+).

Example 45g (E)-3-(4-amino-7-(3-hydroxypropyl)-5-p-tolyl-7H-pyrrolo[2,3-d]pyrimidin-6-yl)-2-(4-methylpiperazine-1-carbonyl)acrylonitrile

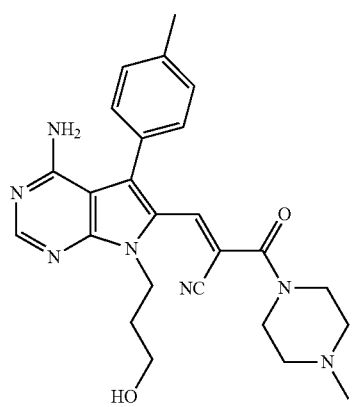 [SMILES: Cc1ccc(-c2c(/C=C(\C#N)C(=O)N3CCN(C)CC3)n(CCCO)c3ncnc(N)c23)cc1]

Compound prepared from N-(2-cyanoacetyl)-N'-methylpiperazine. See Proenca, F.; Costa, M. *Green Chem.* 2008, 10, 995-998. Yield: 15.7 mg (25%), ESI-MS: 460.2 (MH+)

Example 46

3-(4-amino-7-(3-hydroxypropyl)-5-p-tolyl-7H-pyrrolo[2,3-d]pyrimidin-6-yl)-2-cyano-N-cyclopropylacrylamide

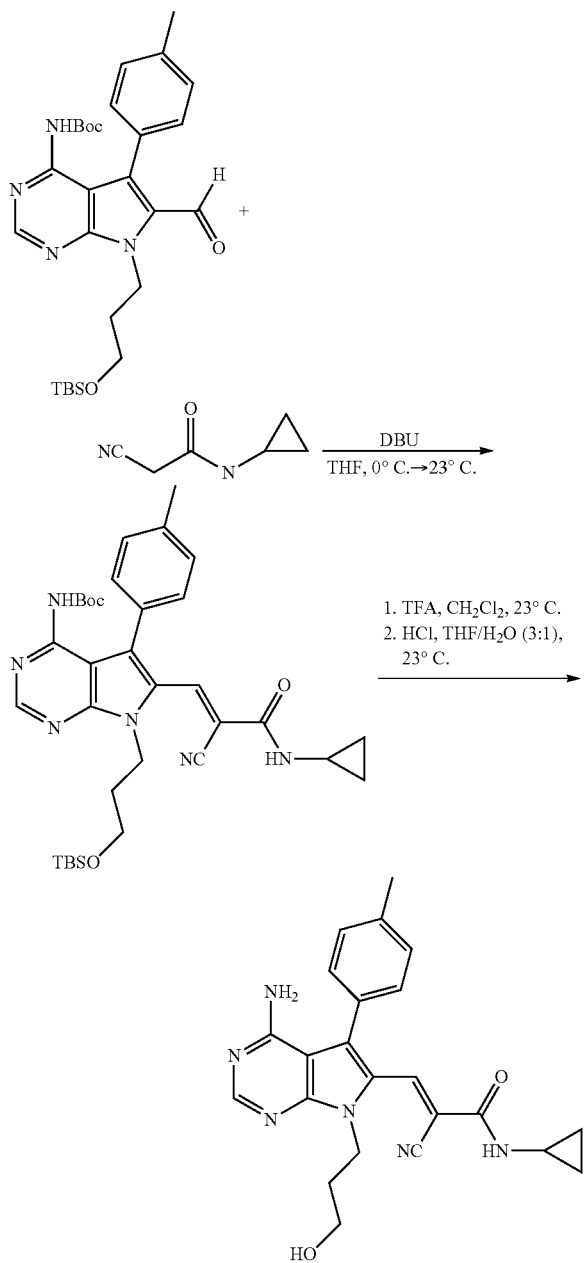

To a solution of 4-tert-butyloxycarbonylamino-7-(3-tert-butyldimethylsiloxypropyl)-5-p-tolyl-7H-pyrrolo[2,3-d]pyrimidine-6-carbaldehyde (101 mg, 0.1925 mmol) and N-cyclopropylcyanoacetamide3 (47.8 mg, 2.0 equiv.) in THF (2.2 mL) that had been pre-cooled to 0-5° C. was added DBU (58 µL, 2.0 equiv.). The reaction mixture was allowed to warm to ambient temperature and stirred for 1 hour, then maintained at −20° C. for 12 hours. The reaction mixture was concentrated and purified by silica gel chromatography (2:1 Hexanes/EtOAc) to afford 53.2 mg (E:Z=2:1, 44% yield) of the intermediate protected cyanoacrylamide as a yellow oil. This oil was dissolved in CH$_2$Cl$_2$ (3 mL) and TFA (1.5 mL) was added. After 16 hours at 20-25° C., the reaction mixture was concentrated and the residue was redissolved in THF (6 mL) and 1M aq. HCl (2 mL) was added. The reaction mixture was maintained at ambient temperature for 8 hours, then quenched with satd. aq. NaHCO3 (20 mL) and brine (30 mL) and extracted with EtOAc (3×50 mL). The combined EtOAc extracts were dried (MgSO4) and concentrated and the oil afforded was purified by preparative TLC (3:1 Toluene/IPA, 0.5 cm plate, 2 elutions) to afford the cyanoacrylamide (26 mg, 74% yield over 2 steps) as a yellow oil.

Example 47

1-(4-chlorophenyl)-2-(3-(hydroxymethyl)phenylamino)ethanone

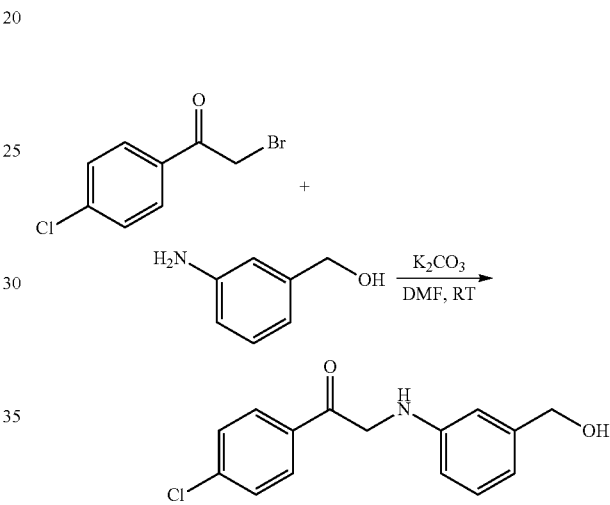

A 100 mL round-bottom flask fitted with a magnetic stir bar was charged with 3-aminobenzyl alcohol (1.58 g, 12.85 mmol), potassium carbonate (3.05 g, 22.1 mmol), and N,N'-dimethylformamide (10 mL). The slurry was stirred while adding 2-bromo-4'-chloroacetophenone (2.85 g, 12.2 mmol) portionwise. The mixture was stirred at room temperature for 2 h. The reaction was diluted with water (80 mL) and the resulting precipitate was collected by filtration, washed with water, and dried in vacuo, providing the product (2.89 g, 86% yield).

Example 48

2-amino-4-(4-chlorophenyl)-1-(3-(hydroxymethyl)phenyl)-1H-pyrrole-3-carbonitrile

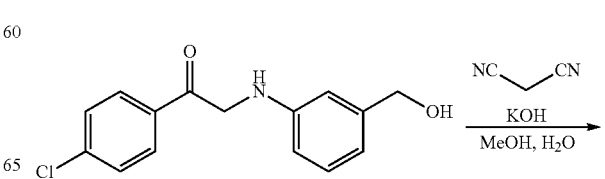

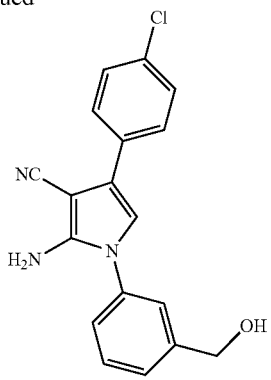

A 250 mL round-bottom flask fitted with a magnetic stir bar was charged with 1-(4-chlorophenyl)-2-(3-(hydroxymethyl)phenylamino)ethanone (2.88 g, 10.4 mmol), potassium hydroxide (85%) (1.8 g, 27 mmol), malononitrile (1.32 g, 20 mmol), water (5 mL), and methanol (50 mL). The mixture was refluxed for 1.5 h, during which time a precipitate formed. The mixture was diluted with water (50 mL) and the precipitate was collected by filtration, washed with water, and dried in vacuo, providing the product (1.68 g, 50% yield).

Example 49

(3-(4-amino-5-(4-chlorophenyl)-7H-pyrrolo[2,3-d]pyrimidin-7-yl)phenyl)methanol

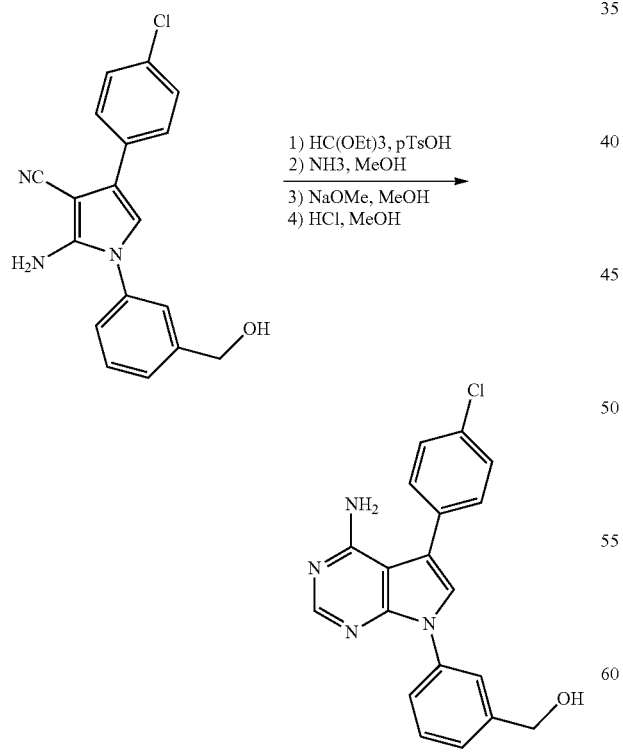

A 250 mL round-bottom flask fitted with a magnetic stir bar was charged with 2-amino-4-(4-chlorophenyl)-1-(3-(hydroxymethyl)phenyl)-1H-pyrrole-3-carbonitrile (1.60 g, 4.9 mmol), triethyl orthoformate (5 mL), and p-toluenesulfonic acid monohydrate (5 mg). The solution was heated to 100° C. for 45 min. Excess triethyl orthoformate was removed under reduced pressure and the resulting oil was dried briefly in vacuo. To the resulting solid was added ammonia (7 M in methanol, 20 mL) and the flask was tightly capped. The solution was stirred at room temperature for 3 h. The solution was concentrated under reduced pressure and redissolved in methanol (10 mL). The solution was heated to 80° C. and sodium methoxide (25% w/v in methanol, 1 mL) was added dropwise. The mixture was refluxed for 2 h, cooled to room temperature and quenched by the addition of water. The solution was extracted with ethyl acetate (3×50 mL). The organic layer was dried over sodium sulfate, filtered, and concentrated under reduced pressure. The resulting oil was purified by Si-gel chromatography (elute 1:1 EtOAc/Hex to 100% EtOAc). Intermediate product containing fractions were combined and concentrated under reduced pressure. The resulting red-brown oil was dissolved in methanol (50 mL) and hydrochloric acid, 1M (50 mL) was added. The solution was stirred at room temperature for 1 h. The solution was partitioned between ethyl acetate and water and extracted with ethyl acetate. The organic layer was dried over sodium sulfate, filtered, and concentrated under reduced pressure to yield the product as a light yellow solid.

Example 50

3-(4-amino-5-(4-chlorophenyl)-7H-pyrrolo[2,3-d]pyrimidin-7-yl)benzaldehyde

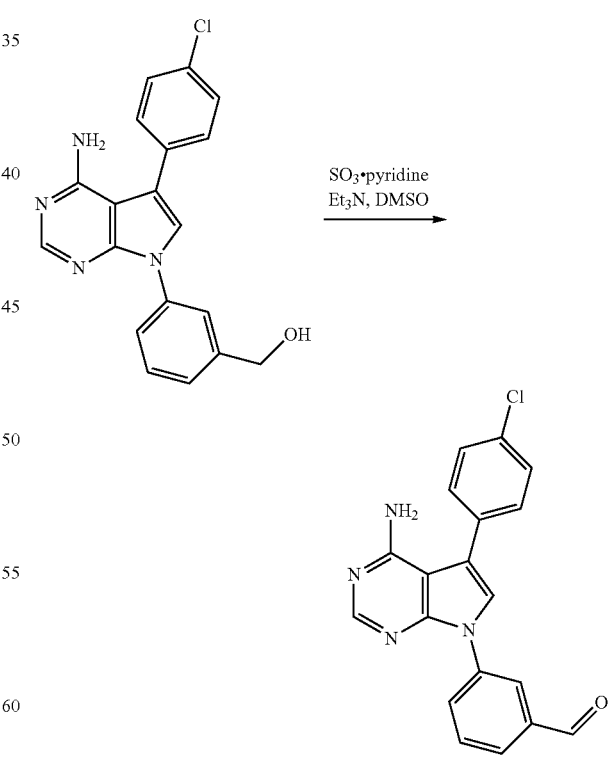

A 20 mL vial fitted with a magnetic stir bar was charged with (3-(4-amino-5-(4-chlorophenyl)-7H-pyrrolo[2,3-d]pyrimidin-7-yl)phenyl)methanol (145 mg, 0.4 mmol), triethylamine (0.4 mL, 2.8 mmol), and dimethyl sulfoxide (2 mL).

A solution of sulfur trioxide.pyridine (200 mg, 1.3 mmol) in DMSO (1.2 mL) was added to the vial and the resulting solution was stirred for 1 h at room temperature. Hydrochloric acid (1 M, 10 mL) was added and the solution stirred for an additional 10 minutes. The resulting precipitate was collected by filtration, washed with water, and dried in vacuo, providing the product as a white solid (162 mg, >99% yield).

Example 51

(E)-3-(3-(4-amino-5-(4-chlorophenyl)-7H-pyrrolo[2,3-d]pyrimidin-7-yl)phenyl)-2-cyanoacrylamide

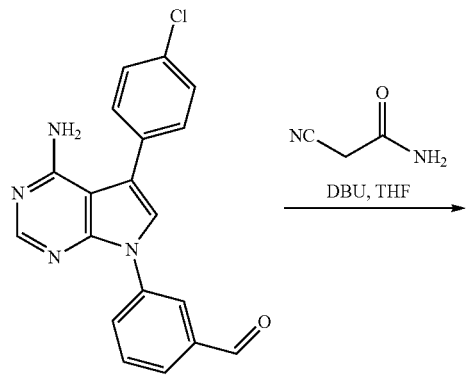

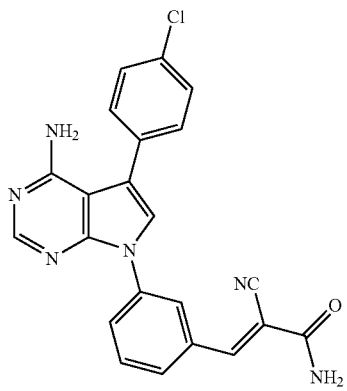

A 20 mL vial fitted with a magnetic stir bar was charged with 3-(4-amino-5-(4-chlorophenyl)-7H-pyrrolo[2,3-d]pyrimidin-7-yl)benzaldehyde (13 mg, 0.04 mmol), 2-cyanoacetamide (4 mg, 0.05 mmol), 1,8-diazabicyclo[5.4.0]undec-7-ene (5 mg, 0.03 mmol), and tetrahydrofuran (1 mL). The reaction mixture was heated to 50° C. for 24 h. Starting material remained as determined by thin layer chromatography, so piperidinium acetate (5 mg, 0.03 mmol) and 2-propanol (0.5 mL) were added and the solution was heated to 60° C. for an additional 24 h. The resulting solution was partitioned between dilute NaHCO$_3$ and EtOAc. The solution was extracted with EtOAc, and the organic layer was dried over sodium sulfate, filtered, and concentrated under reduced pressure. The resulting residue was purified by Si-gel chromatography (elute 3:1 EtOAc/Hex to 100% EtOAc) to yield the product as a white solid (2 mg, 13% yield). Exact Mass: 414.10. M/z found: 415.1 (M+H)$^+$ Example 52

(E)-3-(3-(4-amino-5-(4-chlorophenyl)-7H-pyrrolo[2,3-d]pyrimidin-7-yl)phenyl)-2-cyano-N,N-dimethylacrylamide

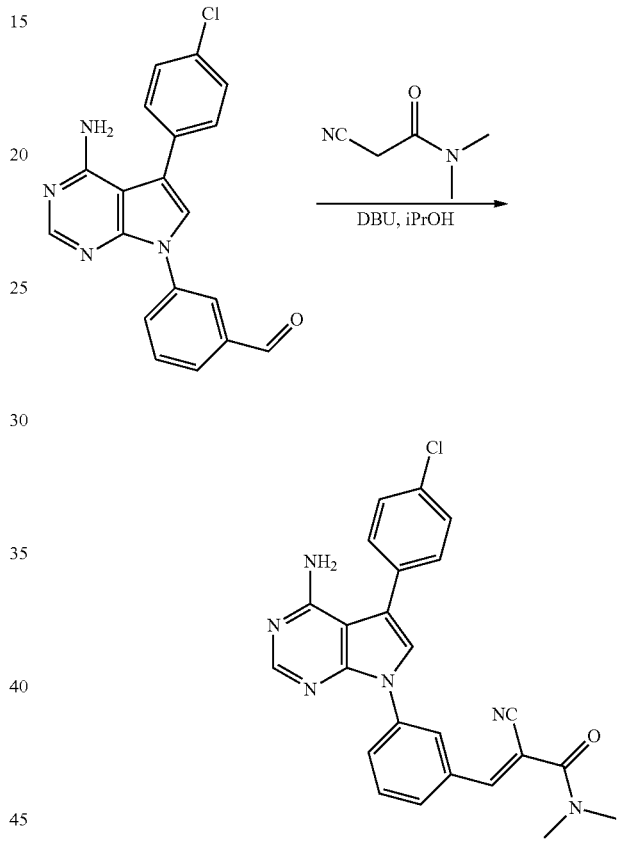

A 20 mL vial fitted with a magnetic stir bar was charged with 3-(4-amino-5-(4-chlorophenyl)-7H-pyrrolo[2,3-d]pyrimidin-7-yl)benzaldehyde (35 mg, 0.10 mmol), N,N'-dimethyl-2-cyanoacetamide (12 mg, 0.11 mmol), 1,8-diazabicyclo[5.4.0]undec-7-ene (5 mg, 0.03 mmol), and 2-propanol (1 mL). The reaction mixture was heated to 60° C. for 24 h. Only starting material was present as determined by thin layer chromatography, so the solution was heated to 80° C. for an additional 24 h. The solution was concentrated under reduced pressure and the resulting residue was redissolved in DMSO (0.8 mL) and the product was purified by RP-HPLC (gradient: 20-95% MeCN/water with 0.1% TFA over 25 min, retention time ~6.8 min). Product containing fractions were combined and the solvent removed under reduced pressure and the resulting solid was purified by Si-gel chromatography (elute with EtOAc). Collect the product as a white solid (6.1 mg, 14% yield). Exact Mass: 442.13. M/z found: 443.0 (M+H)$^+$.

Example 53

(E)-3-(3-(4-amino-5-(4-chlorophenyl)-7H-pyrrolo[2,3-d]pyrimidin-7-yl)phenyl)-2-(azetidine-1-carbonyl)acrylonitrile

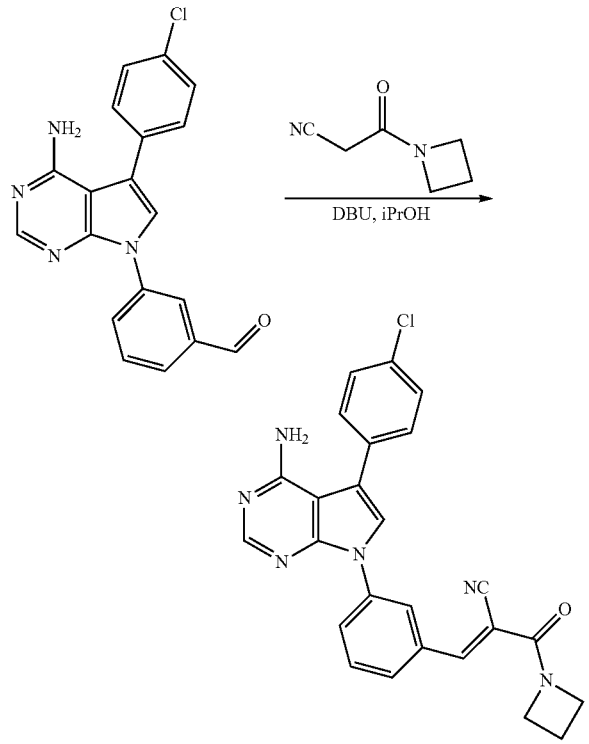

A 20 mL vial fitted with a magnetic stir bar was charged with 3-(4-amino-5-(4-chlorophenyl)-7H-pyrrolo[2,3-d]pyrimidin-7-yl)benzaldehyde (15 mg, 0.04 mmol), 3-(azetidin-1-yl)-3-oxopropanenitrile (12 mg, 0.1 mmol), 1,8-diazabicyclo[5.4.0]undec-7-ene (5 mg, 0.03 mmol), and 2-propanol (1 mL). The reaction mixture was heated to 60° C. for 24 h. The solution was concentrated under reduced pressure and the resulting residue was purified by Si-gel chromatography (elute 100% EtOAc to 10% MeOH/EtOAc). Collect the product as a white solid (16 mg, 82% yield). Exact Mass: 454.13. M/z found: 455.0 (M+H)$^+$.

Example 54

(E)-3-(3-(4-amino-5-(4-chlorophenyl)-7H-pyrrolo[2,3-d]pyrimidin-7-yl)phenyl)-2-(pyrrolidine-1-carbonyl)acrylonitrile

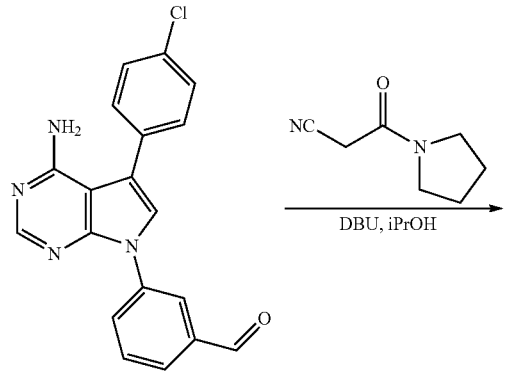

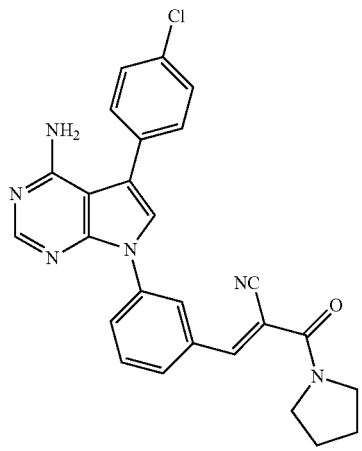

A 20 mL vial fitted with a magnetic stir bar was charged with 3-(4-amino-5-(4-chlorophenyl)-7H-pyrrolo[2,3-d]pyrimidin-7-yl)benzaldehyde (15 mg, 0.04 mmol), 3-oxo-3-(pyrrolidin-1-yl)propanenitrile (14 mg, 0.1 mmol), 1,8-diazabicyclo[5.4.0]undec-7-ene (5 mg, 0.03 mmol), and 2-propanol (1 mL). The reaction mixture was heated to 60° C. for 24 h. The solution was concentrated under reduced pressure and the resulting residue was purified by Si-gel chromatography (elute 100% EtOAc to 10% MeOH/EtOAc). Collect the product as a white solid (12 mg, 59% yield). Exact Mass: 468.15. M/z found: 469.1 (M+H)$^+$.

Example 55

(E)-3-(3-(4-amino-5-(4-chlorophenyl)-7H-pyrrolo[2,3-d]pyrimidin-7-yl)phenyl)-2-(3-hydroxyazetidine-1-carbonyl)acrylonitrile

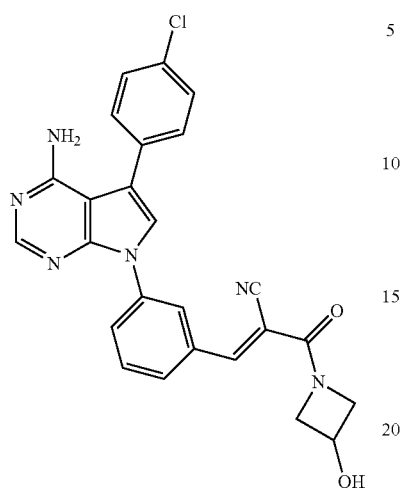

A 20 mL vial fitted with a magnetic stir bar was charged with 3-(4-amino-5-(4-chlorophenyl)-7H-pyrrolo[2,3-d]pyrimidin-7-yl)benzaldehyde (15 mg, 0.04 mmol), 3-(3-hydroxyazetidin-1-yl)-3-oxopropanenitrile (14 mg, 0.1 mmol), 1,8-diazabicyclo[5.4.0]undec-7-ene (5 mg, 0.03 mmol), and 2-propanol (1 mL). The reaction mixture was heated to 60° C. for 24 h. The solution was concentrated under reduced pressure and the resulting residue was purified by Si-gel chromatography (elute 100% EtOAc to 10% MeOH/EtOAc). The product was collected as a white solid (13 mg, 64% yield). Exact Mass: 470.13. M/z found: 471.0 (M+H)$^+$.

Example 56

(E)-3-(3-(4-amino-5-(4-chlorophenyl)-7H-pyrrolo[2,3-d]pyrimidin-7-yl)phenyl)-2-(4-methylpiperazine-1-carbonyl)acrylonitrile

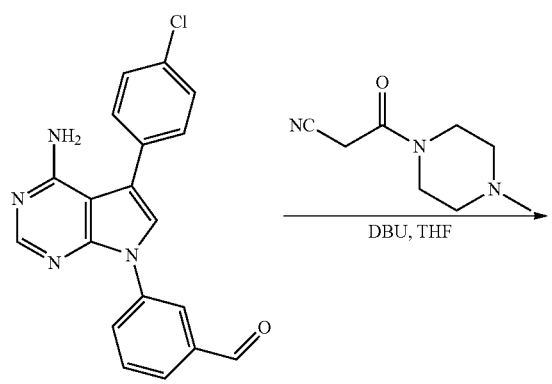

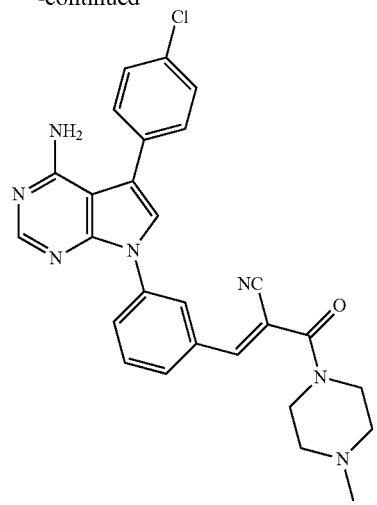

A 20 mL vial fitted with a magnetic stir bar was charged with 3-(4-amino-5-(4-chlorophenyl)-7H-pyrrolo[2,3-d]pyrimidin-7-yl)benzaldehyde (16 mg, 0.05 mmol), 3-(4-methylpiperazin-1-yl)-3-oxopropanenitrile (17 mg, 0.11 mmol), 1,8-diazabicyclo[5.4.0]undec-7-ene (5 mg, 0.03 mmol), and 2-propanol (1 mL). The reaction mixture was heated to 60° C. for 24 h. Only starting material was present as determined by thin layer chromatography, so the solution was heated to 70° C. for an additional 24 h. The solution was concentrated under reduced pressure and the resulting residue was redissolved in DMSO (0.8 mL) and the product was purified by RP-HPLC (gradient: 5-80% MeCN/water with 0.1% TFA over 25 min). Collect the product as a white solid (3 mg, 13% yield). Exact Mass: 497.17. M/z found: 498.1 (M+H)$^+$.

Example 57

2-(3-(hydroxymethyl)phenylamino)-1-(4-phenoxyphenyl)ethanone

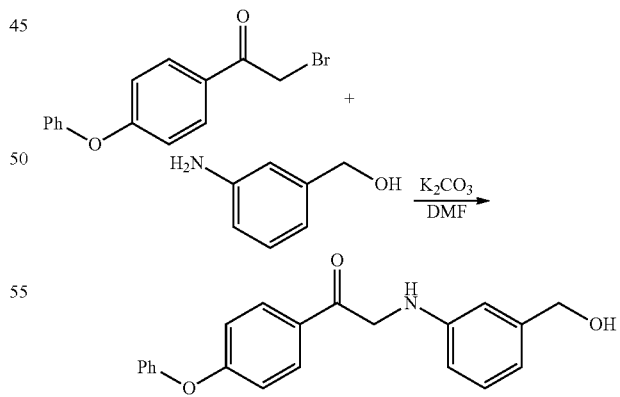

A 100 mL round-bottom flask fitted with a magnetic stir bar was charged with 3-aminobenzyl alcohol (1.3 g, 10.6 mmol), potassium carbonate (1.4 g, 10.1 mmol), and N,N'-dimethylformamide (15 mL). The slurry was stirred while adding 2-bromo-4'-chloroacetophenone (3.04 g, 10.4 mmol) portionwise. The mixture was heated to 50° C. and stirred for 2 h. The reaction mixture was partitioned between EtOAc and water, and then extracted with EtOAc. The organic layers were combined, dried over sodium sulfate, filtered, and concentrated under reduced pressure. The resulting residue was purified by Si-gel chromatography (elute 1:3 EtOAc/hexanes to 1:1 EtOAc/hexanes). The product was collected as a white solid (1.39 g, 40% yield).

Example 58

2-amino-1-(3-(hydroxymethyl)phenyl)-4-(4-phenoxyphenyl)-1H-pyrrole-3-carbonitrile

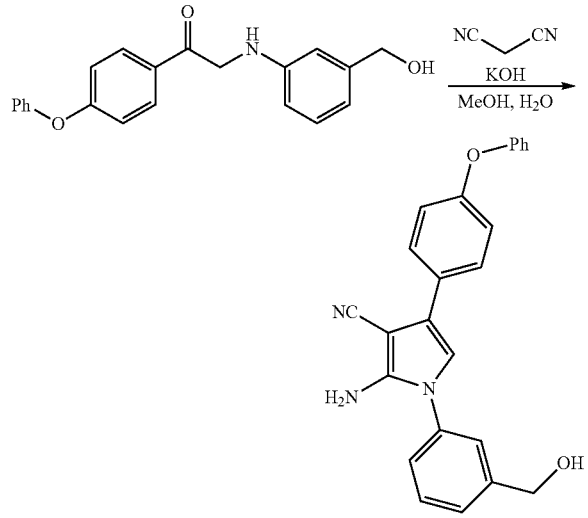

A round-bottom flask fitted with a magnetic stir bar was charged with 2-(3-(hydroxymethyl)phenylamino)-1-(4-phenoxyphenyl)ethanone (1.39 g, 4.17 mmol), potassium hydroxide (85%) (0.8 g, 12 mmol) dissolved in water (3 mL), malononitrile (0.50 g, 7.6 mmol), and methanol (15 mL). The mixture was heated to 80° C. for 2 h. The reaction mixture was partitioned between EtOAc and water, and then extracted with EtOAc. The organic layers were combined, dried over sodium sulfate, filtered, and concentrated under reduced pressure. The resulting residue was purified by Si-gel chromatography, providing the product (0.91 g, 57% yield). Exact Mass: 381.15. M/z found: 382.1 (M+H)$^+$.

Example 59

(3-(4-amino-5-(4-phenoxyphenyl)-7H-pyrrolo[2,3-d]pyrimidin-7-yl)phenyl)methanol

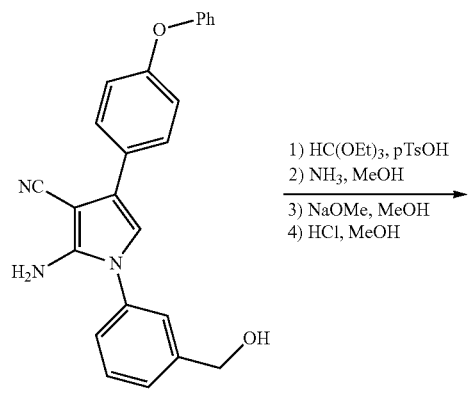

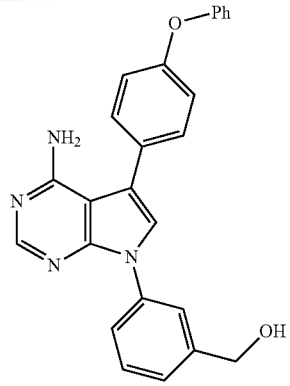

A 100 mL round-bottom flask fitted with a magnetic stir bar was charged with 2-amino-143-(hydroxymethyl)phenyl)-4-(4-phenoxyphenyl)-1H-pyrrole-3-carbonitrile 2-amino-4-(4-chlorophenyl)-1-(3-(hydroxymethyl)phenyl)-1H-pyrrole-3-carbonitrile (0.91 g, 2.7 mmol), triethyl orthoformate (3 mL), and p-toluenesulfonic acid monohydrate (10 mg). The solution was heated to 100° C. for 1.5 h. The reaction mixture was partitioned between EtOAc and water. The organic layer was washed with 5% NaHCO$_3$ and then dried over sodium sulfate, filtered, and concentrated under reduced pressure. The resulting residue was purified by Si-gel chromatography (elute 20% to 40% EtOAc/Hex). The resulting oil was concentrated under reduced pressure and redissolved in ammonia/methanol solution (7 M, 10 mL) and the flask was tightly capped and stirred at room temperature over night. The reaction mixture was concentrated under reduced pressure and redissolved ammonia/methanol solution (7 M, 10 mL), the flask tightly capped and stirred at room temperature for an additional 2 h. The solution was concentrated under reduced pressure and redissolved in methanol (20 mL) and sodium methoxide (25% w/v in methanol, 1 mL) was added. The mixture was refluxed for 2 h, cooled to room temperature and quenched by the addition of hydrochloric acid (1M, 10 mL). The solution was stirred for 1 h at room temperature. The reaction solution was neutralized by the addition of sodium bicarbonate and then was extracted with ethyl acetate (3×50 mL). The organic layer was dried over sodium sulfate, filtered, and concentrated under reduced pressure. The resulting oil was purified by Si-gel chromatography (elute 100% EtOAc to 10% MeOH/EtOAc) to yield the product as a light yellow solid (0.38 g, 38% yield).

Example 60

3-(4-amino-5-(4-phenoxyphenyl)-7H-pyrrolo[2,3-d]pyrimidin-7-yl)benzaldehyde

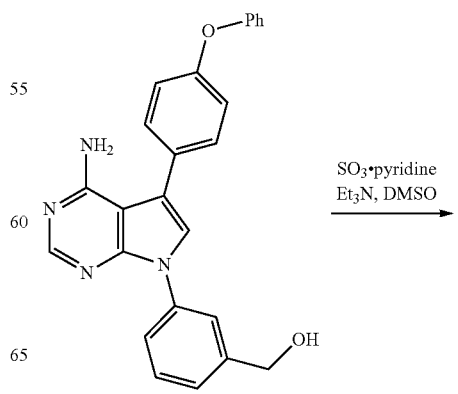

-continued

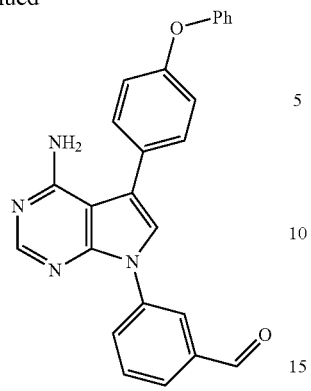

A 20 mL vial fitted with a magnetic stir bar was charged with (3-(4-amino-5-(4-phenoxyphenyl)-7H-pyrrolo[2,3-d]pyrimidin-7-yl)phenyl)methanol (207 mg, 0.51 mmol), triethyl amine (0.5 mL, 3.6 mmol), and dimethyl sulfoxide (2.5 mL). A solution of sulfur trioxide.pyridine (245 mg, 1.6 mmol) in DMSO (1.5 mL) was added to the vial and the resulting solution was stirred for 1 h at room temperature. Hydrochloric acid (1 M, 5 mL) was added and the solution stirred for an additional 5 minutes. The resulting solution was partitioned between EtOAc and water and the organic layer was washed with hydrochloric acid (1 M, 2×), sodium bicarbonate (5%, 1×), water (3×), and brine (1×). The organic layer was then dried over sodium sulfate, filtered, and concentrated under reduced pressure. The resulting residue was purified by Si-gel chromatography (elute 100% EtOAc to 10% MeOH/EtOAc), providing the product as a white solid (141 mg, 68% yield). Exact Mass: 406.14. M/z found: 407.1 (M+H)+.

Example 61

General methods for the synthesis of (E)-3-(3-(4-amino-5-(4-phenoxyphenyl)-7H-pyrrolo[2,3-d]pyrimidin-7-yl)phenyl)-2-cyanoacrylamides Example 61a (E)-3-(3-(4-amino-5-(4-phenoxyphenyl)-7H-pyrrolo[2,3-d]pyrimidin-7-yl)phenyl)-2-cyano-N,N-dimethylacrylamide

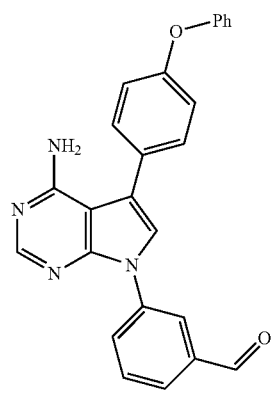 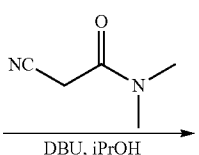

-continued

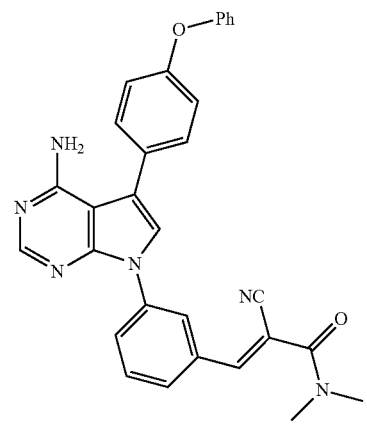

A 20 mL vial fitted with a magnetic stir bar was charged with 3-(4-amino-5-(4-phenoxyphenyl)-7H-pyrrolo[2,3-d]pyrimidin-7-yl)benzaldehyde (20 mg, 0.05 mmol), the appropriate cyanoacetamide (0.05 mmol), 1,8-diazabicyclo[5.4.0]undec-7-ene (5 mg, 0.03 mmol), and 2-propanol (1 mL). The reaction mixture was heated to 60° C. for 18 h. The solution was concentrated under reduced pressure and the resulting residue was redissolved in DMSO (0.8 mL) and the product was purified by RP-HPLC (gradient: 20-95% MeCN/water with 0.1% TFA over 25 min). The product is a white solid (4.2 mg, 17% yield). Exact Mass: 500.20. M/z found: 501.3 (M+H)+.

Example 61b (E)-3-(3-(4-amino-5-(4-phenoxyphenyl)-7H-pyrrolo[2,3-d]pyrimidin-7-yl)phenyl)-2-(4-methylpiperazine-1-carbonyl)acrylonitrile

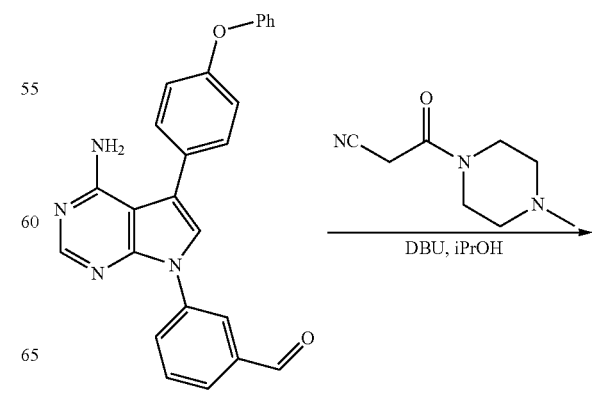

-continued

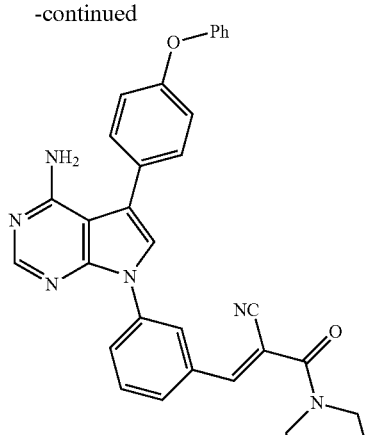

Employing the procedure described above, the named compound was synthesized. The compound is a white solid (9.2 mg, 34% yield). Exact Mass: 555.24. M/z found: 556.1 (M+H)+.

Example 61c (E)-3-(3-(4-amino-5-(4-phenoxyphenyl)-7H-pyrrolo[2,3-d]pyrimidin-7-yl)phenyl)-2-(3-hydroxyazetidine-1-carbonyl)acrylonitrile

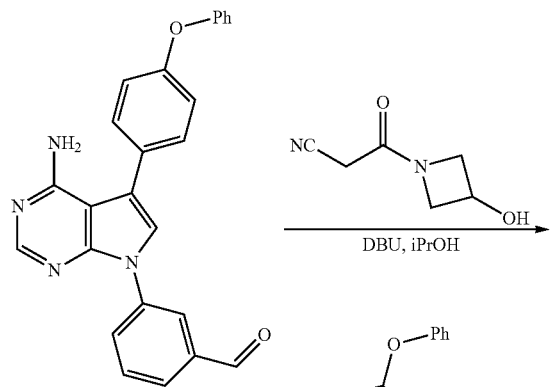

Employing the procedure described above, the named compound was synthesized. The product is a white solid (9.7 mg, 37% yield). Exact Mass: 528.19. M/z found: 529.2 (M+H)+.

Example 61d (E)-3-(3-(4-amino-5-(4-phenoxyphenyl)-7H-pyrrolo[2,3-d]pyrimidin-7-yl)phenyl)-2-cyanoacrylamide

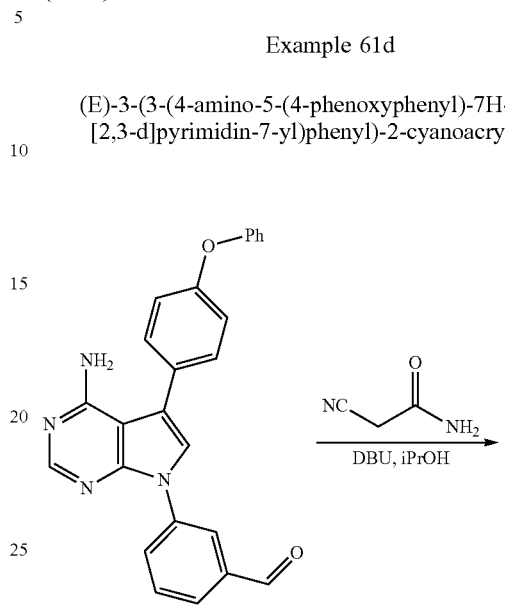

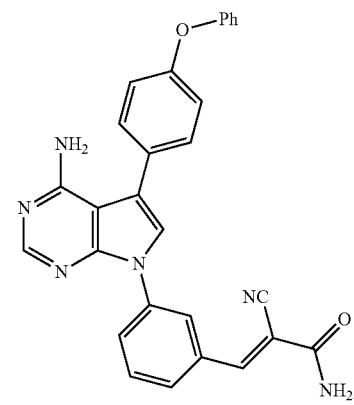

Employing the procedure described above, the named compound was synthesized. The compound is a light yellow solid (6.8 mg, 29% yield). Exact Mass: 472.16. M/z found: 473.0 (M+H)+.

Example 62

2-cyano-N-(2-hydroxyethyl)acetamide

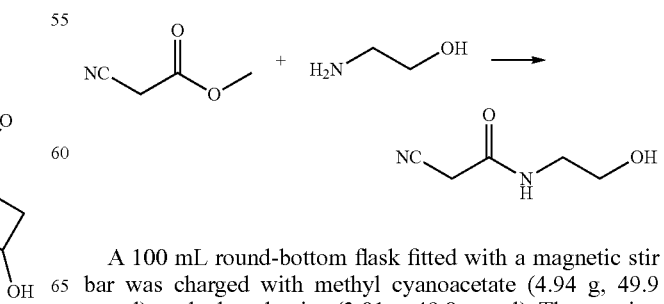

A 100 mL round-bottom flask fitted with a magnetic stir bar was charged with methyl cyanoacetate (4.94 g, 49.9 mmol), and ethanolamine (3.01 g, 49.8 mmol). The reaction mixture was stirred for 2 h at room temperature, at which point the solution was concentrated under reduced pressure and dried in vacuo to yield the product as a white solid (6.91 g, >99% yield).

Example 63

(E)-3-(3-(4-amino-5-(4-phenoxyphenyl)-7H-pyrrolo[2,3-d]pyrimidin-7-yl)phenyl)-2-cyano-N-(2-hydroxyethyl)acrylamide

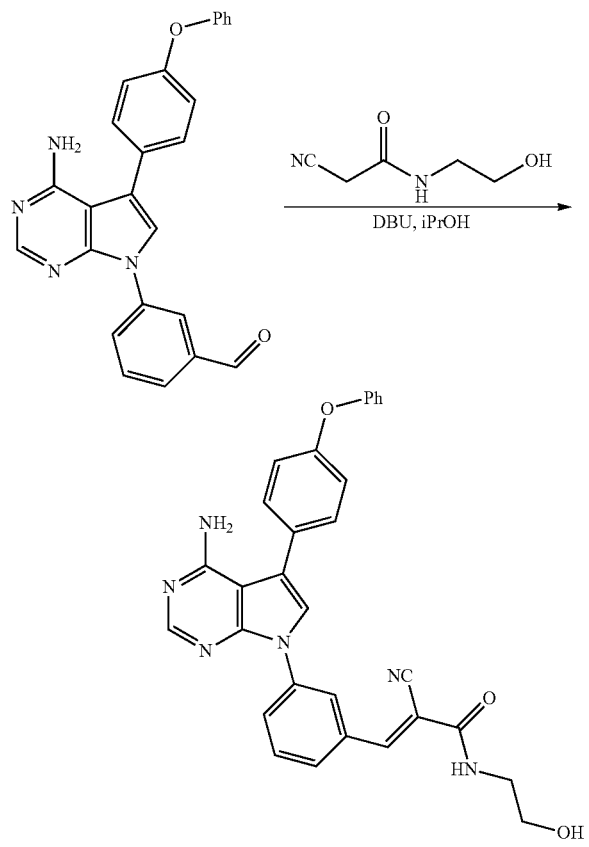

A 4 mL vial fitted with a magnetic stir bar was charged with 3-(4-amino-5-(4-phenoxyphenyl)-7H-pyrrolo[2,3-d]pyrimidin-7-yl)benzaldehyde (9 mg, 0.02 mmol), 2-cyano-N-(2-hydroxyethyl)acetamide (4 mg, 0.03 mmol), piperidinium acetate (1 mg, 0.01 mmol), and 2-propanol (0.5 mL). The reaction mixture was heated to 60° C. for 24 h. The solution was concentrated under reduced pressure and the resulting residue was purified by Si-gel chromatography (elute 100% EtOAc to 10% MeOH/EtOAc) to yield the product, which was further purified by RP-HPLC (gradient: 20-95% MeCN/water with 0.1% TFA over 25 min) to yield the product as a white solid (3.1 mg, 27% yield). Exact Mass: 516.19. M/z found: 517.0 (M+H)$^+$.

Example 64

Determination of Inhibitory Constants

Methods.

RSK2 CTD and His6-ERK2 were expressed and purified as described (Cohen et al., *Science*, 308: 1318). The C436V mutant of RSK2 CTD was generated by Quikchange mutagenesis (Stratagene) and was indistinguishable from WT RSK2 CTD in kinase activity assays, as described previously. WT and C436V RSK2 CTD (10 μM) were activated by His6-ERK2 (10 μM) in 20 mM HEPES [pH 8.0], 10 mM $MgCl_2$, 2.5 mM tris(2-carboxyethyl)phosphine (TCEP), 0.2 mg/mL BSA and 200 μM ATP for 30 min at 22° C. Activated RSK2 CTD (5 nM) in 20 mM HEPES [pH 8.0], 10 mM $MgCl_2$, 2.5 mM tris(2-carboxyethyl)phosphine (TCEP), 0.25 mg/mL BSA, and 100 μM ATP were pre-incubated with inhibitors (ten concentrations, in duplicate) for 30 min. Kinase reactions were initiated by the addition of 5 μCi of [$\gamma$-$^{32}$P]ATP (6000 Ci/mmol, NEN) and 167 μM peptide substrate (RRQLFRGFSFVAK) (SEQ ID NO:1) and performed for 30 min at room temperature. Kinase activity was determined by spotting 5 μL of each reaction onto dried sheets of nitrocellulose that had been pre-washed with 1 M NaCl in 0.1% $H_3PO_4$. The nitrocellulose sheets were washed once with 1% AcOH solution and twice with a solution of 1 M NaCl in 0.1% $H_3PO_4$ (5-10 min per wash). Dried blots were exposed for 30 min to a storage phosphor screen and scanned by a Typhoon imager (GE Life Sciences). Data were quantified using the SPOT program (Knight, Z. et al. *Nature Protocols*, 2: 2459-66), and $IC_{50}$ values were determined using GraphPad Prism 4.0 software.

Results.

Table 1 provides half-maximal inhibitory concentrations ($IC_{50}$ in μM) for electrophilic pyrrolo[2,3-d]pyrimidines 1-8 toward WT RSK2 and C436V RSK2 C-terminal kinase domain (CTD). Compounds 4-6 were additionally tested for RSK2 CTD inhibition in the presence of 10 mM reduced glutathione (GSH). Despite reacting reversibly with cyanoacrylates/cyanoacrylamides 4-6 (GSH reaction with compounds 4-6 was monitored by UV/visible spectroscopy at 350-400 nm) and being present at one million times the concentration of RSK2 CTD, glutathione had no effect on the inhibitory potency of 4-6. Consistent with the formation of a covalent adduct between Cys436 and the electrophilic beta-carbon of the cyanoacrylate and cyanoacrylamide moieties of 4-8, mutation of cysteine-436 to valine (C436V) resulted in a >1000-fold loss in inhibitory potency. Finally, cyanoacrylates and cyanoacrylamides 4-8 were significantly more potent than compounds I-3, which are based on more conventional Michael acceptors (vinyl ketone, acrylate ester, acrylonitrile). N/d, not determined.

TABLE 1

$IC_{50}$ value for selected compounds and RSK2 species.

| | $IC_{50}$ (μM) | | WT RSK2 + |
| --- | --- | --- | --- |
| | WT RSK2 | C436V RSK2 | 10 mM GSH |
| Me enone (1) | 0.087 | 1.7 | n/d |
| Me acrylate (2) | 0.25 | 0.19 | n/d |
| acrylonitrile (3) | 0.75 | 1.5 | n/d |
| CN—OMe (4) | 0.013 | >10 | 0.015 |
| CN—OtBu (5) | 0.007 | >10 | 0.006 |
| CN—NH2 (6) | 0.003 | 5 | 0.004 |
| CN—NHiPr (7) | 0.005 | 5.5 | n/d |
| CN—NHBn (8) | 0.040 | n/d | n/d |

TABLE 1-continued
IC$_{50}$ value for selected compounds and RSK2 species.
| IC$_{50}$ (µM) | | WT RSK2 + |
|---|---|---|
| WT RSK2 | C436V RSK2 | 10 mM GSH |
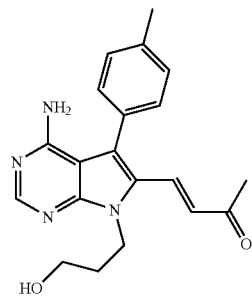
Me enone
(1)
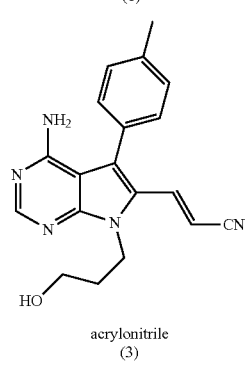
acrylonitrile
(3)
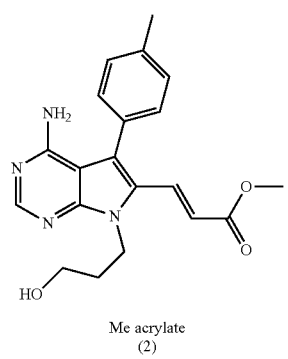 [SMILES: COC(=O)/C=C/c1c(-c2ccc(C)cc2)c2c(N)ncnc2n1CCCO]
Me acrylate
(2)
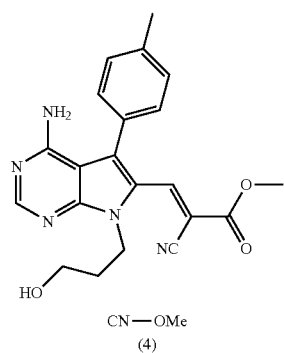
CN—OMe
(4)
TABLE 1-continued
IC$_{50}$ value for selected compounds and RSK2 species.
| IC$_{50}$ (µM) | | WT RSK2 + |
|---|---|---|
| WT RSK2 | C436V RSK2 | 10 mM GSH |
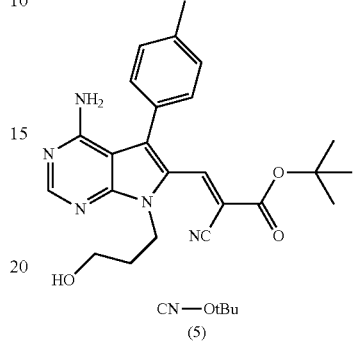
CN—OtBu
(5)
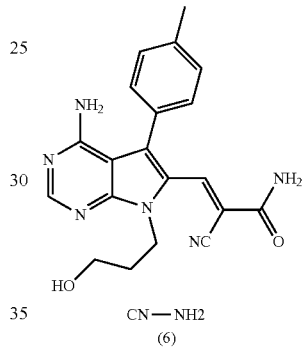
CN—NH2
(6)
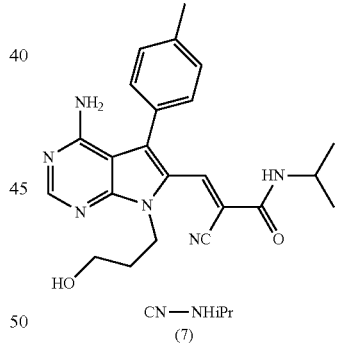
CN—NHiPr
(7)
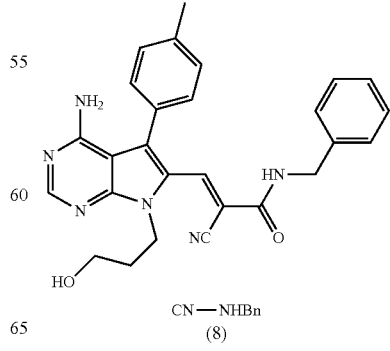
CN—NHBn
(8)

Example 65

Mass spectrometry of RSK2 CTD reaction with compounds 1-8

Methods.

RSK2 CTD (human RSK2, 399-740) was expressed in *E. coli* as a His$_6$-tagged fusion protein and purified by Ni/NTA affinity chromatography, followed by cleavage of the His$_6$-tag and further purification by size exclusion chromatography. RSK2 CTD (5 μM) was incubated with the indicated compounds (25 μM, 5 equiv) for 1 h at room temperature in buffer (20 mM HEPES [pH 8.0], 100 mM NaCl, 10 mM MgCl$_2$). The reaction was stopped by adding an equal volume of 0.4% formic acid, and the samples were analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of RSK2 CTD and electrophilic pyrrolo[2,3-d]pyrimidine adducts were determined with MassLynx deconvolution software and are shown in histogram format.

Results.

Figure 1B:
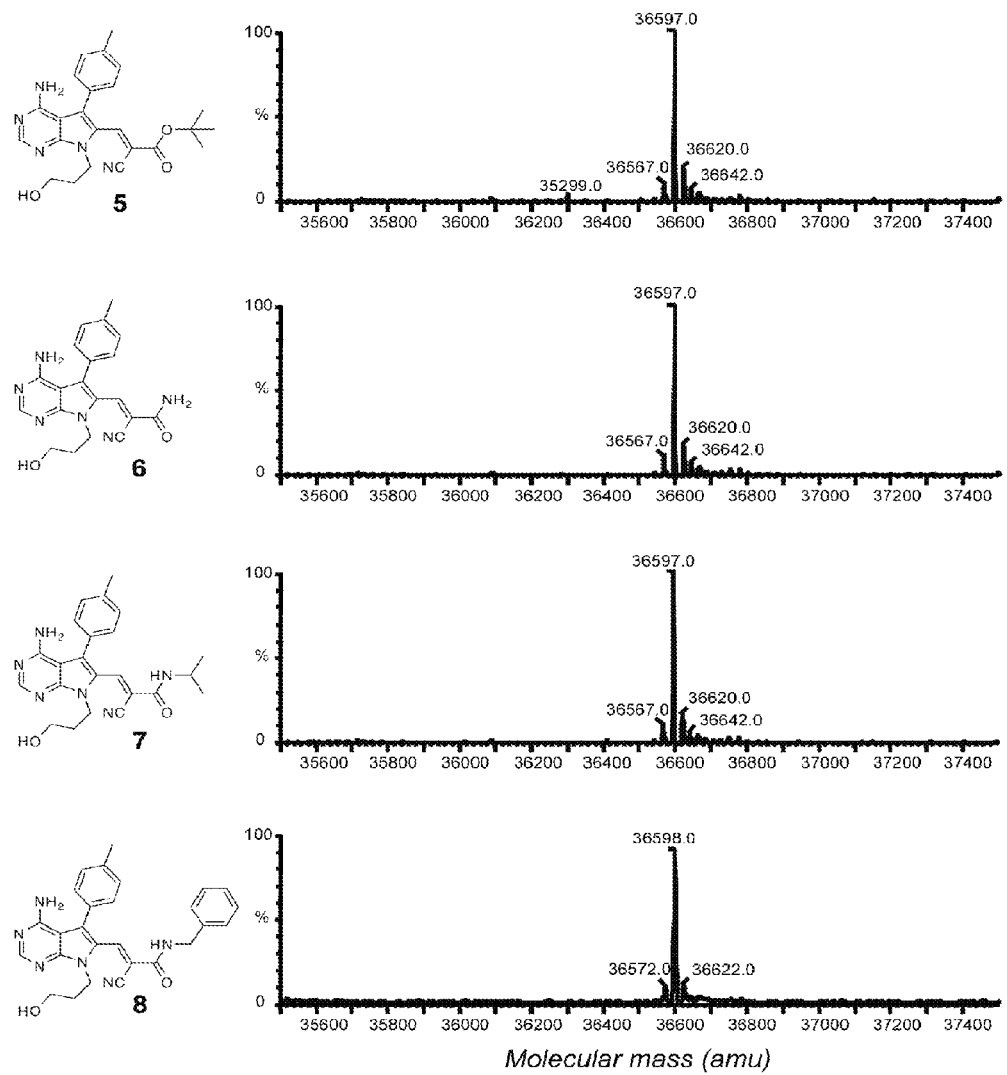

As depicted in FIG. 1A and FIG. 1B, despite their higher potency as RSK2 inhibitors, cyanoacrylates and cyanoacrylamides 4-8 do NOT irreversibly modify the RSK2 C-terminal kinase domain (CTD), as revealed by high-resolution mass spectrometry analysis. Pyrrolo[2,3-c]pyrimidines 1-3 contain conventional electrophilic "warheads" and, as expected, formed irreversible 1:1 adducts with RSK2. This conclusion is supported by the formation of a new peak in the mass spectrum corresponding to the molecular mass of RSK2 CTD plus the molecular mass of the electrophilic compound (FIG. 1A). Note that modification of RSK2 CTD by acrylate 2 and acrylonitrile 3 was somewhat slower relative to enone 1, due to the lower intrinsic electrophilicity of the acrylate/acrylonitrile warheads.

In contrast to compounds 1-3, the cyanoacrylate and cyanoacrylamide inhibitors 4-8 did not form irreversible adducts with RSK2 CTD, as shown by the presence of a single peak in the mass spectra corresponding to the unmodified RSK2 CTD. Despite the lack of irreversible RSK2 modification, compounds 4-8 are significantly more potent inhibitors of RSK2 kinase activity than the irreversible inhibitors 1-3 (Table 1). The Cys436Val mutant of RSK2 (C436V) was ~1000-fold less sensitive to compounds 4-8 (Table 1), demonstrating that potent inhibition requires Cys436. Together, these data suggest that compounds 4-8, all of which contain a cyanoacrylate or cyanoacrylamide electrophile, inhibit RSK2 kinase activity by forming a reversible covalent bond between the electrophilic beta-carbon of the cyanoacrylate/cyanoacrylamide moiety and Cys436 of RSK2. Additional evidence for a reversible covalent mechanism of inhibition for this class of electrophiles (cyanoacrylates and cyanoacrylamides) is provided below.

Example 66

Recovery of RSK2 CTD Activity Upon Dialysis

Methods.

The indicated pyrrolo[2,3-d]pyrimidines (1 μM) were added to a solution of RSK2 CTD (50 nM, pre-activated with 1 equiv of ERK2) in a buffer containing 20 mM HEPES [pH 8.0], 10 mM MgCl$_2$, 2.5 mM tris(2-carboxyethyl)phosphine (TCEP), 0.25 mg/mL BSA, and 100 μM ATP. After 60 min at rt, the reactions were transferred to a dialysis cassette (0.1-0.5 mL Slide-A-Lyzer, MWCO 10 kDa, Pierce) and dialyzed against 2 L of buffer (20 mM Hepes [pH 8.0], 10 mM MgCl$_2$, 1 mM DTT) at 4° C. The dialysis buffer was exchanged after 2 h, and then was exchanged every 24 h until the end of the experiment. Aliquots were removed from the dialysis cassettes every 24 h, flash frozen in liquid nitrogen, and subsequently analyzed for RSK2 kinase activity in triplicate. Kinase activity for each sample was normalized to the DMSO control for that time point and expressed as the mean±SD.

Results.

Figure 2:
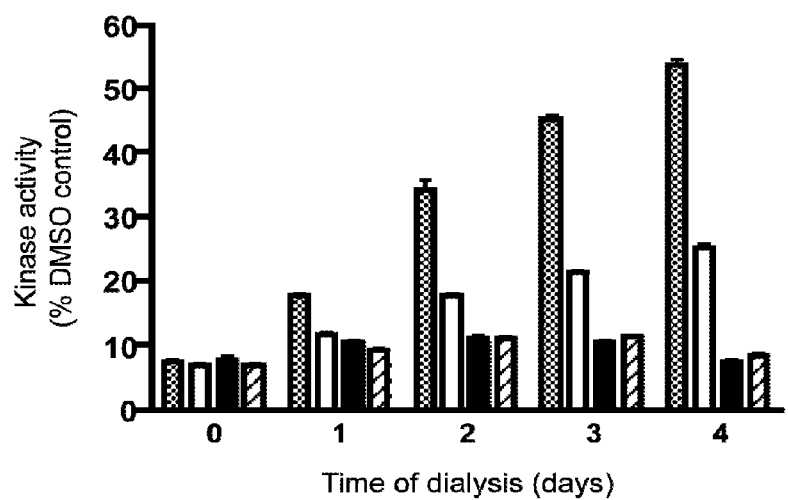
FIG. 2 depicts recovery of kinase activity of RSK2 CTD after inhibition by a selection of compounds disclosed herein and subsequent dialysis. Legend: Cmpd 6: checked; Cmpd 7: open box; Cmpd 1: Black box; Cmpd 9: diagonal stripes.
Figure 2:
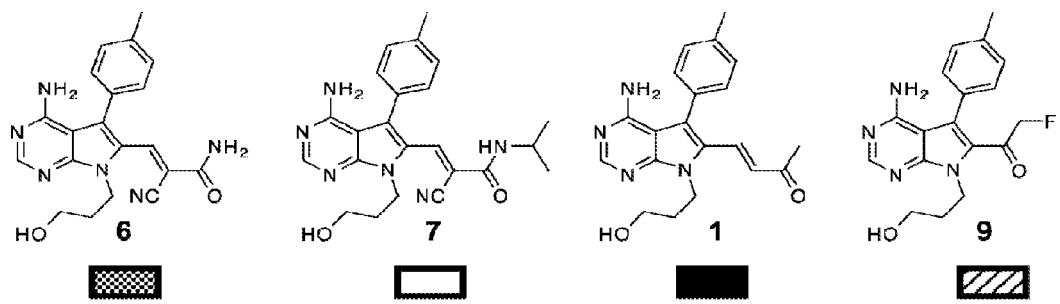

As depicted in FIG. 2, RSK2 CTD kinase activity recovers from inhibition by pyrrolo[2,3-d]pyrimidines 6 and 7 upon dialysis, indicating that 6 and 7 are reversible inhibitors. The data in FIG. 2 show that, upon extensive dialysis at 4° C., RSK2 kinase activity recovers in a time-dependent manner from inhibition by an excess (20 equiv, 1.0 μM) of cyanoacrylamides 6 (~60% recovery) and 7 (~25% recovery). Thus, cyanoacrylamides 6 and 7 are slowly dissociating, reversible inhibitors of RSK2 with dissociation half-times of ~3 days and >4 days, respectively, under these conditions (dialysis at 4° C.). Note that dissociation is more rapid at room temperature and proceeds to completion in the presence of an irreversible competitor (see FIG. 3). In contrast to the partial recovery of kinase activity observed with cyanoacrylamides 6 and 7, RSK2 CTD remained completely inhibited by enone 1 and fluoromethylketone 9 during 4 days of dialysis, further demonstrating that these compounds are irreversible inhibitors. These results are consistent with the LCMS data, which show that enone 1 (FIG. 1A) and fluoromethylketone 9 (FIG. 3) react irreversibly with RSK2, whereas cyanoacrylates and cyanoacrylamides do not form irreversible RSK2 adducts. Further evidence that cyanoacrylate- and cyanoacrylamide-substituted pyrrolo[2,3-c]pyrimidines form slowly dissociating, fully reversible complexes with RSK2 is provided in FIG. 3.

Example 67

Dissociation Kinetics of Reversible Covalent Inhibitors

Methods.

Figure 3:
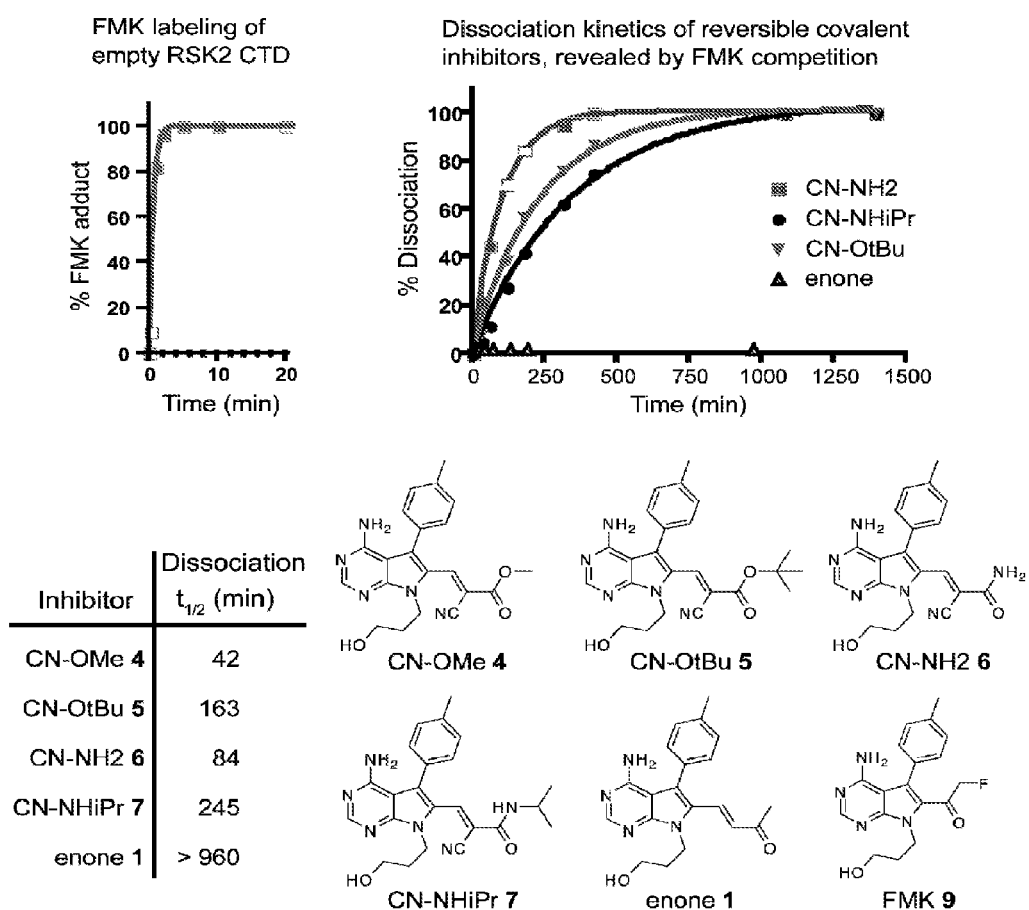
FIG. 3 depicts cyanoacrylate or cyanoacrylamide (Cmpds 4-7) dissociation from intact folded RSK2 CTD, as measured by competitive labeling with fluoromethylketone Cmpd 9 (FMK). Upper left panel: time course of FMK labeling of empty RSK2 CTD. Upper right panel: time course of dissociation of reversible covalent inhibits, Cmpds 4-7. Lower panel: tabular presentation of dissociation half-time (min) for the indicated compounds.

RSK2 CTD (5 μM) in 20 mM HEPES [pH 8.0], 10 mM MgCl$_2$, 100 mM NaCl, 2.5 mM tris(2-carboxyethyl)phosphine (TCEP) and 0.2 mg/mL BSA was preincubated with 10 μM inhibitor 1, 4-7 (or DMSO control) for 60 min at room temperature. FMK 9 (100 μM) was then added, and aliquots were removed at different time points (0.5-1500 min) and immediately quenched by mixing with an equal volume of 0.4% formic acid. Samples were analyzed by LCMS with an LCT Premier mass spectrometer and MassLynx deconvolution software, as described in FIG. 1. Peaks corresponding to empty RSK2 CTD (in the case of pre-treatment with 4-7; pre-treatment with enone 1 produced the expected mass shift, which did not change after FMK addition) and FMK-modified RSK2 CTD were integrated at each time point, and the percent FMK adduct plotted as a function of time (denoted "% Dissociation" in the graph on the left side of FIG. 3). The graph on the right side of FIG. 3 shows FMK labeling kinetics in the absence of any competitor. Kinetic data (% FMK adduct vs. time) were fit to a single exponential (PRISM 4.0) to obtain dissociation half-times depicted in the table. Control experiments showed that C436V RSK2 was not modified by FMK 9 under these conditions.

Results.

As depicted in FIG. 3, cyanoacrylates/cyanoacrylamides 4-7 dissociate with a half-time of hours from intact, folded RSK2 CTD, as measured by competitive labeling with fluoromethylketone 9. A large molar excess of fluoromethylketone 9 (100 µM, 20 equiv; "FMK" in FIG. 3) rapidly and irreversibly modified RSK2 CTD ($t_{1/2}$<2 min), as revealed by LCMS analysis of the RSK2 CTD (FIG. 3, upper left graph). By contrast, when RSK2 CTD was first treated with cyanoacrylates/cyanoacrylamides 4-7 (2.0 equiv), modification resulting from subsequent treatment with FMK 9 (100 µM, 20 equiv) was much slower, occurring with a half-time ($t_{1/2}$) of 42-245 min (FIG. 3, upper right graph). Because modification of apo-RSK2 CTD by FMK 9 occurs in less than 2 min, the observed FMK modification rate of RSK2 pre-bound to compounds 4-7 is approximately equal to the dissociation rate of the pre-bound cyanoacrylate/cyanoacrylamide. Methyl vinyl ketone 1, a conventional Michael acceptor, did not dissociate under these conditions, and FMK labeling was not observed, even after 24 h (FIG. 3). These data are consistent with the dialysis experiments in FIG. 2 and reveal that cyanoacrylates/cyanoacrylamides 4-7 dissociate slowly, yet completely, from the intact, functional RSK2 CTD, with dissociation half-times of 1-4 h. The data further reveal that the "off-rates" of the cyanoacrylates/cyanoacrylamide inhibitors can be tuned by modifying the ester and amide substituents. The N-isopropyl cyanoacrylamide had the slowest off-rate, consistent with potent RSK2 inhibitory activity in vitro and in cell-based assays (see Table 1 and FIG. 6).

Example 68

Covalent Bond Formation Between Cys436 and Cmpd 7

Methods.

To a solution of cyanoacrylamide 7 (1.0 equiv, 100-200 µM) in phosphate-buffered saline (PBS) was added WT RSK2 CTD, C436V RSK2 CTD (1.5 equiv), or buffer alone. After 10 min at rt, the UV/Visible absorbance spectrum was acquired (NanoDrop 1000 Spectrophotometer). SDS (final concentration of 2%), guanidine (final concentration 3 M, pH 8), or proteinase K (0.02 equiv based on RSK2 CTD) was added and the UV/Visible absorbance spectrum was recorded after 1 min at RT (SDS, guanidinium HCl) or 3 h at 37° C. (proteinase K). Spectra from the proteinase K and SDS addition experiments are shown in the middle and lower panels, respectively. In each experiment, absorbance values at 400 nm were normalized to the value of cyanoacrylamide 7 in buffer alone and plotted on the bar graph. Control experiments showed that neither SDS, guanidine, nor proteinase K affected the absorbance spectrum of cyanoacrylamide 7 at 400 nm.

Results.

Figure 4:
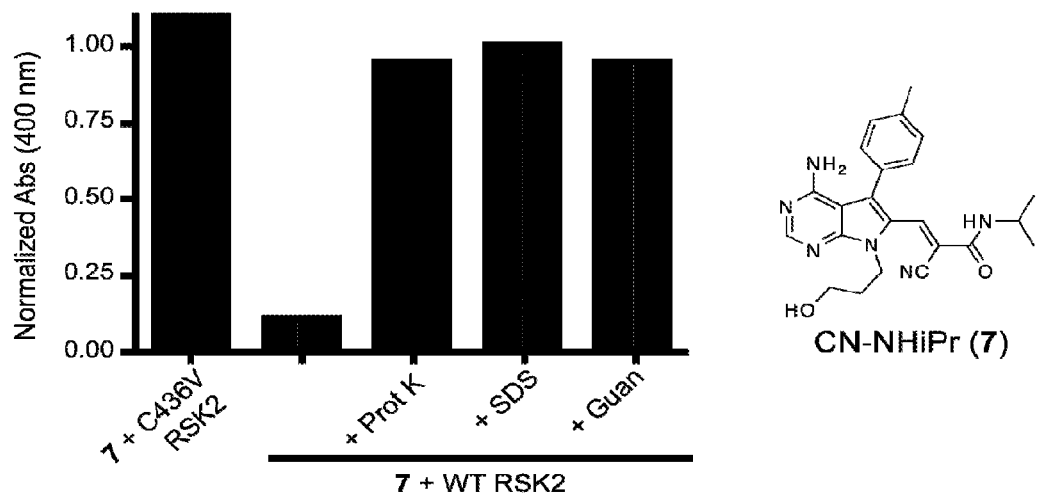
FIG. 4 depicts the formation and reversal of covalent bond formation between RSK2 and Cmpd 7 by UV/Visible spectrophotometry. Upper panel: normalized absorbance (400 nm) attributed to Cmpd 7 after reaction with a) C436V RSK2; b) WT RSK2; c) WT RSK2 plus proteinase K; d) WT RSK2 plus SDS; and e) WT RSK2 plus guanidine HCl. Middle panel: UV/Visible spectra for Cmpd 7, alone in buffer or in the presence of RSK2 or RSK2 plus Proteinase K (3 hr incubation). Lower panel: UV/Visible spectra for Cmpd 7, alone in buffer or in the presence of RSK2 or RSK2 plus SDS (1 min incubation).
Figure 4:
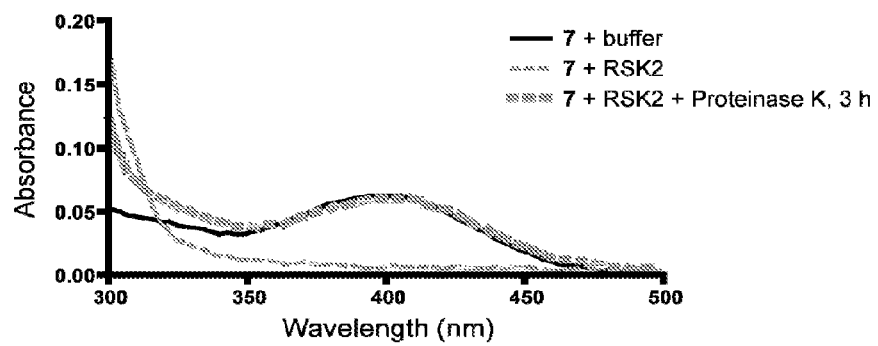
Figure 4:
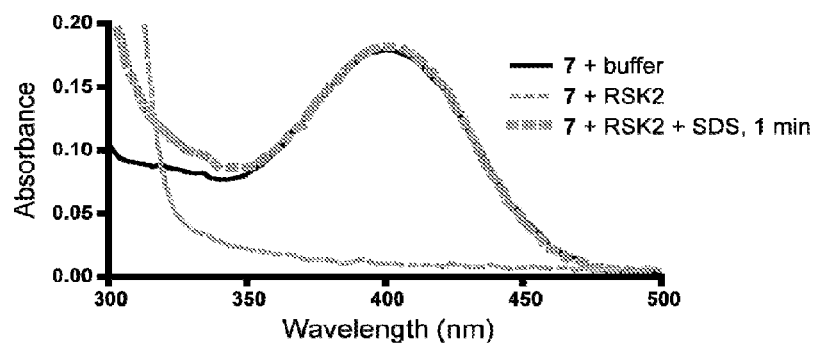

As depicted in FIG. 4, the covalent bond between Cys436 and cyanoacrylamide 7 reverses within seconds upon denaturation or proteolytic digestion of RSK2. We monitored covalent bond formation and reversal between RSK2 and cyanoacrylamide 7 by UV/visible absorption spectroscopy. Cyanoacrylamide 7 absorbs visible light with a peak at ~400 nm (FIG. 4, middle and lower panels), as expected for a cyanoacrylamide moiety conjugated to a heteroaromatic system. Addition of excess RSK2 CTD (1.5 equiv) to cyanoacrylamide 7 resulted in complete disappearance of the 400 nm peak, indicating disruption of the cyanoacrylamide chromophore by nucleophilic attack of Cys436. By contrast, addition of RSK2 CTD carrying the C436V mutation had no effect on the absorbance spectrum of cyanoacrylamide 7 (FIG. 4, bar graph). This control further substantiates our interpretation that loss of the 400 nm peak results from formation of a covalent bond between Cys436 of RSK2 and the electrophilic beta-carbon of the cyanoacrylamide moiety of compound 7.

We used three independent methods to disrupt the folded state of the RSK2 kinase domain bound to cyanoacrylamide 7: (1) 0.02 equiv proteinase K ("Prot K"), a non-specific proteinase that digests folded proteins into small peptides, (2) 2% sodium dodecyl sulfate ("SDS"), a well-characterized protein-denaturing detergent, and (3) 3 M guanidine HCl ("Guan"), a chaotrope that disrupts the native three-dimensional fold of most proteins. All three protein denaturants resulted in the reappearance of the 400 nm absorbance peak, indicating that the covalent bond between Cys436 and cyanoacrylamide 7 had broken. Covalent bond reversal occurred within seconds, concomitant with RSK2 denaturation (by SDS and guanidine HCl) or proteolytic digestion (complete digestion with 0.02 equiv proteinase K proceeded over ~3 h). Absorbance spectra are shown in the middle and lower panels for experiments with proteinase K and SDS, respectively (absolute absorbance values are different in the two experiments because different concentrations of cyanoacrylamide 7 were used). Absorbance values for all three conditions were normalized to the absorbance of cyanoacrylamide 7 in buffer alone and are shown in the bar graph. FIG. 5 shows LCMS chromatograms derived from similar experiments, proving that the addition of protein denaturants to the covalent complex formed between cyanoacrylamide 7 and RSK2 CTD results in the quantitative liberation of cyanoacrylamide 7.

Our data suggest that cyanoacrylamide inhibitors are unlikely to form permanent covalent adducts with cellular proteins, because once the protein is unfolded and/or proteolytically digested (a likely pre-condition for eliciting a delayed immune reaction), the covalent bond becomes kinetically and thermodynamically unstable and rapidly dissociates. We demonstrated this behavior with a high-affinity (nanomolar to picomolar) complex between cyanoacrylamide 7 and RSK2 CTD, in which the dissociation half-time changed from ~3 h in the folded state to less than 1 min upon denaturation of the kinase domain. Consistent with these observations, glutathione, an abundant cysteine-containing peptide, formed covalent adducts with compounds 4-8 (shown by UV/Visible spectroscopy) that rapidly dissociated, as shown by (1) rapid recovery of the cyanoacrylate/cyanoacrylamide chromophore upon dilution, and (2) unperturbed RSK2 inhibitory potency in the presence of 10 mM glutathione (Table 1). The dependence of the rate of covalent bond dissociation of a protein thiol/electrophile adduct on the folded state of the protein has not, to our knowledge, been described.

Example 69

Recovery of Cmpd 7 after Denaturation of RSK2 CTD/Cmpd 7 Complex

Methods.

Cyanoacrylamide 7 (250 µM) was incubated in the absence or presence of RSK2 CTD (300 µM) for 10 min in a total volume of 50 µL. Guanidine hydrochloride (50 µL, 6 M, pH 8) was added and the contents were mixed gently for 1 min, after which acetonitrile was added to a final concentration of 50%. The solution was filtered (0.2 µm pore size)

and analyzed by LCMS (20 µL injection, Waters XTerra MS C18 column, 5-70% MeCN/water+0.1% formic acid over 20 min; Waters 2695 Alliance Separations Module, Waters Micromass ZQ mass spectrometer).

Results.

Figure 5A:
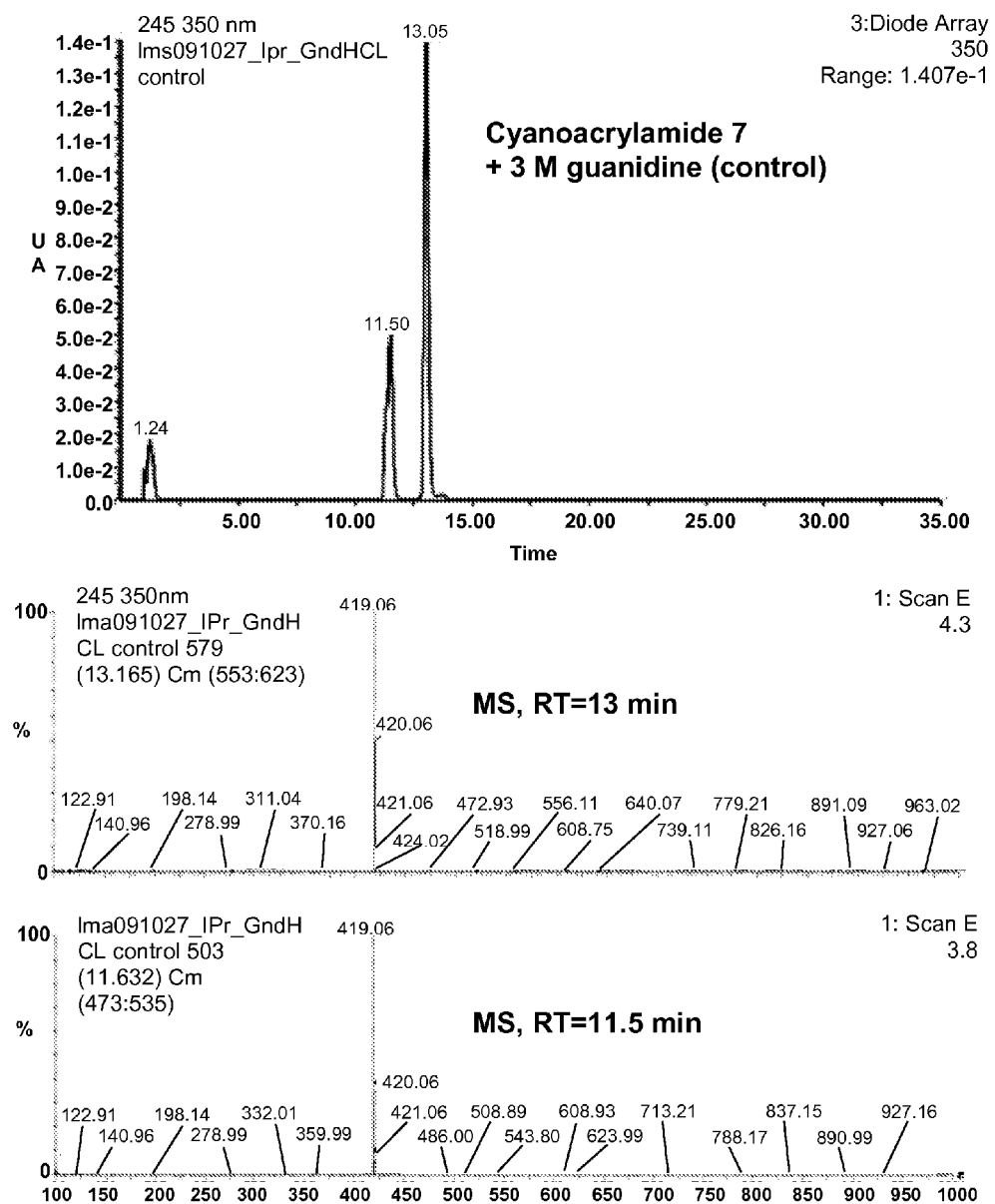
FIG. 5A depicts the mass spectrometric analysis of the incubation of Cmpd 7 with 3 M guanidine HCl.
Figure 5B:
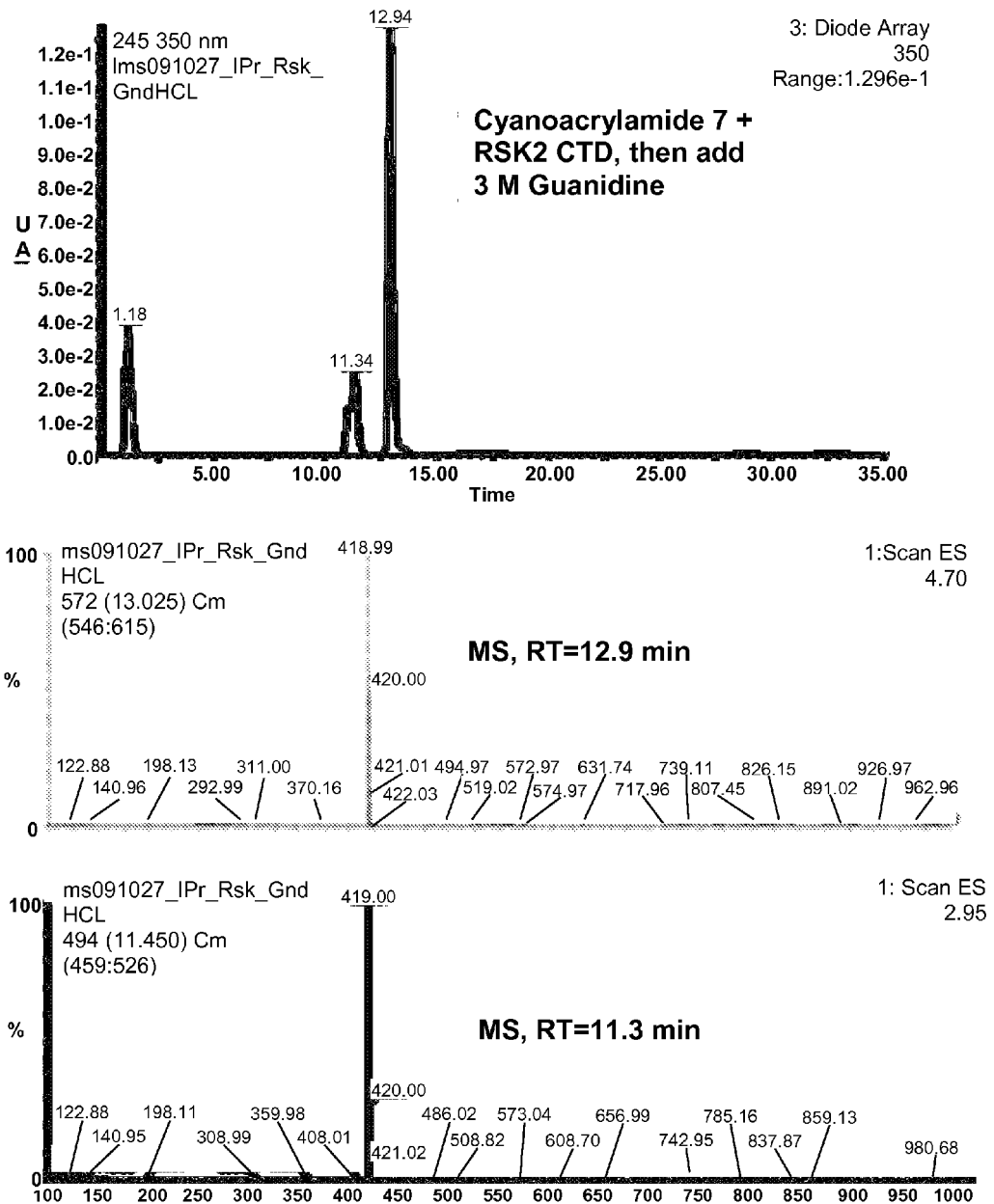
FIG. 5B depicts the mass spectrometric analysis of the incubation of Cmpd 7 incubated with RSK2 CTD prior to addition of 3 M guanidine HCl.

As depicted in FIG. 5A and FIG. 5B, consistent with the spectroscopic data shown in FIG. 4, LCMS analysis revealed quantitative recovery of cyanoacrylamide 7 after denaturation of the RSK2 CTD/cyanoacrylamide 7 complex with 3 M guanidine. The first chromatogram (FIG. 5A) (λ=350 nm) shows cyanoacrylamide 7 dissolved in buffer with 3 M guanidine HCl. The second chromatogram (FIG. 5B) (λ=350 nm) shows recovery of pure cyanoacrylamide 7 after treatment of the RSK2 CTD/cyanoacrylamide 7 complex with 3 M guanidine HCl. Two major peaks, corresponding to E- and Z-isomers of cyanoacrylamide 7, respectively, were observed in both samples. Peak areas were similar in the control and RSK2 CTD-treated samples, indicating quantitative recovery of cyanoacrylamide 7 after denaturation with guanidine. MS analysis of each peak confirmed its identity as E- or Z-cyanoacrylamide 7 (calculated MW, 418.2; observed [M+H], 419.1).

Example 70

Inhibition of RSK2 Autophosphorylation of Ser386

Methods.

HEK-293 cells in a 75 cm² flask (~80% confluent) were transfected with the pMT2 expression vector encoding HA-tagged RSK2 using Lipofectamine 2000 (Invitrogen) according to the manufacturer's protocol. After 12 h, the cells were trypsinized and seeded into 6-well plates at 600,000 cells per well in DMEM with 10% serum. After an additional 16 h, the cells were deprived of serum for 4 h and then treated with the indicated concentrations of inhibitors for 2 h in serum-free DMEM. Following inhibitor treatment, the cells were stimulated for 30 min with phorbol myristate acetate (PMA) (100 ng/ml), then washed with 2 mL cold PBS and frozen onto the plate at −80° C. The cells were thawed and scraped into 80 µL of lysis buffer (20 mM Hepes pH 7.9, 450 mM NaCl, 25% glycerol, 3 mM MgCl₂, 0.5 mM EDTA) with protease (Complete, Roche) and phosphatase (Cocktails 1 and 2, Sigma-Aldrich) inhibitors. The lysates were cleared by centrifugation and normalized via Bradford assay quantification. Laemmli sample buffer was added to the lysates, and the proteins were separated by 10% SDS-PAGE and analyzed by Western blot with phospho-Ser386 RSK2 (1:500 dilution, rabbit mAb, Cell Signaling #9335) and anti-HA (1:1000 dilution, 12CA5 mouse monoclonal, Roche) antibodies. Images were recorded on a LI-COR Odyssey imaging system (LI-COR Biosciences), and band intensities were integrated using LI-COR software. For each condition, the ratio of the phospho-Ser386 signal to the HA-RSK2 signal was calculated and expressed as a percentage of the DMSO control value (+PMA). These data are presented in the graph.

Results.

Figure 6:
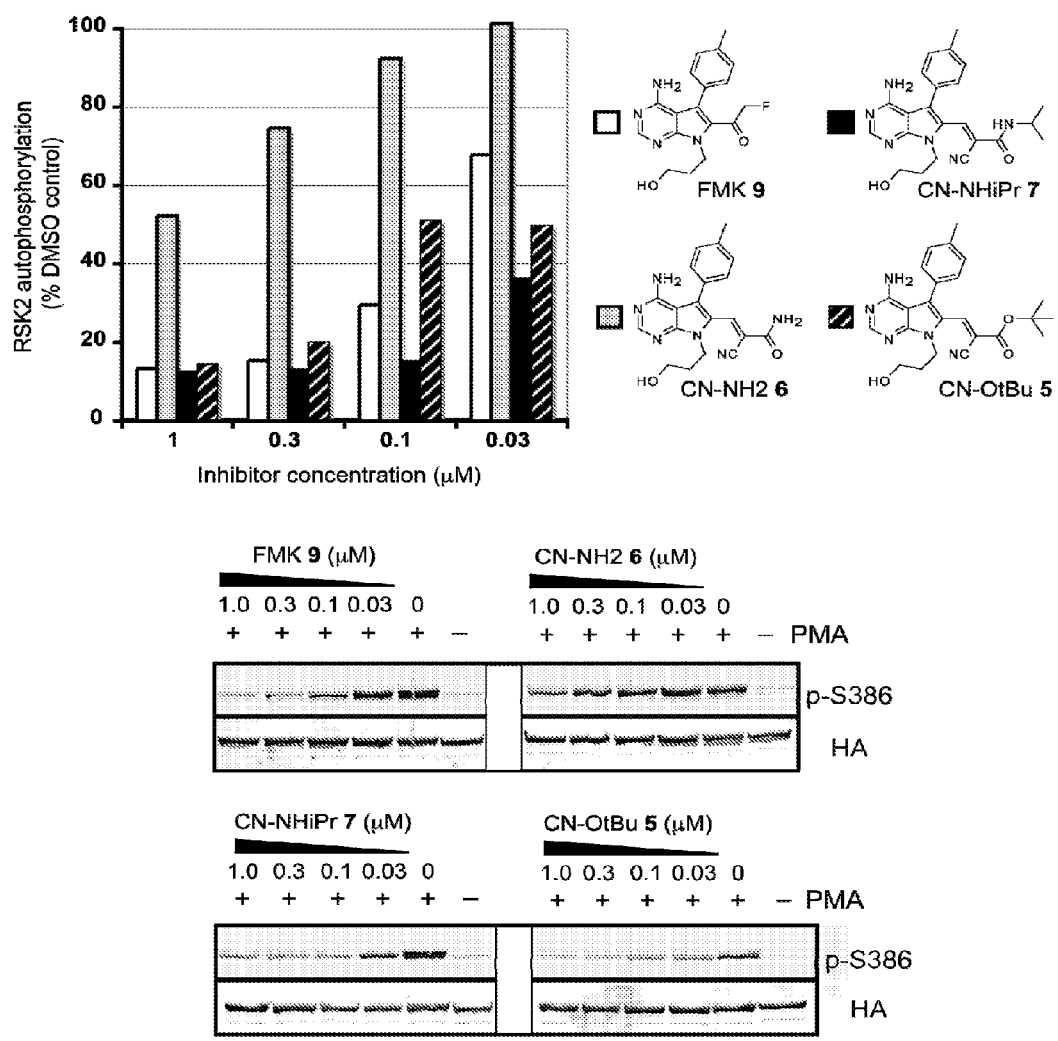
FIG. 6 depicts the inhibition of autophosphorylation of Ser386 of RSK2 by Cmpds 5-7 and Cmpd 9 in HEK-293 cells. Legend: FMK 9 (Cmpd 9): open box; Cmpd 7: black box; Cmpd 6: grayed box; Cmpd 5: diagonal stripes. Lower panel: Western blot analysis with phospho-Ser386 RSK2 and anti-HA antibodies, as described herein.

As depicted in FIG. 6, cyanoacrylate 5 and cyanoacrylamides 6 and 7 inhibit RSK2 autophosphorylation of Ser386 in mammalian cells. Note that the N-isopropyl cyanoacrylamide 7 was the most potent ($IC_{50}$<30 nM) among all the inhibitors tested, whereas cyanoacrylamide 6 had weak activity ($IC_{50}$~1000 nM). The data show that the cyanoacrylate and cyanoacrylamide inhibitors are cell permeable and sufficiently potent to compete with high intracellular concentrations of ATP and glutathione.

Example 71

Determination of General Utility of Activated Olefins for Inhibition of Therapeutically Relevant Proteins Methods.

For RSK2 kinase assays, see Example 64 above. Full-length human T175A NEK2 (referred to as "NEK2") was expressed and purified as previously described (Knapp S. et al. *J. Biol. Chem.*, 2007, 282: 6833-6842). The C22V mutant of NEK2 was generated by Quikchange mutagenesis (Stratagene) and was indistinguishable from NEK2 in kinase activity assays. NEK2 kinases (60 nM) in 20 mM Hepes, pH 7.6, 10 mM MgCl₂, 1 mM EDTA, 0.2 mg/mL BSA, and 100 µM ATP were pre-incubated with inhibitors (8-10 concentrations, in duplicate) for 30 min at room temperature. Kinase reactions were initiated by the addition of 0.4 µCi/µL of γ-³²P-ATP (6000 Ci/mmol, NEN) and 2.37 mg/mL β-casein (Sigma) and incubated for 30 minutes at room temperature.

Human PLK1 (Millipore, catalog number 14-777M) (7.2 nM) in 20 mM Hepes, pH 7.6, 10 mM MgCl₂, 1 mM EDTA, 0.2 mg/mL BSA, and 100 µM ATP was pre-incubated with inhibitors (8-10 concentrations, in duplicate) for 30 min at room temperature. Kinase reactions were initiated by the addition of 0.4 µCi/µL of γ-³²P-ATP (6000 Ci/mmol, NEN) and 0.5 mg/mL dephosphorylated α-casein (Sigma) and incubated for 30 min at room temperature. Kinase activity was determined by spotting 5 µL of each reaction onto dried sheets of nitrocellulose pre-washed with 1M NaCl in 0.1% $H_3PO_4$. After blotting each kinase reaction, the nitrocellulose sheets were washed once with 1% AcOH solution. Kinase activity was determined by spotting 5 µL of each reaction onto dried sheets of nitrocellulose that had been pre-washed with 1 M NaCl in 0.1% $H_3PO_4$. The nitrocellulose sheets were washed once with 1% AcOH solution and twice with a solution of 1 M NaCl in 0.1% $H_3PO_4$ (5-10 minutes per wash). Dried blots were exposed for 30 minutes to a storage phosphor screen and scanned by a Typhoon imager (GE Life Sciences). Data were quantified using the SPOT program (Knight, Z. et al. *Nature Protocols*, 2: 2459-66), and $IC_{50}$ values were determined using GraphPad Prism 4.0 software.

Results.

To test the general utility of activated olefins ("Michael acceptors"), including cyanoacrylamides, as cysteine-targeting moieties for the inhibition of therapeutically relevant proteins, we synthesized a panel of cyanoacrylamides that were substituted with heterocycles commonly found in kinase inhibitor drugs (e.g., azaindoles, indazoles, pyridines, pyrazoles, biaryls). We also synthesized acrylonitriles that were either unsubstituted on the nitrile-bearing carbon (Table 2a, entries 28 and 30) or were substituted with non-carboxamide electron withdrawing groups on the nitrile-bearing carbon (Table 2a, entries 19-21, 31, 32). These novel compounds were evaluated for their ability to inhibit the following kinases in vitro: WT RSK2, C436V RSK2, WT NEK2, C22V NEK2, and/or PLK1. Note that the wild-type versions of these kinases all have a cysteine in a similar location of the ATP binding site, immediately C-terminal to the "glycine-rich" loop.

Figure 7:
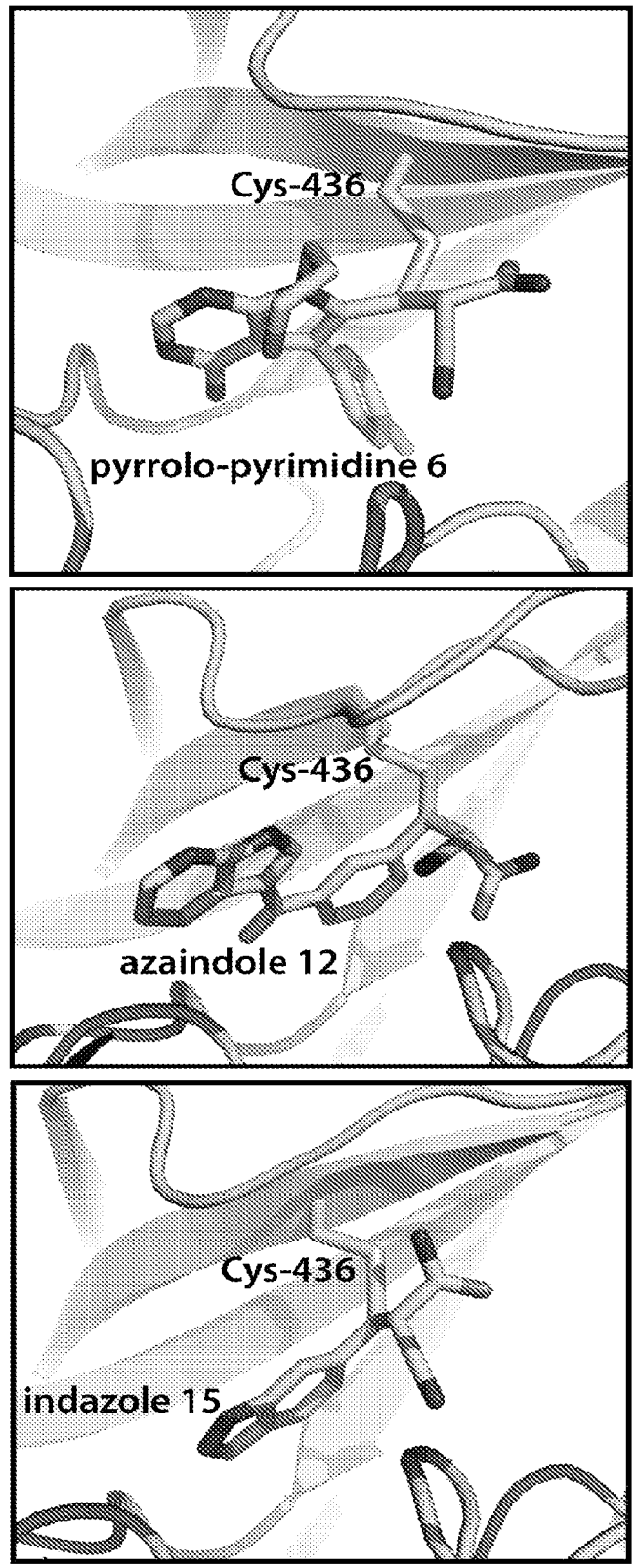
FIG. 7 depicts modes of binding of Cmpds 6, 12 or 15 (top, middle, and lower panels, respectively) to Cys-436 of RSK2, based on X-ray crystallographic structures obtained as described herein.

From these data, we conclude: (1) changing the structure of the heterocycle dramatically affects the kinase inhibitory potency and selectivity of the cyanoacrylamides and acrylonitriles. Thus, even these relatively simple "fragments" (MW<300) show steep structure-activity relationships. (2) Acrylonitriles that are substituted with a second electron withdrawing group (e.g., carboxamide) on the nitrile-bearing carbon are more potent than simple acrylonitriles containing hydrogen on the nitrile-bearing carbon (compare entries 30 vs. 31 and 22 in Table 2a; entries 3 vs. 4-8 in Table 1). (3) Where tested, the Cys to Val mutants of RSK2 and NEK2 were 10-100 times less sensitive than the WT enzymes, consistent with an inhibitory mechanism that involves covalent modification of Cys436 and Cys22 of RSK2 and NEK2, respectively. This notion was further supported by x-ray co-crystal structures of RSK2 bound to two different cyanoacrylamide fragments from Table 2a. The structures show unequivocally that Cys436 of RSK2 forms a covalent bond with the electrophilic beta-carbon of the cyanoacrylamide moiety (see FIG. 7).

TABLE 2a

| | | IC50 values (uM). | | | | |
|---|---|---|---|---|---|---|
| Entry | | RSK2 WT | RSK2 C436V | NEK2 WT | NEK2 C22V | PLK1 WT |
| 10 | [structure] | 5 | 100 | 0.90 | >10 | 30 |
| 11 | [structure] | <0.75 | 150 | 0.109 | 10 | 1 |
| 12 | [structure] | 0.124 | 40 | 3 | >10 | |
| 13 | [structure] | 0.250 | >150 | 3 | >10 | |

TABLE 2a-continued

| | IC50 values (uM). | | | | |
|---|---|---|---|---|---|
| Entry | RSK2 WT | RSK2 C436V | NEK2 WT | NEK2 C22V | PLK1 WT |
| 14 | 1 | | >10 | | |
| 15 | 0.183 | >150 | 3 | >10 | |
| 16 | 0.092 | | | | |
| 17 | 0.630 | | >10 | | |
| 18 | 0.758 | | 0.211 | >10 | |

TABLE 2a-continued
| | IC50 values (uM). | | | | |
|---|---|---|---|---|---|
| Entry | RSK2 WT | RSK2 C436V | NEK2 WT | NEK2 C22V | PLK1 WT |
| 19 | | | | | |
| 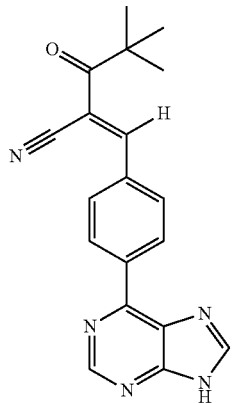 [SMILES: CC(C)(C)C(=O)/C(C#N)=C/c1ccc(-c2ncnc3[nH]cnc23)cc1] | | | | | |
| 20 | | 60 | 0.2 | >10 | |
| 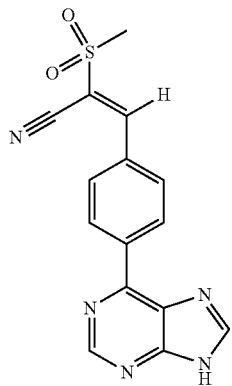 [SMILES: CS(=O)(=O)/C(C#N)=C/c1ccc(-c2ncnc3[nH]cnc23)cc1] | | | | | |
| 21 | | 60 | 1 | >10 | |
| 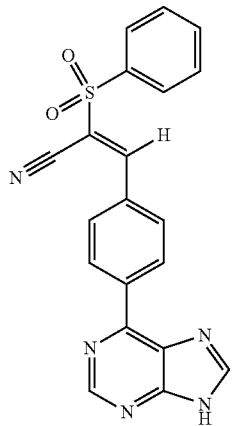 [SMILES: N#C/C(=C\c1ccc(-c2ncnc3[nH]cnc23)cc1)S(=O)(=O)c1ccccc1] | | | | | |

TABLE 2a-continued

| | IC50 values (uM). | | | | |
|---|---|---|---|---|---|
| Entry | RSK2 WT | RSK2 C436V | NEK2 WT | NEK2 C22V | PLK1 WT |
| 22 (structure) | 10 | 150 | 8 | >300 | 100 |
| 23 (structure) | 3 | >10 | 1 | | |
| 24 (structure) | 5 | >150 | | | 10 |
| 25 (structure) | 2.6 | | 6.5 | | |

TABLE 2a-continued
| | IC50 values (uM). | | | | |
|---|---|---|---|---|---|
| Entry | RSK2 WT | RSK2 C436V | NEK2 WT | NEK2 C22V | PLK1 WT |
| 26 | | | | | |
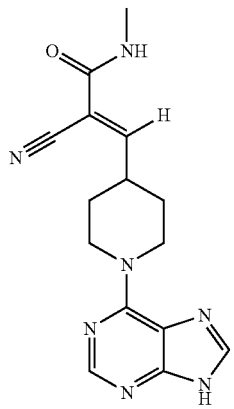 [SMILES: CNC(=O)/C(C#N)=C/C1CCN(c2ncnc3[nH]cnc23)CC1]
| 27 | | | | | |
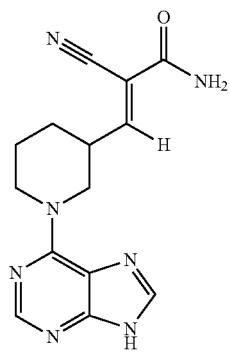 [SMILES: N#C/C(=C\C1CCCN(c2ncnc3[nH]cnc23)C1)C(N)=O]
| 28 | | | | | |
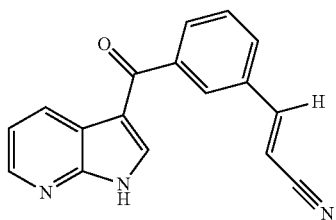 [SMILES: N#C/C=C/c1cccc(C(=O)c2c[nH]c3ncccc23)c1]
| 29 | | | 1 | 1 | |
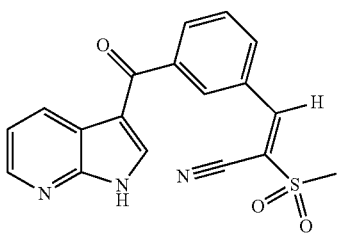 [SMILES: CS(=O)(=O)/C(C#N)=C/c1cccc(C(=O)c2c[nH]c3ncccc23)c1]

TABLE 2a-continued
| | | IC50 values (uM). | | | | |
|---|---|---|---|---|---|---|
| Entry | | RSK2 WT | RSK2 C436V | NEK2 WT | NEK2 C22V | PLK1 WT |
| 30 | 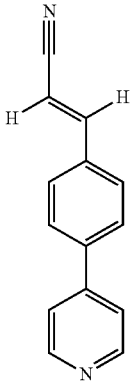 [SMILES: N#C/C=C/c1ccc(-c2ccncc2)cc1] | | | >300 | >300 | >300 |
| 31 | 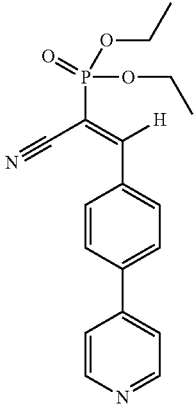 [SMILES: CCOP(=O)(OCC)/C(C#N)=C/c1ccc(-c2ccncc2)cc1] | 20 | >150 | 40 | >300 | 300 |
| 32 | 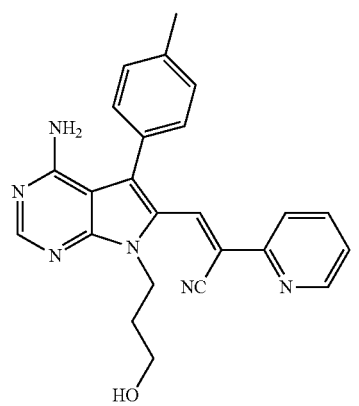 [SMILES: Cc1ccc(-c2c(/C=C(\C#N)c3ccccn3)n(CCCO)c3ncnc(N)c23)cc1] | 0.142 | >10 | | | |
| 33 | 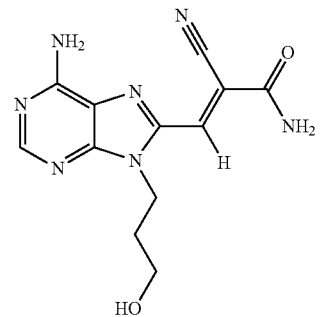 [SMILES: N#C/C(=C\c1nc2c(N)ncnc2n1CCCO)C(N)=O] | 80 | >150 | 10 | | 10 |

TABLE 2a-continued
| | IC50 values (uM). | | | | |
|---|---|---|---|---|---|
| Entry | RSK2 WT | RSK2 C436V | NEK2 WT | NEK2 C22V | PLK1 WT |
| 34 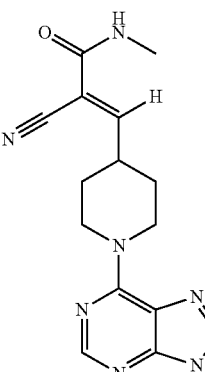 | 0.129 | | | | |
| 35 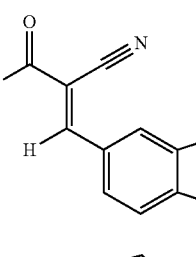 | 0.493 | | | | |
TABLE 2b
| | IC50 values of compounds (μM). | | | | | | |
|---|---|---|---|---|---|---|---|
| Cmpd | RSK2 WT | RSK2 C436V | NEK2 WT | NEK2 C22V | PLK1 WT | JAK2 WT | JAK3 WT |
| 36 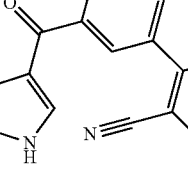 | | | | 0.440 | | | |
| 37 | 0.747 | | | | | | |
| 38 | 0.386 | | | | | | |

TABLE 2b-continued

IC50 values of compounds (μM).

| Cmpd | Structure | RSK2 WT | RSK2 C436V | NEK2 WT | NEK2 C22V | PLK1 WT | JAK2 WT | JAK3 WT |
|------|-----------|---------|------------|---------|-----------|---------|---------|---------|
| 39 | | 2 | | | | | | |
| 40 | | 0.014 | | 0.189 | | 0.650 | | |
| 41 | | 0.014 | | 1.14 | | 0.650 | | |
| 42 | | 0.089 | | 3.8 | | 10 | | |
| 43 | | 0.0038 | | | | | | |

TABLE 2b-continued

IC50 values of compounds (μM).

| Cmpd | RSK2 WT | RSK2 C436V | NEK2 WT | NEK2 C22V | PLK1 WT | JAK2 WT | JAK3 WT |
|---|---|---|---|---|---|---|---|
| 44 | 0.0024 | | | | | | |
| 45 | 0.0243 | | | | | | |
| 46 | 0.0232 | | | | | | |

TABLE 2b-continued
| | IC50 values of compounds (μM). | | | | | | |
|---|---|---|---|---|---|---|---|
| Cmpd | RSK2 WT | RSK2 C436V | NEK2 WT | NEK2 C22V | PLK1 WT | JAK2 WT | JAK3 WT |
| 47 | 0.0413 | | | | | | |
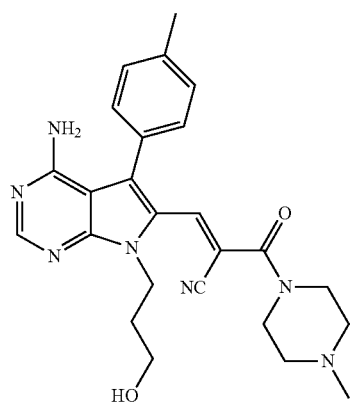 [SMILES: Cc1ccc(-c2c(/C=C(\C#N)C(=O)N3CCN(C)CC3)n(CCCO)c3ncnc(N)c23)cc1]
| 48 | 0.0047 | | | | | | |
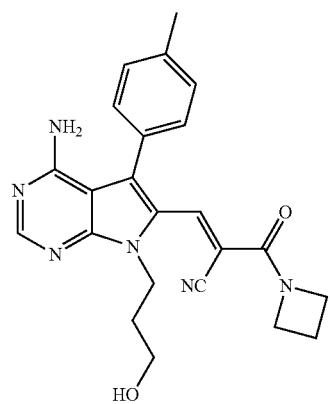 [SMILES: Cc1ccc(-c2c(/C=C(\C#N)C(=O)N3CCC3)n(CCCO)c3ncnc(N)c23)cc1]
| 49 | 0.0065 | | | | | | |
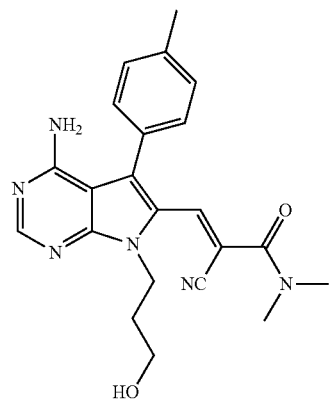 [SMILES: Cc1ccc(-c2c(/C=C(\C#N)C(=O)N(C)C)n(CCCO)c3ncnc(N)c23)cc1]

TABLE 2b-continued

IC50 values of compounds (μM).

| Cmpd | RSK2 WT | RSK2 C436V | NEK2 WT | NEK2 C22V | PLK1 WT | JAK2 WT | JAK3 WT |
|---|---|---|---|---|---|---|---|
| 50 | 0.0132 | | | | | | |

TABLE 2c

IC50 values of compounds (μM).

| Cmpd | Btk | JAK2 | JAK3 | WT cSrc | S345C cSrc |
|---|---|---|---|---|---|
| 51 | 0.09 | >10 | 0.273 | 5.9 | 0.52 |
| 52 | 0.13 | >10 | 0.141 | 0.64 | 0.08 |

TABLE 2c-continued
IC50 values of compounds (μM).
| Cmpd | Btk | JAK2 | JAK3 | WT cSrc | S345C cSrc |
|------|-----|------|------|---------|------------|
| 53   | 1.5 |      |      | >5.0    | 2.5        |
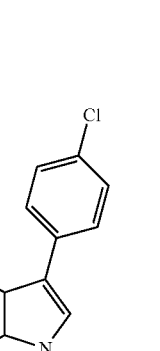
| 54 | 0.78 | | | | |
| 55 | 0.70 | | | >5.0 | 0.49 |

TABLE 2c-continued
IC50 values of compounds (μM).
| Cmpd | | Btk | JAK2 | JAK3 | WT cSrc | S345C cSrc |
|---|---|---|---|---|---|---|
| 56 | 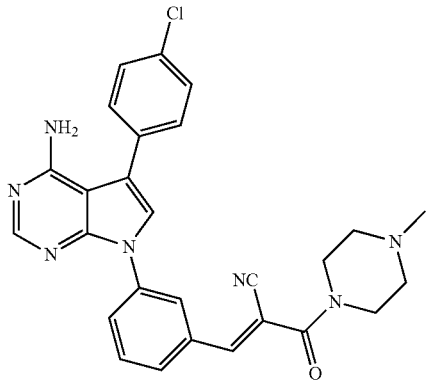 [SMILES: CN1CCN(C(=O)/C(C#N)=C/c2cccc(-n3cc(-c4ccc(Cl)cc4)c4c(N)ncnc43)c2)CC1] | 0.23 | >10 | 0.660 | >5.0 | 1.2 |
| 57 | 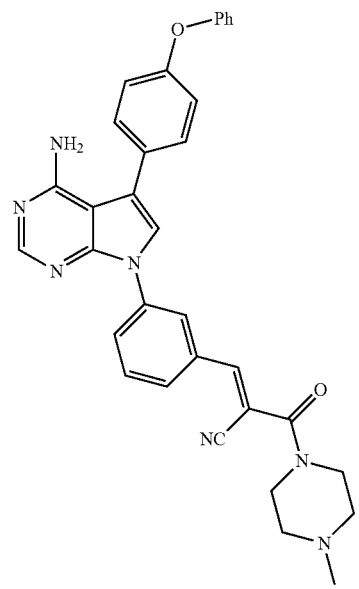 [SMILES: CN1CCN(C(=O)/C(C#N)=C/c2cccc(-n3cc(-c4ccc(Oc5ccccc5)cc4)c4c(N)ncnc43)c2)CC1] | 0.62 | | | N/I | 2.1 |
| 58 | 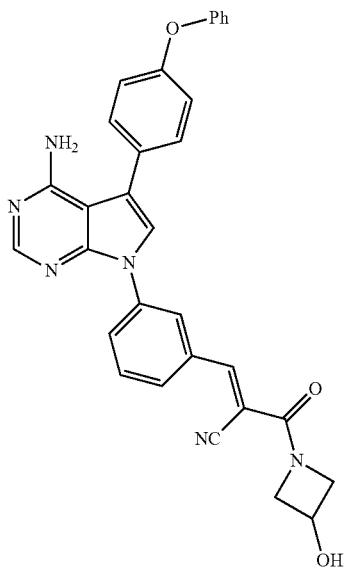 [SMILES: N#C/C(=C\c1cccc(-n2cc(-c3ccc(Oc4ccccc4)cc3)c3c(N)ncnc32)c1)C(=O)N1CC(O)C1] | 0.07 | | | N/I | 0.29 |

TABLE 2c-continued
| | IC50 values of compounds (μM). | | | | |
|---|---|---|---|---|---|
| Cmpd | | Btk | JAK2 | JAK3 | WT cSrc | S345C cSrc |
| 59 | 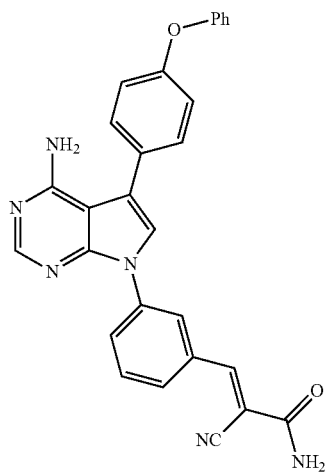 [SMILES: N#C/C(=C\c1cccc(-n2cc(-c3ccc(Oc4ccccc4)cc3)c3c(N)ncnc32)c1)C(N)=O] | 0.04 | | | | |
| 60 | 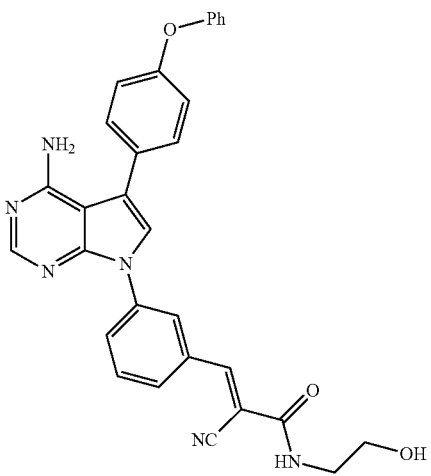 [SMILES: N#C/C(=C\c1cccc(-n2cc(-c3ccc(Oc4ccccc4)cc3)c3c(N)ncnc32)c1)C(=O)NCCO] | 0.24 | | | | |
| 61 | 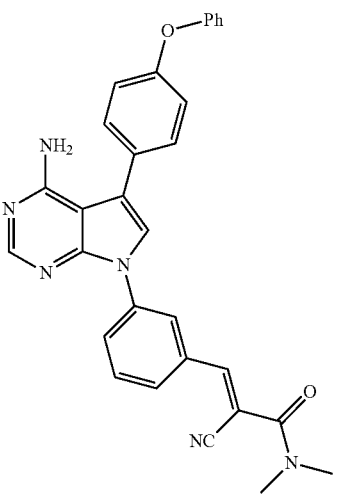 [SMILES: CN(C)C(=O)/C(C#N)=C/c1cccc(-n2cc(-c3ccc(Oc4ccccc4)cc3)c3c(N)ncnc32)c1] | 0.63 | | | N/I | N/I |

TABLE 2d
IC50 values of compounds (μM).
| Cmpd | | RSK2 WT |
|---|---|---|
| 62 | 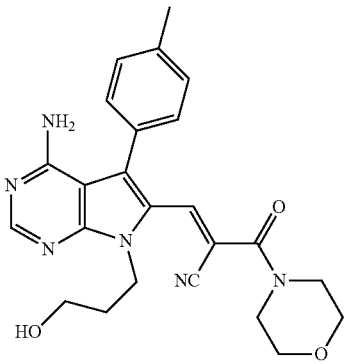 [SMILES: Cc1ccc(-c2c(/C=C(\C#N)C(=O)N3CCOCC3)n(CCCO)c3ncnc(N)c23)cc1] | 0.0105 |
| 63 | 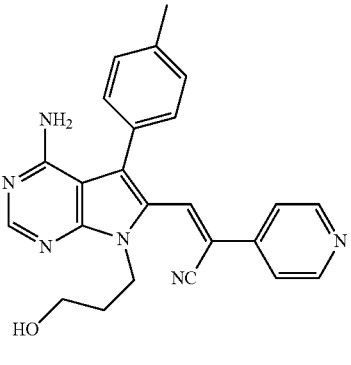 [SMILES: Cc1ccc(-c2c(/C=C(\C#N)c3ccncc3)n(CCCO)c3ncnc(N)c23)cc1] | 0.071 |
| 64 | 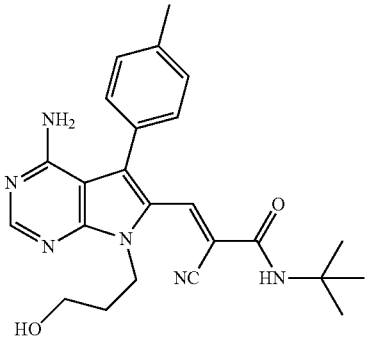 [SMILES: Cc1ccc(-c2c(/C=C(\C#N)C(=O)NC(C)(C)C)n(CCCO)c3ncnc(N)c23)cc1] | 0.0045 |
| 65 | 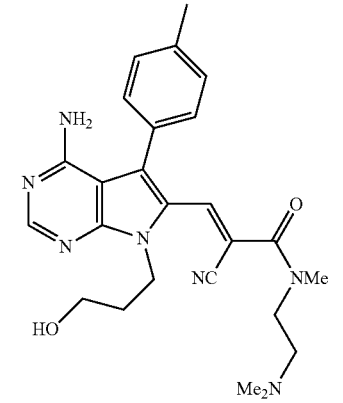 [SMILES: Cc1ccc(-c2c(/C=C(\C#N)C(=O)N(C)CCN(C)C)n(CCCO)c3ncnc(N)c23)cc1] | 0.0413 |
| 66 | 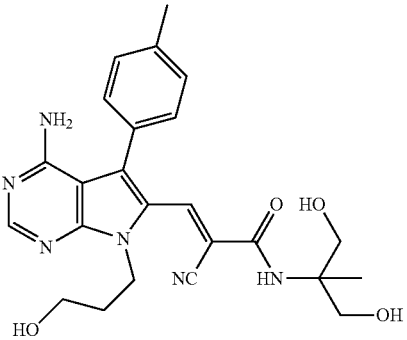 [SMILES: Cc1ccc(-c2c(/C=C(\C#N)C(=O)NC(C)(CO)CO)n(CCCO)c3ncnc(N)c23)cc1] | 0.0036 |
| 67 | 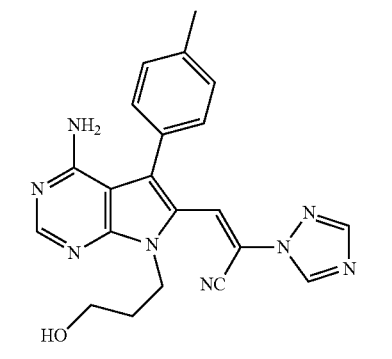 [SMILES: Cc1ccc(-c2c(/C=C(\C#N)n3cncn3)n(CCCO)c3ncnc(N)c23)cc1] | 0.0148 |
| 68 | 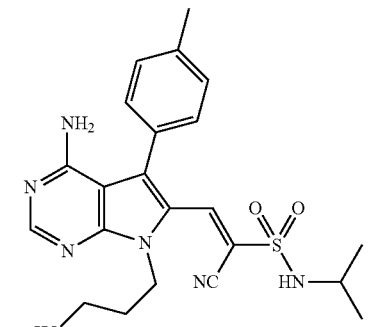 | 0.002 |
| 69 | 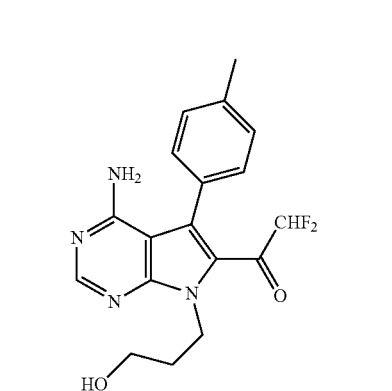 [SMILES: Cc1ccc(-c2c(C(=O)C(F)F)n(CCCO)c3ncnc(N)c23)cc1] | >0.500 |

TABLE 2d-continued

IC50 values of compounds (μM).

| Cmpd | RSK2 WT |
|---|---|
| 70 (structure) | >0.500 |
| 71 (structure) | >0.500 |
| 72 (structure) | 0.017 |
| 73 (structure) | 0.0261 |
| 74 (structure) | >0.500 |
| 75 (structure) | 0.0048 |
| 76 (structure) | 0.224 |
| 77 (structure) | 0.0126 |

TABLE 2d-continued

IC50 values of compounds (μM).

| Cmpd | | RSK2 WT |
|---|---|---|
| 78 | [structure] | 0.0304 |
| 79 | [structure] | 0.274 |
| 80 | [structure] | 0.0209 |
| 81 | [structure] | 0.003 |
| 82 | [structure] | 0.041 |

TABLE 2e

IC50 values of compounds (μM).

| Cmpd | | Btk | Wt cSrc | S345C cSrc |
|---|---|---|---|---|
| 83 | [structure] | 0.08 | >10 | >10 |

Example 72

X-Ray Crystallography and Binding Models at the RSK2 CTD ATP Site

Methods.

RSK2 CTD was expressed and purified as described above (see description for FIG. 1A AND FIG. 1B) and concentrated to 20 mg/ml in 20 mM HEPES pH 8.0, 50 mM NaCl. Cyanoacrylamide 6, 12, or 15 (1 μl of a 10 mM stock solution in 100% DMSO) was then added to 19 μl of RSK2 CTD, to give 19 mg/ml protein and 0.5 mM inhibitor in 5% DMSO. Crystals of the complexes were then grown in hanging drops by mixing 1 μl of protein/inhibitor complex with 1 μl of precipitant solution composed of 0.1M HEPES pH 7.0, 10% PEG3350, 50 mM ammonium sulphate at 20° C. Typically, crystals grew to maximal dimensions in 1-2 days. Crystals were then transferred to a cryoprotectant solution (LV Cryo Oil, Mitegen LLC, Ithaca, N.Y.) and frozen in a stream of liquid nitrogen at 100° K. The crystals belonged to the space group $P4_12_12$ with unit cell parameters a=47.5 Å; b=47.5 Å; c=291.5 Å. All datasets were collected on the 8.2.1 beamline of the Advanced Light Source at the Lawrence Berkeley National Laboratory. Diffraction data were integrated and scaled with the program XDS (Kabsh, W. 1993). The structure of the RSK2 CTD/inhibitor complex was solved by molecular replacement using data to 2.4 Å (cyanoacrylamide 6), 2.1 Å (cyanoacrylamide 12), and 2.1 Å (cyanoacrylamide 15) and Protein Data Bank structure 2qr8 as a search model in program MolRep (Vagin et al., 1997), followed by several rounds of manual rebuilding and restrained refinement with programs COOT (Emsley P, Cowtan K., Acta Crystallogr D Biol Crystallogr. 2004) and REFMAC5 (G N, Vagin A A, Dodson E J. Acta Crystallogr D Biol Crystallogr. 1997).

Figure 8:
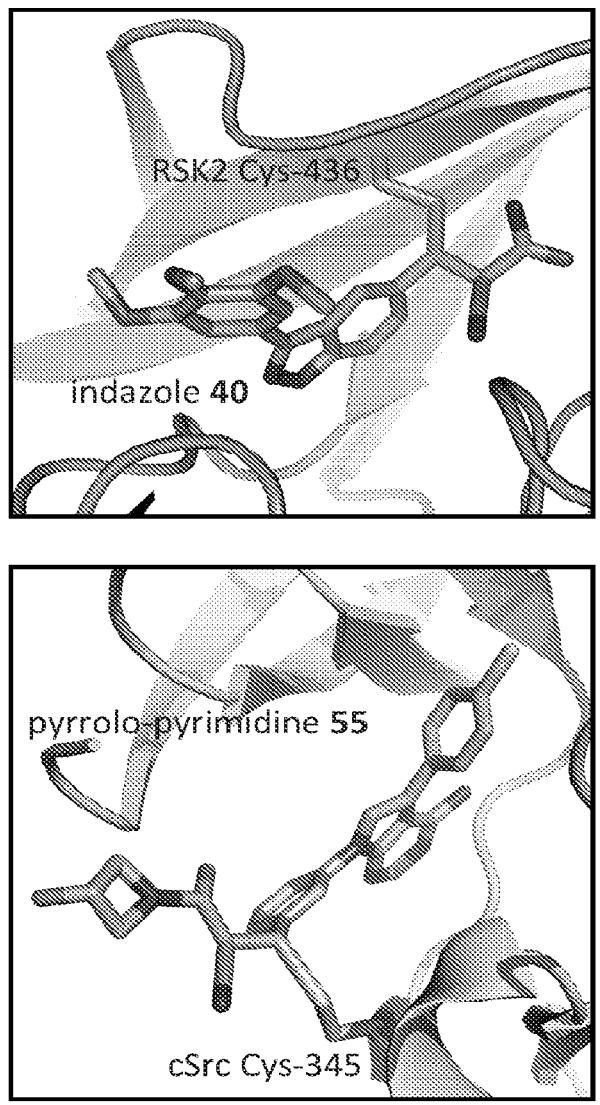
FIG. 8 depicts modes of binding of Cmpd 40 (top panel) to Cys-436 of RSK2, and Cmpd 55 to Cys-345 of cSrc.

Cyanoacrylamides, when appended to three different kinase inhibitor scaffolds, bind to the ATP binding pocket of RSK2 CTD and form a covalent bond with Cys-436. We solved co-crystal structures of RSK2 CTD bound to three cyanoacrylamide inhibitors: pyrrolo-pyrimidine 6 (Table 1), azaindole 12 (Table 2), and indazole 15 (Table 2). These compounds are potent inhibitors of RSK2 kinase activity, and mutation of Cys-436 to Val confers significant resistance (Table 1 and Table 2). The co-crystal structures of 6, 12, and 15 reveal non-covalent interactions that are typically observed in kinase/inhibitor co-crystal structures; e.g., hydrogen bonding between a heteroatom in the inhibitor and the backbone NH of RSK2 Met-496. For each of the cyanoacrylamide inhibitors, a covalent bond between the thiol of Cys-436 and the beta-carbon of the cyanoacrylamide moiety is clearly visible (FIG. 7, created from the structure coordinate files with PyMol). In addition to the data presented in Table 2, the co-crystal structures shown in FIG. 7 support the notion that an acrylonitrile, when substituted on the nitrile-bearing carbon with an electron withdrawing group (e.g., carboxamide), is a "portable" cysteine-targeting moiety that can be appended to diverse kinase-binding scaffolds to achieve potent inhibitors (nanomolar affinity) that make a reversible covalent bond with an active site cysteine. Binding of indazole Cmpd 40 to Cys-436 of RSK2 is depicted in the top panel of FIG. 8.

Example 73

Cloning, Protein Expression, Purification, and Crystallization of cSrc

The kinase domain of chicken cSrc (S345C mutant) was expressed and purified as described (Blair et al., Nat. Chem. Biol., 2007) and concentrated to 3 mg/ml in 20 mM Tris pH 7.5, 100 mM NaCl, 1 mM DTT, 5% Glycerol. Protein (3 mg/mL) was incubated for 10 minutes on ice with inhibitor (200 µM) with 2% DMSO. Crystals of the complex were then grown in hanging drops by mixing 1 µl of protein/inhibitor-complex with 1 µl of precipitant solution composed of 100 mM MES, 50 mM NaOAc, 2% PEG(4000), pH 6.5 at 20° C. Typically crystals grew as thin plates to maximal dimensions in 1-2 days. Crystals were then transferred to a cryoprotectant solution consisting of mother liquor supplemented with 25% glycerol and frozen in a stream of liquid nitrogen at 100 K.

Data Collection and Structure Solution.

The crystals belonged to the space group P1 with unit cell parameters a=42.0 Å; b=63.2 Å; c=73.1 Å; α=100.9°; β=90.8°; γ=90.0°. All datasets were collected on the 8.2.1. beamline of the Advanced Light Source at the Berkeley National Laboratory. Diffraction data were integrated and scaled with the program XDS (Kabsh, W. 1993). The structure of the cSRC/inhibitor complex was solved by molecular replacement using data to 2.3 Å and structure 3en4 as search model in program MolRep, followed by several rounds of manual rebuilding and restrained refinement with programs COOT and REFMAC5. Binding of pyrrolopyrimdine Cmpd 55 to Cys-345 of cSrc is depicted in the bottom panel of FIG. 8.

Example 74

General Procedure for cSrc Kinase Assay

Wild-type and S345C mutant cSrc kinase domains were expressed and purified as described (Blair et al., Nat. Chem. Biol., 2007). The purified cSrc kinase (2 nM final concentration) was pre-incubated with inhibitors (six or ten concentrations, in duplicate) for 30 minutes at room temperature in kinase reaction buffer (20 mM HEPES pH 7.4, 10 mM $MgCl_2$ 0.2 mM EDTA) with 200 µM ATP, and 1 mg/mL BSA. Kinase reactions were initiated by the addition of 0.05 µCi/µt of $\gamma$-$^{32}$P-ATP (6000 Ci/mmol, NEN) and 0.1 mM substrate peptide (LEIYGEFKKK) (SEQ ID NO:2) and incubated for 30 minutes at room temperature. Kinase activity was determined by spotting 6 µL of each reaction onto sheets of phosphocellulose. Each blot was washed once with 1% AcOH solution, twice with 0.1% $H_3PO_4$ solution, and once with MeOH (5-10 minutes per wash). Dried blots were exposed for 30 minutes to a storage phosphor screen and scanned by a Typhoon imager (GE Life Sciences). The data were quantified using ImageQuant (v. 5.2, Molecular Dynamics) and plotted using GraphPad Prism 4.0 software.

Example 75

2-cyano-N-(1-hydroxy-2-methylpropan-2-yl)-3-(3-(3,4,5-trimethoxyphenyl)-1H-indazol-5-yl)acrylamide

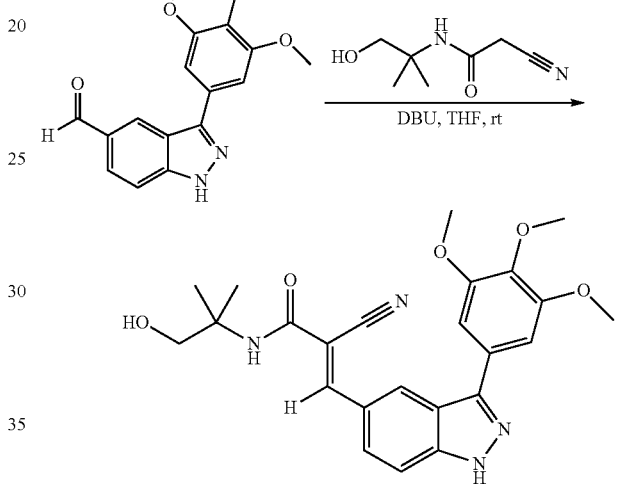

To a solution of 3-(3,4,5-trimethoxyphenyl)-1H-indazole-5-carbaldehyde (48 mg, 0.16 mmol) and 2-cyano-N-(1-hydroxy-2-methylpropan-2-yl)acetamide (23 mg, 0.16 mmol) in THF (1 mL) was added DBU (16 µL, 0.16 mmol). The colorless solution slowly became bright orange after 1 hour. The reaction mixture concentrated and purified by preparative TLC, eluting with EtOAc, to afford 44 mg (61%) of 2-cyano-N-(1-hydroxy-2-methylpropan-2-yl)-3-(3-(3,4,5-trimethoxyphenyl)-1H-indazol-5-yl)acrylamide a bright yellow solid. Exact mass: 450.19, M/z found: 451.23 (M+H)$^+$.

Example 76

3-(pyridin-3-yl)-1H-indazole-5-carbaldehyde

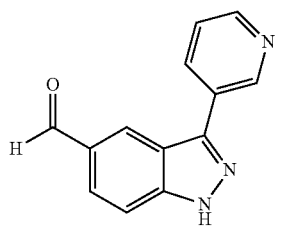

3-iodo-5-formylindazole (206 mg, 0.735 mmol), pyridin-3-ylboronic acid (106 mg, 0.882 mmol) and K₂CO₃ (330 mg, 2.21 mmol) were combined in 5:1 Dioxane:H₂O (2 mL) and degassed with bubbling argon for 20 minutes. Pd(PPh₃)₄ (91 mg, 0.074 mmol) was added, and the reaction vessel purged with argon again. The reaction was then microwaved at 130° C. for 45 minutes. The crude reaction mixture was diluted with EtOAc (20 mL) and washed twice with 1M HCl (20 mL). The combined aqueous washings were neutralized with 1M NaOH and extracted with three portions of EtOAc (75 mL) which were concentrated under reduced pressure to afford 42 mg (26%) of 3-(pyridin-3-yl)-1H-indazole-5-carbaldehyde as a yellow solid.

Example 77

2-cyano-3-(3-(pyridin-3-yl)-1H-indazol-5-yl)acrylamide

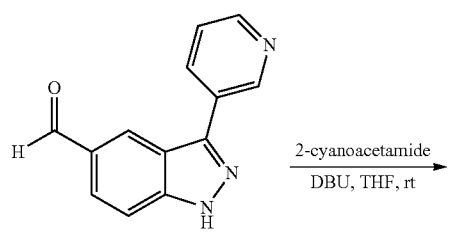

To a solution of 3-(pyridin-3-yl)-1H-indazole-5-carbaldehyde (30 mg, 0.134 mmol) and 2-cyano-N-methylacetamide (12 mg, 0.134 mmol) in THF (1 mL) was added DBU (13 μL, 0.134 mmol). The colorless slurry slowly turned bright yellow and soluble upon addition of DBU. When all solids had dissolved, the crude reaction mixture was concentrated and purified by preparative TLC, eluting with 95:5:1 EtOAc: MeOH:TEA, to afford 7 mg (18%) of 2-cyano-3-(3-(pyridin-3-yl)-1H-indazol-5-yl)acrylamide as a bright yellow solid. Exact mass: 289.10, M/z found: 290.01 (M+H)⁺.

Example 78

(E)-3-(3-(4-amino-5-(4-phenoxyphenyl)-7H-pyrrolo [2,3-d]pyrimidin-7-yl)phenyl)-2-cyano-N-(1-hydroxy-2-methylpropan-2-yl)acrylamide

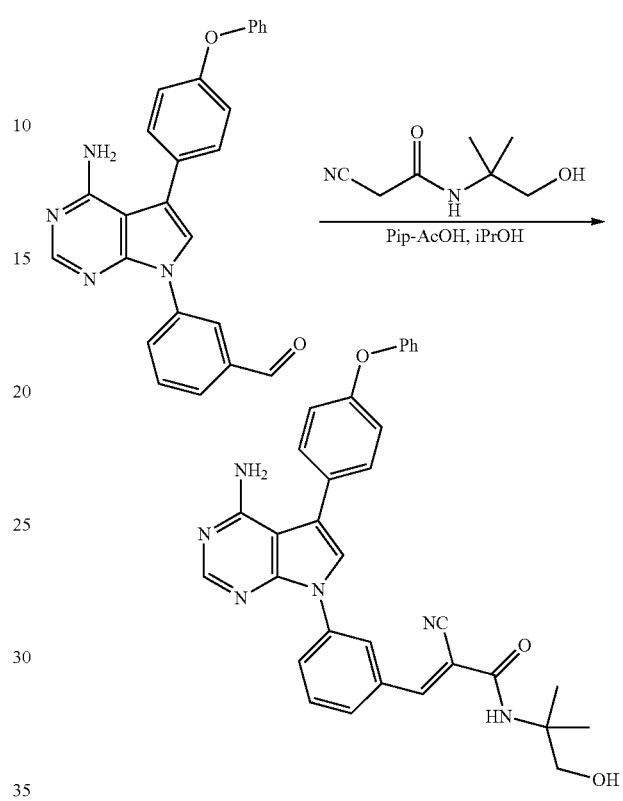

A 4 mL vial fitted with a magnetic stir bar was charged with 3-(4-amino-5-(4-phenoxyphenyl)-7H-pyrrolo[2,3-d] pyrimidin-7-yl)benzaldehyde (5 mg, 0.01 mmol), 2-cyano-N-(1-hydroxy-2-methylpropan-2-yl)acetamide (5 mg, 0.03 mmol), piperidinium acetate (2 mg, 0.02 mmol), and 2-propanol (0.5 mL). The reaction mixture was heated to 60° C. for 24 h. The solution was concentrated under reduced pressure and the resulting residue was purified by Si-gel chromatography (elute 100% EtOAc to 10% MeOH/EtOAc) to yield the product, which was further purified by RP-HPLC (gradient: 20-95% MeCN/water with 0.1% TFA over 25 min) to yield the product as a white solid (1.5 mg, 22% yield). Exact Mass: 544.22. M/z found: 545.0 (M+H)⁺.

Example 79

4-Amino-7-(3-hydroxypropyl)-5-p-tolyl-7H-pyrrolo [2,3-d]pyrimidine-6-carbaldehyde

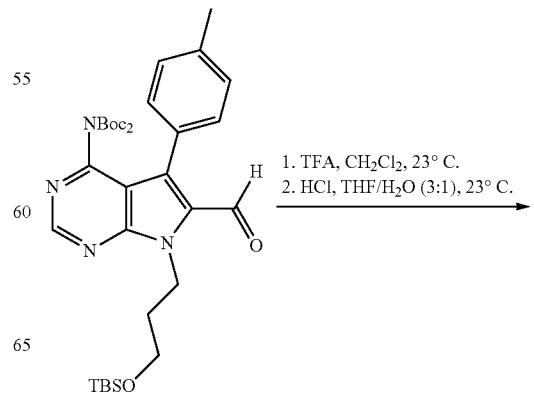

-continued

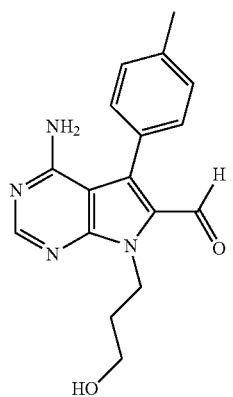

To a solution of 4-Di-tert-butyloxycarbonylamino-7-(3-tert-butyldimethylsiloxypropyl)-5-p-tolyl-7H-pyrrolo[2,3-d]pyrimidine-6-carbaldehyde (1.43 g, 2.28 mmol) in dichloromethane (12 mL) was added TFA (5 mL). The reaction mixture was maintained at ambient temperature for 12 hours, then concentrated under reduced pressure. The residue was redissolved in THF (12 mL), and 1M aq. HCl (4 mL) was added. The reaction mixture was stirred at ambient temperature for 24 hours and then diluted with EtOAc (50 mL) and satd. aq. NaHCO₃ (50 mL). The phases were separated and the aqueous phase was extracted with EtOAc (50 mL). The combined organic extracts were washed with brine (50 mL), then concentrated under reduced pressure. The residue was azeotroped with benzene (50 mL) and dried in vacuo to afford 0.99 g of the deprotected aldehyde (wet), which was used without further purification.

Example 80

Synthesis of Cyanoacetamides and Heteroaryl Acetonitriles 3-morpholino-3-oxopropanenitrile, 2-cyano-N-(2-(dimethylamino)ethyl)-N-methylacetamide (Wang, K.; Nguyen, K.; Huang, Y.; Domling, A. *J. Comb. Chem.* 2009, 11, 920-927) and 2-cyano-N-(1,3-dihydroxy-2-methylpropan-2-yl)acetamide (Santilli, A. A.; Osdene, T. S. *J. Org. Chem.* 1964, 29, 2066-2068) were synthesized as previously described.

1. 4-Cyanomethylpyridine-1-oxide

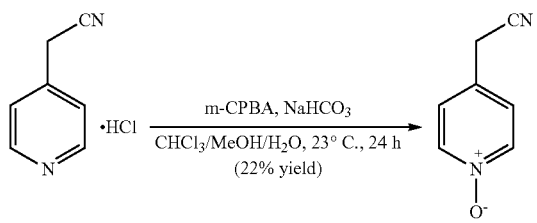

To a slurry of 4-cyanomethylpyridine hydrochloride (689.2 mg, 4.458 mmol) in Chloroform (12 mL) was added NaHCO₃ (538 mg, 5.35 mmol, 1.4 equiv) in H₂O (2 mL) leading to effervescence. Once gas evolution subsided, meta-chloroperbenzoic acid (1.25 g, 6.69 mmol, 1.6 equiv) was added in one portion. The reaction mixture was stirred at ambient temperature for 24 hours, then concentrated with silica gel and purified by silica gel chromatography (12.5 to 25% IPA in CH₂Cl₂) afforded 129 mg (22% yield) of the N-oxide as a red semi-solid.

2. 2-Cyano-N-(2-hydroxyethyl)-N-methylacetamide

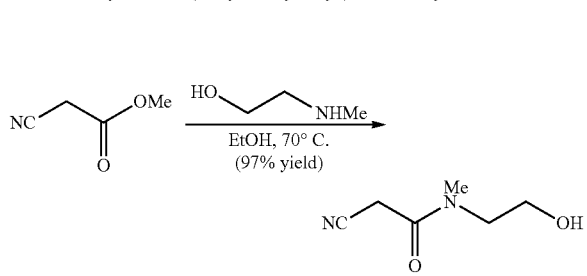

To a solution of methyl cyanoacetate (6.27 g, 63.3 mmol) in ethanol (12 mL) was added 2-(methylamino)ethanol (5.6 mL, 69.6 mmol, 1.1 equiv). The reaction mixture was heated to 70° C. for 4 hours, then cooled to ambient temperature and concentrated under reduced pressure. Silica gel chromatography of the crude residue (EtOAc) afforded 8.76 g (97% yield) of 2-cyano-N-(2-hydroxyethyl)-N-methylacetamide as an amber oil.

3. N-tert-butyl-2-cyanoacetamide

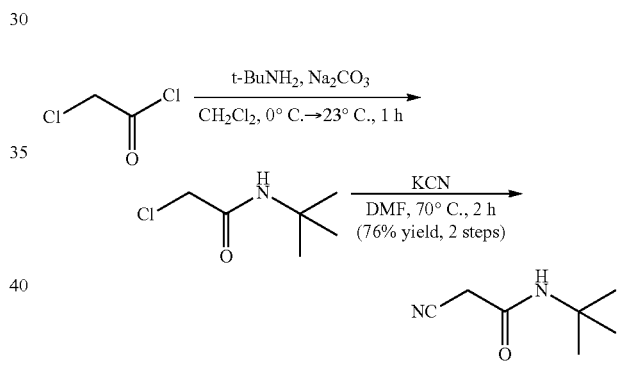

To a slurry of tert-butylamine (3.7 mL, 35.4 mmol, 2.0 equiv) and sodium carbonate (3.75 g, 35.4 mmol, 2.0 equiv) in CH₂Cl₂ (20 mL) cooled to 0° C. was added a solution of chloroacetyl chloride (1.4 mL, 17.7 mmol, 1.0 equiv) in CH₂Cl₂ (10 mL) over 5 minutes. Once the addition was complete, the reaction mixture was allowed to warm to ambient temperature and stirred for 45 minutes, then filtered. The filter cake was washed with CH₂Cl₂ (50 mL). The combined filtrate and wash were concentrated to afford the intermediate tert-butyl-2-chloroacetamide as white solid, which was carried on to the next step without any further purification. The tert-butyl-2-chloroacetamide was dissolved in DMF (12 mL), and 2.31 g (35.4 mmol, 2.0 equiv) of finely crushed KCN was added. The reaction mixture was heated to 70° C. for 2 hours and then filtered. The filter cake was washed with EtOAc (2×30 mL). The combined washes and filtrate were concentrated to afford an amber oil. Purification by silica gel chromatography (40% EtOAc in Hexanes) afforded the tert-butyl-2-cyanoacetamide as a semi-solid with DMF as an impurity. This semi-solid was dissolved in EtOAc (100 mL) and washed with water (3×70 mL). The combined aqueous washes were extracted with EtOAc (100 mL). The combined EtOAc solutions were washed with brine (70 mL), dried (MgSO$_4$) and concentrated to afford the analytically pure tert-butyl-2-cyanoacetamide (1.88 g, 76% yield, 2 steps) as an off-white solid.

4. N-1-adamantyl-2-cyanoacetamide

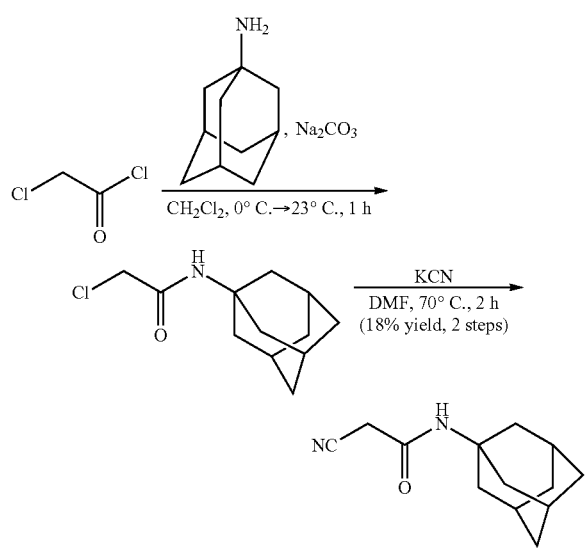

To a slurry of 1-adamantylamine (2.80 g, 18.5 mmol, 1.5 equiv) and sodium carbonate (2.62 g, 24.7 mmol, 2.0 equiv) in CH$_2$Cl$_2$ (17 mL) at 20-25° C. was added a solution of chloroacetyl chloride (1.24 mL, 12.3 mmol, 1.0 equiv) in CH$_2$Cl$_2$ (5 mL) over 5 minutes. Once the addition was complete, the reaction mixture was stirred for 10 minutes and diluted with CH$_2$Cl$_2$ (10 mL) for more efficient stirring. After 2 hours, the reaction mixture was filtered. The filter cake was washed with CH$_2$Cl$_2$ (20 mL). The combined filtrate and wash were concentrated to afford the intermediate 1-adamantyl-2-chloroacetamide as white solid, which was carried on to the next step without any further purification. The 1-adamantyl-2-chloroacetamide was dissolved in DMF (6 mL), and 1.61 g (24.7 mmol, 2.0 equiv) of finely crushed KCN was added. The reaction mixture was heated to 70° C. for 14 hours and then cooled to ambient temperature. The reaction mixture was diluted with EtOAc (100 mL) and washed with water (3×60 mL). The combined aqueous washes were extracted with EtOAc (70 mL). The combined EtOAc solutions were washed with brine (100 mL), dried (MgSO$_4$) and concentrated to afford a residue. Purification by silica gel chromatography (25% EtOAc in Hexanes) afforded 1-adamantyl-2-chloroacetamide (500 mg, 18% yield) and 1-adamantyl-2-cyanoacetamide (491 mg, 18% yield, 2 steps) as white solids.

5. 1-Cyano-N-isopropylmethanesulfonamide

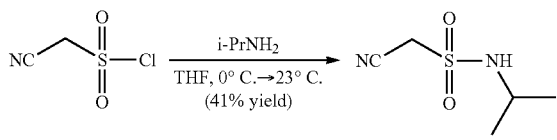

To a solution of 1-cyanomethanesulfonyl chloride (Sammes, M. P.; Wylie, C. M.; Hoggett, J. G. *J. Chem. Soc. (C)*, 1971, 2151-2155) (3.25 g, 23.3 mmol, 1.0 equiv) in THF (20 mL) cooled to 0-5° C. was added isopropylamine (5.0 mL, 58.2 mmol, 2.5 equiv) over 10 minutes. The reaction mixture was then allowed to warm to ambient temperature. After 12 hours, the reaction mixture was filtered through Celite. The filter cake was washed with MeCN (50 mL). The wash was combined with the filtrate and concentrated to afford a residue, which after purification by silica gel chromatography (25% EtOAc in Hexanes), afforded 1.55 g (41% yield) of 1-cyano-N-isopropylmethanesulfonamide as an amber oil.

6. Allyl-2-(2-cyanoacetamido)-2-methylpropanoate

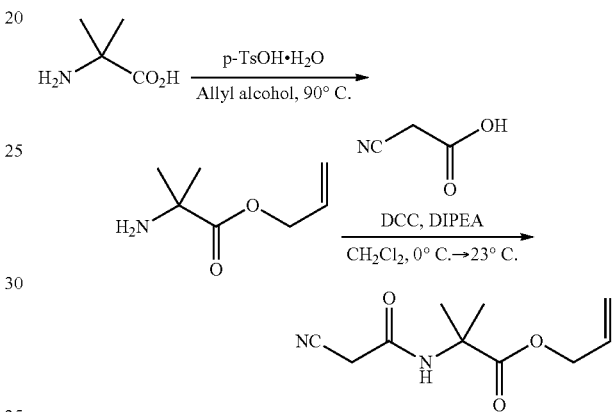

A slurry of 2-amino-2-methylpropanoic acid (Aib, 2.05 g, 19.9 mmol) and p-toluenesulfonic acid monohydrate (5.11 g, 26.9 mmol, 1.35 equiv) in allyl alcohol (30 mL) was heated to 90° C. for 24 hours, then cooled to ambient temperature. The reaction mixture was concentrated to remove allyl alcohol and then diluted with CH$_2$Cl$_2$ (100 mL), and saturated aqueous sodium carbonate (100 mL). The phases were separated and the aqueous phase was extracted with CH$_2$Cl$_2$ (100 mL). The combined organic extracts were washed with brine (100 mL), dried (Na$_2$SO$_4$) and concentrated to afford the crude Aib-allyl ester (2.84 g, quantitative yield) as a brown oil, which was carried on to the next step without further purification.

To a solution of cyanoacetic acid (500 mg, 5.88 mmol, 1.0 equiv), N,N-diisopropylethylamine (3.1 mL, 17.6 mmol, 3.0 equiv) and Aib-allyl ester (1.26 g, 8.82 mmol, 1.5 equiv) in CH$_2$Cl$_2$ (8 mL) cooled to 0-5° C. was added a solution of N,N'-dicyclohexylcarbodiimide (1.82 g, 8.82 mmol, 1.5 equiv) in CH$_2$Cl$_2$ (7 mL) over 3 minutes. The reaction mixture was stirred at 0-5° C. for 40 minutes and then allowed to warm to ambient temperature. After 24 hours, the reaction mixture was diluted with EtOAc (100 mL) and washed with 0.5 M HCl (50 mL) and the organic phase was filtered through Celite to remove precipitated solids. The filtrate was washed with brine (50 mL), dried (Na$_2$SO$_4$) and concentrated to afford a brown solid, which was purified by silica gel chromatography (50% EtOAc in Hexanes), to afford 648 mg (53% yield) of allyl-2-(2-cyanoacetamido)-2-methylpropanoate as a white solid.

7. 2-Cyano-N',N'-dimethylacetohydrazide

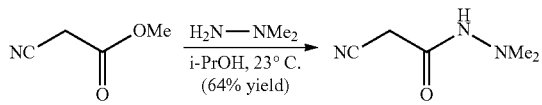

To a solution of methyl cyanoacetate (5.48 g, 55.3 mmol, 1.0 equiv) in 2-propanol (12 mL) was added N,N-dimethylhydrazine (8.4 mL, 110.6 mmol, 2.0 equiv). The reaction mixture was stirred at ambient temperature for 20 hours, then concentrated to afford a red solid, which was slurried in Et2O (50 mL), filtered and dried to afford the hydrazide as an orange red solid (4.52 g, 64% yield). Additional purification of a portion of the solid by silica gel chromatography (50% EtOAc in Hexanes, then EtOAc) afforded 1.68 g of analytical pure hydrazide as an off-white solid.

8. 2-Cyano-N-methoxyacetamide

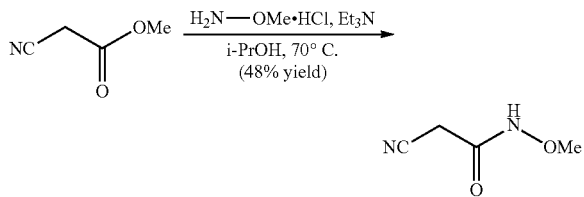

To a slurry of methyl cyanoacetate (1.21 g, 12.2 mmol, 1.0 equiv) and O-methylhydroxylamine hydrochloride (2.02 g, 24.2 mmol, 1.9 equiv) in 2-propanol (5 mL) was added triethylamine (5.1 mL, 36.3 mmol, 3.0 equiv). The reaction mixture was heated to 70° C. for 3 hours and then filtered hot. The filter cake was washed with 2-propanol (3×5 mL). The combined washes and filtrate were concentrated and the residue afforded was purified by silica gel chromatography (70% EtOAc in Hexanes) to afford 2-cyano-N-methoxyacetamide (673 mg, 48% yield) as a white solid.

9. 2-(1H-pyrazol-1-yl)acetonitrile

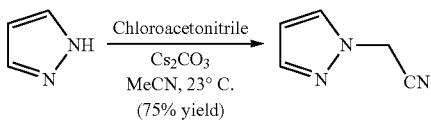

To a slurry of pyrazole (1.04 g, 15.3 mmol, 1.0 equiv) and cesium carbonate (7.47 g, 22.9 mmol, 1.5 equiv) in MeCN (21 mL) was added chloroacetonitrile (1.16 mL, 18.3 mmol, 1.2 equiv) over 3 minutes. The reaction mixture was stirred at ambient temperature for 2 hours and filtered. The filter cake was washed with MeCN (2×20 mL). The combined filtrate and washes were concentrated and the residue obtained was purified by silica gel chromatography (25% EtOAc in Hexanes) to afford 1.23 g (75% yield) of 2-(1H-pyrazol-1-yl)acetonitrile as a colorless oil.

10. 2-(1H-1,2,3-triazol-1-yl)acetonitrile

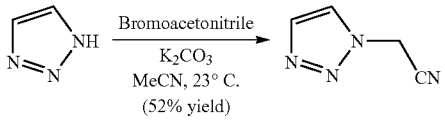 [SMILES: c1c[nH]nn1 ; N#CCn1ccnn1]

To a slurry of 1H-1,2,3-triazole (261.4 mg, 3.79 mmol, 1.0 equiv) and potassium carbonate (785 mg, 5.68 mmol, 1.5 equiv) in MeCN (8 mL) was added a solution of bromoacetonitrile (303 µL, 4.54 mmol, 1.2 equiv) in MeCN (4 mL) over 3 minutes. The reaction mixture was stirred at ambient temperature for 2 hours and filtered. The filter cake was washed with MeCN (30 mL). The combined filtrate and washes were concentrated and the residue obtained was purified by silica gel chromatography (50% EtOAc in Hexanes) to afford 211 mg (52% yield) of 2-(1H-1,2,3-triazol-1-yl)acetonitrile as a colorless oil.

11. Azetidine (X=H), and 3-hydroxyazetidine (X=OH) cyanoacetamides

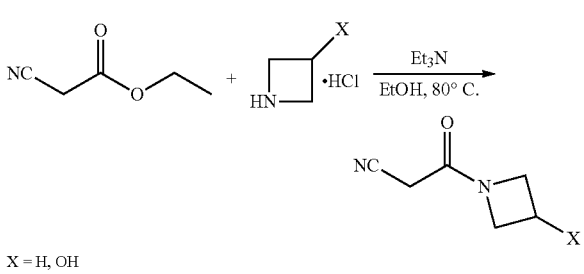

X = H, OH

Ethylcyanoacetate (1.0 equiv.), azetidine (X=H), or 3-hydroxyazetidine (X=OH) hydrochloride (1.1 equiv.) and triethylamine (1. 5 equiv.) in EtOH (6 mL) were heated at 80° C. for 6 hours. The reaction mixture was concentrated and the residue was partitioned between EtOAc (25 mL) and DI water (25 mL). The aqueous phase was extracted with EtOAc (2×30 mL). The combined organic extracts were dried (Na2SO4) and concentrated to afford a residue, which was purified by silica gel chromatography (4:1 EtOAc/Hexanes for X=H; 16:1 EtOAc/MeOH for X=OH) to afford the desired cyanoacetamide.

Ethylcyanoacetate (550 mg, 4.86 mmol) and azetidine hydrochloride (500 mg) afforded 196.5 mg (33% yield) of azetidine cyanoacetamide.

Ethylcyanoacetate (469.4 mg, 4.15 mmol) and 3-hydroxyazetidine hydrochloride (500 mg) afforded 89 mg (15% yield) of azetidine cyanoacetamide.

Example 81

Synthesis of Cyanoacrylamides or Heteroaryl Acrylonitriles

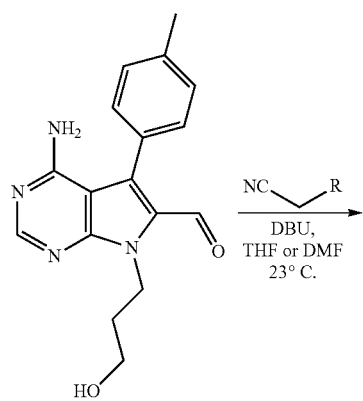

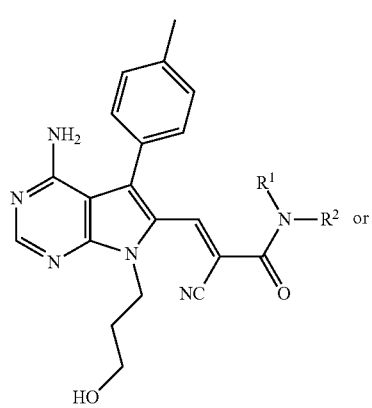

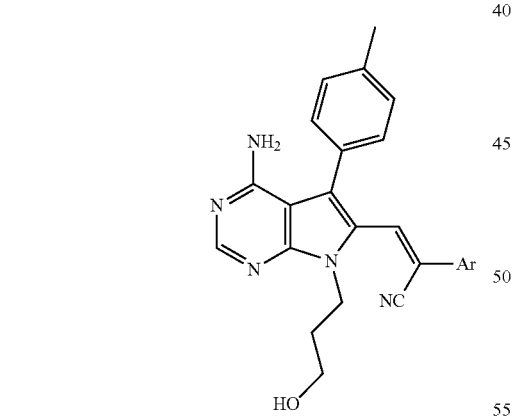

General procedure for synthesis of cyanoacrylamide or heteroarylacrylonitrile derivatives: 4-Amino-7-(3-hydroxypropyl)-5-p-tolyl-7H-pyrrolo[2,3-d]pyrimidine-6-carbaldehyde (1.0 equiv.), the appropriate cyanoacetamide or heteroaryl acetonitrile (1.2-1.5 equiv.) and DBU (1.5-2.0 equiv.) were stirred in THF or DMF (2 mL) at ambient temperature for 1-3 days. The reaction mixture was then concentrated and purified by preparative TLC or HPLC to afford the cyanoacrylamide or heteroaryl acrylonitrile as a mixture of (E)- and (Z)-isomers.

3-(4-amino-7-(3-hydroxypropyl)-5-p-tolyl-7H-pyrrolo[2,3-d]pyrimidin-6-yl)-2-(morpholine-4-carbonyl)acrylonitrile

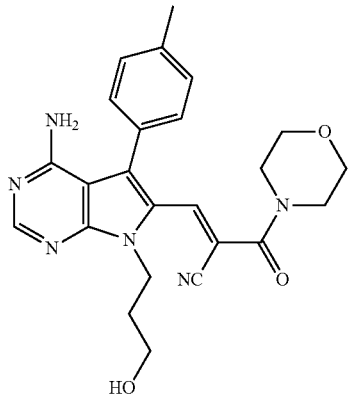 [SMILES: Cc1ccc(-c2c(/C=C(\C#N)C(=O)N3CCOCC3)n(CCCO)c3ncnc(N)c23)cc1]

Yield: 12.1 mg (21% yield). ESI-MS: 447.7 (MH⁺).

3-(4-amino-7-(3-hydroxypropyl)-5-p-tolyl-7H-pyrrolo[2,3-d]pyrimidin-6-yl)-2-(pyridin-4-yl)acrylonitrile

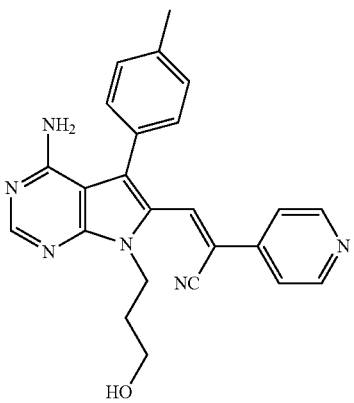 [SMILES: Cc1ccc(-c2c(/C=C(\C#N)c3ccncc3)n(CCCO)c3ncnc(N)c23)cc1]

Yield: 7.3 mg (25% yield). ESI-MS: 411.7 (MH⁺).

3-(4-amino-7-(3-hydroxypropyl)-5-p-tolyl-7H-pyrrolo[2,3-d]pyrimidin-6-yl)-N-tert-butyl-2-cyanoacrylamide

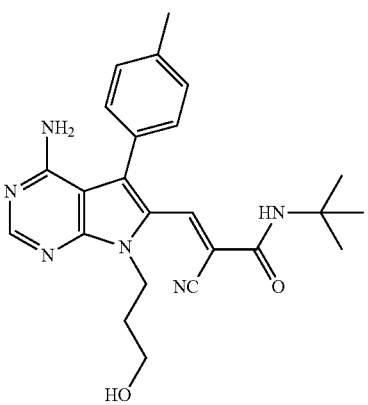 [SMILES: Cc1ccc(-c2c(/C=C(\C#N)C(=O)NC(C)(C)C)n(CCCO)c3ncnc(N)c23)cc1]

Yield: 19.9 mg (38% yield). ESI-MS: 433.2 (MH⁺).

173

3-(4-amino-7-(3-hydroxypropyl)-5-p-tolyl-7H-pyrrolo[2,3-d]pyrimidin-6-yl)-2-cyano-N-(2-(dimethylamino)ethyl)-N-methylacrylamide

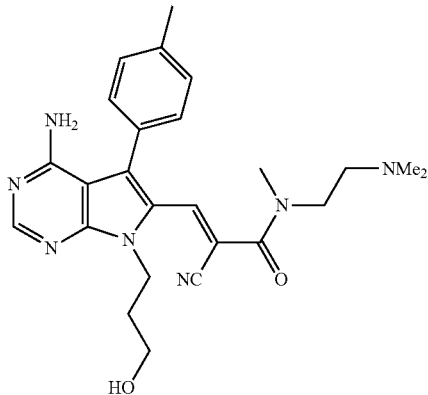 [SMILES: Cc1ccc(-c2c(/C=C(\C#N)C(=O)N(C)CCN(C)C)n(CCCO)c3ncnc(N)c23)cc1]

Yield: 9.8 mg (29%). ESI-MS: 462.5 (MH$^+$).

3-(4-amino-7-(3-hydroxypropyl)-5-p-tolyl-7H-pyrrolo[2,3-d]pyrimidin-6-yl)-2-cyano-N-(2-hydroxyethyl)-N-methylacrylamide

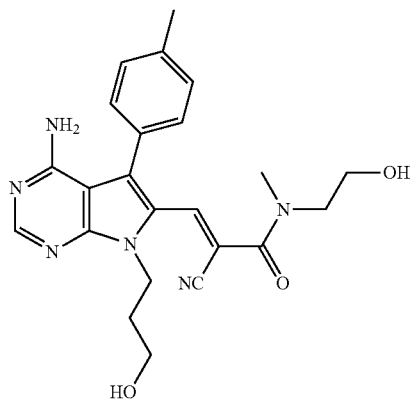 [SMILES: Cc1ccc(-c2c(/C=C(\C#N)C(=O)N(C)CCO)n(CCCO)c3ncnc(N)c23)cc1]

Yield: 2.3 mg (5%). ESI-MS: 435.6 (MH$^+$).

3-(4-amino-7-(3-hydroxypropyl)-5-p-tolyl-7H-pyrrolo[2,3-d]pyrimidin-6-yl)-2-cyano-N-(1,3-dihydroxy-2-methylpropan-2-yl)acrylamide

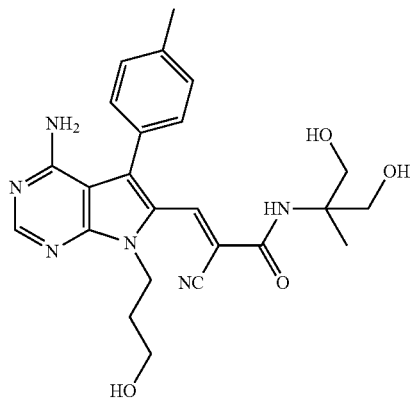 [SMILES: Cc1ccc(-c2c(/C=C(\C#N)C(=O)NC(C)(CO)CO)n(CCCO)c3ncnc(N)c23)cc1]

Yield: 12.3 mg (35% yield). ESI-MS: 464.5 (MH$^+$).

174

3-(4-amino-7-(3-hydroxypropyl)-5-p-tolyl-7H-pyrrolo[2,3-d]pyrimidin-6-yl)-2-(1H-1,2,4-triazol-1-yl)acrylonitrile

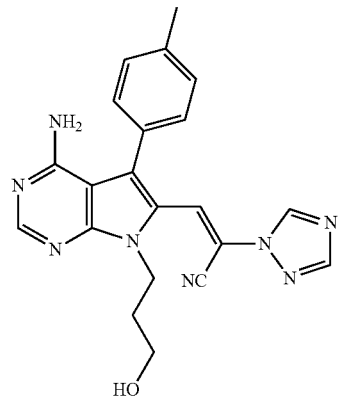 [SMILES: Cc1ccc(-c2c(/C=C(\C#N)n3cncn3)n(CCCO)c3ncnc(N)c23)cc1]

Yield: 7.1 mg (27% yield). ESI-MS: 401.5 (MH$^+$).

2-(4-amino-7-(3-hydroxypropyl)-5-p-tolyl-7H-pyrrolo[2,3-d]pyrimidin-6-yl)-1-cyano-N-isopropylethenesulfonamide

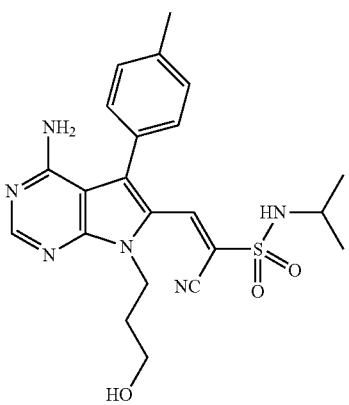 [SMILES: Cc1ccc(-c2c(/C=C(\C#N)S(=O)(=O)NC(C)C)n(CCCO)c3ncnc(N)c23)cc1]

Yield: 17.8 mg (49% yield). ESI-MS: 455.5 (MH$^+$).

3-(4-amino-7-(3-hydroxypropyl)-5-p-tolyl-7H-pyrrolo[2,3-d]pyrimidin-6-yl)-N-(1-adamantyl)-2-cyanoacrylamide

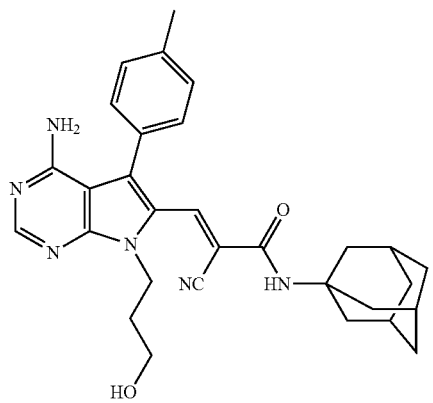 [SMILES: Cc1ccc(-c2c(/C=C(\C#N)C(=O)NC34CC5CC(CC(C5)C3)C4)n(CCCO)c3ncnc(N)c23)cc1]

Yield: 11.3 mg (27% yield). ESI-MS: 511.6 (MH$^+$).

175

3-(4-amino-7-(3-hydroxypropyl)-5-p-tolyl-7H-pyrrolo[2,3-d]pyrimidin-6-yl)-2-(4-methylthiazol-2-yl)acrylonitrile

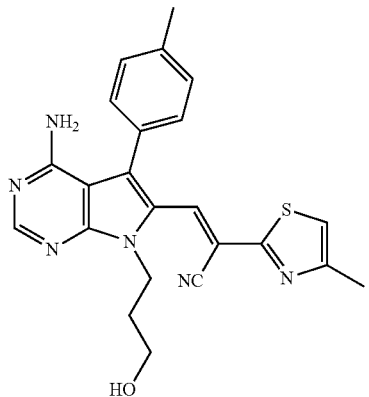 [SMILES: Cc1ccc(-c2c(/C=C(\C#N)c3nc(C)cs3)n(CCCO)c3ncnc(N)c23)cc1]

Yield: 12.7 mg (48% yield). ESI-MS: 431.5 (MH+).

3-(4-amino-7-(3-hydroxypropyl)-5-p-tolyl-7H-pyrrolo[2,3-d]pyrimidin-6-yl)-2-(1H-pyrazol-1-yl)acrylonitrile

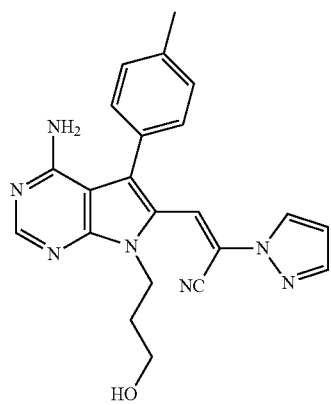 [SMILES: Cc1ccc(-c2c(/C=C(\C#N)n3cccn3)n(CCCO)c3ncnc(N)c23)cc1]

Yield: 6.6 mg (25% yield). ESI-MS: 400.3 (MH+).

3-(4-amino-7-(3-hydroxypropyl)-5-p-tolyl-7H-pyrrolo[2,3-d]pyrimidin-6-yl)-2-(1H-1,2,3-triazol-1-yl)acrylonitrile

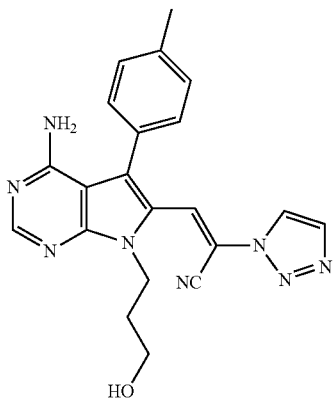 [SMILES: Cc1ccc(-c2c(/C=C(\C#N)n3ccnn3)n(CCCO)c3ncnc(N)c23)cc1]

Yield: 5.2 mg (21% yield). ESI-MS: 401.5 (MH+).

176

Allyl-2-(3-(4-amino-7-(3-hydroxypropyl)-5-p-tolyl-7H-pyrrolo[2,3-d]pyrimidin-6-yl)-2-cyanoacrylamido)-2-methylpropanoate

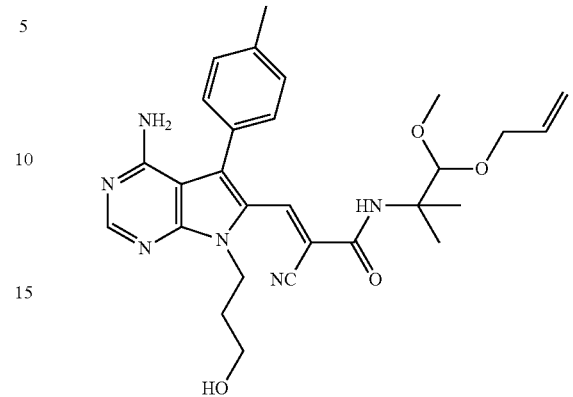

Yield: 11.1 mg (19% yield). ESI-MS: 503.6 (MH+).

3-(4-amino-7-(3-hydroxypropyl)-5-p-tolyl-7H-pyrrolo[2,3-d]pyrimidin-6-yl)-2-(pyridin-3-yl)acrylonitrile

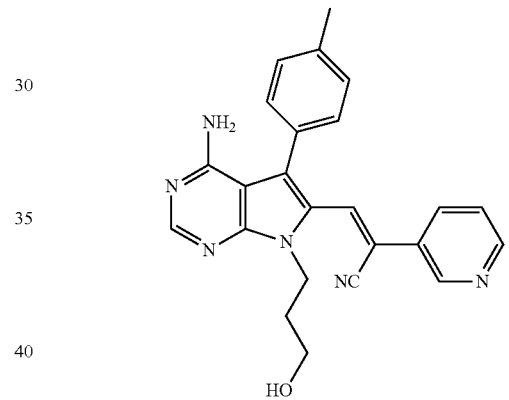

Yield: 21.3 mg (62% yield). ESI-MS: 411.3 (MH+).

4-(2-(4-amino-7-(3-hydroxypropyl)-5-p-tolyl-7H-pyrrolo[2,3-d]pyrimidin-6-yl)-1-cyanovinyl)pyridine 1-oxide

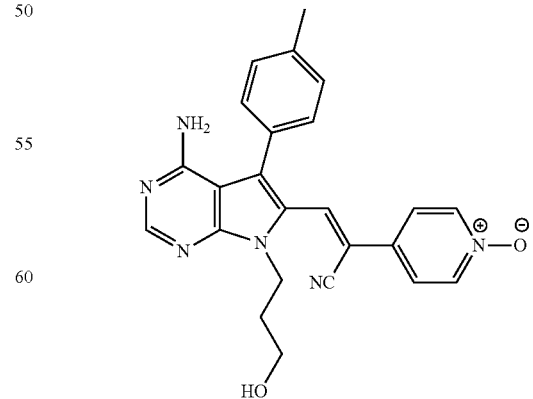

Yield: 3.3 mg (7% yield). ESI-MS: 427.7 (MH+).

177

3-(4-amino-7-(3-hydroxypropyl)-5-p-tolyl-7H-pyr-rolo[2,3-d]pyrimidin-6-yl)-2-cyano-N',N'-dimethyl-acrylohydrazide

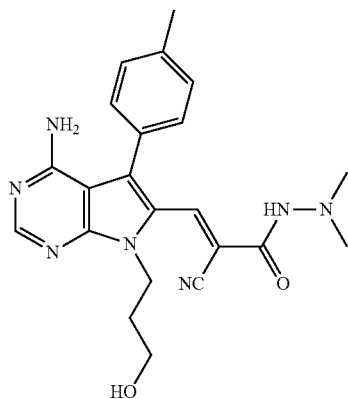 [SMILES: Cc1ccc(-c2c(/C=C(\C#N)C(=O)NN(C)C)n(CCCO)c3ncnc(N)c23)cc1]

Yield: 6.1 mg (18% yield). ESI-MS: 420.5 (MH⁺).

3-(4-amino-7-(3-hydroxypropyl)-5-p-tolyl-7H-pyr-rolo[2,3-d]pyrimidin-6-yl)-2-cyano-N-methoxyacry-lamide

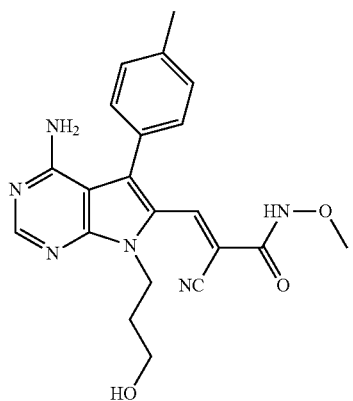 [SMILES: CONC(=O)/C(C#N)=C/c1c(-c2ccc(C)cc2)c2c(N)ncnc2n1CCCO]

Yield: 19 mg (49% yield). ESI-MS: 407.4 (MH⁺).

3-(4-amino-7-(3-hydroxypropyl)-5-p-tolyl-7H-pyr-rolo[2,3-d]pyrimidin-6-yl)-2-cyano-N,N-dimethyl-acrylamide Prepared from N,N-dimethylcyanoacetamide (Basheer, A.; Yamataka, H.; Ammal, S. C.; Rappoport, Z. *J. Org. Chem.* 2007, 72, 5297-5312).

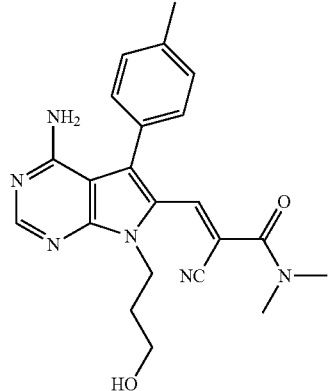 [SMILES: Cc1ccc(-c2c(/C=C(\C#N)C(=O)N(C)C)n(CCCO)c3ncnc(N)c23)cc1]

Yield: 33.8 mg (24%, E:Z=1.7:1). ESI-MS: 405.2 (MH⁺).

178

3-(4-amino-7-(3-hydroxypropyl)-5-p-tolyl-7H-pyr-rolo[2,3-d]pyrimidin-6-yl)-2-cyano-N-(1-hydroxy-2-methylpropan-2-yl)acrylamide Prepared from 2-cyano-N-(1-hydroxy-2-methylpropan-2-yl)acetamide (Santilli, A. A.; Osdene, T. S. *J. Org. Chem.* 1964, 29, 2066-2068).

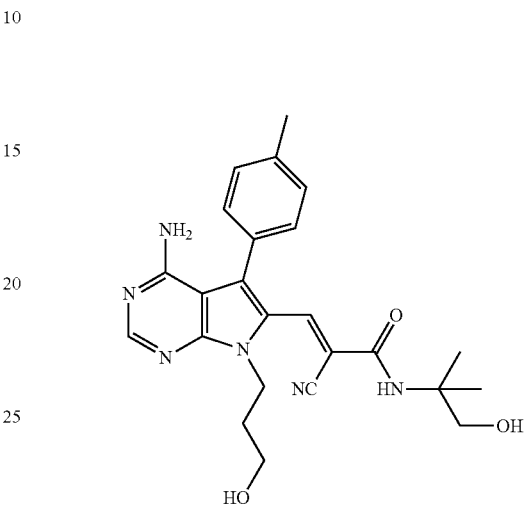

Yield: 17.2 mg (39%), ESI-MS: 449.2 (MH⁺)

3-(4-amino-7-(3-hydroxypropyl)-5-p-tolyl-7H-pyr-rolo[2,3-d]pyrimidin-6-yl)-2-cyano-N,N-diethylacry-lamide Prepared from N,N-diethylcyanoacetamide (Wang, K.; Nguyen, K.; Huang, Y.; Domling, A. *J. Comb. Chem.* 2009, 11, 920-927).

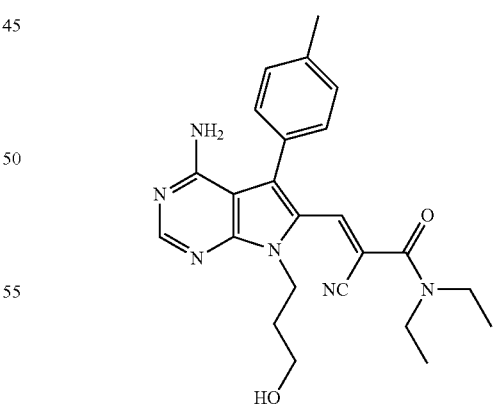

Yield: 9.2 mg (8%), ESI-MS: 433.2 (MH⁺) 3-(4-amino-7-(3-hydroxypropyl)-5-p-tolyl-7H-pyrrolo[2,3-d]pyrimidin-6-yl)-2-(pyrrolidine-1-carbonyl)acrylonitrile Prepared from N-(2-cyanoacetyl)pyrrolidine (Wang, K.; Nguyen, K.; Huang, Y.; Domling, A. *J. Comb. Chem.* 2009, 11, 920-927).

179

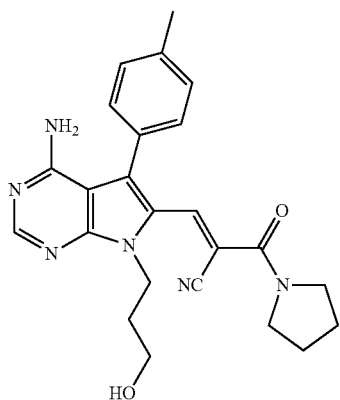 [SMILES: Cc1ccc(-c2c(/C=C(\C#N)C(=O)N3CCCC3)n(CCCO)c3ncnc(N)c23)cc1]

Yield: 1.6 mg (3%), ESI-MS: 431.2 (MH+)

3-(4-amino-7-(3-hydroxypropyl)-5-p-tolyl-7H-pyrrolo[2,3-d]pyrimidin-6-yl)-2-(azetidine-1-carbonyl)acrylonitrile

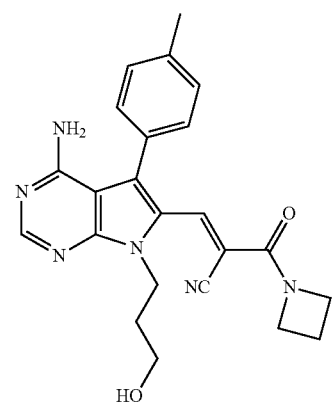 [SMILES: Cc1ccc(-c2c(/C=C(\C#N)C(=O)N3CCC3)n(CCCO)c3ncnc(N)c23)cc1]

Yield: 16.5 mg (32%), ESI-MS: 417.2 (MH+)

3-(4-amino-7-(3-hydroxypropyl)-5-p-tolyl-7H-pyrrolo[2,3-d]pyrimidin-6-yl)-2-(3-hydroxyazetidine-1-carbonyl)acrylonitrile

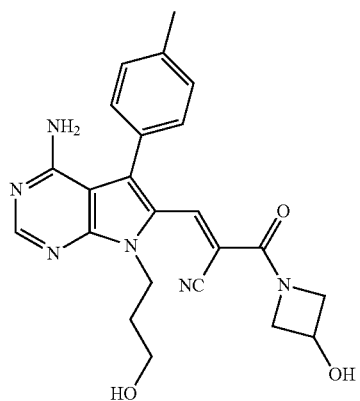 [SMILES: Cc1ccc(-c2c(/C=C(\C#N)C(=O)N3CC(O)C3)n(CCCO)c3ncnc(N)c23)cc1]

Yield: 20.1 mg (38%), ESI-MS: 433.2 (MH+)

180

(E)-3-(4-amino-7-(3-hydroxypropyl)-5-p-tolyl-7H-pyrrolo[2,3-d]pyrimidin-6-yl)-2-(4-methylpiperazine-1-carbonyl)acrylonitrile Prepared from N-(2-cyanoacetyl)-N'-methylpiperazine (Proenca, F.; Costa, M. *Green Chem.* 2008, 10, 995-998).

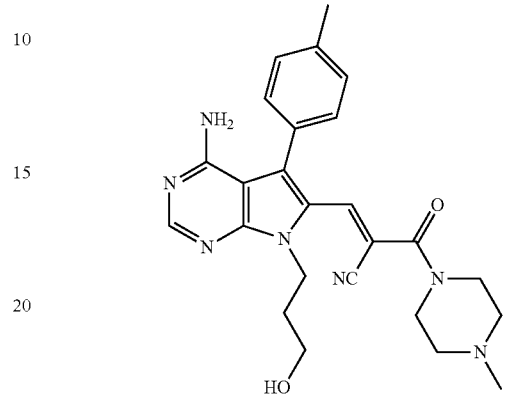

Yield: 15.7 mg (25%), ESI-MS: 460.2 (MH+)

3-(4-amino-7-(3-hydroxypropyl)-5-p-tolyl-7H-pyrrolo[2,3-d]pyrimidin-6-yl)-2-cyano-N-cyclopropylacrylamide

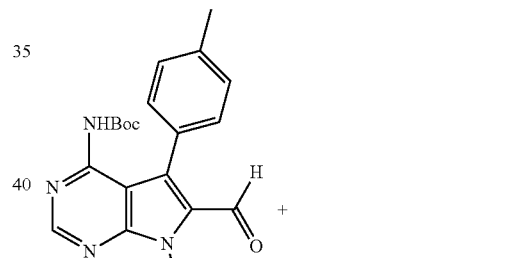

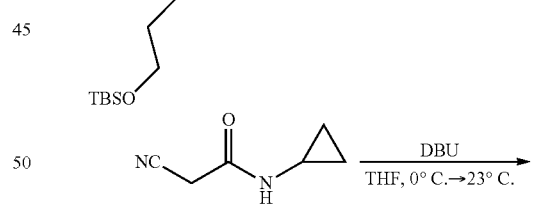

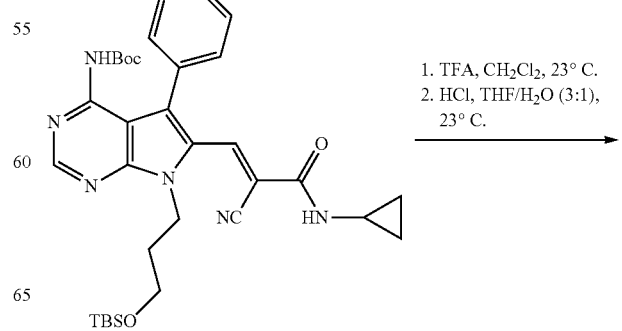

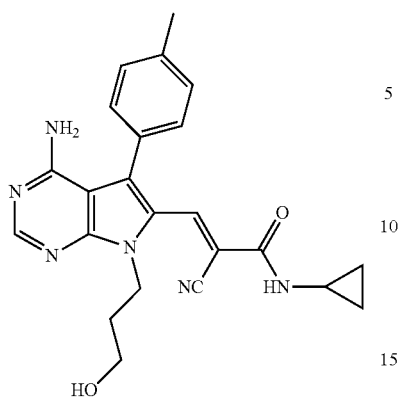

To a solution of 4-tert-butyloxycarbonylamino-7-(3-tert-butyldimethylsiloxypropyl)-5-p-tolyl-7H-pyrrolo[2,3-d]pyrimidine-6-carbaldehyde (101 mg, 0.1925 mmol) and N-cyclopropylcyanoacetamide[3] (47.8 mg, 2.0 equiv.) in THF (2.2 mL) that had been pre-cooled to 0-5° C. was added DBU (58 μL, 2.0 equiv.). The reaction mixture was allowed to warm to ambient temperature and stirred for 1 hour, then maintained at −20° C. for 12 hours. The reaction mixture was concentrated and purified by silica gel chromatography (2:1 Hexanes/EtOAc) to afford 53.2 mg (E:Z=2:1, 44% yield) of the intermediate protected cyanoacrylamide as a yellow oil. This oil was dissolved in $CH_2Cl_2$ (3 mL) and TFA (1.5 mL) was added. After 16 hours at 20-25° C., the reaction mixture was concentrated and the residue was redissolved in THF (6 mL) and 1M aq. HCl (2 mL) was added. The reaction mixture was maintained at ambient temperature for 8 hours, then quenched with satd. aq. $NaHCO_3$ (20 mL) and brine (30 mL) and extracted with EtOAc (3×50 mL). The combined EtOAc extracts were dried ($MgSO_4$) and concentrated and the oil afforded was purified by preparative TLC (3:1 Toluene/IPA, 0.5 cm plate, 2 elutions) to afford the cyanoacrylamide (26 mg, 74% yield over 2 steps) as a yellow oil. ESI-MS: 417.1 ($MH^+$).

1-(4-amino-7-(3-hydroxypropyl)-5-p-tolyl-7H-pyrrolo[2,3-d]pyrimidin-6-yl)-2,2-difluoroethanone

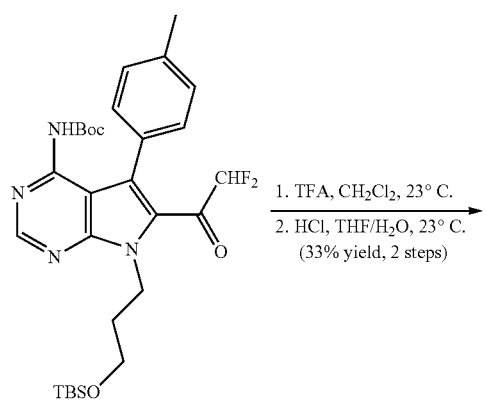

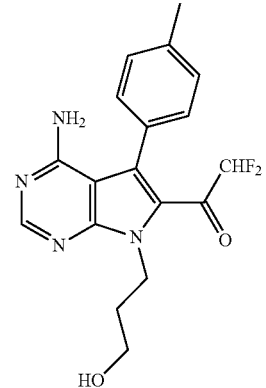

To a solution of the corresponding Di-tert-butyloxycarbonylamino tert-butyldimethylsflyloxydifluoromethyl ketone (39.0 mg, 57.8 μmol) in $CH_2Cl_2$ (2 mL) was added TFA (2 mL). The reaction mixture was maintained at ambient temperature for 17 hours, then concentrated and the residue was redissolved in THF (3 mL). HCl (1M, 1 mL) was added and the reaction mixture was stirred at ambient temperature for 12 hours, then quenched with saturated aqueous sodium bicarbonate (5 mL) and extracted with EtOAc (3×10 mL). The combined organic extracts were dried ($Na_2SO_4$) and concentrated to afford a white solid, which was slurried in MeCN (10 mL). The suspension was filtered and the filtrate was concentrated to afford the difluoromethylketone (6.9 mg, 33% yield, 2 steps) as a white solid. ESI-MS: 361.3 ($MH^+$).

3-(4-amino-7-(3-hydroxypropyl)-5-p-tolyl-7H-pyrrolo[2,3-d]pyrimidin-6-yl)-2-cyano-N-isopropylpropanamide

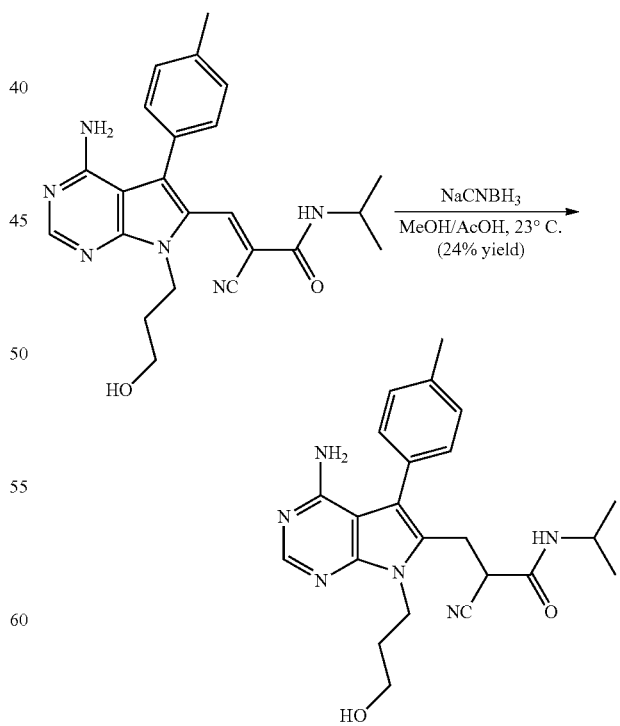

To a solution of the corresponding cyanoacrylamide (31.7 mg, 75.8 μmol) in MeOH (1.8 mL) was added glacial AcOH (0.2 mL), followed by sodium cyanoborohydride (14.3 mg, 227 µmol, 3.0 equiv). The reaction mixture was stirred at ambient temperature for 24 hours, then concentrated and the residue purified by preparative HPLC (0.1% TFA in H₂O: 0.1% TFA in MeCN, 95:5 to 20:80 v/v gradient over 20 minutes) to afford the desired amide (9.8 mg, 24% yield) as a colorless oil. ESI-MS: 421.5 (MH⁺).

Example 82

Assays for Reversible Thiol Addition to Electrophilic, Nitrile-Substituted Olefins

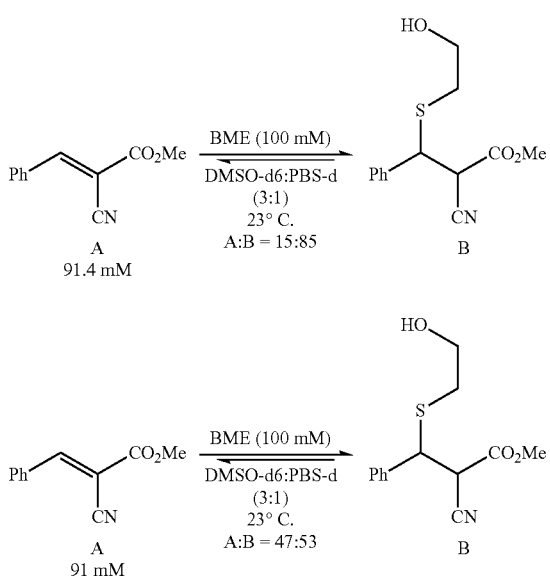

Deuterated Phosphate Buffered Saline (PBS-d) was prepared by dissolution of NaCl (400 mg), KCl (10 mg), Na₂DPO₄ (30.7 mg) and KD₂PO₄ (9.7 mg) in 40 mL D₂O. The pH of the solution was adjusted to 7.4 using NaOD (solution in D₂O) and DCl in D₂O.

To a solution of cyanoacrylate A (5.1 mg, 27.3 µmol) in 0.75 mL of DMSO-d6 was added a solution of 400 mM 2-mercaptoethanol (BME) in PBS-d (0.25 mL). Analysis of the reaction mixture by ¹H NMR indicated >95% conversion to the thiol adduct B.

A ratio of the starting cyanoacrylate to the adduct can be readily determined by integration of the diagnostic peaks at 8.30 ppm for the cyanoacrylate A and 4.52 ppm for the thioether B.

Cyanoacrylate A: ¹H NMR (400 MHz, 3:1 v/v DMSO-d6:PBS-d): δ 8.30 (s, 1H), 7.91 (m, 2H), 7.60-7.49 (m, 3H), 3.78 (s, 3H).

Figure 9:
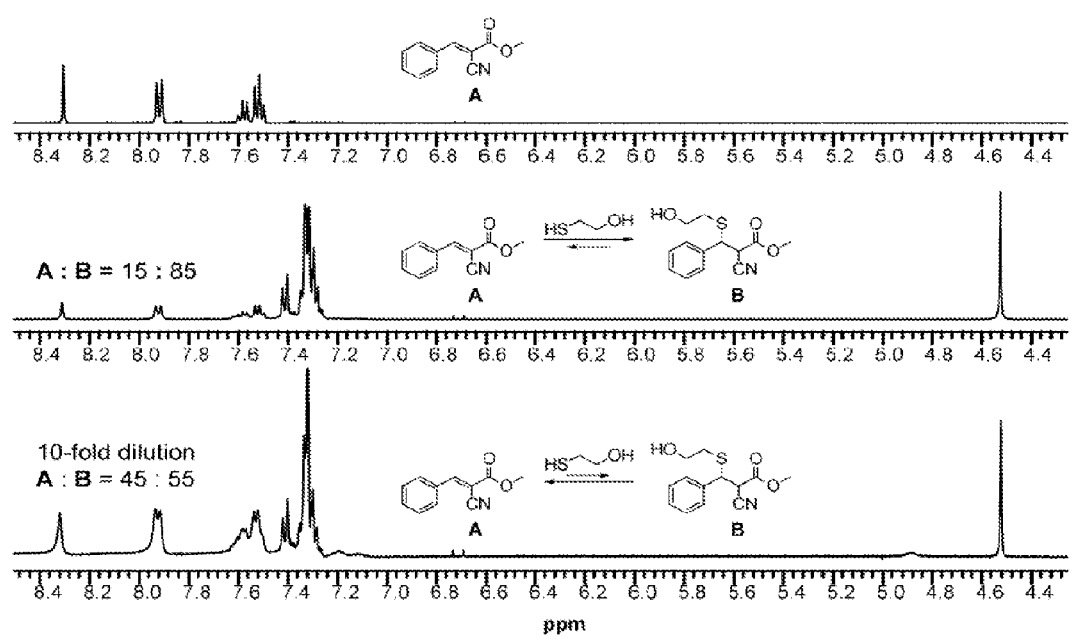
FIG. 9 depicts $^1$H NMR spectrum before and after dilution of reaction mixture.
Figure 10:
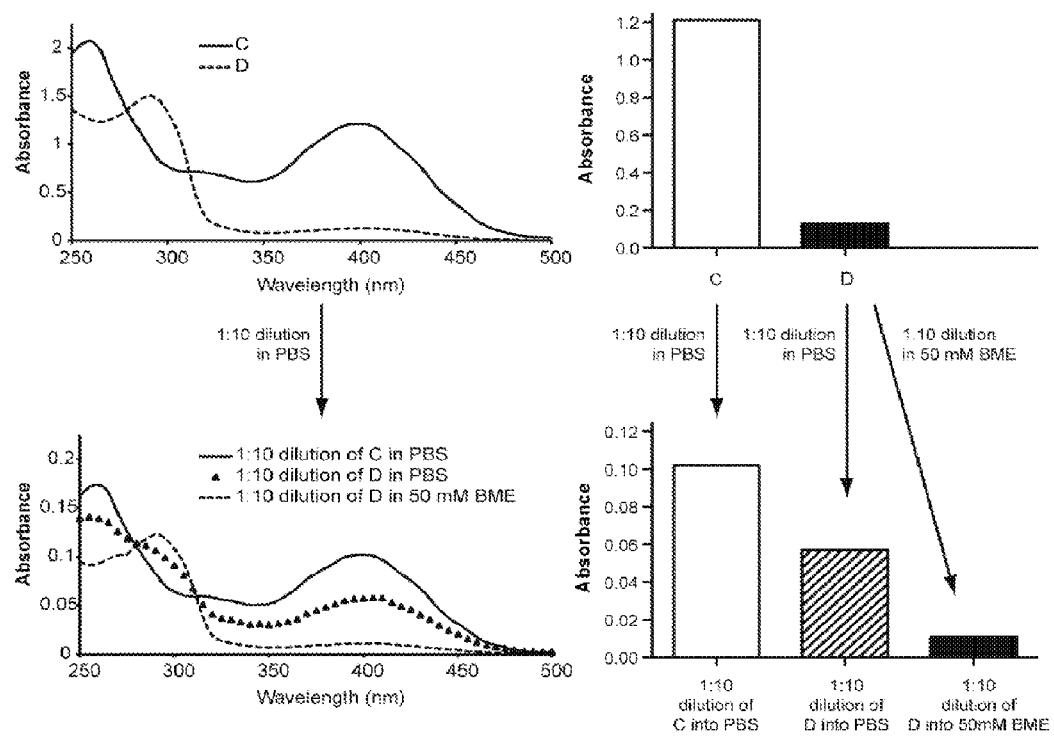
FIG. 10 depicts cyanoacrylamide absorbance spectrum and graphical representation of the absorbance values before and after dilution.

Addition of BME causes the formation of adduct B (a ca. 61:39 mixture of diastereomers) with the following resonances: 1H NMR (400 MHz, 3:1 v/v DMSO-d6:PBS-d): 7.41 (m, 1H), 7.35-7.28 (m, 4H), 4.52 (s, 1H), 3.64 (s, 3H, major diastereomer), 3.56 (s, 3H, minor diastereomer), 3.46 (t, J=6.3 Hz, 2H, major diastereomer, overlaps with signal for excess BME), 3.38 (t, J=6.7 Hz, 2H, minor diastereomer), 2.58-2.40 (m, 2H, overlaps with signal for excess BME). The formation of the thiol adduct was found to be reversible as demonstrated by the following experiment:

To a solution of cyanoacrylate A (17.1 mg, 91.4 µmol) in 0.75 mL of DMSO-d6 was added a solution of 400 mM BME in PBS-d (0.25 mL). Analysis of the reaction mixture by ¹H NMR indicated an 85:15 ratio of the thiol adduct B to the starting cyanoacrylate A. The reaction mixture was then diluted 10-fold by addition of 100 µL of the reaction mixture into 900 µL of 3:1 v/v DMSO-d6:deuterated PBS. Analysis of the solution by ¹H NMR indicated a 53:47 ratio of the thiol adduct B to the starting cyanoacrylate A; the ratio of cyanoacrylate A to adduct B being determined by the integrals of the diagnostic peaks 8.30 ppm for the cyanoacrylate A and 4.52 ppm for the thioether B (FIG. 9).

Example 83

Thiol Reversibility Assay by UV/Visible Spectroscopy

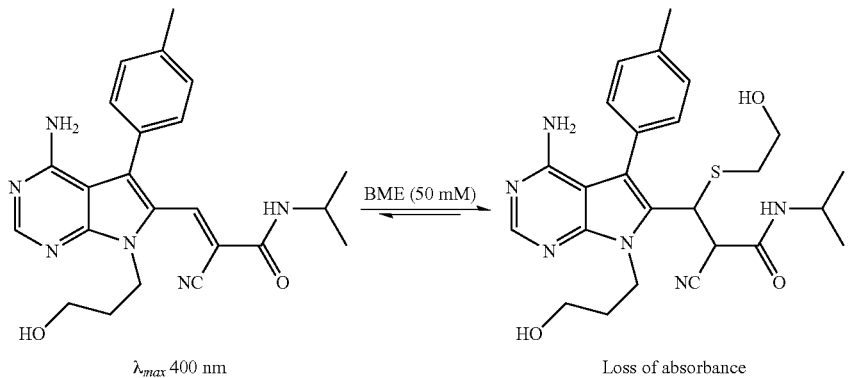

-continued

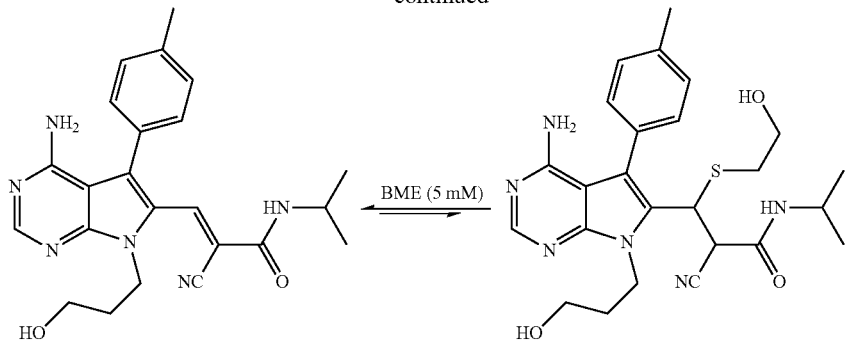

Reversible reactions of UV-active electrophiles with BME can be characterized spectrophotometrically using a Spectramax M5 (Molecular Devices, Sunnyvale Calif.) UV-VIS spectrophotometer over the range of 250-500 nm at 20° C. Equilibrium reactions were initiated by mixing equal volumes of the N-isopropyl cyanoacrylamide depicted above (400 µM solution in PBS, pH 7.4) with a solution of 2-mercaptoethanol (100 mM BME solution in PBS, pH 7.4).

Solutions C (200 µM cyanoacrylamide in PBS at pH 7.4, control) and D (200 µM cyanoacrylamide plus 50 mM BME in PBS at pH 7.4) were analyzed spectrophotometrically (Costar clear flat bottom 96-well plate, 100 µL per well for each reaction) by monitoring the cyanoacrylamide absorbance peak at 400 nm. Disappearance of this peak (solution D, FIG. 2) indicates reaction with BME. Solution D was then diluted 10-fold by mixing 10 µL aliquots with 90 µL of either PBS (pH 7.4) or 50 mM BME in PBS (pH 7.4). Solution C was also diluted 10-fold in PBS (pH 7.4) and was used as a reference for the absorbance signal. Dilution of solution D into PBS results in rapid recovery (within seconds) of the cyanoacrylamide absorbance at 400 nm, indicating rapid reversal of the BME-cyanoacrylamide adduct. These data are consistent with the NMR assay described above. For electrophiles (e.g., cyanoacrylamides) that absorb light at wavelengths above 300 nm, the spectrophotometric assay is more convenient than NMR and is more readily implemented in a high-throughput format (e.g., 96-well plates).

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A compound having the formula:

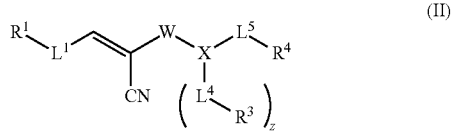

(II)

wherein
W is —C(O)— or S(O)$_2$—;
z is 0 or 1;
X is O or N, wherein if X is O, then z is 0;
R$^1$ is R$^7$-substituted 7H-pyrrolo[2,3-d]pyrimidin-6-yl, R$^7$-substituted 7H-pyrrolo[2,3-d]pyrimidin-7-yl or R$^7$-substituted pyrazolopyrimidin-1-yl;
R$^7$ is independently halogen, —CN, —OH, —NH$_2$, —COOH, —CF$_3$, R$^8$-substituted or unsubstituted alkyl, R$^8$-substituted or unsubstituted heteroalkyl, R$^8$-substituted or unsubstituted cycloalkyl, R$^8$-substituted or unsubstituted heterocycloalkyl, R$^8$-substituted or unsubstituted aryl, R$^8$-substituted or unsubstituted heteroaryl, or -L$^6$-R$^{7A}$;
L$^6$ is —O—, —C(O)—, —C(O)NH—, —S(O)$_m$—, or —S(O)$_m$NH—;
m is 0, 1, or 2;
R$^{7A}$ is hydrogen, halogen, —CN, —OH, —NH$_2$, —COOH, —CF$_3$, R$^8$-substituted or unsubstituted alkyl, R$^8$-substituted or unsubstituted heteroalkyl, R$^8$-substituted or unsubstituted cycloalkyl, R$^8$-substituted or unsubstituted heterocycloalkyl, R$^8$-substituted or unsubstituted aryl, or R$^8$-substituted or unsubstituted heteroaryl;
R$^8$ is independently hydrogen, halogen, —CN, —OH, —NH$_2$, —COOH, —CF$_3$, R$^9$-substituted or unsubstituted alkyl, R$^9$-substituted or unsubstituted heteroalkyl, R$^9$-substituted or unsubstituted cycloalkyl, R$^9$-substituted or unsubstituted heterocycloalkyl, R$^9$-substituted or unsubstituted aryl, or R$^9$-substituted or unsubstituted heteroaryl;
R$^9$ is independently hydrogen, halogen, —CN, —OH, —NH$_2$, —COOH, —CF$_3$, R$^{10}$-substituted or unsubstituted alkyl, R$^{10}$-substituted or unsubstituted heteroalkyl, R$^{10}$-substituted or unsubstituted cycloalkyl, R$^{10}$-substituted or unsubstituted heterocycloalkyl, R$^{10}$-substituted or unsubstituted aryl, or R$^{10}$-substituted or unsubstituted heteroaryl;
R$^{10}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl;
R$^3$ and R$^4$ are independently hydrogen, unsubstituted alkyl, alkyl substituted with one or two hydroxy or di(unsubstituted alkyl)amino, substituted or unsubstituted heteroalkyl, substituted or unsubstituted cycloalkyl, substituted or unsubstituted heterocycloalkyl, or substituted or unsubstituted aryl, wherein R$^3$ and R$^4$ are optionally joined together with X to form a substituted or unsubstituted heterocycloalkyl or substituted or unsubstituted heteroaryl;
L$^1$ is a bond or unsubstituted phenylene;
L$^4$ and L$^5$ are independently a bond, unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and wherein if L$^1$ is a bond and R$^1$ is (3-(4-amino-5-p-tolyl-7H-pyrrolo[2,3-d]pyrimidin-7-yl)propan-1-ol)-6-yl, then at least one of R$^3$ and R$^4$ are not hydrogen.

2. The compound of claim 1, wherein X is N.

3. The compound according to claim 1, having the structure

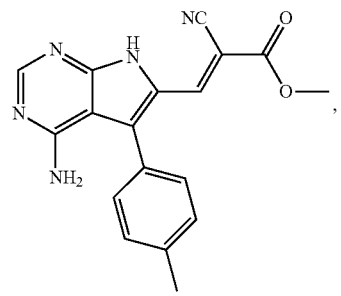
,

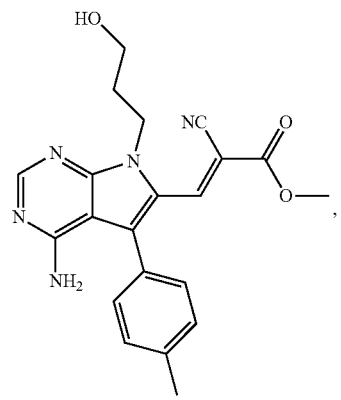
,

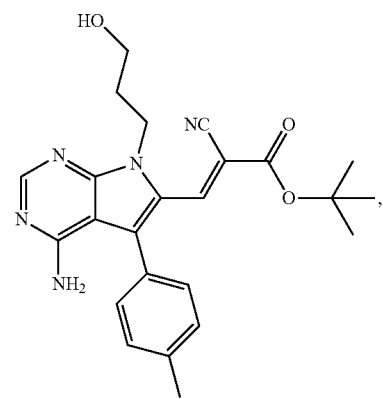
,

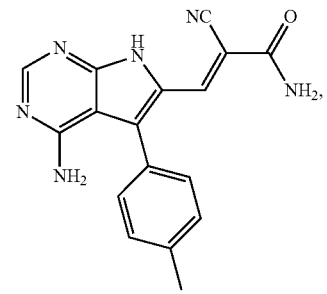
,

189
-continued
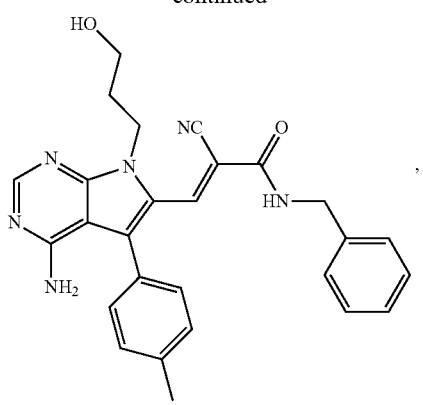
,
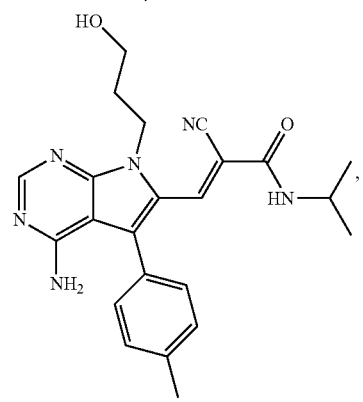
,
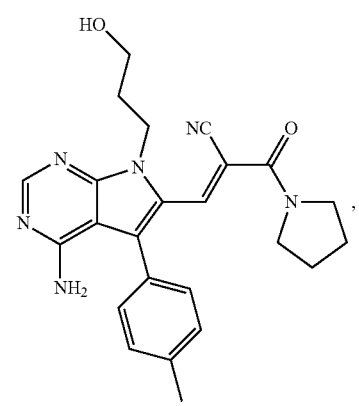
,
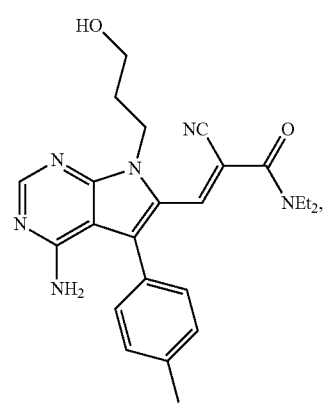
,
190
-continued
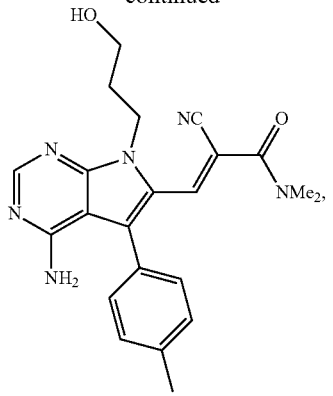
,
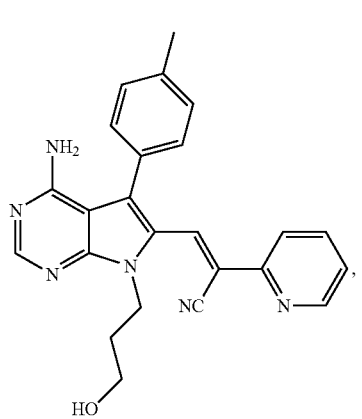
,
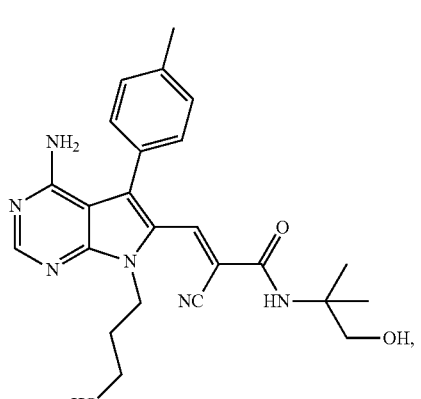
,
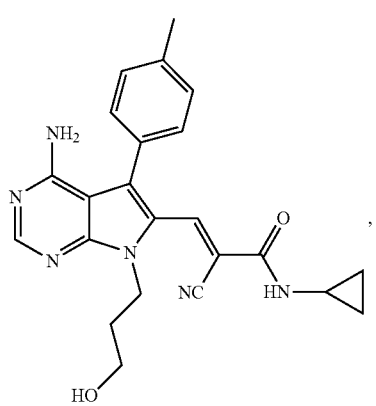
, 191
-continued
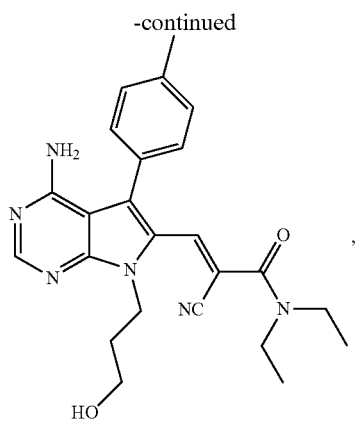
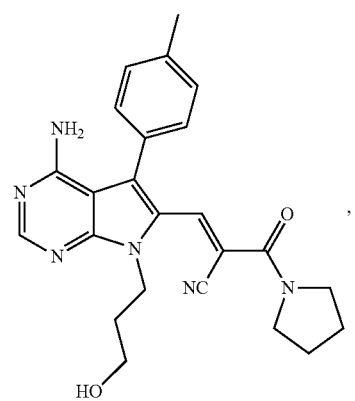
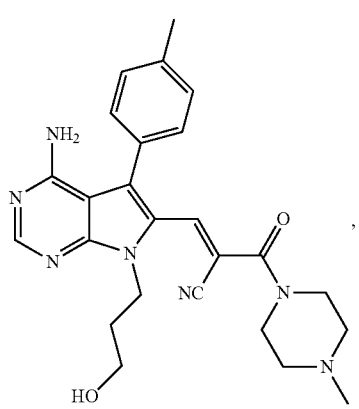
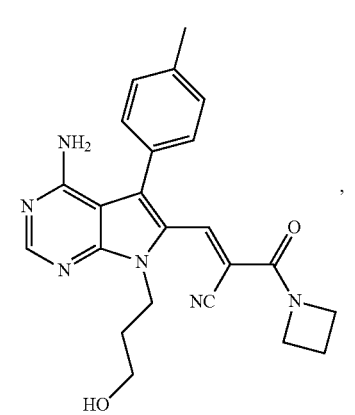
192
-continued
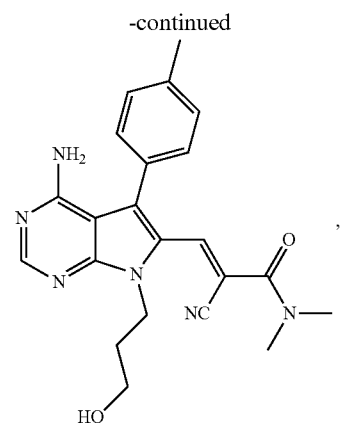
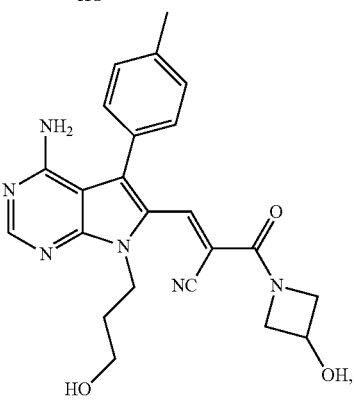
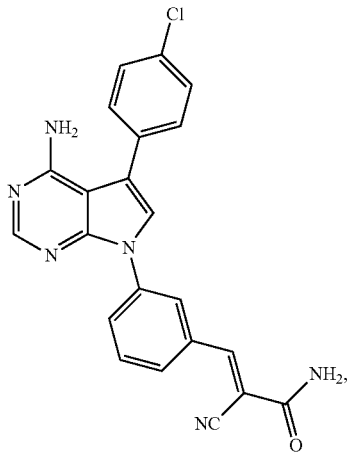
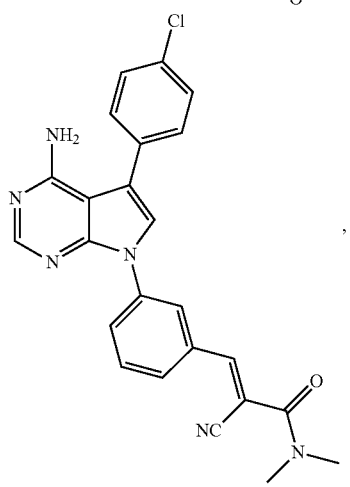

-continued
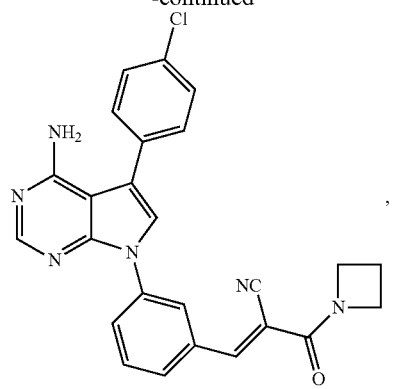
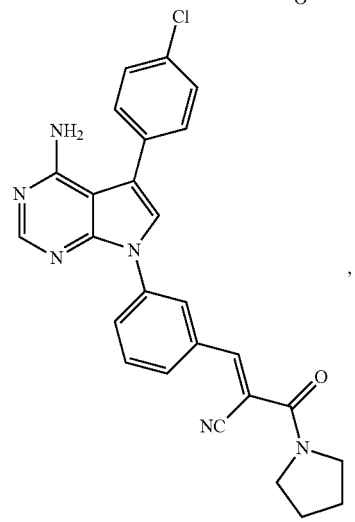
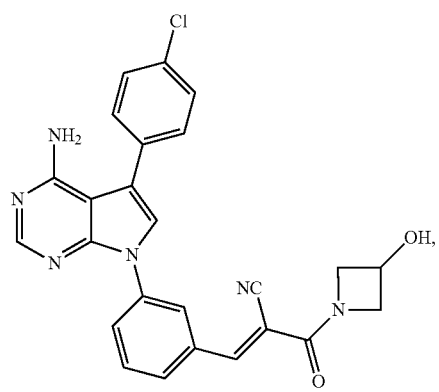
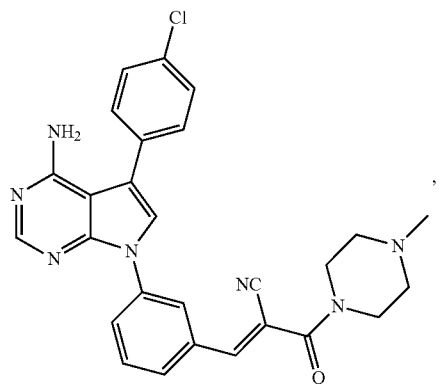
-continued
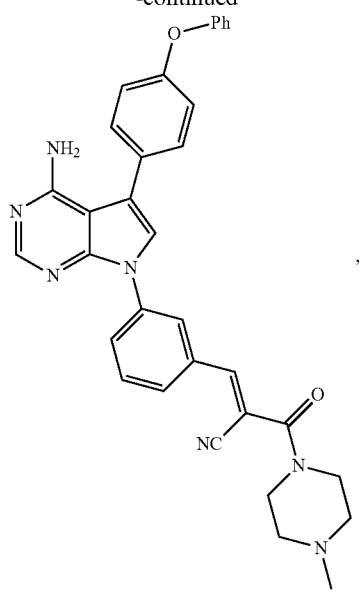
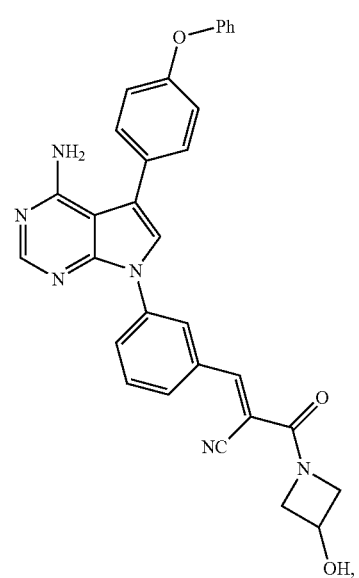
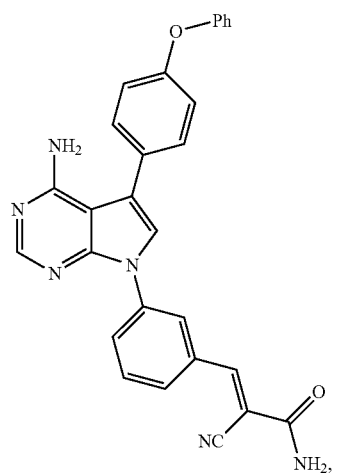

195
-continued
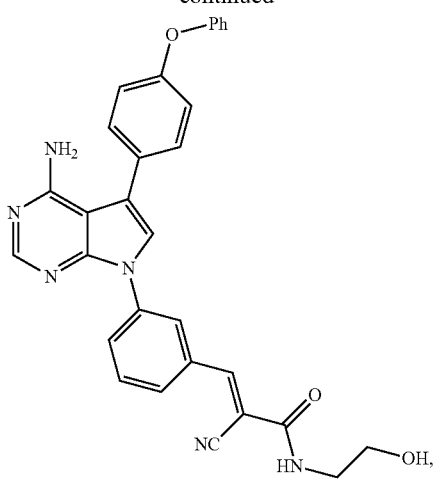
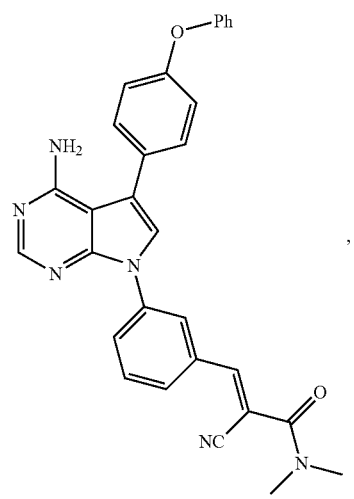
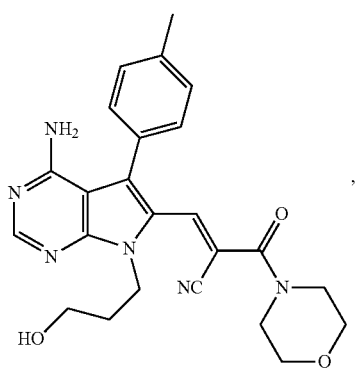
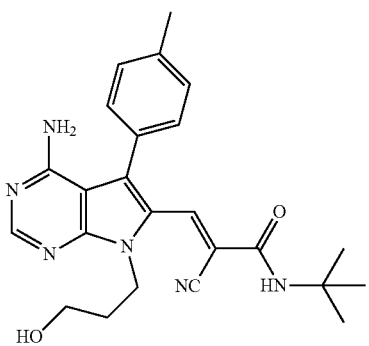
196
-continued
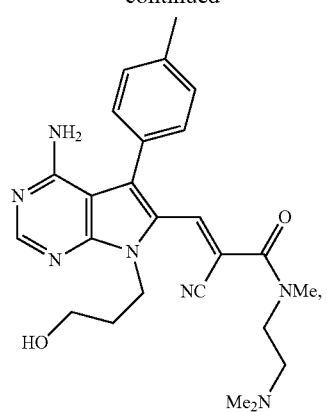
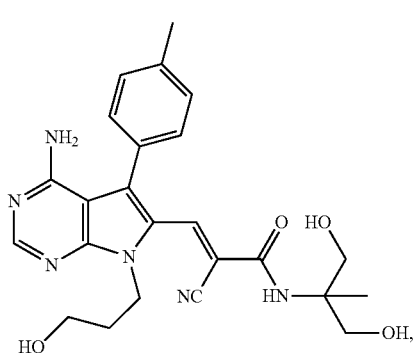
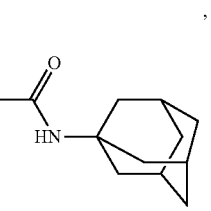
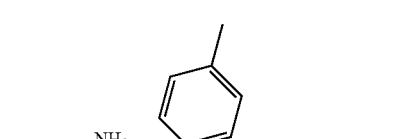
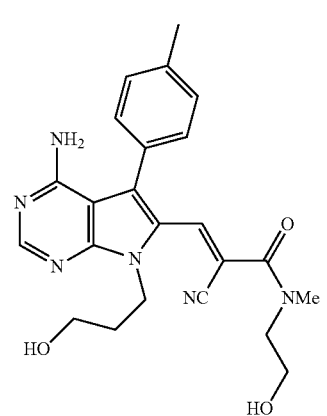

-continued

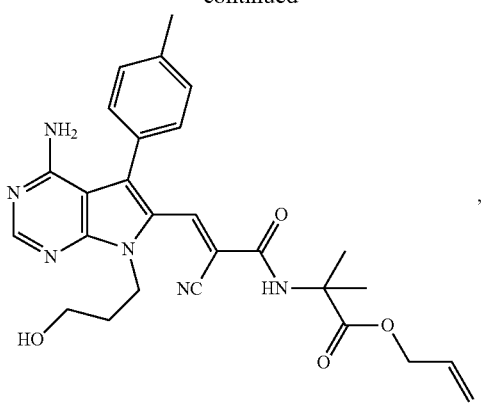

,

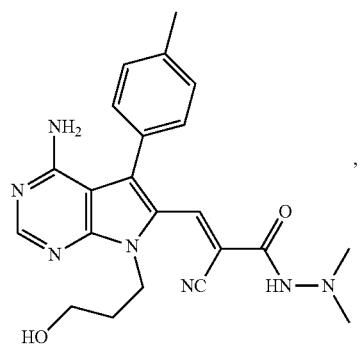

,

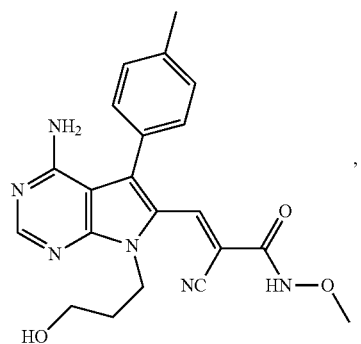

,

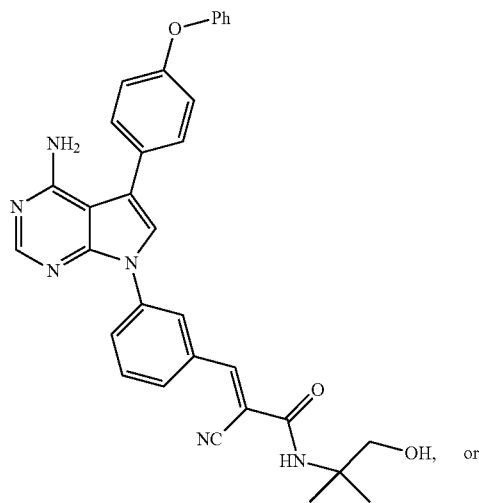 or

-continued

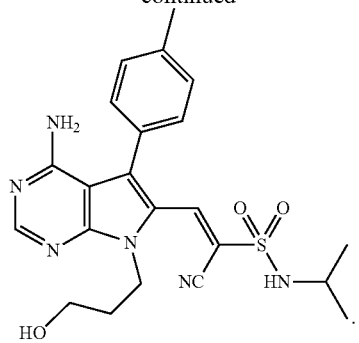

.

4. A pharmaceutical composition comprising a compound of claim 1 and a pharmaceutically acceptable excipient.

5. A compound having the formula:

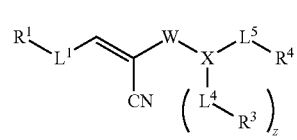

(II)

wherein

W is —C(O)— or —S(O)$_2$—;

z is 1;

R$^1$ is R$^7$-substituted 7H-pyrrolo[2,3-d]pyrimidin-6-yl, R$^7$-substituted 7H-pyrrolo[2,3-d]pyrimidin-7-yl or R$^7$-substituted pyrazolopyrimidin-1-yl;

R$^7$ is halogen, —CN, —OH, —NH$_2$, —COOH, —CF$_3$, R$^8$-substituted or unsubstituted alkyl, R$^8$-substituted or unsubstituted heteroalkyl, R$^8$-substituted or unsubstituted cycloalkyl, R$^8$-substituted or unsubstituted heterocycloalkyl, R$^8$-substituted or unsubstituted aryl, R$^8$-substituted or unsubstituted heteroaryl, or -L$^6$-R$^{7A}$;

L$^6$ is —O—, —C(O)—, —C(O)NH—, —S(O)$_m$—, or —S(O)$_m$NH—;

m is 0, 1, or 2;

R$^{7A}$ is hydrogen, halogen, —CN, —OH, —NH$_2$, —COOH, —CF$_3$, R$^8$-substituted or unsubstituted alkyl, R$^8$-substituted or unsubstituted heteroalkyl, R$^8$-substituted or unsubstituted cycloalkyl, R$^8$-substituted or unsubstituted heterocycloalkyl, R$^8$-substituted or unsubstituted aryl, or R$^8$-substituted or unsubstituted heteroaryl;

R$^8$ is independently hydrogen, halogen, —CN, —OH, —NH$_2$, —COOH, —CF$_3$, R$^9$-substituted or unsubstituted alkyl, R$^9$-substituted or unsubstituted heteroalkyl, R$^9$-substituted or unsubstituted cycloalkyl, R$^9$-substituted or unsubstituted heterocycloalkyl, R$^9$-substituted or unsubstituted aryl, or R$^9$-substituted or unsubstituted heteroaryl;

R$^9$ is independently hydrogen, halogen, —CN, —OH, —NH$_2$, —COOH, —CF$_3$, R$^{10}$-substituted or unsubstituted alkyl, R$^{10}$-substituted or unsubstituted heteroalkyl, R$^{10}$-substituted or unsubstituted cycloalkyl, R$^{10}$-substituted or unsubstituted heterocycloalkyl, R$^{10}$-substituted or unsubstituted aryl, or R$^{10}$-substituted or unsubstituted heteroaryl;

R$^{10}$ is independently halogen, —CN, —OH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl;

$R^3$ and $R^4$ are independently hydrogen, unsubstituted alkyl, alkyl substituted with one or two hydroxy or di-(unsubstituted alkyl)amino, substituted or unsubstituted heteroalkyl, substituted or unsubstituted cycloalkyl, substituted or unsubstituted heterocycloalkyl, or substituted or unsubstituted aryl wherein $R^3$ and $R^4$ are optionally joined together with X to form a substituted or unsubstituted heterocycloalkyl or substituted or unsubstituted heteroaryl;

$L^1$ is a bond or unsubstituted phenylene;

$L^4$ and $L^5$ are independently a bond, unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and wherein if $L^1$ is a bond and $R^1$ is (3-(4-amino-5-p-tolyl-7H-pyrrolo[2,3-d]pyrimidin-7-yl)propan-1-ol)-6-yl, then at least one of $R^3$ and $R^4$ are not hydrogen.

6. The compound according to claim 5, wherein $R^1$ is $R^7$-substituted 7H-pyrrolo[2,3-d]pyrimidinyl.

7. The compound according to claim 6, wherein $R^3$ and $R^4$ are hydrogen.

8. The compound according to claim 6,
wherein
$R^3$ is unsubstituted alkyl; and
$R^4$ is hydrogen.

9. The compound according to claim 6, wherein $R^3$ and $R^4$ join with N to form $R^{23}$-substituted or unsubstituted pyrrolidinyl.

10. The compound according to claim 5,
wherein
$R^1$ is $R^7$-substituted 7H-pyrrolo[2,3-d]pyrimidinyl; and
$R^7$ is —$NH_2$, $R^8$-substituted or unsubstituted alkyl, or $R^8$-substituted or unsubstituted phenyl.

\* \* \* \* \*